US011253585B2

(12) United States Patent
Smith et al.

(10) Patent No.: US 11,253,585 B2
(45) Date of Patent: Feb. 22, 2022

(54) VACCINE COMPOSITIONS HAVING IMPROVED STABILITY AND IMMUNOGENICITY

(71) Applicant: Novavax, Inc., Gaithersburg, MD (US)

(72) Inventors: Gale Smith, Germantown, MD (US); Ye Liu, Clarksville, MD (US); Jing-Hui Tian, Germantown, MD (US); Michael J. Massare, Mt. Airy, MD (US); Sarathi Boddapati, Germantown, MD (US); Erica Shane, McLean, VA (US); Cynthia Oliver, Potomac, MD (US); Gregory Glenn, Potomac, MD (US)

(73) Assignee: Novavax, Inc., Gaithersburg, MD (US)

( * ) Notice: Subject to any disclaimer, the term of this patent is extended or adjusted under 35 U.S.C. 154(b) by 229 days.

(21) Appl. No.: 16/545,424

(22) Filed: Aug. 20, 2019

(65) Prior Publication Data

US 2020/0101151 A1 Apr. 2, 2020

Related U.S. Application Data

(62) Division of application No. 15/257,436, filed on Sep. 6, 2016, now Pat. No. 10,426,829.

(60) Provisional application No. 62/350,973, filed on Jun. 16, 2016, provisional application No. 62/309,216, filed on Mar. 16, 2016, provisional application No. 62/255,786, filed on Nov. 16, 2015, provisional application No. 62/213,947, filed on Sep. 3, 2015.

(51) Int. Cl.
| | |
|---|---|
| *A61K 39/155* | (2006.01) |
| *A61K 39/12* | (2006.01) |
| *C12N 7/00* | (2006.01) |
| *A61K 9/00* | (2006.01) |
| *A61K 9/16* | (2006.01) |
| *A61K 39/00* | (2006.01) |

(52) U.S. Cl.
CPC .......... *A61K 39/155* (2013.01); *A61K 9/0019* (2013.01); *A61K 9/1611* (2013.01); *A61K 9/1617* (2013.01); *A61K 39/12* (2013.01); *C12N 7/00* (2013.01); *A61K 2039/54* (2013.01); *A61K 2039/55505* (2013.01); *A61K 2039/55555* (2013.01); *C12N 2710/14143* (2013.01); *C12N 2760/14134* (2013.01); *C12N 2760/14171* (2013.01); *C12N 2760/16122* (2013.01); *C12N 2760/16134* (2013.01); *C12N 2760/16151* (2013.01); *C12N 2760/16222* (2013.01); *C12N 2760/16234* (2013.01); *C12N 2760/16251* (2013.01); *C12N 2760/18522* (2013.01); *C12N 2760/18534* (2013.01)

(58) Field of Classification Search
None
See application file for complete search history.

(56) References Cited

U.S. PATENT DOCUMENTS

| | | |
|---|---|---|
| 4,900,549 A | 2/1990 | De Vries et al. |
| 5,057,540 A | 10/1991 | Kensil et al. |
| 5,149,650 A | 9/1992 | Wertz et al. |
| 5,620,690 A | 4/1997 | Kersten et al. |
| 6,231,859 B1 | 5/2001 | Kensil |
| 6,245,532 B1 | 6/2001 | Smith et al. |
| 6,352,697 B1 | 3/2002 | Cox et al. |
| 6,428,807 B1 | 8/2002 | MacFarlan et al. |
| 6,558,670 B1 | 5/2003 | Friede et al. |
| 8,563,002 B2 | 10/2013 | Baudoux et al. |
| 8,715,692 B2 | 5/2014 | Pushko et al. |
| 8,821,881 B2 | 9/2014 | Morein et al. |
| 9,675,685 B2 | 6/2017 | Pushko et al. |
| 9,708,373 B2 | 7/2017 | Garcia-Sastre et al. |
| 9,717,786 B2 | 8/2017 | Pushko et al. |
| 9,731,000 B2 | 8/2017 | Pushko et al. |
| 10,022,437 B2 | 7/2018 | Pushko et al. |
| 10,426,829 B2 | 10/2019 | Smith et al. |
| 10,729,764 B2 | 8/2020 | Morein et al. |
| 2004/0028698 A1 | 2/2004 | Colau et al. |
| 2005/0142148 A1 | 6/2005 | Fouchier et al. |
| 2006/0121065 A1 | 6/2006 | Morein et al. |
| 2006/0171917 A1 | 8/2006 | Campbell et al. |
| 2006/0239963 A1 | 10/2006 | Morein et al. |
| 2008/0233150 A1 | 9/2008 | Smith et al. |
| 2010/0239617 A1 | 9/2010 | Pushko et al. |
| 2010/0239671 A1 | 9/2010 | Edelman et al. |
| 2010/0285135 A1 | 11/2010 | Wendorf et al. |
| 2010/0291147 A1 | 11/2010 | Baudoux et al. |
| 2012/0107353 A1 | 5/2012 | Morein et al. |
| 2013/0122032 A1 | 5/2013 | Smith et al. |

(Continued)

FOREIGN PATENT DOCUMENTS

| | | |
|---|---|---|
| AU | 200324520 B2 | 4/2009 |
| AU | 2014100888 A4 | 9/2014 |

(Continued)

OTHER PUBLICATIONS

"Safety Evaluation of Certain Food Additives and Contaminants Quillaia Extracts," WHO Food Additives, WHO (first draft, Eastwood et al., Series:48, pp. 1-14 (2001).

(Continued)

*Primary Examiner* — Agnieszka Boesen
(74) *Attorney, Agent, or Firm* — Cooley LLP

(57) ABSTRACT

Disclosed herein are nanoparticles suitable for use in vaccines. The nanoparticles present antigens from pathogens surrounded to and associated with a detergent core resulting in enhanced stability and good immunogenicity. Dosages, formulations, and methods for preparing the vaccines and nanoparticles are also disclosed.

27 Claims, 103 Drawing Sheets

Specification includes a Sequence Listing.

(56) References Cited

U.S. PATENT DOCUMENTS

| | | | |
|---|---|---|---|
| 2013/0123333 A1 | 5/2013 | Mirkin et al. |
| 2013/0337005 A1 | 12/2013 | Rademacher et al. |
| 2014/0227309 A1 | 8/2014 | Smith et al. |
| 2014/0294879 A1 | 10/2014 | Pushko et al. |
| 2014/0335049 A1 | 11/2014 | Morein et al. |
| 2015/0202283 A1 | 7/2015 | Steff et al. |
| 2015/0209425 A1 | 7/2015 | Morein et al. |
| 2015/0265698 A1 | 9/2015 | Pushko et al. |
| 2015/0266930 A1 | 9/2015 | Pushko et al. |
| 2015/0306207 A1 | 10/2015 | Smith et al. |
| 2015/0335730 A1 | 11/2015 | Smith et al. |
| 2015/0359872 A1 | 12/2015 | Pushko et al. |
| 2016/0184427 A1 | 6/2016 | Morein et al. |
| 2017/0202948 A1 | 7/2017 | Smith et al. |
| 2017/0319682 A1 | 11/2017 | Smith et al. |
| 2018/0133308 A1 | 5/2018 | Smith et al. |
| 2018/0369368 A1 | 12/2018 | Morein et al. |
| 2019/0134187 A1 | 5/2019 | Pushko et al. |
| 2019/0314487 A1 | 10/2019 | Boddapati et al. |
| 2020/0030436 A1 | 1/2020 | Pushko et al. |
| 2020/0215189 A1 | 7/2020 | Morein et al. |

FOREIGN PATENT DOCUMENTS

| | | |
|---|---|---|
| CA | 2491457 C | 9/2012 |
| CN | 101090711 A | 12/2007 |
| CN | 102107003 A | 6/2011 |
| EP | 0109942 A2 | 5/1984 |
| EP | 0362279 B1 | 1/1995 |
| EP | 1539231 B1 | 6/2009 |
| WO | WO 88/09336 A1 | 12/1988 |
| WO | WO 90/03184 A1 | 4/1990 |
| WO | WO 96/11711 A1 | 4/1996 |
| WO | WO 97/30728 A1 | 8/1997 |
| WO | WO 2001/0066137 A1 | 9/2001 |
| WO | WO 2004/004762 A1 | 1/2004 |
| WO | WO 2005/002620 A1 | 1/2005 |
| WO | WO 2005/080417 A2 | 9/2005 |
| WO | WO 2007/149490 A1 | 12/2007 |
| WO | WO 2008/114149 A2 | 9/2008 |
| WO | WO 2008/133663 A2 | 11/2008 |
| WO | WO 2009/012487 A2 | 1/2009 |
| WO | WO 2009/108689 A1 | 9/2009 |
| WO | WO 2010/077717 A1 | 7/2010 |
| WO | WO 2010/138193 A2 | 12/2010 |
| WO | WO 2010/138193 A3 | 12/2010 |
| WO | WO2011/008974 A1 | 1/2011 |
| WO | WO2011/008974 A3 | 1/2011 |
| WO | WO 2012/061815 A2 | 5/2012 |
| WO | WO 2012/061815 A3 | 5/2012 |
| WO | WO 2013/006842 A2 | 1/2013 |
| WO | WO 2013/006842 A3 | 1/2013 |
| WO | WO 2013/049342 A1 | 4/2013 |
| WO | WO 2014/024024 A1 | 2/2014 |
| WO | WO 2014/124423 A1 | 8/2014 |
| WO | WO 2014/174018 A1 | 10/2014 |
| WO | WO 2015/042373 A1 | 3/2015 |

OTHER PUBLICATIONS

Adjuvanting Viral Vectored Malaria Vaccines with Matrix M, Identifier NCT01669512, ClinicaiTrials.gov, U.S. National Institutes of Health; available at http://clinicaltrials.gov/ct2/show/NCT01669512?term=MatrixM+or+Matrix+M&rank=1, Mar. 9, 2014, pp. 1-4.

Ahlberg et al., Global transcriptional response to ISCOM-Matrix adjuvant at the site of administration and in the draining lymph node early after intramuscular injection in pigs, Developmental and Comparative Immunology, vol. 38, pp. 17-26 (2012), Elsevier Ltd.

Barr et al., "ISCOMs and other saponin based adjuvants," Advanced Drug Delivery Reviews, (1998), 32: 247-271.

Behboudi et al., "Quillaja Saponin Formulations that Stimulate Proinflammatory Cytokines Elicit a Potent Acquired Cell-Mediated Immunity," Scand. J. Immunol. 50:371-377 (1999).

Bengtsson et al., Matrix-M adjuvant increases immunogenicity of seasonal influenza vaccine for the elderly, manuscrip in preparation, pp. 1-27 (2014).

Boulter, et al., Evaluation of recombinant sporozoite antigen SPAG-1 as a vaccine candidate against Theileria annulata by the use of different delivery systems, Tropical Medicine and International Health, vol. 4, pp. A71-A77 (1999), Blackwell Science, Ltd.

Copland et al., "Hydration of lipid films with an aqueous solution of Quil A: a simple method for the preparation of immune-stimulating complexes," International Journal of Pharmaceutics 196:135-139 (2000).

Coulter, et al., Studies on experimental adjuvanted influenza vaccines: comparison of immune stimulating complexes(Iscoms) and oil-in-water vaccines; Vaccine, vol. 16, No. 11/12, pp. 1243-1253 (1998), Elsevier Science Ltd., Great Britain.

Cox, et al., Development of an Influenza-ISCOM Vaccine, in Vaccine Design (eds. G. Gregoriadis et al.), Springer Science+Business Media, New York (1997), pp. 33-49.

Cox, et al., Evaluation of a virosomal H5N1 vaccine formulated with Maxtrix M adjuvant in phase I clinical trial, Elsevier Ltd, Vaccine, 29, pp. 8049-8059, Aug. 22, 2011.

Cox, et al., Prospects for the Development of New Vaccine Adjuvants, BioDrugs, vol. 12(6), pp. 439-453 (1999), Ad is International Limited.

Demana et al., "Pseudo-ternary phase diagrams of aqueous mixtures of Quil A, cholesterol and phospholipid prepared by the lipid-film hydration method," International Journal of Pharmaceutics 270:229-239 (2004).

Drane et al., "Iscomatrix™ adjuvant for prophylactic and therapeutic vaccines," Expert Rev. Vaccines 6:761-772 (2007).

Ekstrom et al., "Iscom and iscom-matrix enhance by intranasal route the IgA responses to OVA and rCTB in local and remote mucosal secretions," Vaccine 17:2690-2701 (1999).

EMEA (European Agency for the Evaluation of Medicinal Products), "Committee for Veterinary Medicinal Products. Quillaia Saponins. Summary Report ," EMEA/MRL/055/95-FINAL, pp. 1-2 (1996).

Ennis et al., "Augmentation of Human Influenza A Virus-Specific Cytotoxic T Lymphocyte Memory by Influenza Vaccine and Adjuvanted Carriers (ISCOMS)," Virology 25:256-261 (1999).

Eyles et al., "Immunodominant Francisella tularensis antigens identified using proteome microarray," Proteomics 7:2172-2183 (2007).

Fossum et al., Early inflammatory response to the saponin adjuvant Matrix-M in the pig, Veterinary Immunology and Immunopathology, http://dx.doi.org/10.1016/j.vetimm.2013.07.007 (2013), pp. 1-9, Elsevier B.V.

Genocea Biosciences, Genocea Reports Positive Initial Phase 1/2A Results for GEN-003, It's Pioneering Therapeutic Vaccine Candidate for the Treatment of Herpes Simplex Virus-2 (HSV-2), at ICAAC 2013, press release, Cambridge MA, Sep. 12, 2013, pp. 1-3.

Johansson et al., "Iscoms with different quillaja saponin components differ in their immunomodulating activities," Vaccine 17:2894-2900 (1999).

Kensil, Saponins as Vaccine Adjuvants, Critical Reviews in Therapeutic Drug Carrier Systems, vol. 13(1&2), pp. 1-55 (1996), Begell House, Inc.

Kersten et al., On the structure of immune-stimulating saponin-lipid complexes (iscoms) Biochimica et Biophysica Acta, 1062:165-171 (1991).

Lavelle et al., "Cholera Toxin Promotes the Induction of Regulatory T Cells Specific for Bystander Antigens by Modulating Dendritic Cell Activation," Journal of Immunology 171:2384-2392 (2003).

Lovgren-Bengtsson et al., "4.5 Preparation and Use of Adjuvants," Methods in Microbiology 32:551-588 (2002).

Lovgren-Bengtsson, 6 Preparation and Use of Adjuvants; Methods in Microbiology, vol. 25, pp. 471-502 (1998), Academic Press Ltd.

Lucy et al., "Structure and Assembly of Macromolecular Lipid Complexes Composed of Globular Micelles," Journal of Molecular Biology, (1964), 8: 727-748.

Magnusson et al., Immune enhancing properties of the novel Matrix-M adjuvant leads to potentiated immune responses to an influenza vaccine in mice, Vaccine, http://dx.doi.org/10.1 016/j.vaccine.2013.01.039 (2013), pp. 1-9, Elsevier Ltd.

(56) References Cited

OTHER PUBLICATIONS

Magnusson et al., Matrix-M adjuvanted envelope protein vaccine protects against lethal lineage 1 and 2 West Nile virus infection in mice, Vaccine vol. 32, pp. 800-808 (2014), Elsevier Ltd.
McKenzie et al., ISCOMATRIX vaccines: Safety in human clinical studies, Human Vaccines, vol. 6, No. 3, pp. 237-246 (2010), Landes BioScience.
Morein et al., "Current status and potential application of ISCOMs in veterinary medicine," Advanced Drug Delivery Reviews 56:1367-1382 (2004).
Nord et al., "Novel acetylated triterpenoid saponins in a chromatographic fraction from Quillaja saponaria Molina," Carbohydrate Research 329:817-829 (2000).
Ozel et al., "Quaternary Structure of the Immunostimulating Complex (Iscom),"Journal of Ultrastructure and Molecular Structure Research 102:240-248 (1989).
Pedersen et al., Matrix-M adjuvanted virosomal H5N1 vaccine confers protection against lethal viral challenge in a murine model, Influenza and Other Respiratory Viruses. DOI: 1 0.1111/j.1750-2659.2011.00256.x (2011 ), pp. 1-12, Blackwell Publishing Ltd.
Pedersen, et al.; T-Helper 1 Cells Elicited by H5N1 Vaccination Predict Seroprotection, Journal of Infectious Disease, 206, pp. 158-166, Jul. 15, 2016.
Rimmelzwaan et al., "A randomized, double blind study in young healthy adults comparing cell mediated and humoral immune responses induced by influenza ISCOM™ vaccines and conventional vaccines,"Vaccine 19:1180-1187 (2001).
Ronnberg et al., "Adjuvant activity of non-toxic Quillaja saponaria Molina components for use in ISCOM matrix," Vaccine, vol. 13, No. 14, pp. 1375-1382 (1995).
Safety and Immunogenicity Study of Therapeutic HSV-2 Vaccine, Identifier NCT01667341, ClinicaiTrials.gov, U.S. National Institutes of Health; available at http://clinicaltrials.gov/ct2/show/NCT01667341 ?term=matrix+m&rank=3, Mar. 9, 2014, pp. 1-4.
Sjolander, et al., ISCOMs: an adjuvant with multiple functions, Journal of Leukocyte Biology, vol. 64, pp. 713-723 (1998).
Sjolander, et al., Uptake and adjuvant activity of orally delivered saponin and ISCOM vaccines, Advanced Drug Delivery Reviews, vol. 34, pp. 321-338 (1998), Elsevier Science B.V.
Skoberne et al., An adjuvanted herpes simplex virus 2 subunit vaccine elicits a T cell response in mice and is an effective therapeutic vaccine in Guinea pigs, J. Virol. 87:3930-3942 (2013).
Sun et al., "Advances in saponin-based adjuvants," Vaccine 27:1787-1796 (2009).
Sun et al., "ISCOMs and ISOMATRIX™," Vaccine 27:4388-4401 (2009).
Wald et al., Novel Therapeutic Vaccine for Genital Herpes Reduces Genital HSV-2 Shedding, in ICAAC 2013, Denver, CO, Sep. 2013, cover page and p. 279, Abstract 183(G).
Wald, "A Novel Therapeutic Vaccine (GEN003) for Genital Herpes Reduces HSV-2 Shedding: Initial Results of Clinical Trial GEN003-001," Presented at Interscience Conference on Antimicrobial Agents and Chemotherapy (ICAAC 2013), Denver, CO, Sep. 12, 2013, pp. 1-21.
Wang et al., "Expression and purification of an influenza he1nagglutinin-one step closer to a recombinant protein-based influenza vaccine," Vaccine vol. 24, Issue 12, pp. 2176-2185 (2006).
Anderson et al., "Intracellular processing of the human respiratory syncytial virus fusion glycoprotein: amino acid substitutions affecting folding, transport and cleavage," J. Gen. Virol. 73:1177-118 (1992).
Brandenburg et al., Respiratory Syncytial Virus Specific Serum Antibodies in Infants Under Six Months of Age: Limited Serological Response Upon Infection, J. Med. Virol. 52:97-104 (1997).
Calder et al., "Electron Microscopy of the Human Respiratory Syncytial Virus Fusion Protein and Complexes That It Forms with Monoclonal Antibodies," Virol. 271:122-131 (2000).
Creemers et al., "Endoproteolytic Cleavage of Its Propeptide Is a Prerequisite for Efficient Transport of Furin Out of the Endoplasmic Reticulum," J. Biol. Chem. 270(6):2695-2702 (1995).

Crowe, Jr. "Influence of Maternal Antibodies on Neonatal Immunization against Respiratory Viruses," Clin. Infect. Dis. 33:1720-1727 (2001).
Crowe, Jr. et al. "Passively Acquired Antibodies Suppress Humoral But Not Cell-Mediated Immunity in Mice Immunized with Live Attenuated Respiratory Syncytial Virus Vaccines," J. Immunol. 167:3910-3918 (2001).
Demirjian and Levy, "Safety and Efficacy of Neonatal Vaccination," Eur. J. Immunol. 39(1):36-46 (2009).
European Search Report, EP Appl. No. 16166033.7, 8 pages (dated Aug. 10, 2016).
Genbank Accession No. AAC55970.1, "fusion glycoprotein precursor [Human respiratory syncytial virus]" (1996).
Glenn, "Recombinant, Insect Cell-Derived RSV Nanoparticle Vaccine," Novavax.com, 34 pages (Jul. 4, 2012) https://www.novavax.com/download/file/RSV nanoparticle Vaccine-MVADsJuly4(2).pdf.
Glenn et al., "Safety and immunogenicity of a Sf9 insect cell-derived respiratory syncytial virus fusion protein nanoparticle vaccine," Vaccine. Jan. 7, 2013;31(3):524-532.
Gonzalez-Reyes et al., "Cleavage of the human respiratory syncytial virus fusion protein at two distinct sites is required for activation of membrane fusion," Proc. Natl. Acad. Sci. USA 98(17):9859-9864 (2001).
Halsey and Galazka, "The efficacy of DPT and oral poliomyelitis immunization schedules initiated from birth to 12 weeks of age," Bull. World Health Org. 63(6):1151-1169 (1985).
Higgins et al., "Advances in RSV vaccine research and development—A global agenda," Vaccine 34:2870-2875 (2016).
International Search Report, 4 pages, PCT appl. No. PCT/US09/67269 (dated Mar. 4, 2010).
International Search Report, 5 pages, PCT appl. No. PCT/US2012/057546 (dated Jan. 22, 2013).
International Search Report, 6 pages, PCT appl. No. PCT/US2016/050413 (dated Feb. 21, 2017).
Kim et al., "Respiratory Syncytial Virus Disease in Infants Despite Prioir Administration of Antigenic Inactivated Vaccine," Am. J. Epidemil. 89(4):422-434 (1969).
Lieberman et al., "Preparation and immunogenic properties of a recombinant West Nile subunit vaccine," Vaccine 25:414-423 (2007).
Martin et al., "Sequence elements of the fusion peptide of human respiratory syncytial virus fusion protein required for activity," J. Gen. Virol. 87:1649-1658 (2006).
Martinez et al., "Combining DNA and protein vaccines for early life immunization against respiratory syncytial virus in mice," Eur. J. Immunol. 29:3390-3400 (1999).
Murphy et al., "An update on approaches to the development of respiratory syncytial virus (RSV) and parainfluenza virus type 3 (PIV3) vaccines," Virus Res. 32:13-26 (1994).
Murphy et al., "Effect of Age and Preexisting Antibody on Serum Antibody Response of Infants and Children to the F and G Glycoproteins during Respiratory Syncytial Virus Infection," J. Clin. Microbiol. 24(5):894-898 (1986).
Murphy et al., "Effect of passive antibody on the immune repspone of cotton rats to purified F and G glycoproteins of repiratory suncytial virus (RSV)," Vaccine 9:185-189 (1991).
Murphy et al., "Passive Transfer of Respiratory Syncytial Virus (RSV) Antiserum Suppresses the Immune Response to the RSV Fusion (F) and Large (G) Glycoproteins Expressed by Recombinant Vacccinia Viruses," J. Virol. 62(10):3907-3910 (1988).
Parrington et al., "Baculovirus expression of the respiratory syncytial virus fusion protein using Trichoplusia ni insect cells," Virus Genes 14:63-72 (1997).
Ruiz-Arguello et al., "Thermostability of the human respiratory syncytial virus fusion protein before and after activation: implications for the membrane-fusion mechanism," J. Gen. Virol. 85:3677-3687 (2004).
Ruiz-Arguello et al., "Effect of Proterlytic Processing at Two Distinct Sites on Shape and Aggregation of an Anchorless Fusion Protein of Human Respiratory Syncytial Virus and Fate of the Intervening Segment," Virol. 298:317-326 (2002).
Sales and Wang, "Respiratory syncytial virus vaccine: Is it coming?" Paediatr. Child Health 8(10):605-608 (2003).

(56) References Cited

OTHER PUBLICATIONS

Siegrist, "Mechanisms by which maternal antibodies influence infant vaccine responses: review of hypotheses and definition of main determinants," Vaccine 21:3406-3412 (2003).

Siegrist et al., "Protective Efficacy against Respiratory Syncytial Virus following Murine Neonatal Immunization with BBG2Na Vaccine: Influence of Adjuvants and Maternal Antibodies," J. Infect. Dis. 179:1326-1333(1999).

Smith et al., "Respiratory Syncytial Virus Fusion Glycoprotein Expressed in Insect Cells Form Protein Nanoparticles That Induce Protective Immunity in Cotton Rats," PLOS ONE 7(11):e50852, 12 pages (2012).

Smith et al., "Novel hemagglutinin nanoparticle influenza vaccine with Matrix-M™ adjuvant induces hemagglutination inhibition, neutralizing, and protective responses in ferrets against homologous and drifted A(H3N2) subtypes," Vaccine 35:5366-5372 (2017).

Supplementary European Search Report, EP Appl. No. 09836751.9, 9 pages (dated Apr. 29, 2013).

Supplementary European Search Report, EP Appl. No. 12835033.7, 7 pages (dated Feb. 17, 2015).

Weisshaar et al., "Blocking Respiratory Syncytial Virus Entry: A Story with Twists," DNA Cell Biol. 34:505-510 (2015).

Widjaja et al., "Recombinant Soluble Respiratory Syncytial Virus F Protein That Lacks Heptad Repeat B, Contains a GCN4 Trimerization Motif and Is Not Cleaved Displays Prefusion-Like Characteristics," PLoS One 10(6):e0130829, 19 pages (2015).

Whitehead et al., "Recombinant Respiratory Syncytial Virus (RSV) Bearing a Set of Mutations from Cold-Passaged RSV is Attenuated in Chimpanzees," J. Virol. 72(5):4467-4471 (1998).

Written Opinion of the International Searching Authority, 4 pages, PCT appl. No. PCT/US09/67269 (dated Mar. 4, 2010).

Written Opinion of the International Searching Authority, 5 pages, PCT appl. No. PCT/US2012/057546 (dated Jan. 22, 2013).

Written Opinion of the International Searching Authority, 11 pages, PCT appl. No. PCT/US2016/050413 (dated Feb. 21, 2017).

Lovgren et al., The Requirement of Lipids for the Formation of Immunostimulating Complexes (Iscoms), Biotechnol. Appl. Biochem. 10:161-172 (1988).

Demana et al., "A comparison of pseudo-ternary diagrams of aqueous mixtures of Quil A, cholesterol and phospholipid prepared by lipid-film hydration and dialysis," Journal of Pharmacy and Pharmacology 56:573-580 (2004).

Shi et al., "Stabilization of Human Papillomavirus Virus-Like Particles by Non-Ionic Surfactants," Journal of Pharmaceutical Sciences, 2005, p. 1538-1551.

Kanekiyo et al., "Self-assembling influenza nanoparticle vaccines elicit broadly neutralizing HlNl antibodies," Nature 2013, vol. 499 p. 102-108.

Wu et al., "Active 1918 pandemic flu viral neuraminidase has distinct N-glycan profile and is resistant to trypsin digestion," Biochemical and Biophysical Research, 2009, vol. 379. p. 749-753.

Karin Lovgren Bengtsson, Bror Morein & Albert DME Osterhaus (2011) ISCOM technology-based Matrix M™ adjuvant: success in future vaccines relies on formulation, Expert Review of Vaccines, 10:4, 401-403, DOI: 10.1586/erv.11.25.

Tekewe et al., A rapid and simple screening method to identify conditions for enhanced stability of modular vaccine candidates, Biochemical Engineering Journal 100:50-58 (2015).

Iyer et al., Purified, Proteolytically Mature HIV Type 1 SOSIP gp140 Envelope Trimers, AIDS Research and Human Retroviruses 23(6):817-828 (2007).

European Search Report, EP Appl. No. 16843191.4, 13 pages, dated Mar. 14, 2019.

Rama et al., "An insect cell derived respiratory syncytial virus (RSV) F nanoparticle vaccine induces antigenic site II antibodies and protects against RSV challenge in cotton rats by active and passive immunization", Vaccine, Elsevier, Amsterdam, NL, 32(48)6485-6492 (2014).

International Search Report and Written Opinion issued by the International Searching Authority for Application No. PCT/US2019/022930, dated Aug. 8, 2019, 14 pages.

Giannos et al., Formulation Stabilization and Disaggregatoin of Bevacizumab, Ranibizumab and Aflibercept in Dilute Solutions, Pharm Res 35:78 (2018), 15 pages.

Makwana et al., "Prefilled Syringes: An Innovation in Parenteral Packaging," International Journal of Pharmaceutical Investigation 1 (4):200-206 (2011).

Shinde et al., "Improved Titers Against Influenza Drift Variants with a Nanoparticle Vaccine," N Engl Med 378:24 (2018), 3 pages.

Shinde et al, Induction of Broadly Cross-Reactive Immune Responses Against A(H3N2) Viruses: Results of a Phase 2 Trial of a Novel Recombinant Hemagglutinin Saponin-Adjjvanted nanoparticle Influenza Vaccine ("NanoFlu"), 30 pages (2018).

Lichtenberg et al., "The Mechanism of Detergent Solubilization of Lipid Bilayers," Biophysical Journal, vol. 105:289-299 (2013).

"Novavax' NanoFlu Achieves All Primary Endpoints In Phase 3 Clinical Trial," Press Release dated Mar. 24, 2020, 3 pages.

Citovsky et al., "Fusion of Sendai Virions or Reconstituted Sendai Virus Envelopes with Liposomes or Erythrocyte Membranes Lacking Virus Receptors," The Journal of Biological Chemistry 260(22)12072-12077 (1985).

Nussbaum et al., "Fusion of influenza Virus particles with liposomes: requirement for cholesterol and virus receptors to allow fusion with and lysis of neutral but not of negatively charged liposomes",. Journal of General Virology, 2831-2837 (1992).

Vaarala et al., "Antigenic Differences between AS03 Adjuvanted Influenza A (H1N1) Pandemic Vaccines: Implications for Pandemrix Associated Narcolepsy Risk," PLOS One, 1-23 (2014).

Lee et al., "Recent Advances of Vaccine Adjuvants for Infectious Diseases," Immune Network, 51-57 (2015).

Eckert et al., "Mechanisms of Viral Membrane Fusion and Its Inhibition," Annual Review of Biochemistry 70:770-810 (2001).

Gruenke et al., "New Insights into the Spring-Loaded Conformational Change of Influenza Virus Hemagglutinin," Journal of Virology, May 2002, 76:(9) 4456-4466 (2002).

Hancock et al., "Adjuvants Recognized by Toll-Like Receptors Inhibit the Induction of Polarized Type 2 T Cell Responses by Natural Attachment (G) Protein of Respiratory Syncytial Virus," Vaccine 21(27-30):4348-4358 (2003).

Wang, "Protein aggregation and its inhibition in biopharmaceutics," International Journal of Pharmaceutics 289 (2005) 1-30.

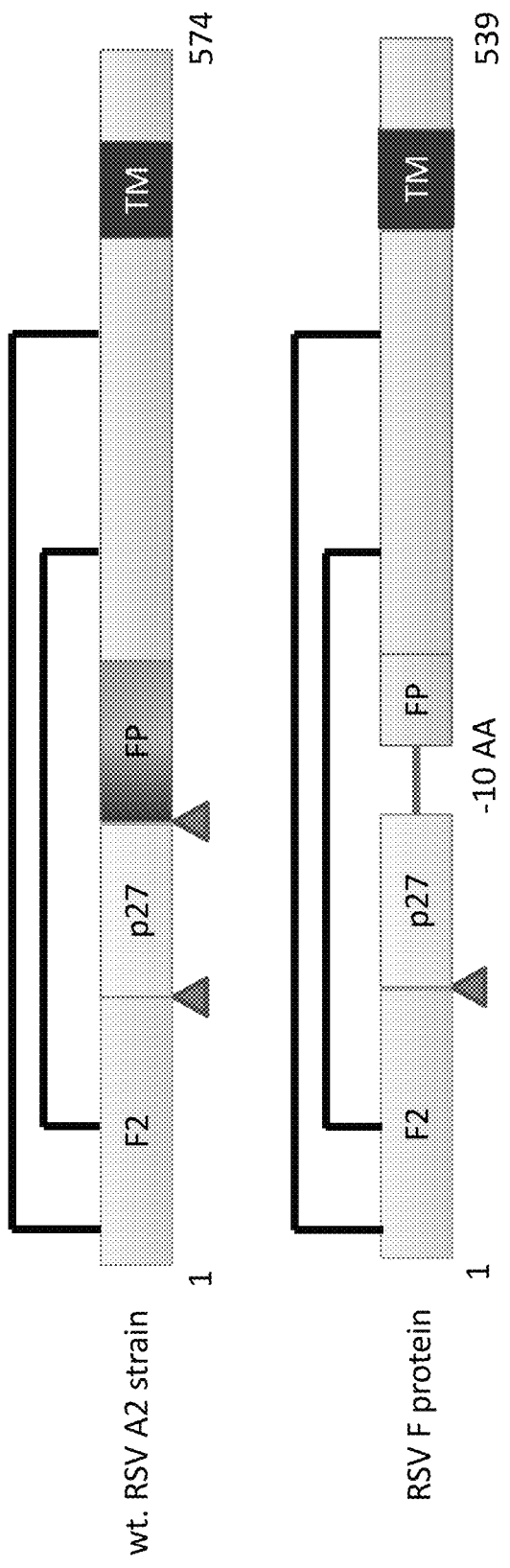
Fig. 1A. RSV F Protein Primary Structure

Fig. 1B. RSV F Protein Functional Sites

```
  1  PQNITEEFYQS TCSAVSKGYL SALRTGWYTS VITIELSNIK ENKCNGTDAK
 51  VKLIKQELDK YKNAVTELQL LMQSTPATNN RARRELPRFM NYTLNNAKKT
101  NVTLSKKQKQ QAIASGVAVS KVLHLEGEVN KIKSALLSTN KAVVSLSNGV
151  SVLTSKVLDL KNYIDKQLLP IVNKQSCSIS NIETVIEFQQ KNNRLLEITR
201  EFSVNAGVTT PVSTYMLTNS ELLSLINDMP ITNDQKKLMS NNVQIVRQQS
251  YSIMSIIKEE VLAYVVQLPL YGVIDTPCWK LHTSPLCTTN TKEGSNICLT
301  RTDRGWYCDN AGSVSFFPQA ETCKVQSNRV FCDTMNSLTL PSEVNLCNVD
351  IFNPKYDCKI MTSKTDVSSS VITSLGAIVS CYGKTKCTAS NKNRGIIKTF
401  SNGCDYVSNK GVDTVSVGNT LYYVNKQEGK SLYVKGEPII NFYDPLVFPS
451  DEFDASISQV NEKINQSLAF IRKSDELLHN VNAGKSTTNI MITTIIVII
501  VILLSLIAVG LLLYCKARST PVTLSKDQLS GINNIAFSN
```

Legend:

F1 domain in blue, F2 domain in black, N-Linked glycosylation site, :-Furin cleavage site, !- major cleavage site
⌐ ⌐ - Disulfide bond

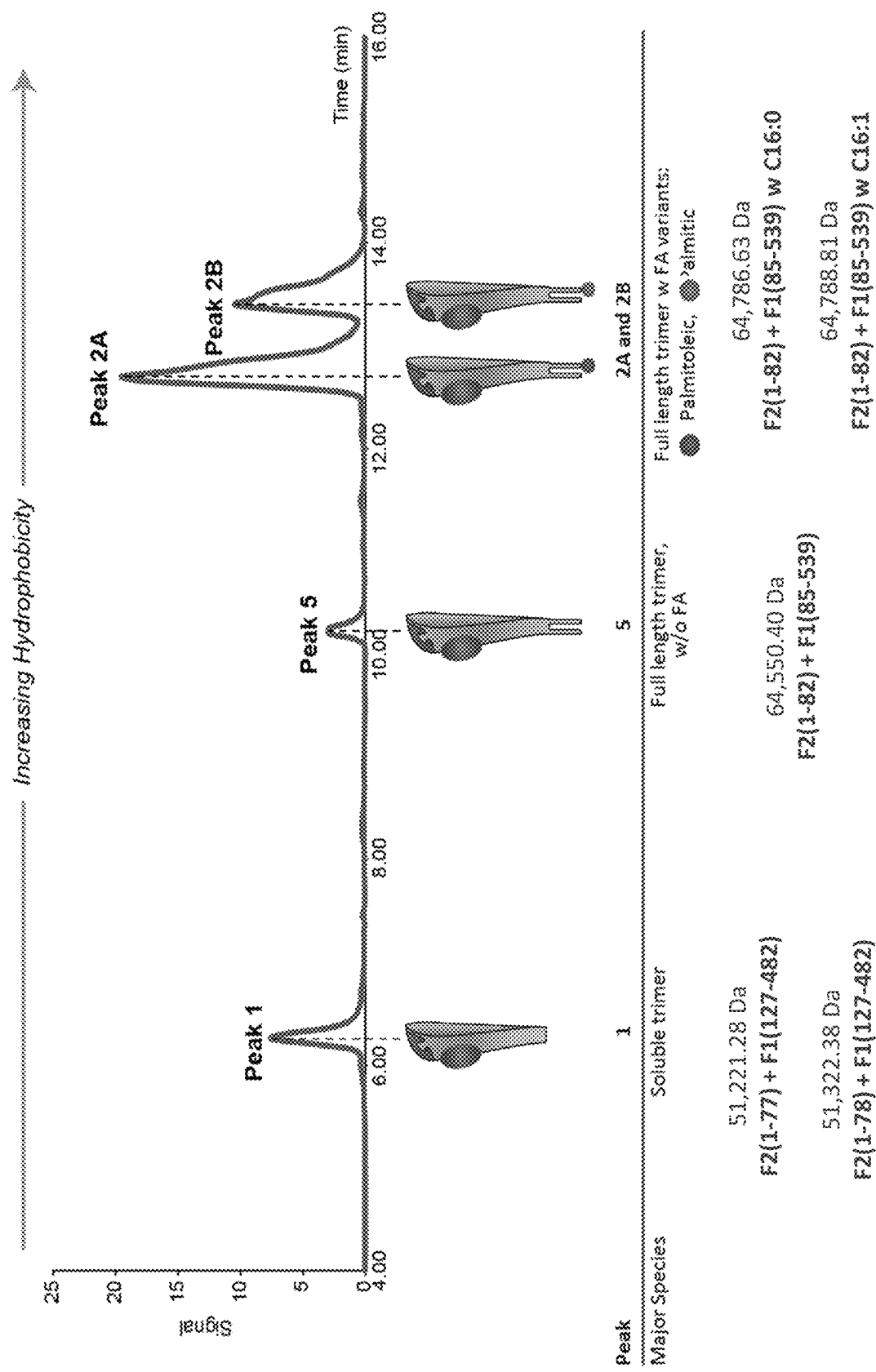

Fig. 3. Separation of RSV F Proteins by rSDS-PAGE

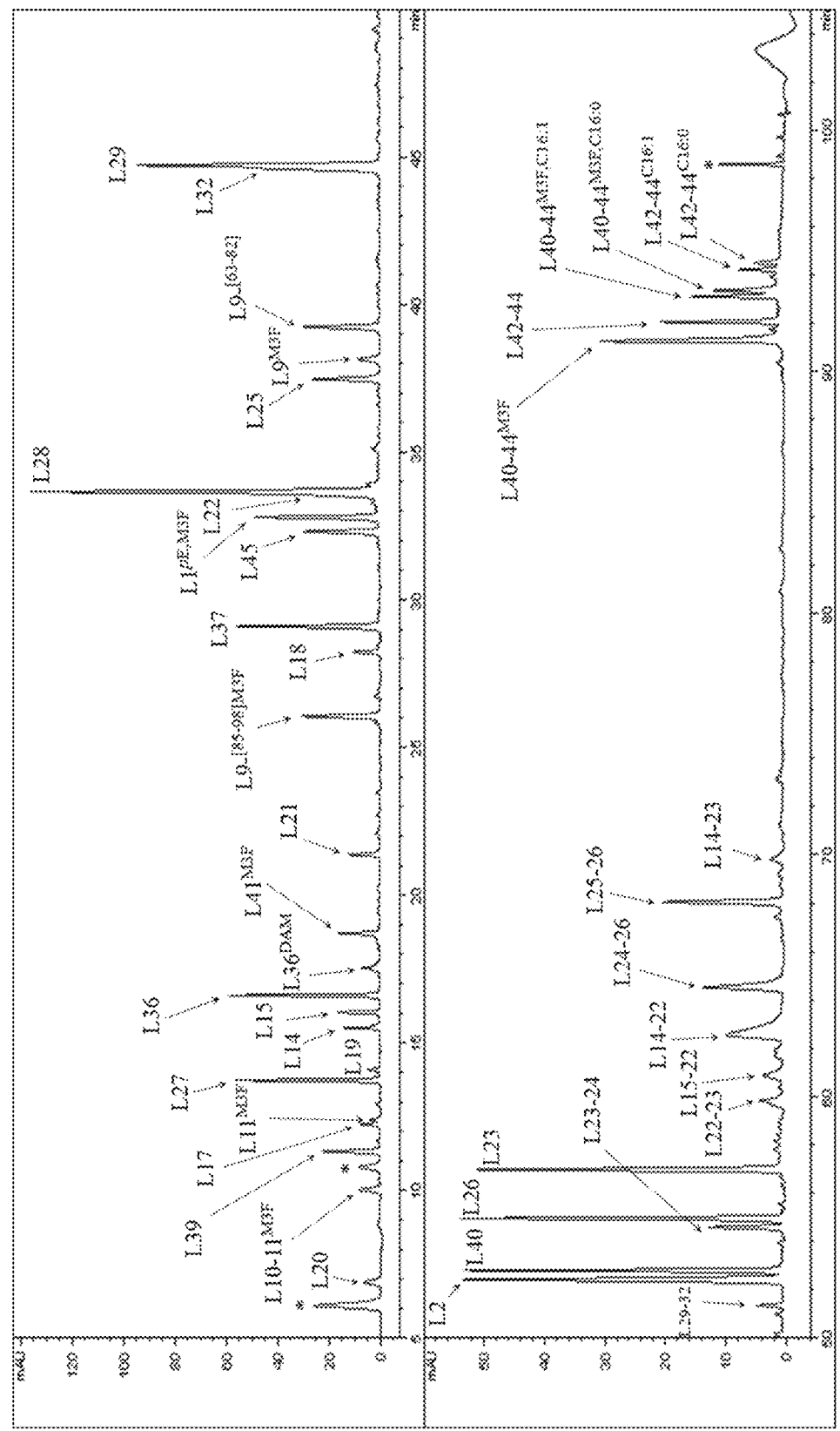
Fig. 4. Primary Structure by Peptide Mapping
Representative reduced and alkylated endoproteinase Lys-C peptide map of RSV F.
* = System peak, DAM – Deamidation, M3F – Fucosylated Mannose 3 glycan.

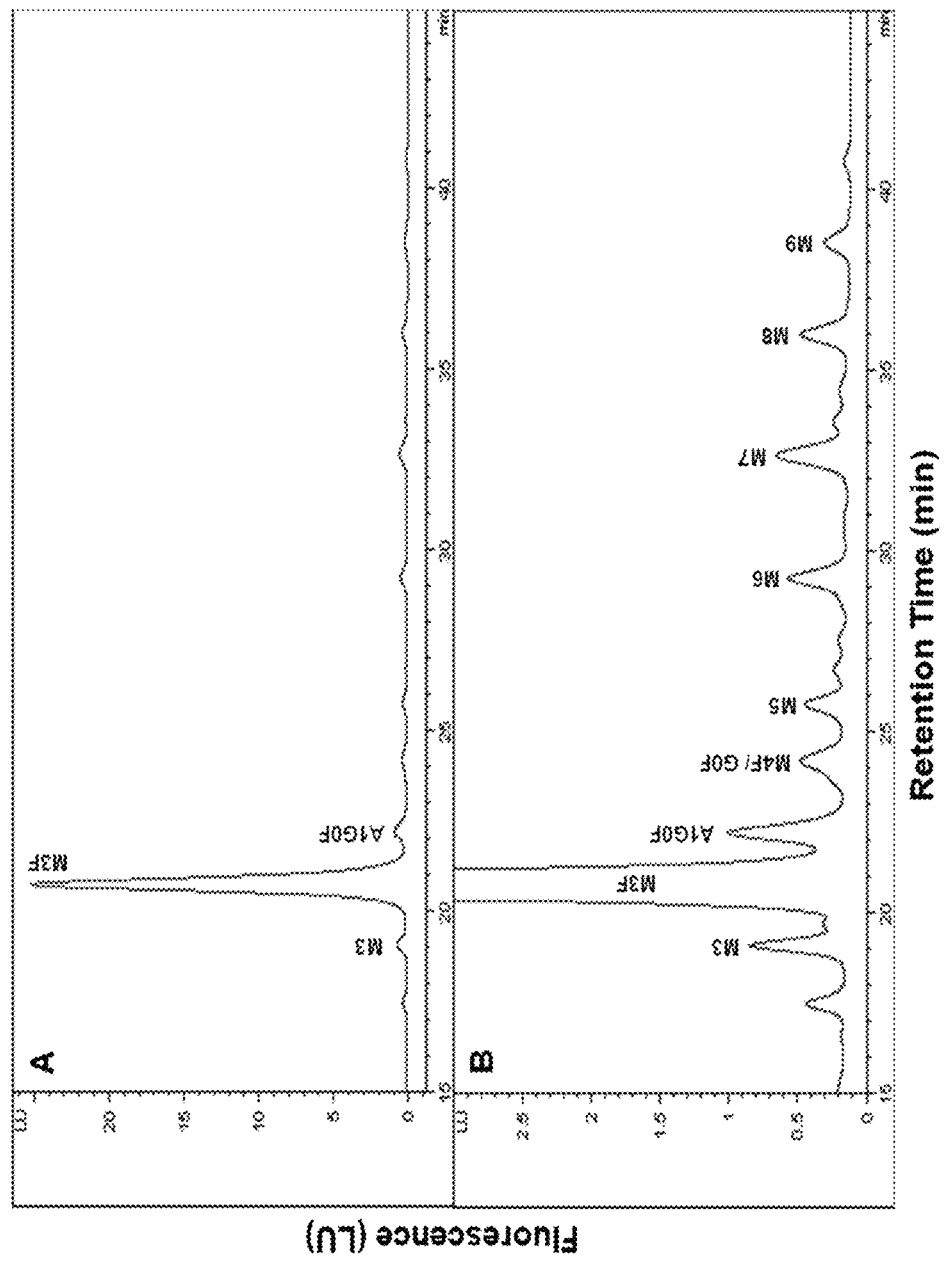
Fig. 5. Glycoanalysis using HPLC-FLD
• Major glycan structures are fucosylated Man3

Fig. 6. Electron Micrograph of RSV F Nanoparticles showing RSV F Protein Trimers attached to the PS-80 core Fig. 7. Dynamic Light Scattering (DLS) measurement of particle size of RSV-F nanoparticles

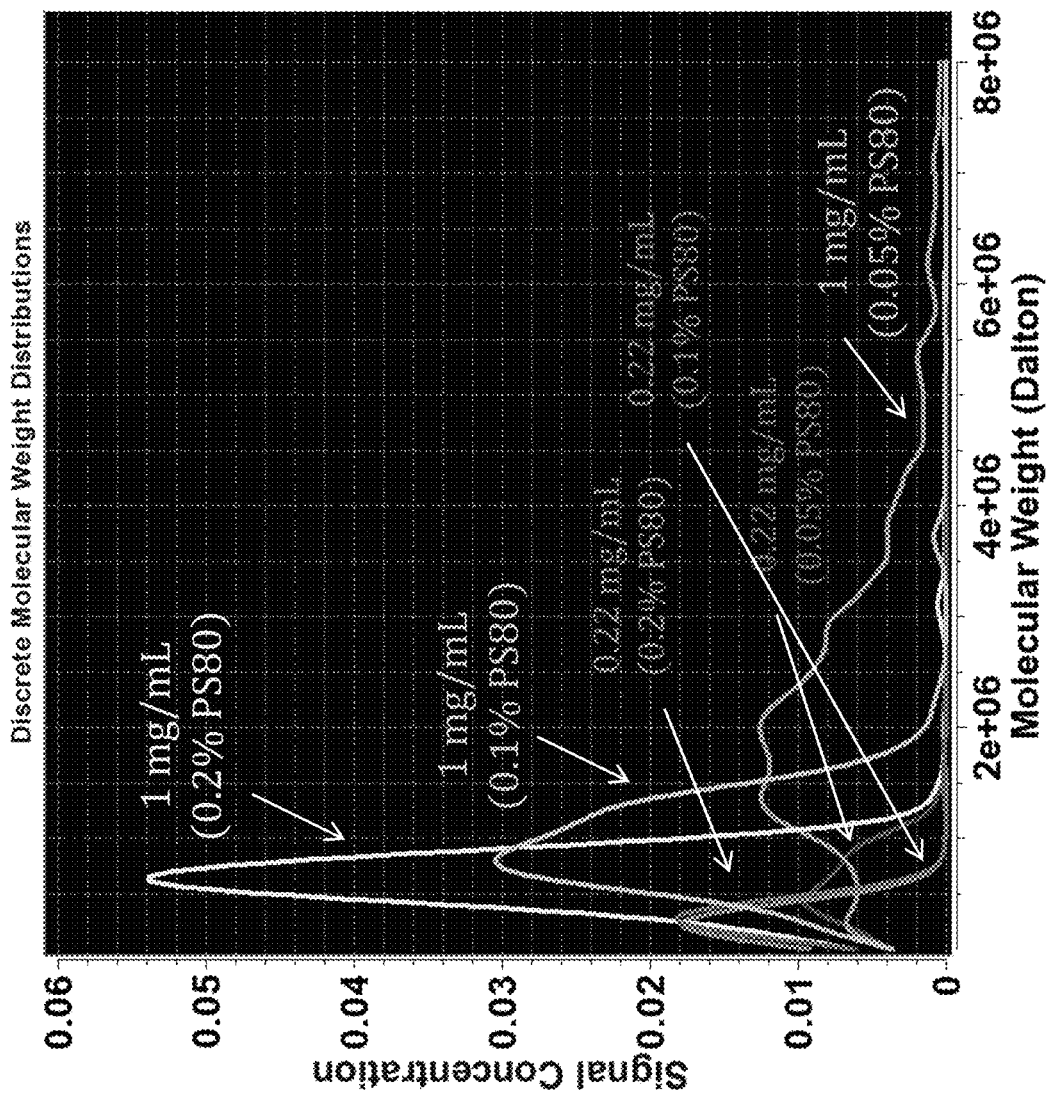
Fig. 8. Particle size determined by Analytical Ultracentrifugation (AUC)

Fig. 9A. Shape of RSV F particles produced with 0.2% PS80, 0.22 mg/mL RSV F

Fig. 9B. Shape of RSV F particles produced with 0.5% PS80, 0.22 mg/mL RSV F or 1 mg/ml RSV F

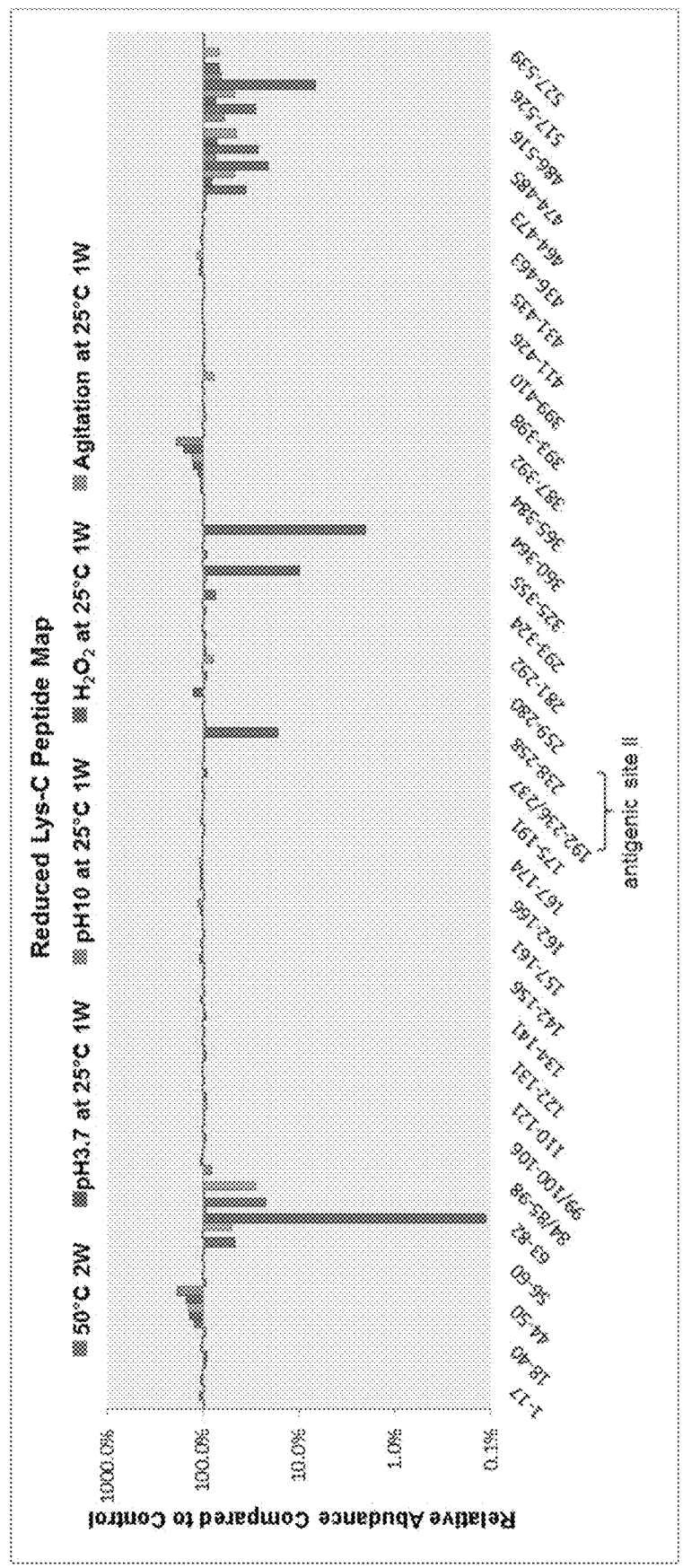
Fig. 10. Stability Studies: Primary Structure Differences after Stress Test Fig. 11. Stability Studies: Antigenic site 2 (palivizumab site) is robust with respect to stress conditions

| Residue | 192-236/237 | 238-258 |
|---|---|---|
| Sequence | ...NSELLSLINDMPITNDQK/K | LMSNN... |
| Thermal Stress | 98.80% | 97.00% |
| Low pH | 102.80% | 95.90% |
| High pH | 101.50% | 95.90% |
| Oxidation | 90.20% | 16.90% |
| Agitation | 102.10% | 93.40% |

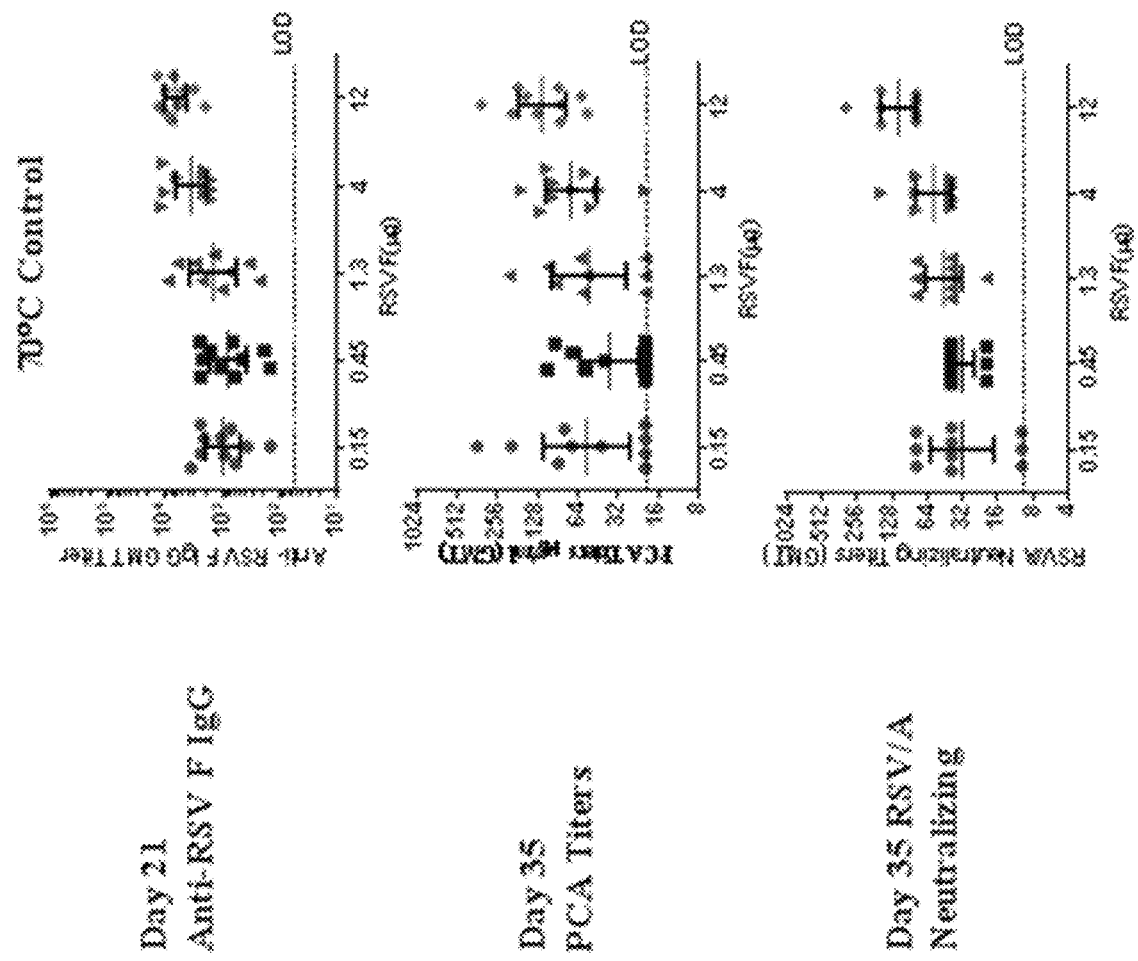

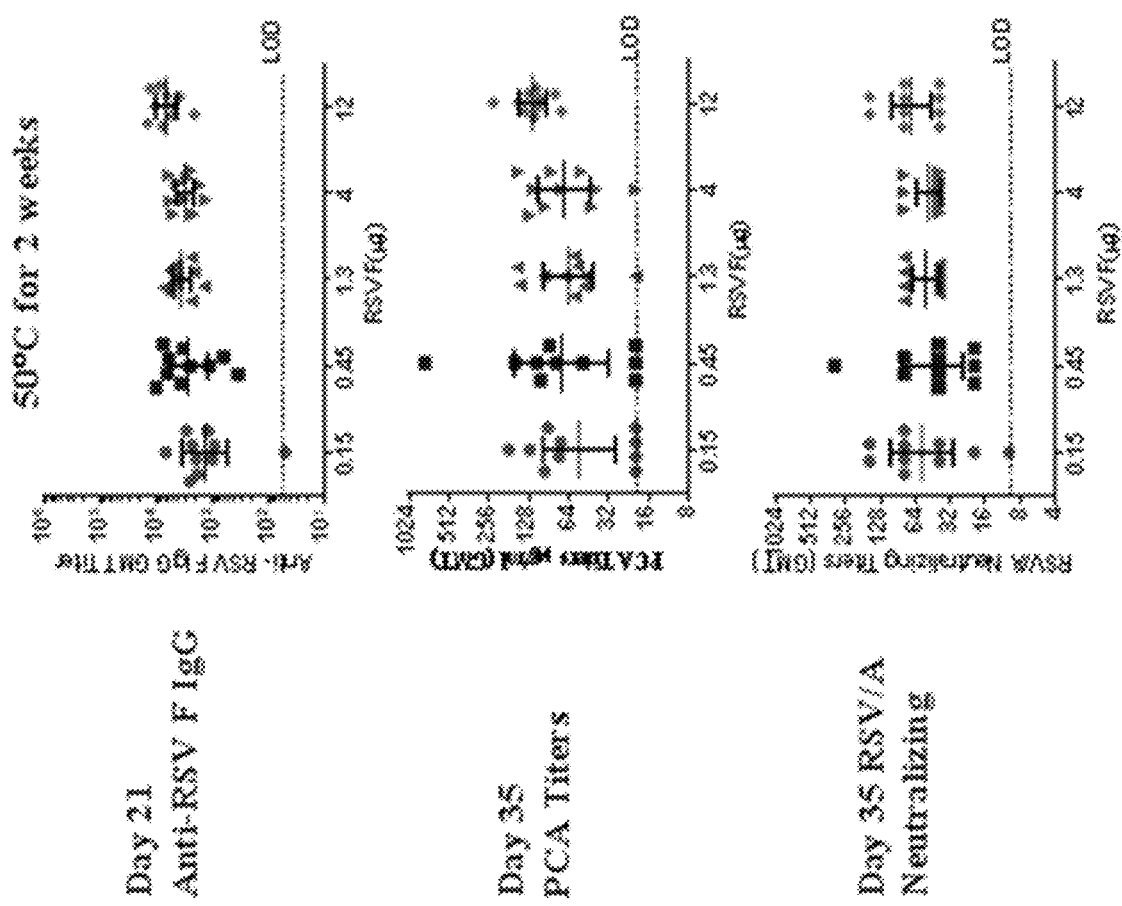

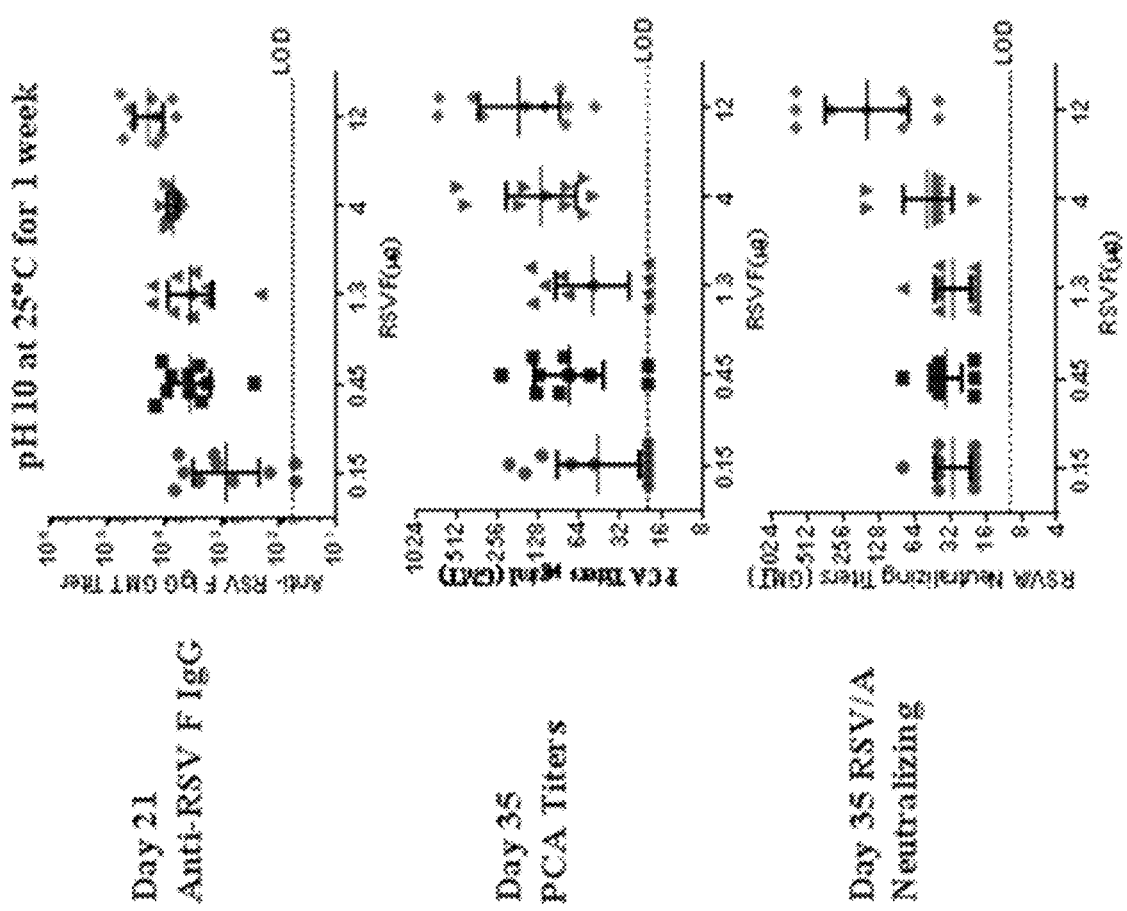
Fig. 12C Stability Studies: Preservation of Mouse Immunogenicity

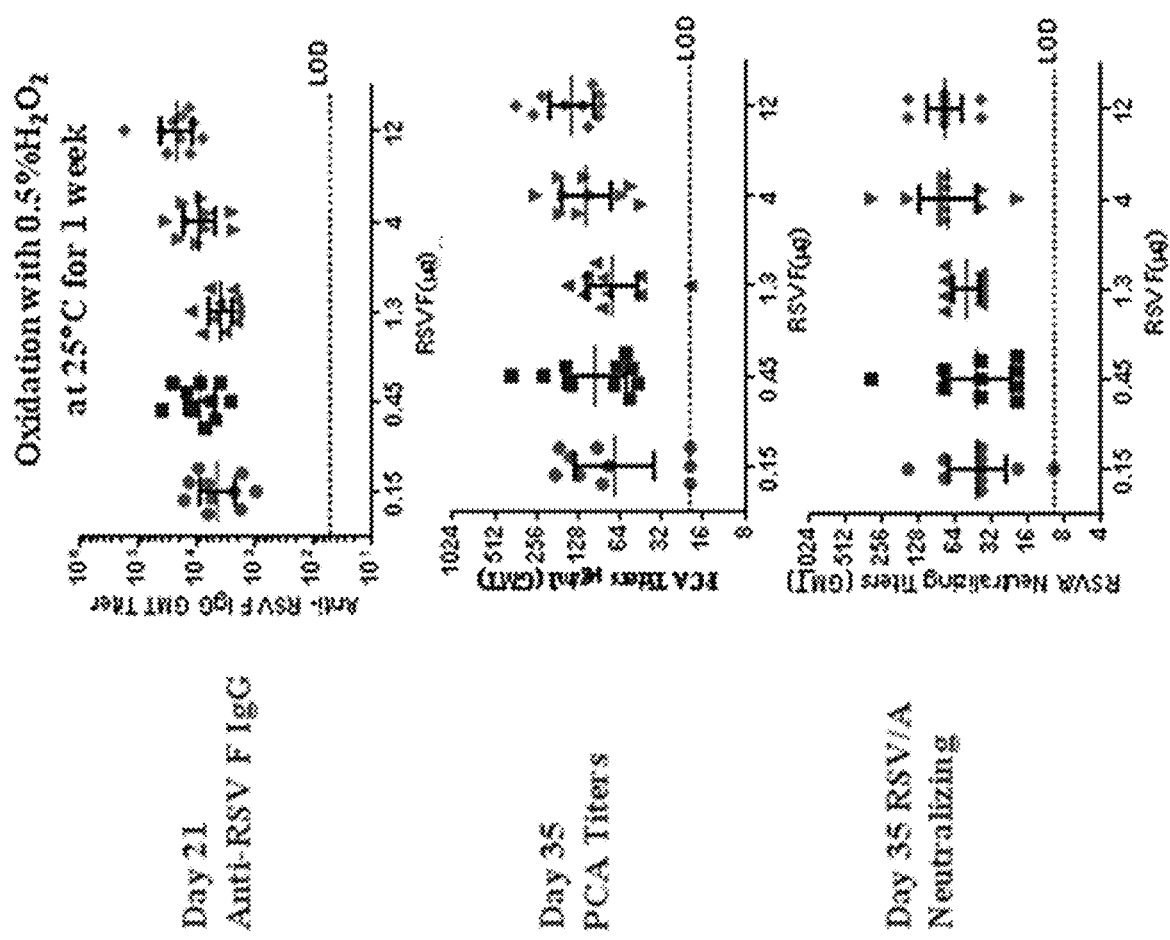
Fig. 12D Stability Studies: Preservation of Mouse Immunogenicity

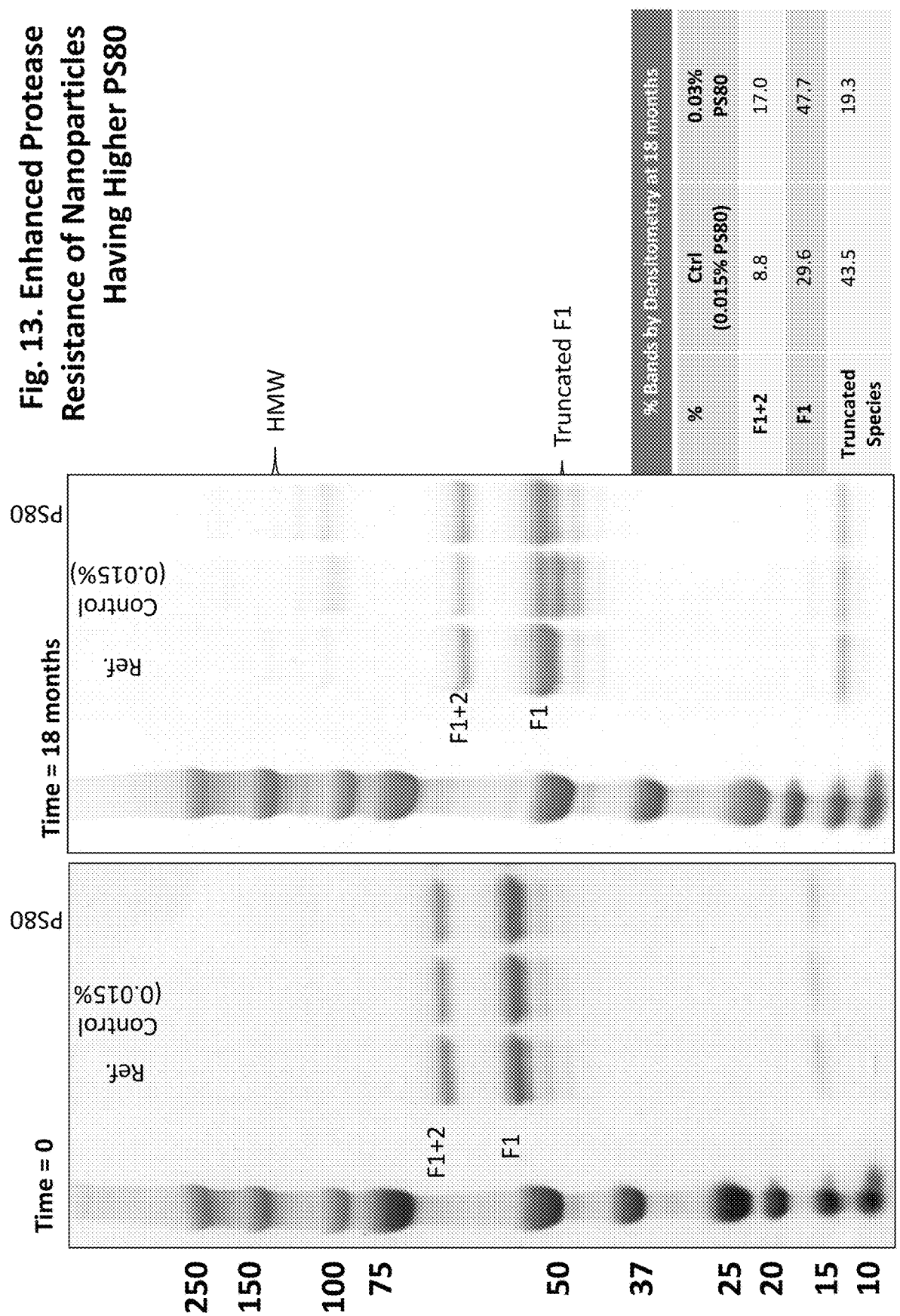

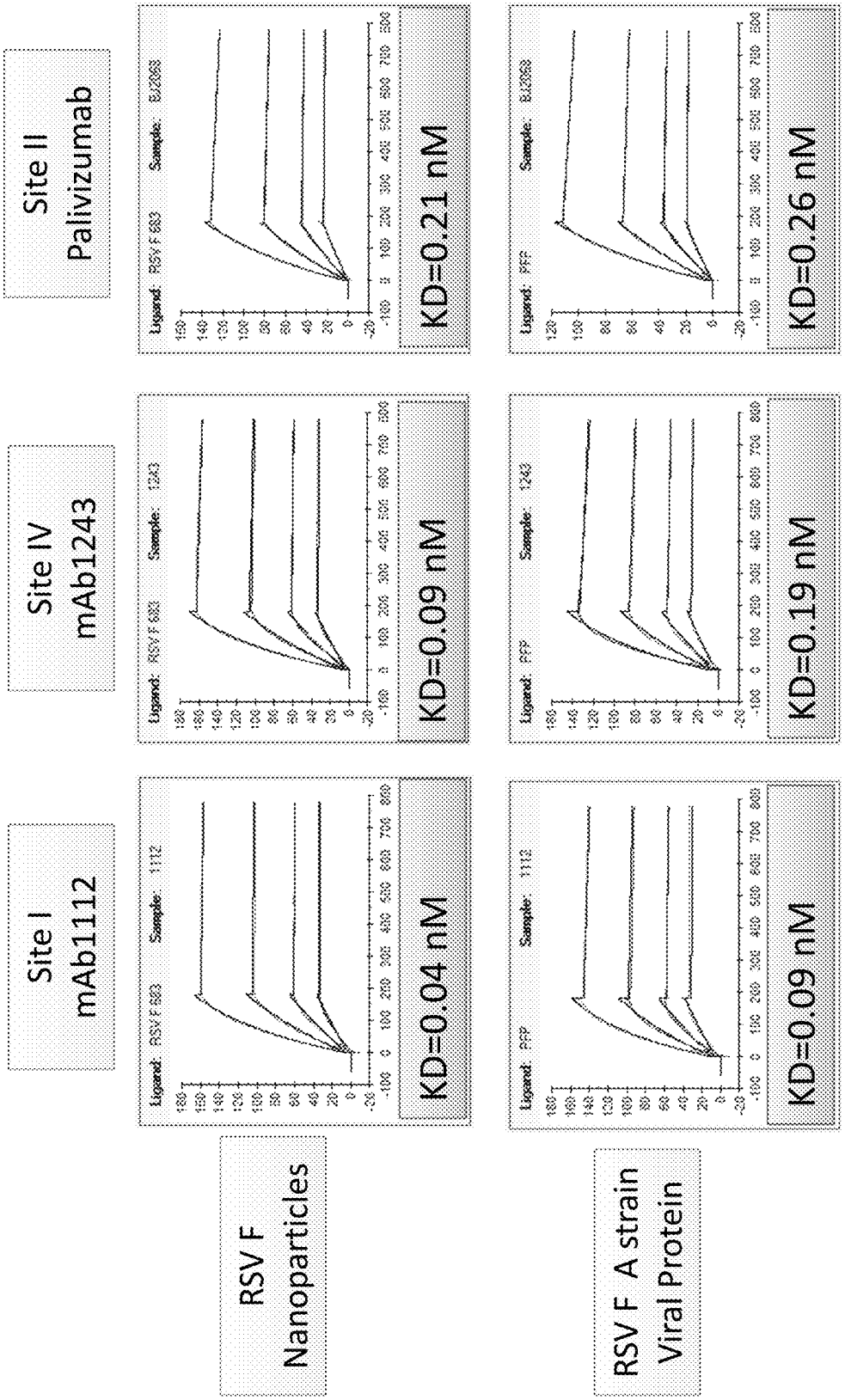
Fig. 14. RSV F Nanoparticles Bind To Site I, II, and IV Neutralizing mAbs Fig. 15. RSV F Nanoparticle Vaccine Induces Antibody Competitive with mAb Binding to Sites I, IV, and II in Cotton Rats

Fig. 16

Production of BV1184 WVS (P3)

- Sf9 Cell Expansion in Rocker-style Bioreactor (50L, 20L wv)
  ↓
- Infection with MVS (P2) and WVS Harvest
  ↓
  BV1184 WVS (P3)

Main Process:

- Sf9 Cell Thawing and Expansion in Flasks
  ↓
- Sf9 Cell Expansion in Bioreactor (20 and 100L wv)
  ↓
- Sf9 Cell Expansion in Production Bioreactor (500 to 1000L wv)
  ↓
- Infection with Recombinant Baculovirus and Production of RSV F Protein
  ↓
- Harvest: Cell Collection and Washing
  ↓
- Lysis and Extraction
  ↓
- Low pH Treatment
  ↓
- Clarification
  ↓
- Anion Exchange Chromatography Fractogel TMAE
  ↓
- Affinity Chromatography Lentil Lectin
  ↓
- Low pH Inactivation
  ↓
- Cation Exchange Chromatography Fractogel SO3
  ↓
- Formulation and 0.2 μm Filtration
  ↓
- Drug Substance
  22 mM sodium phosphate
  150 mM sodium chloride
  1% (w/v) histidine
  0.04% (w/v) polysorbate 80, pH 6.2
  Stored at ≤ −60°C

Preparation of RSV F Nanoparticles from Baculovirus to Drug Substance

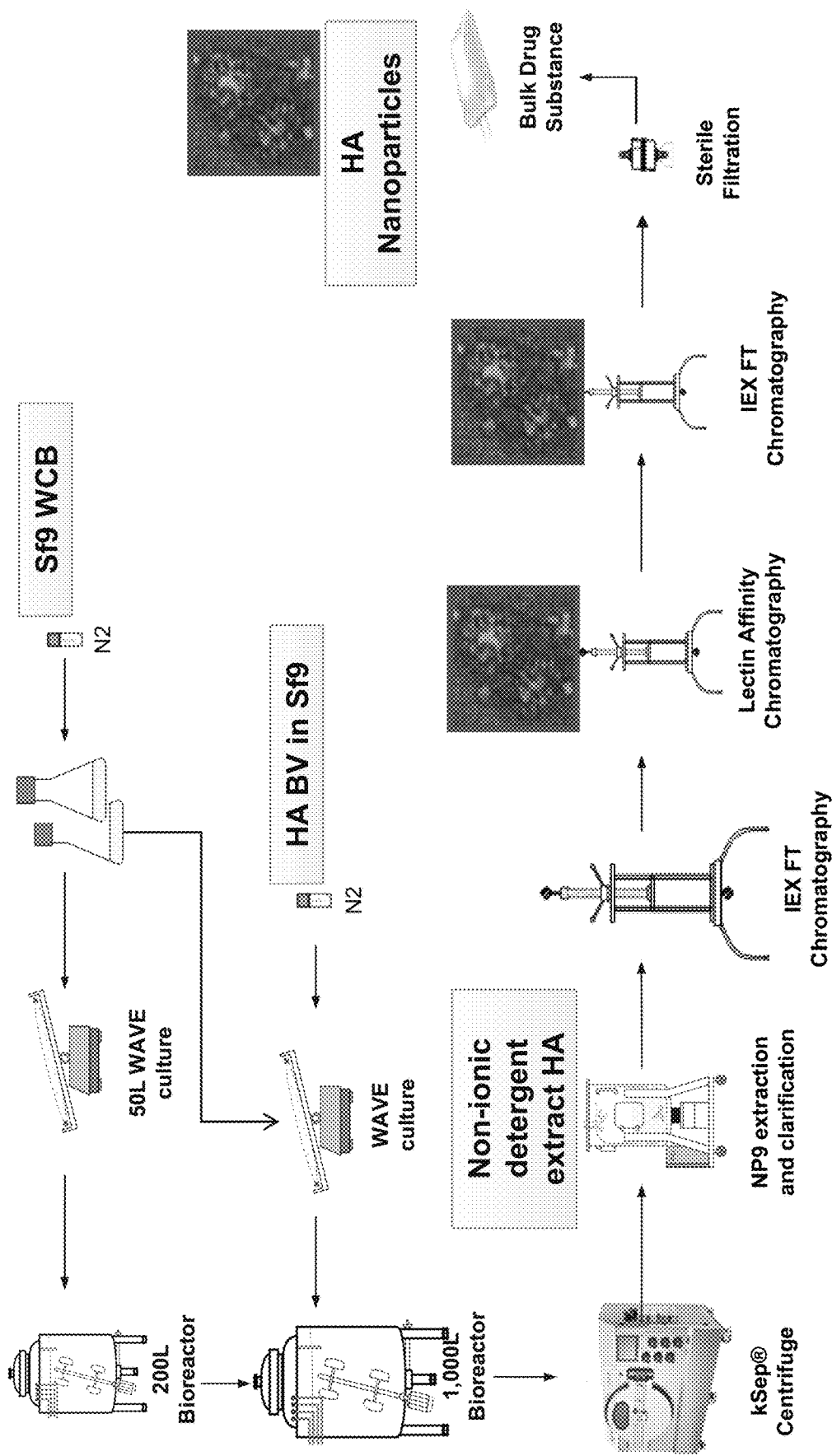
Fig. 17 Preparation of HA Nanoparticles from Baculovirus to Drug Substance

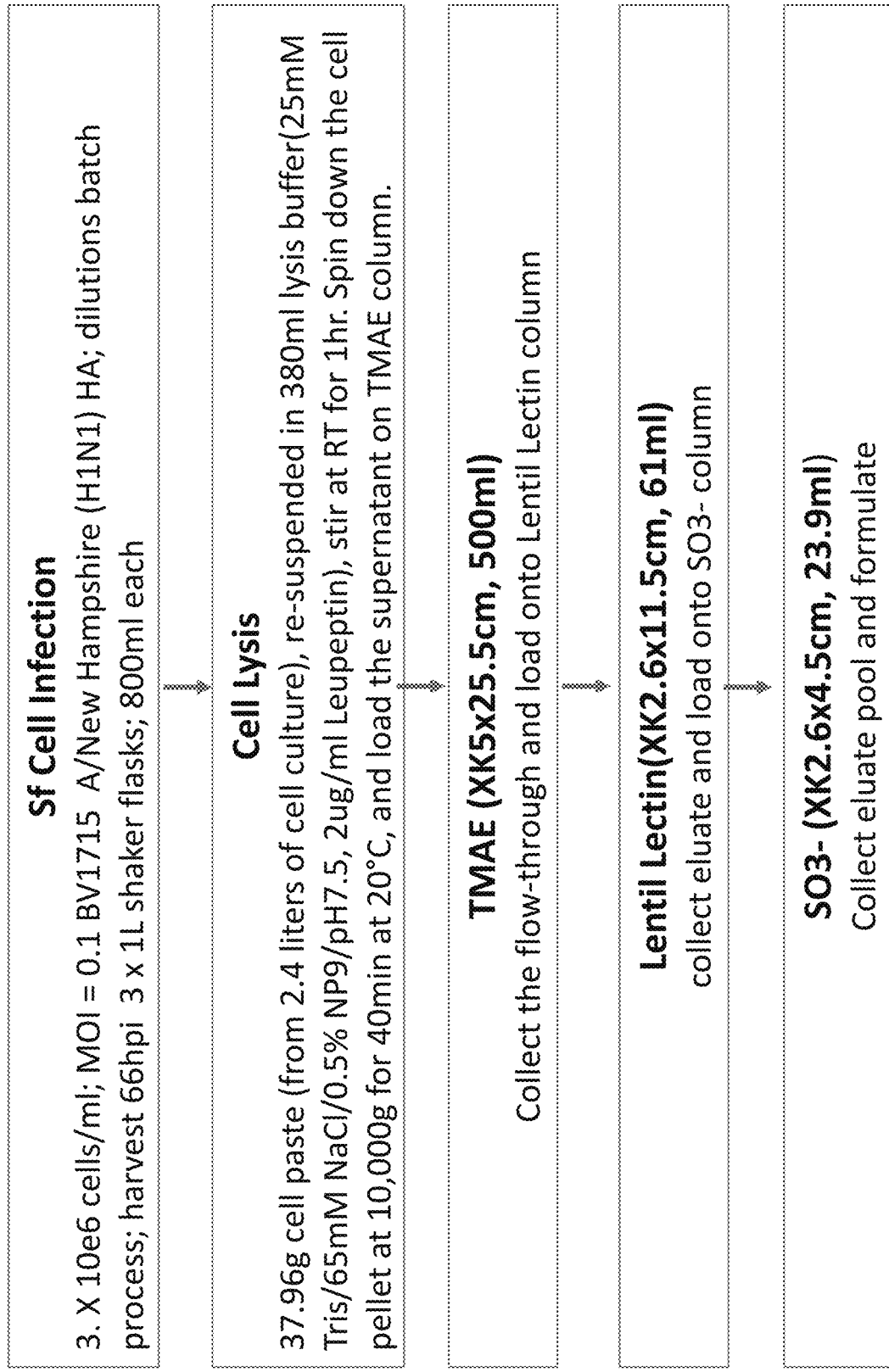
Fig. 18A: HA Nanoparticle Purification flow chart

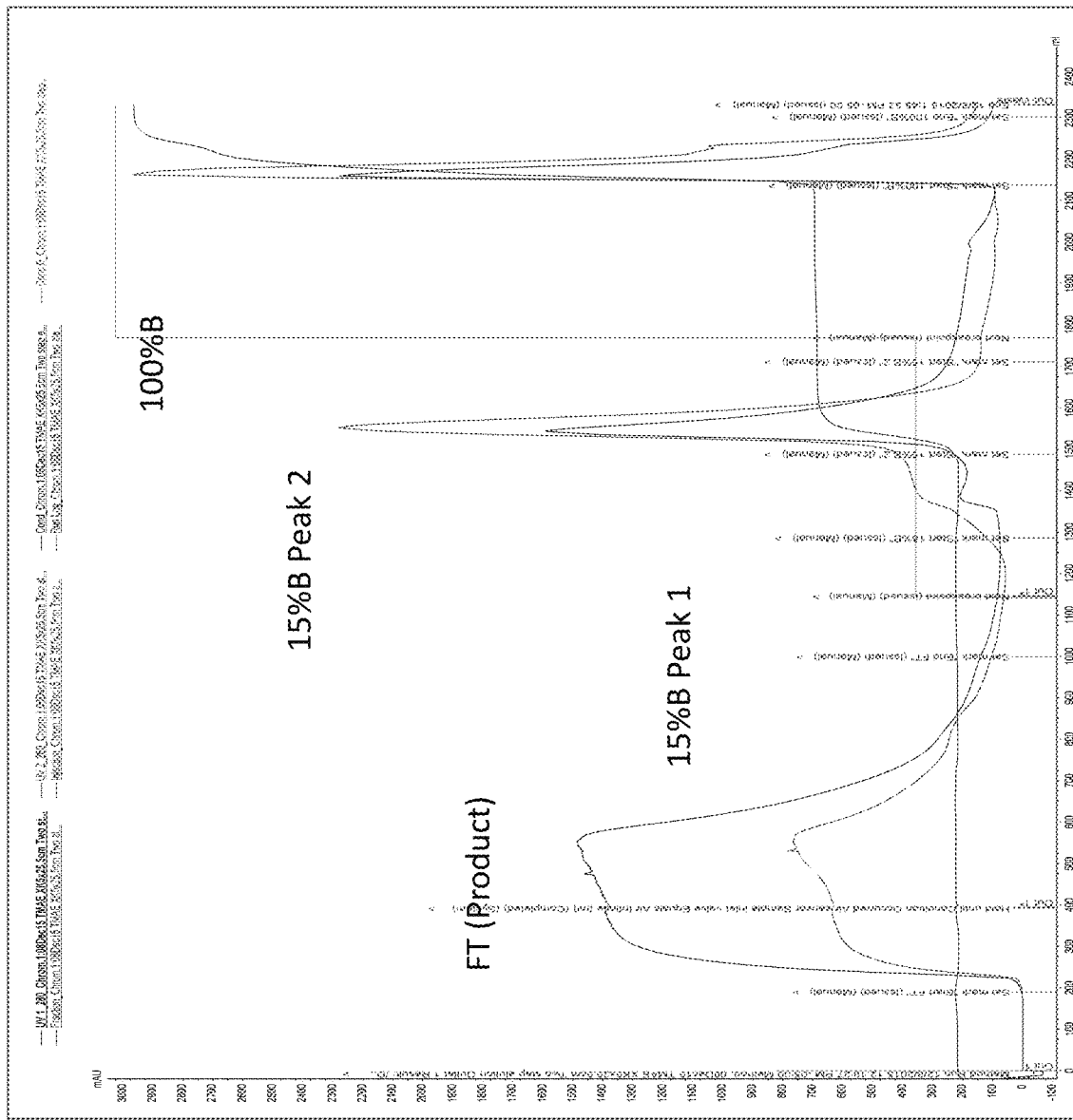
Fig. 18B: HA Nanoparticle: TMAE column chromatogram

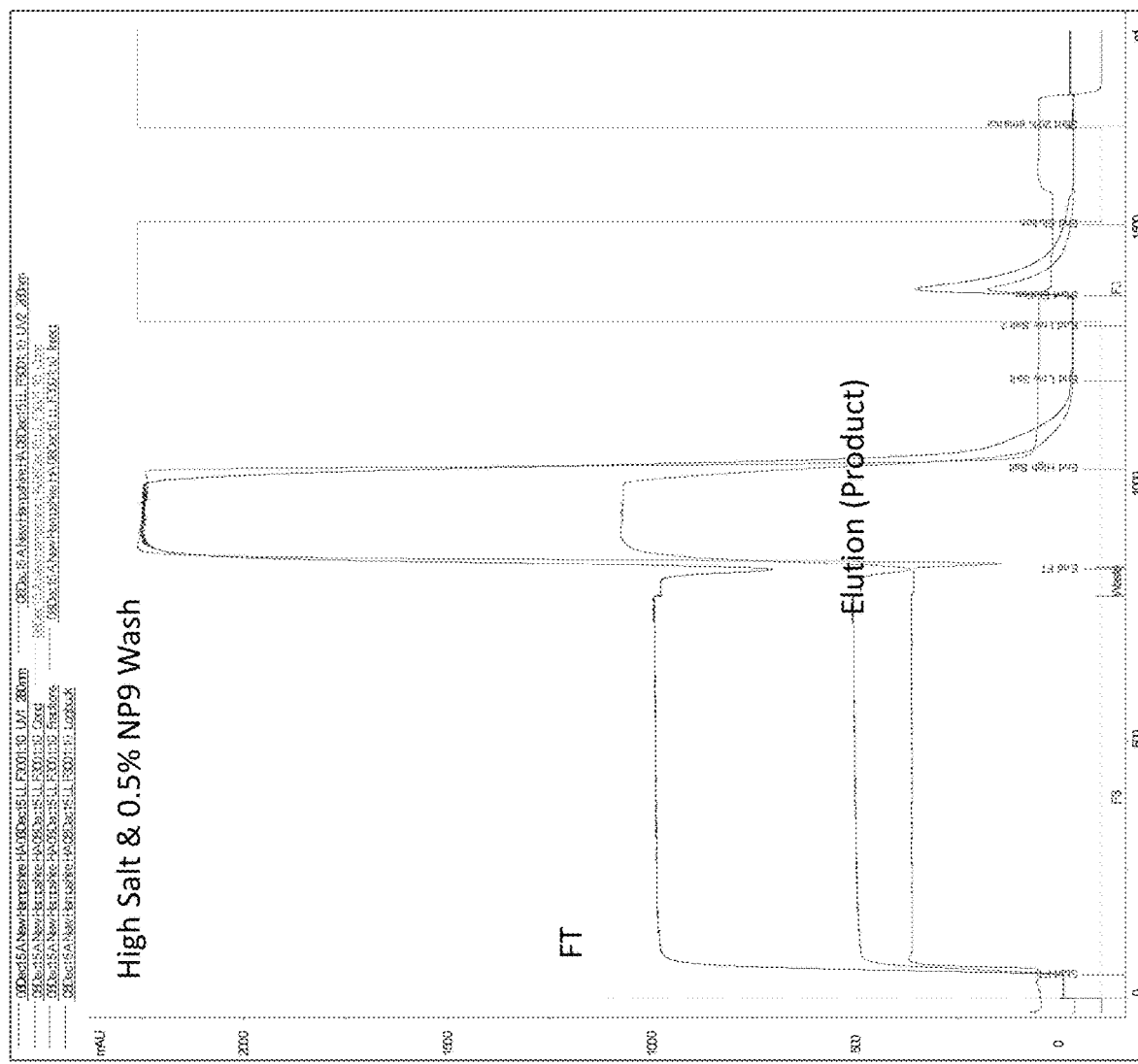
Fig. 18C: HA Nanoparticle: Lentil Lectin Chromatogram

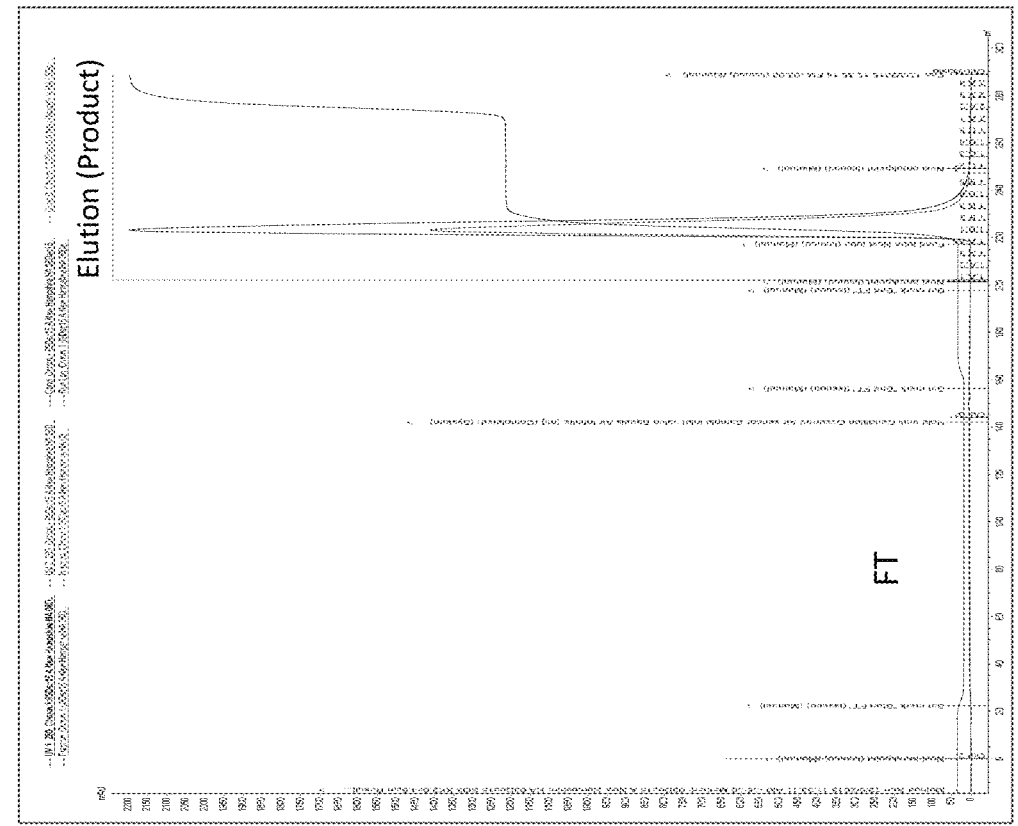
Fig. 18D: HA Nanoparticle: Sulfate (SO3-) Chromatogram

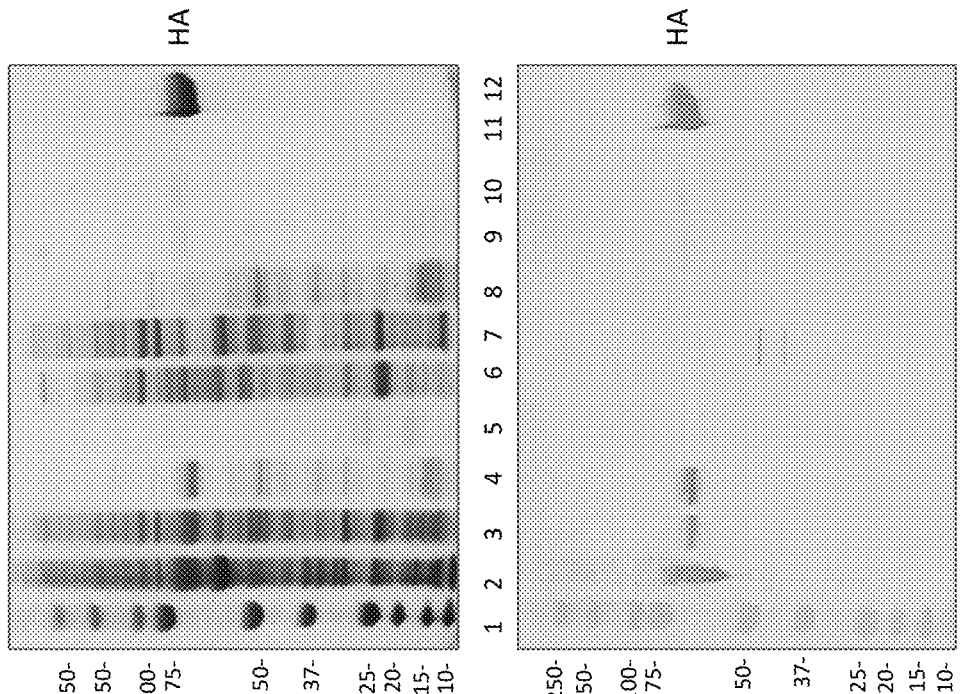
Fig. 18E: HA Nanoparticle: SDS PAGE showing TMAE and LL columns

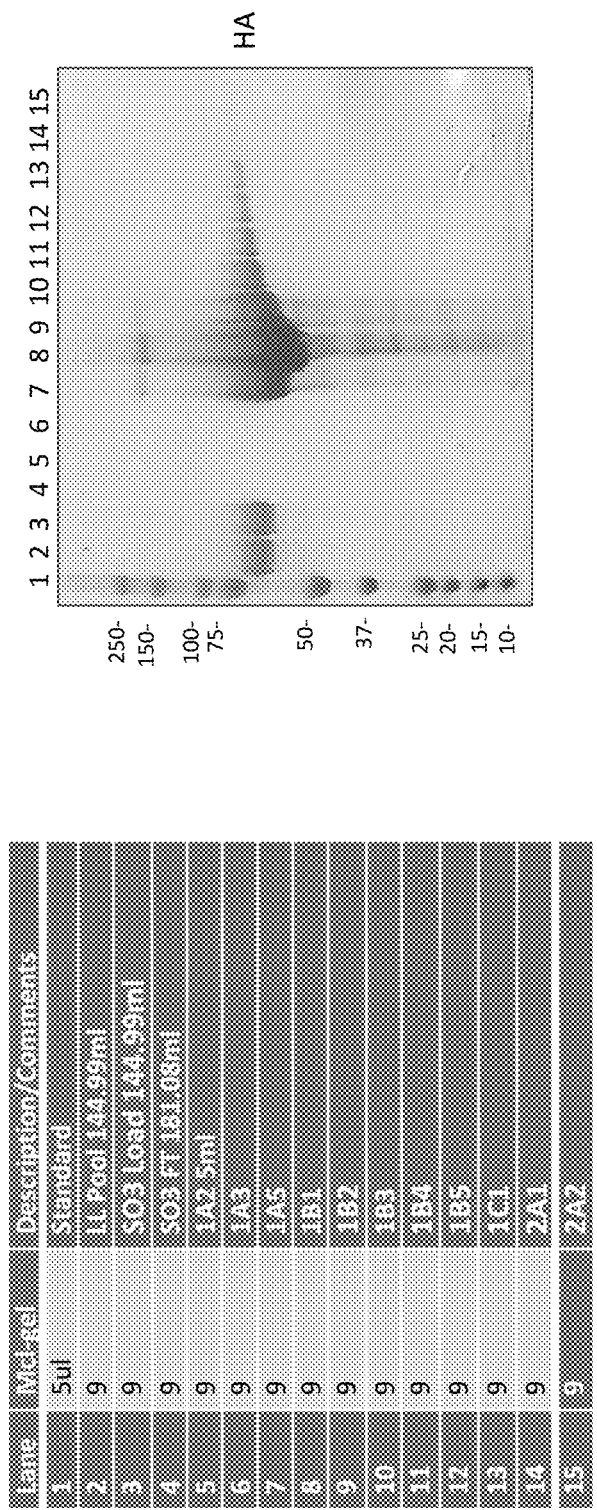
Fig. 18F: HA Nanoparticle: SDS PAGE for SO3- column

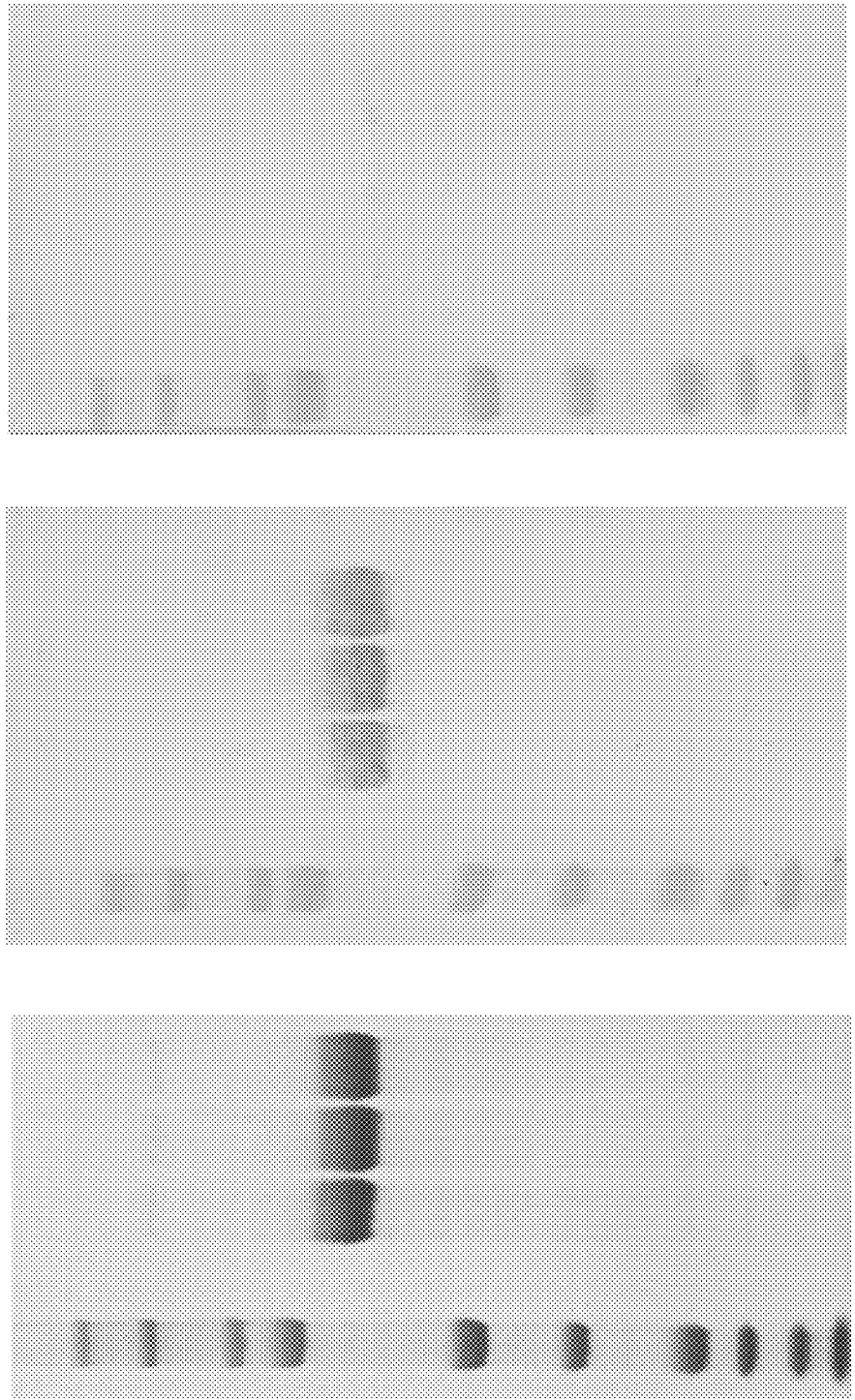
Fig. 19A: HA Nanoparticle Analysis A/New Hampshire/1/2015 (H1N1)

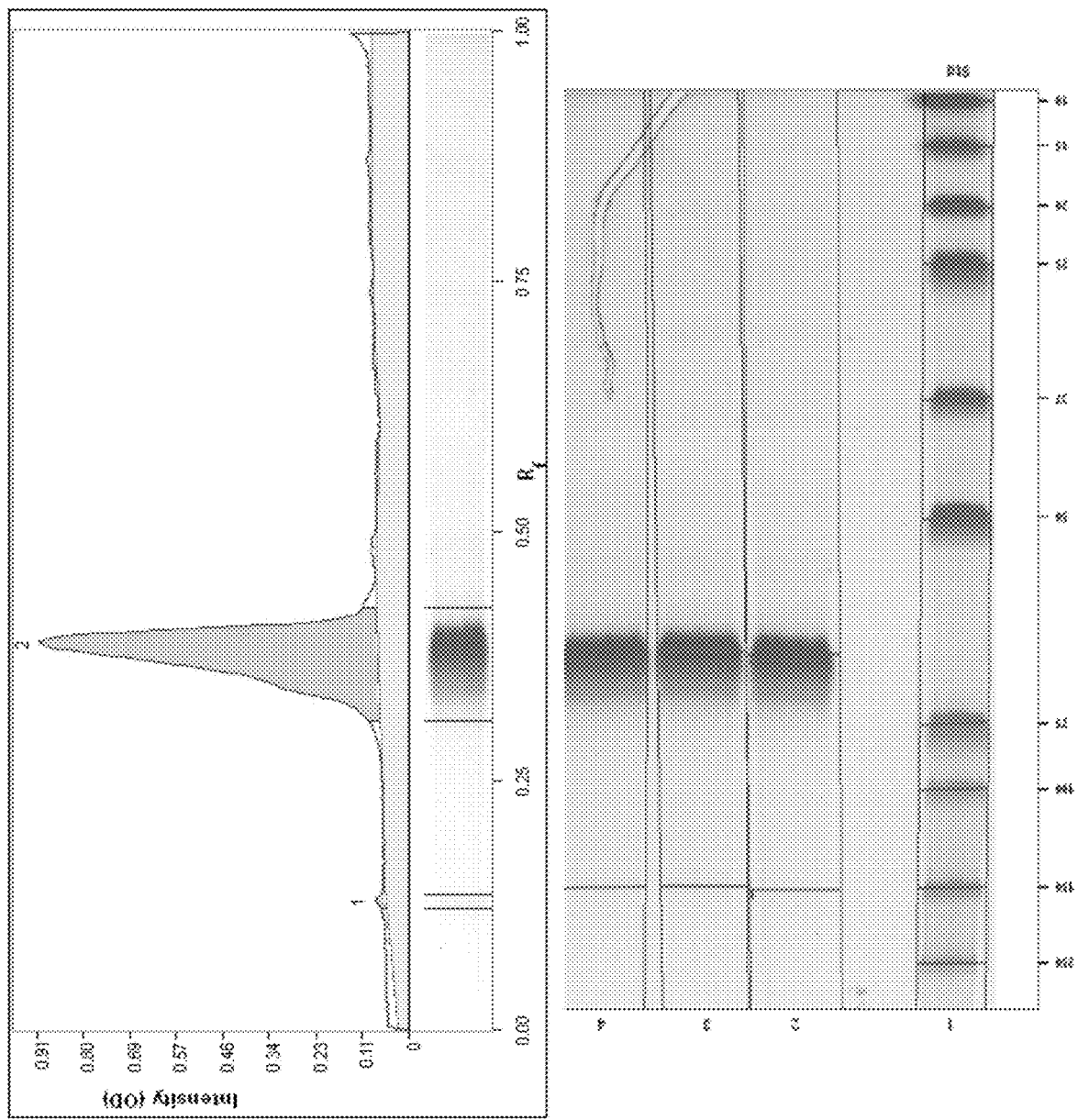
Fig. 19B: HA Nanoparticle Analysis A/New Hampshire/1/2015 (H1N1)
HA 99.1%

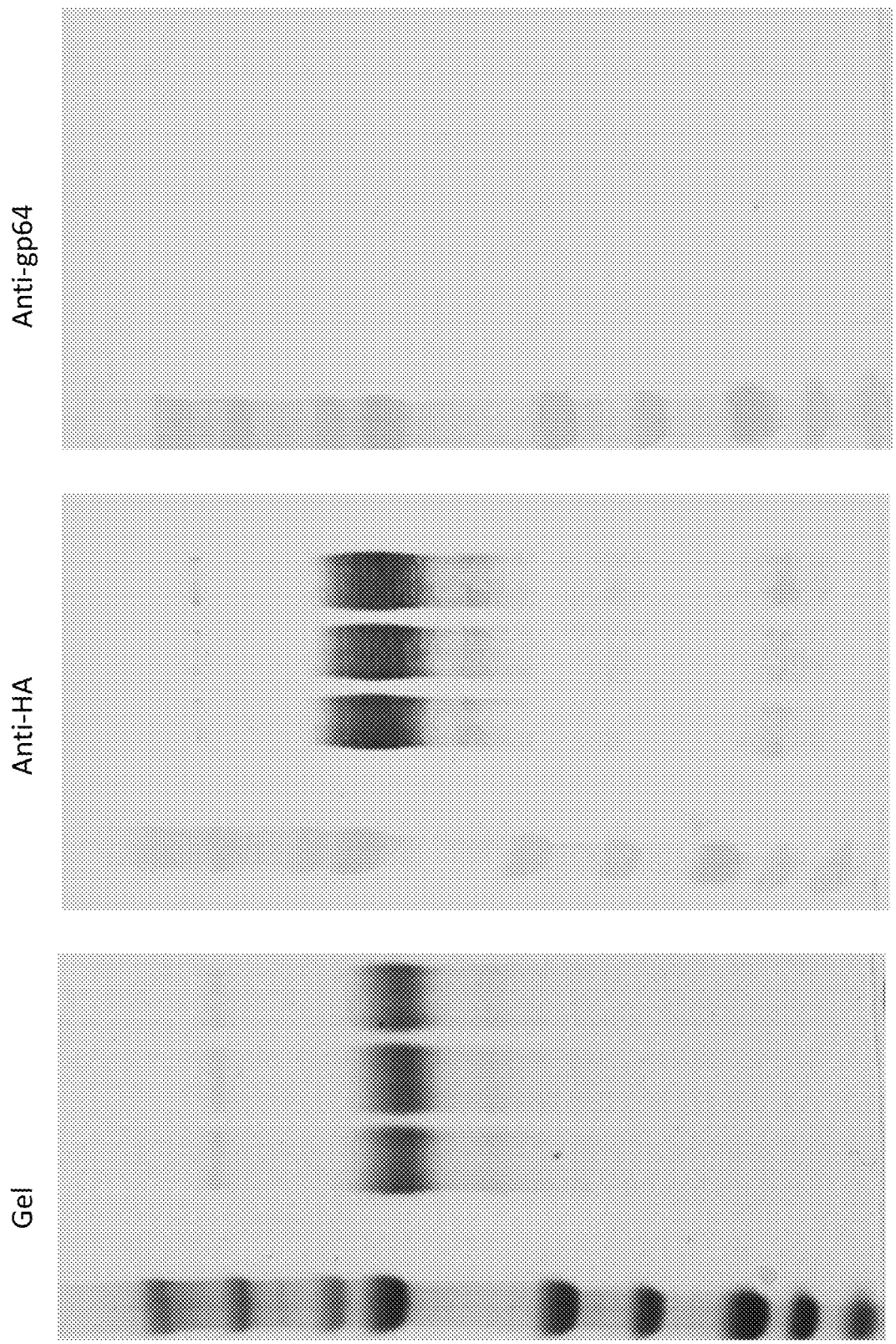
Fig. 19C: HA Nanoparticle Analysis (A/Switzerland/9715293/2013 (H3N2))

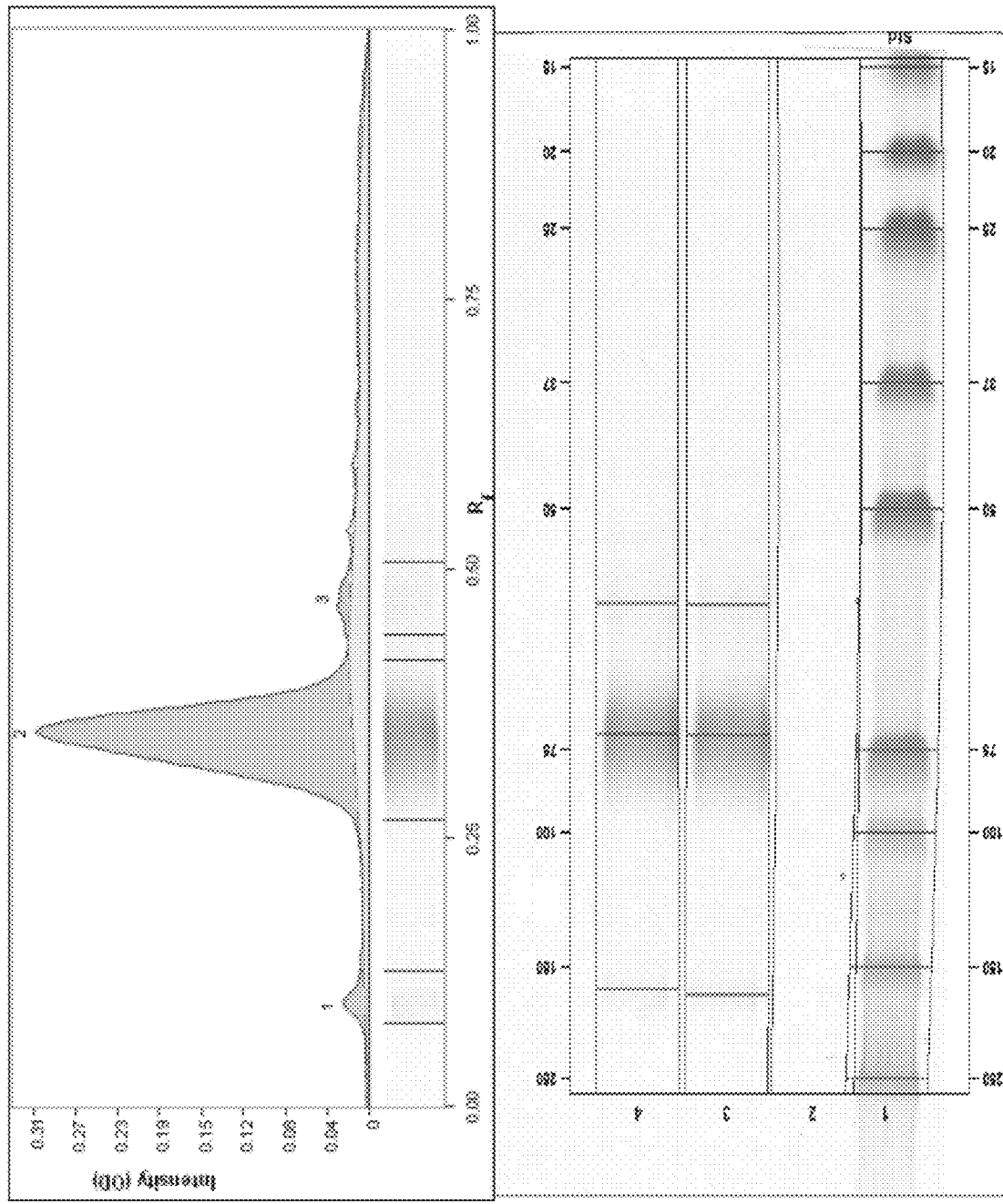
Fig. 19D: HA Nanoparticle Analysis (A/Switzerland/9715293/2013 (H3N2))

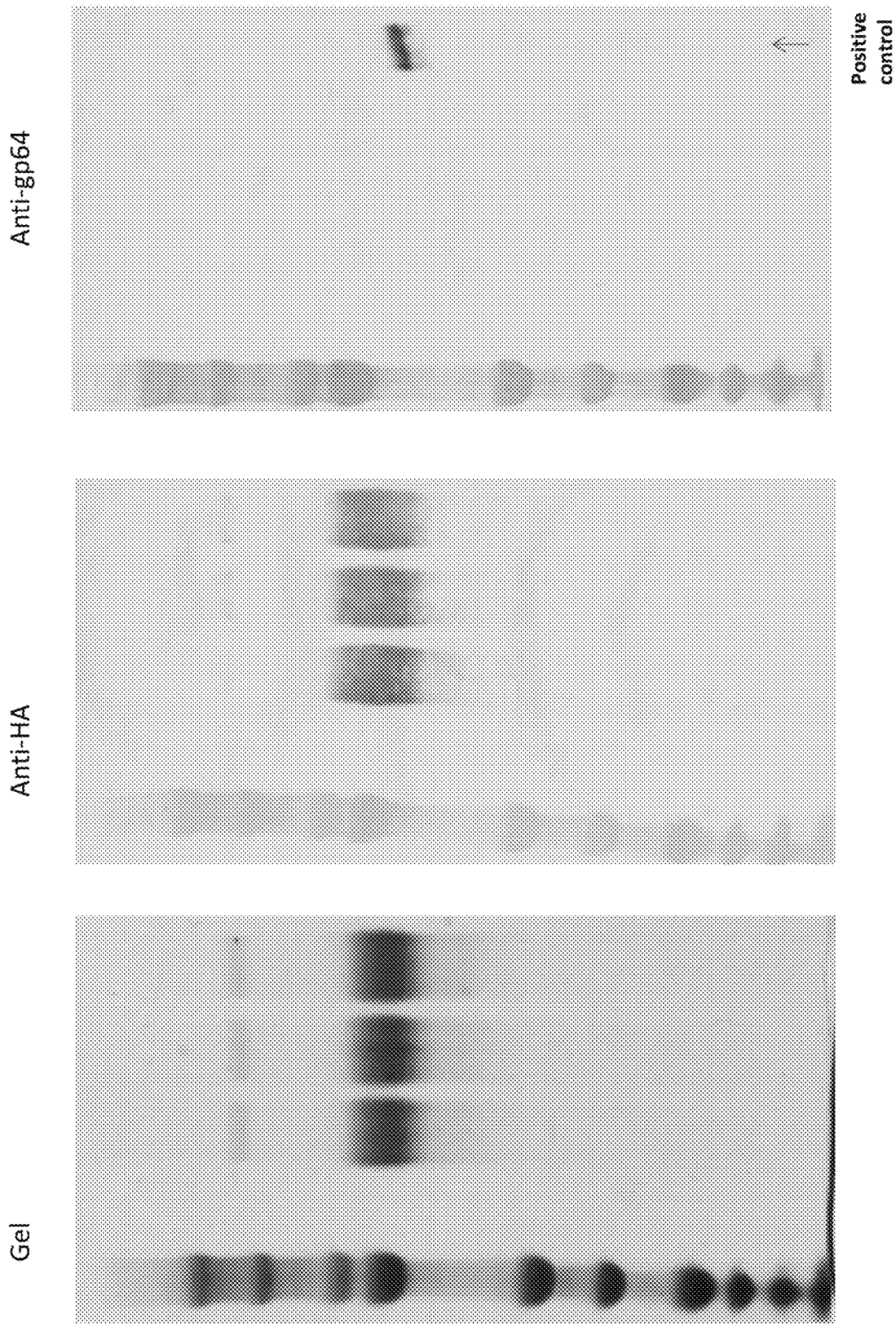
Fig. 19E: HA Nanoparticle Analysis A/Hong Kong/4801/2014 (H3N2)

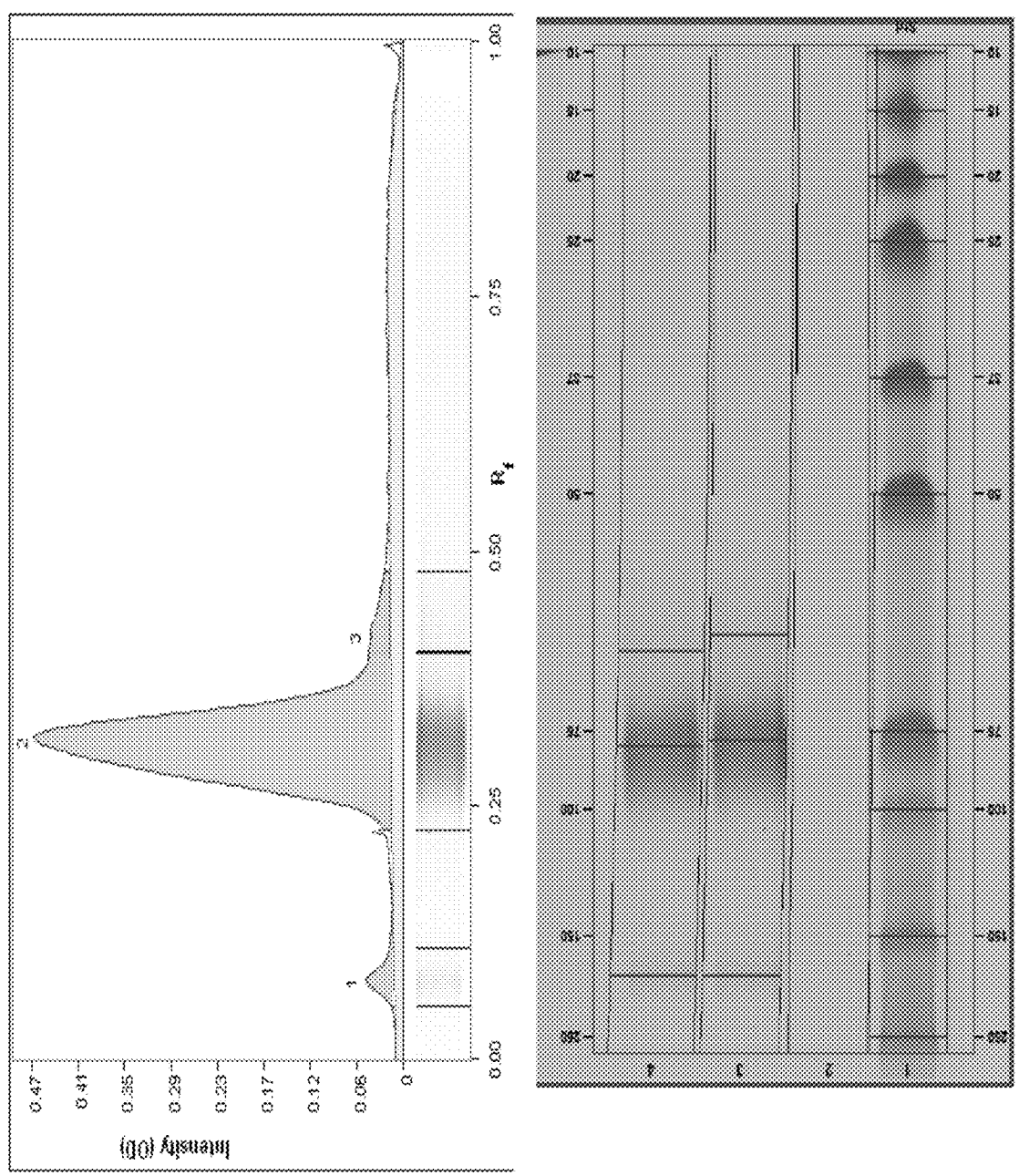
Fig. 19F: HA Nanoparticle Analysis (A/Hong Kong/4801/2014 (H3N2))
HA: 93.3%

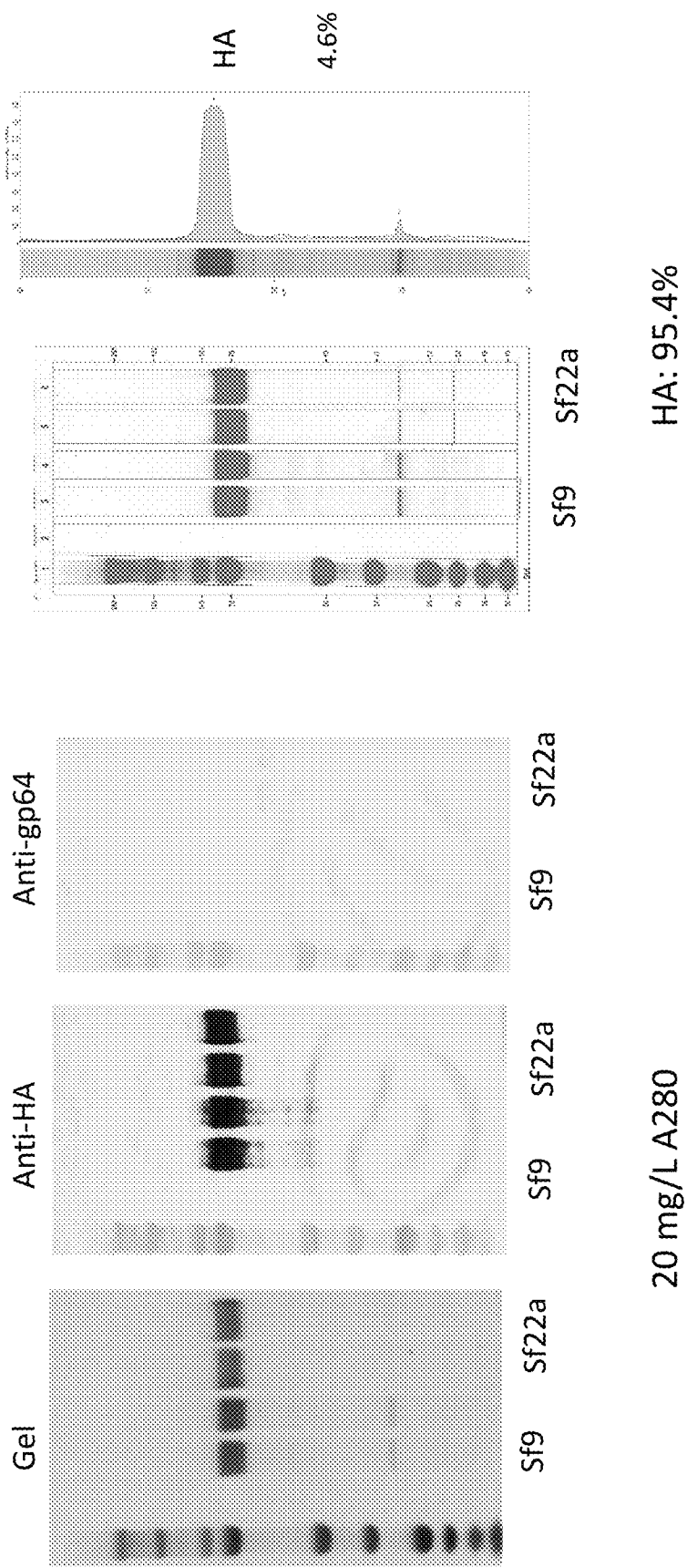
Fig. 19G: HA Nanoparticle Analysis (B/Phuket/3073/2013) in Sf9 and Sf22a c

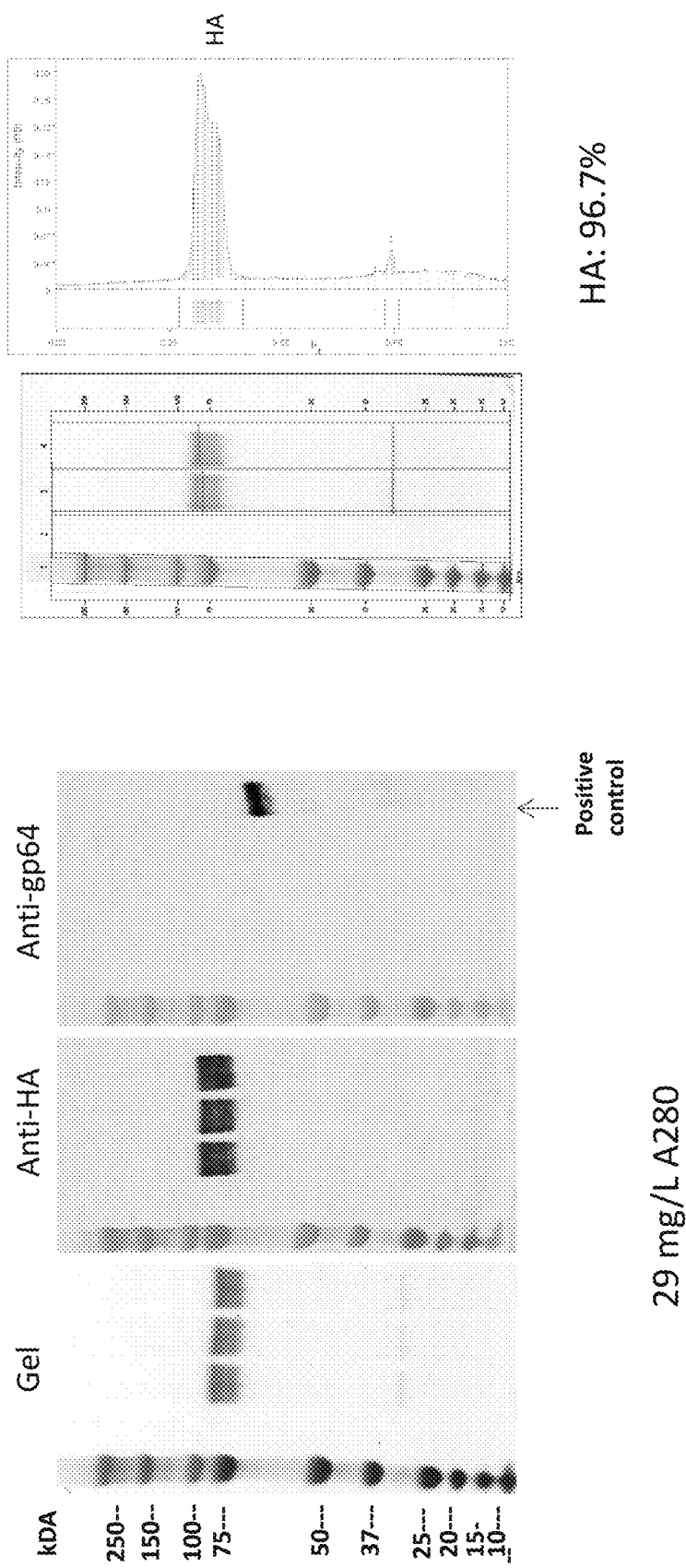
Fig. 19H: HA Nanoparticle Analysis (B/Brisbane/60/2008 HA nanoparticles)

Fig. 19I: HA Nanoparticle Purity by RP-HPLC Scout20-100 with Imtakt Column

Fig. 19J: HA Nanoparticle Analysis Summary of Production and Analysis

| Strains | BCA mg/ml | A280 HA mg/ml | IDMS HA mg/ml | HA% peptide mapping | HA% Densitometry | HA% RP-HPLC | Particle Size d.nm (PDI) | Yield (mg/L A280) |
|---|---|---|---|---|---|---|---|---|
| A/New Hampshire/1/2015 H1N1 | 0.98 | 0.93 | 0.772 | 97.3% | 93.4% | 83.5% | 22.0 (0.126) | 19 |
| A/Switzerland/9715293/2013 H3N2 | 1.06 | 0.93 | 0.891 | 98.1% | 94.5% | 89.4% | 24.7 (0.135) | 18 |
| A/Hong Kong/4801/2014 H3N2 | 0.70 | 0.55 | 0.535 | 95.1% | 93.3% | 85.0% | 24.0 (0.174) | 12 |
| B/Phuket/3073/2013 | 0.60 | 0.60 | 0.389 | 89.6% | 95.4% | | 29.9 (0.118) | 20 |
| B/Brisbane/60/2008 | 1.39 | 1.44 | 1.015 | 90.4% | 96.7% | | 30.5 (0.102) | 29 |

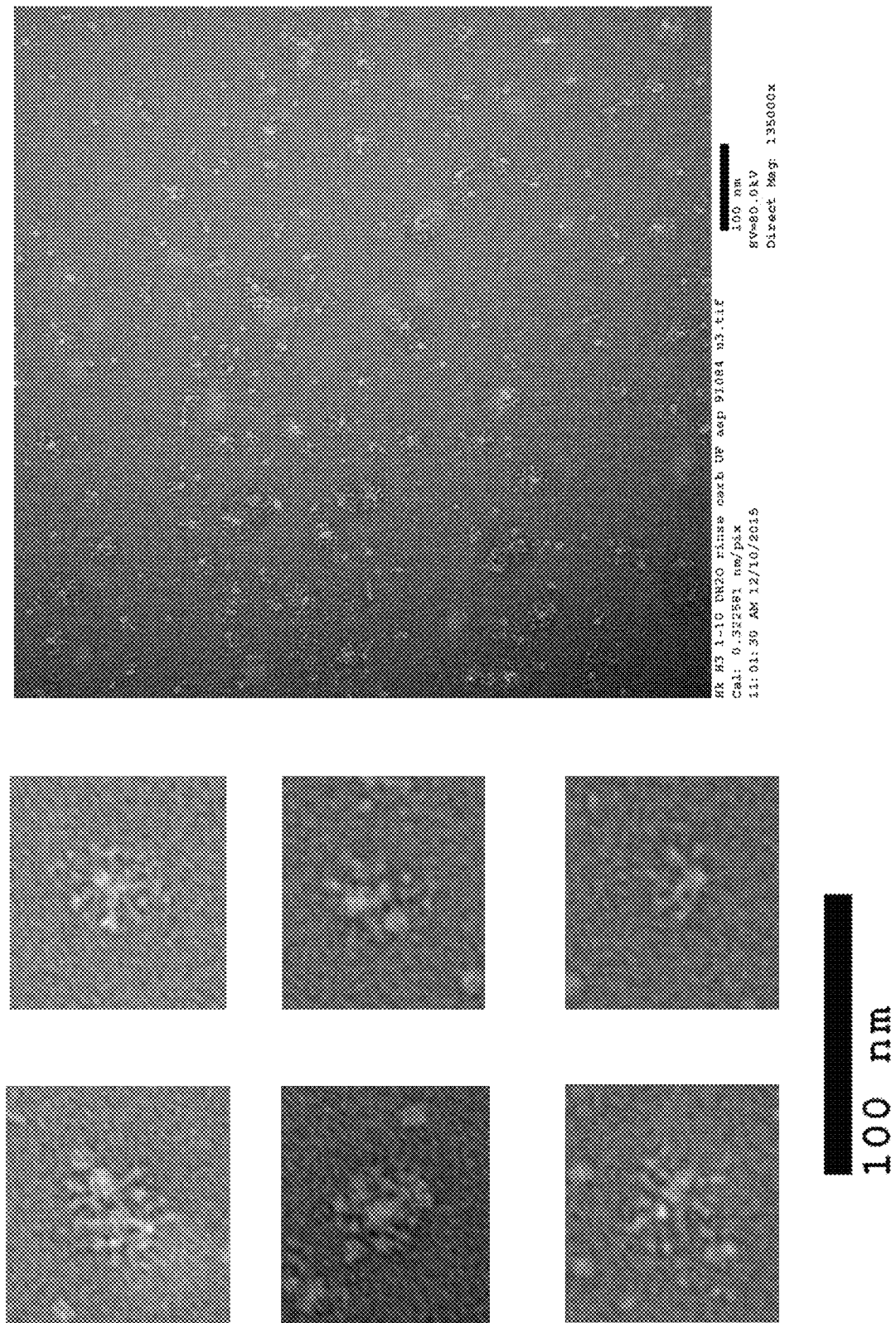

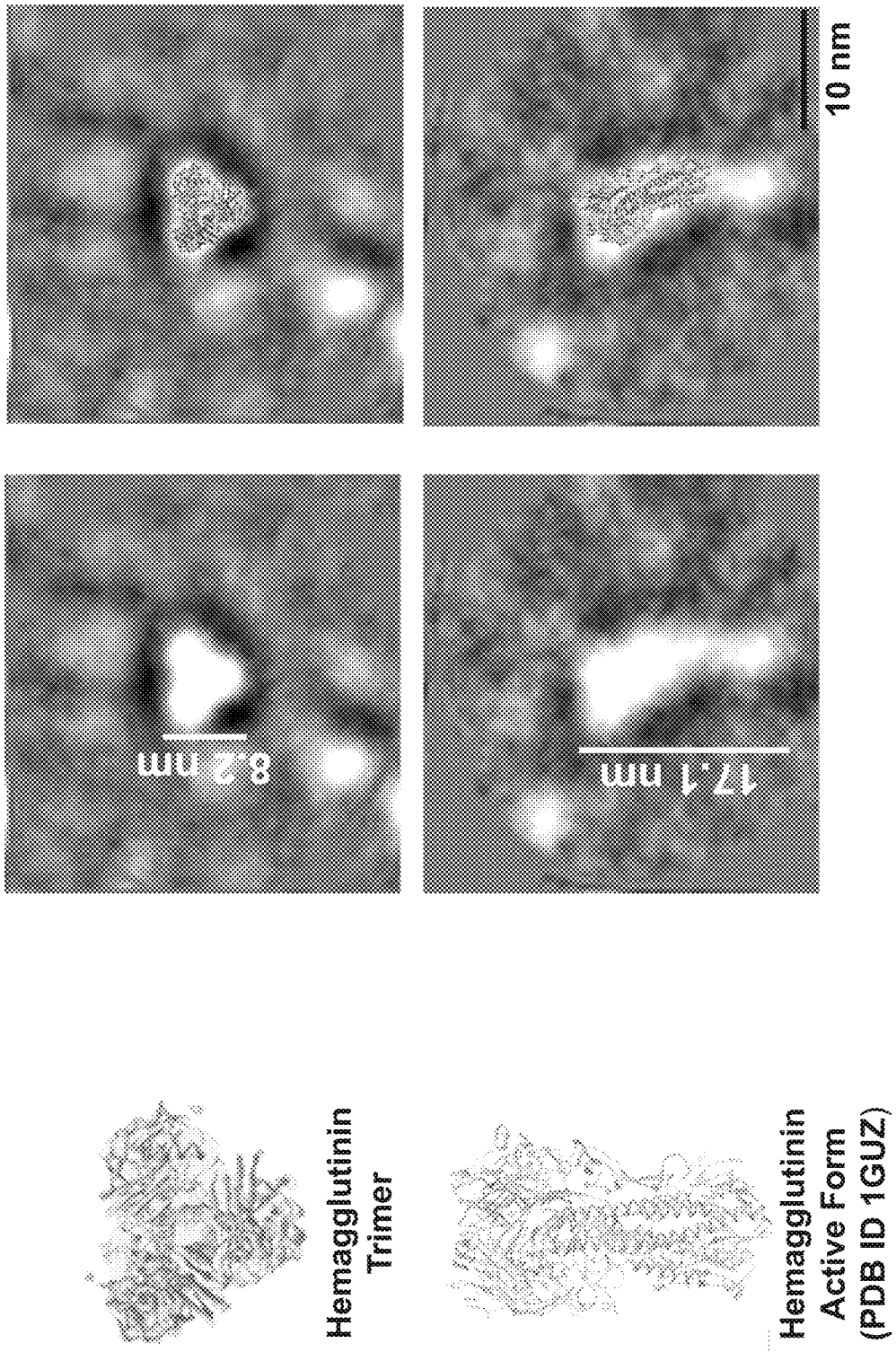

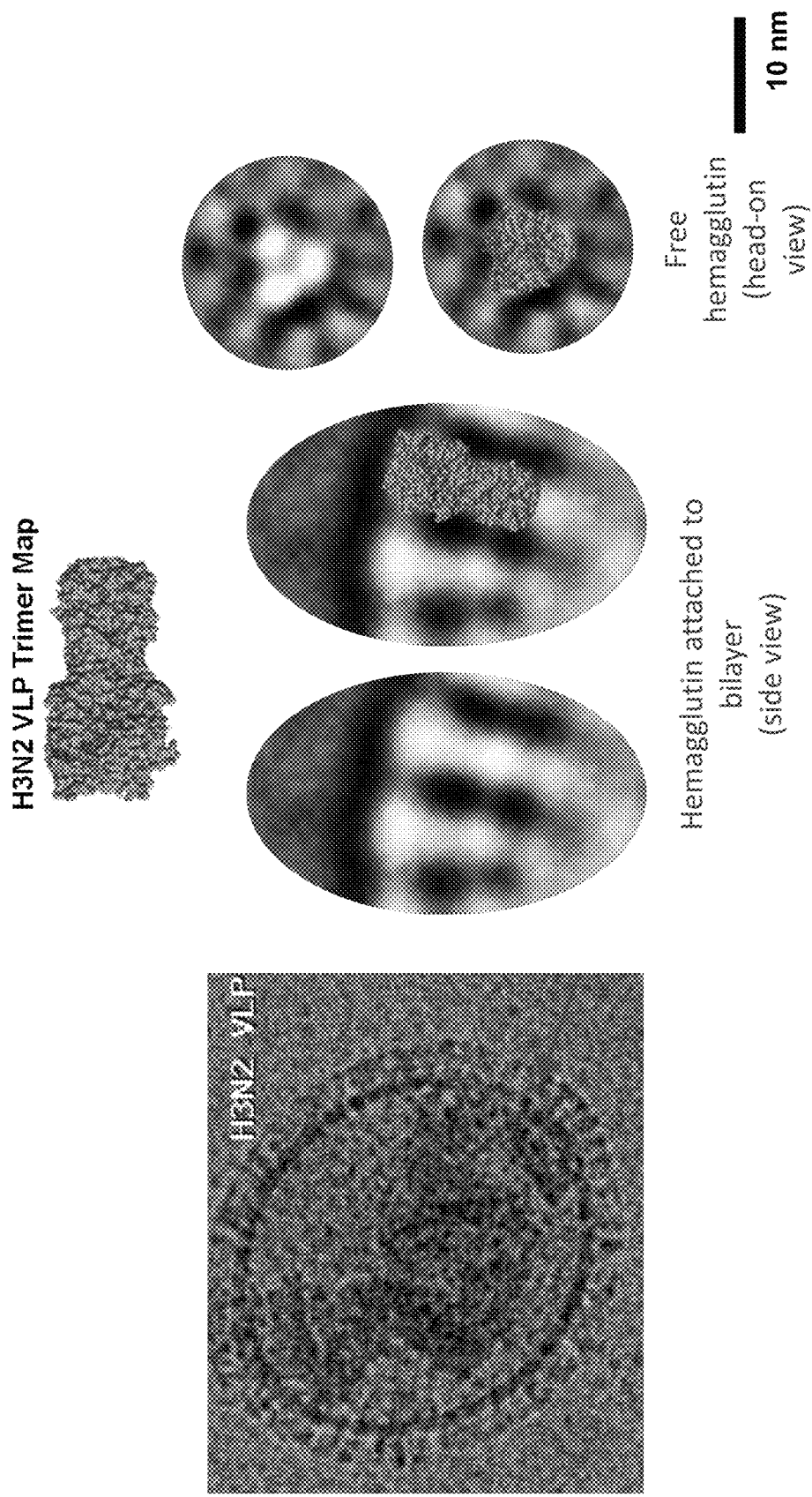
Fig. 21B: A/Switzerland/715293/2014 (H3N2) n15 VLPs: CryoEM 2D class averaging Fig. 22: Immunogenicity : RIC RSV F + A/Switzerland H3 HA Nanoparticle + Matrix M mouse study

| Group | N | RSV F 1.5μg | H3N2 nHA 1.5μg | Matrix M 5μg | AlPO₄ (60μg) | Immunization (Day) | Blood Collection (Day n=10) | Spleen Harvest (Day n=5) |
|---|---|---|---|---|---|---|---|---|
| 1 | 15 | + | - | - | - | 0, 21 | -1, 21, ²28, 35 | 28 |
| 2 | 15 | - | + | - | - | 0, 21 | -1, 21, ²28, 35 | 28 |
| 3 | 15 | + | + | - | - | 0, 21 | -1, 21, ²28, 35 | 28 |
| 4 | 15 | + | - | + | - | 0, 21 | -1, 21, ²28, 35 | 28 |
| 5 | 15 | - | + | + | - | 0, 21 | -1, 21, ²28, 35 | 28 |
| 6 | 15 | + | + | + | - | 0, 21 | -1, 21, ²28, 35 | 28 |
| 7 | 15 | + | - | - | + | 0, 21 | -1, 21, ²28, 35 | 28 |
| 8 | 15 | - | + | - | + | 0, 21 | -1, 21, ²28, 35 | 28 |
| 9 | 15 | + | + | - | + | 0, 21 | -1, 21, ²28, 35 | 28 |
| 10 | 5 | - | - | - | - | - | - | 28 |

[1] A/Switzerland H3 Nanoparticle (nHA) monovalent
[2] Day 28 blood draw only on mice euthanized for spleen collection

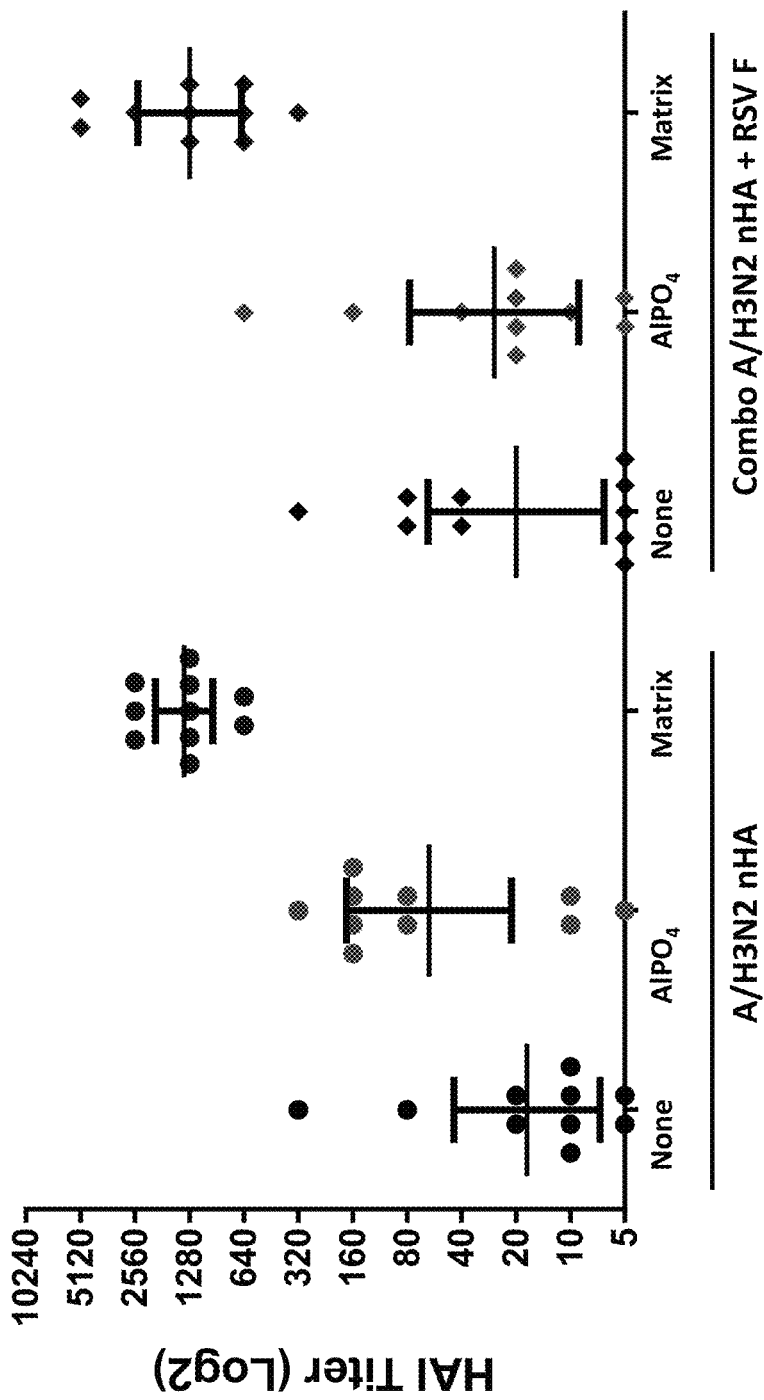

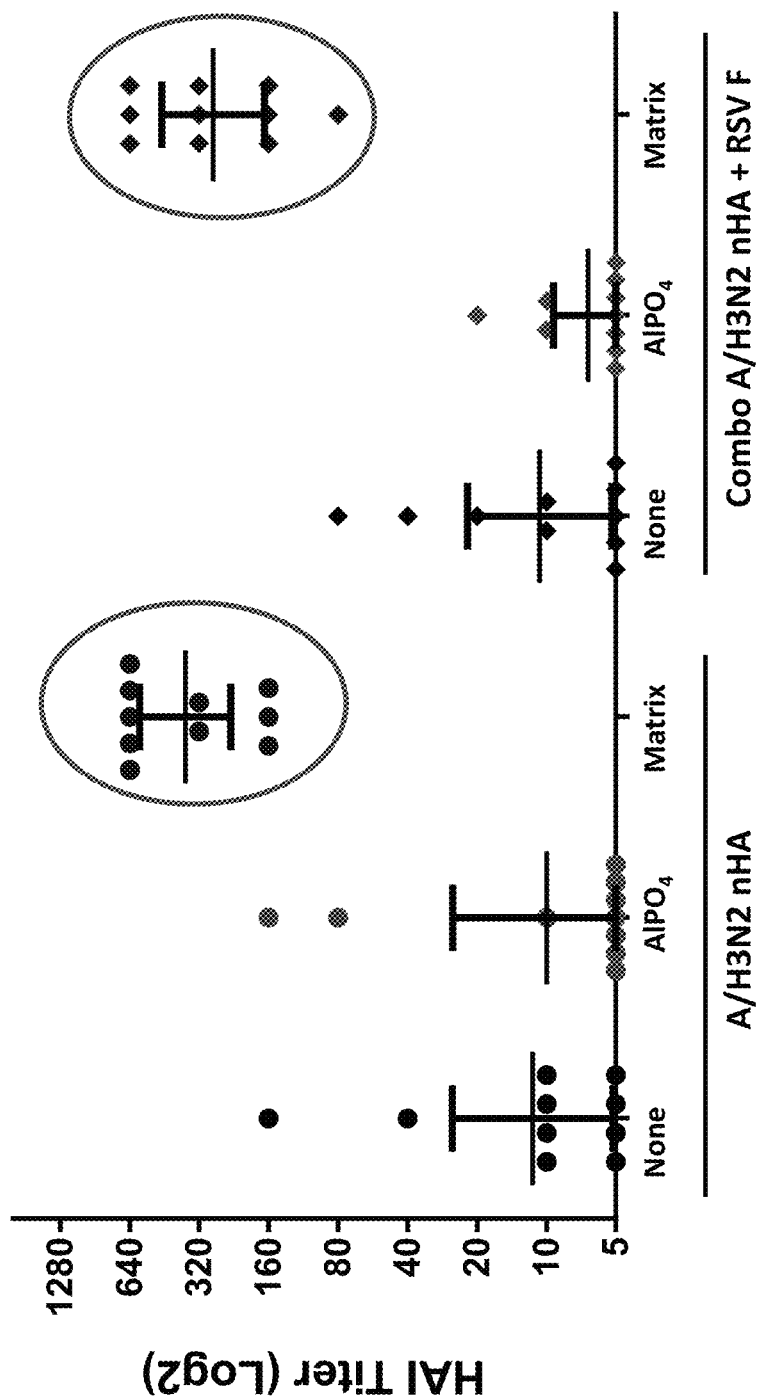

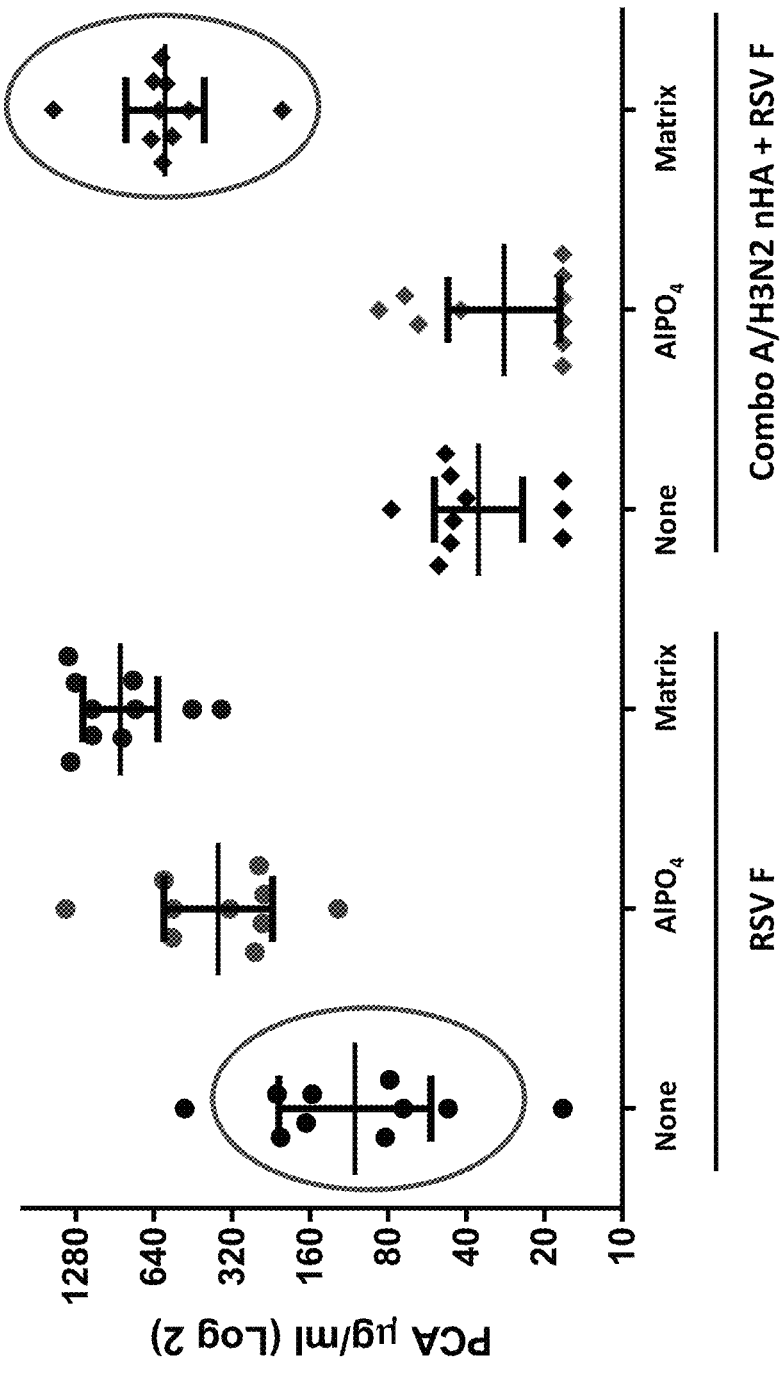
Fig. 23C: RSV F site II Palivizumab Competitive Antibody (PCA) responses

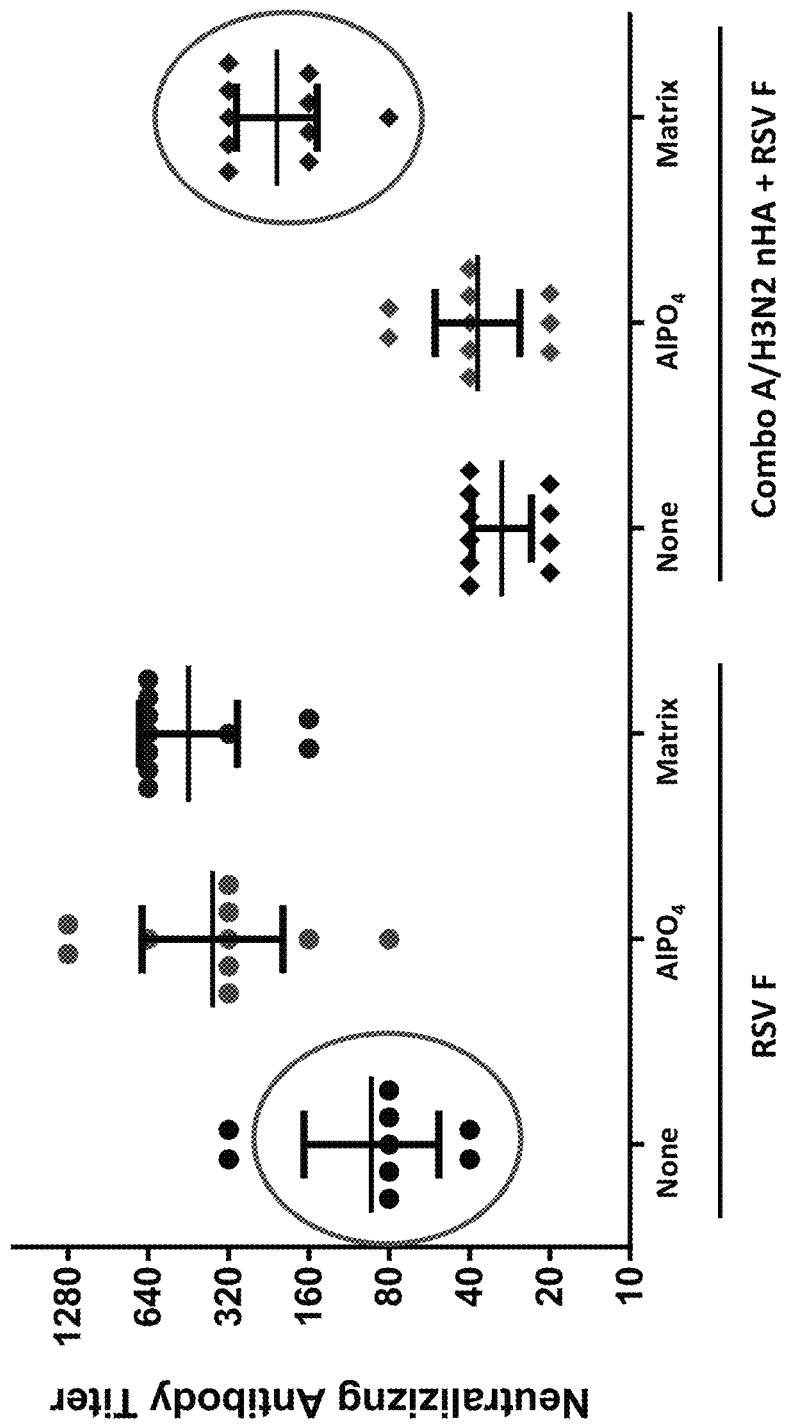
Fig. 23D: RSV A neutralizing antibody responses

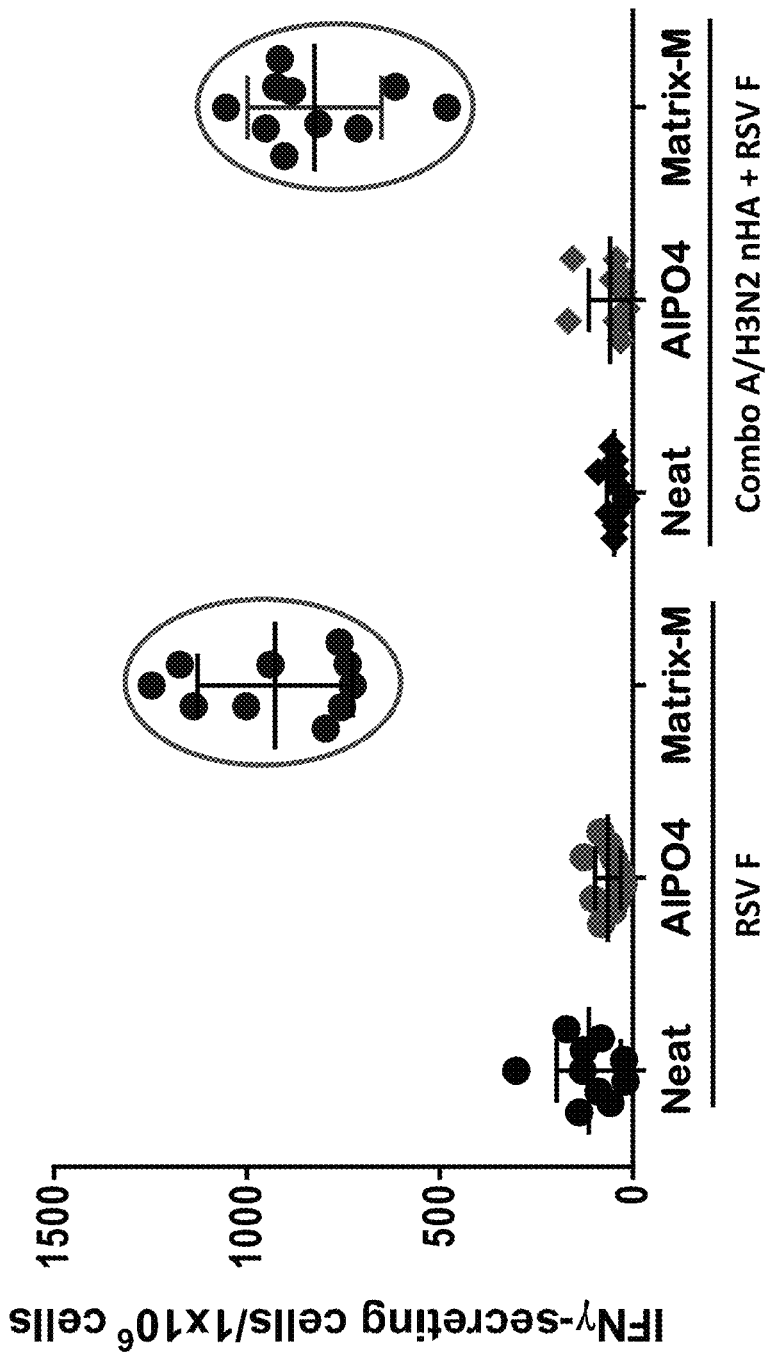

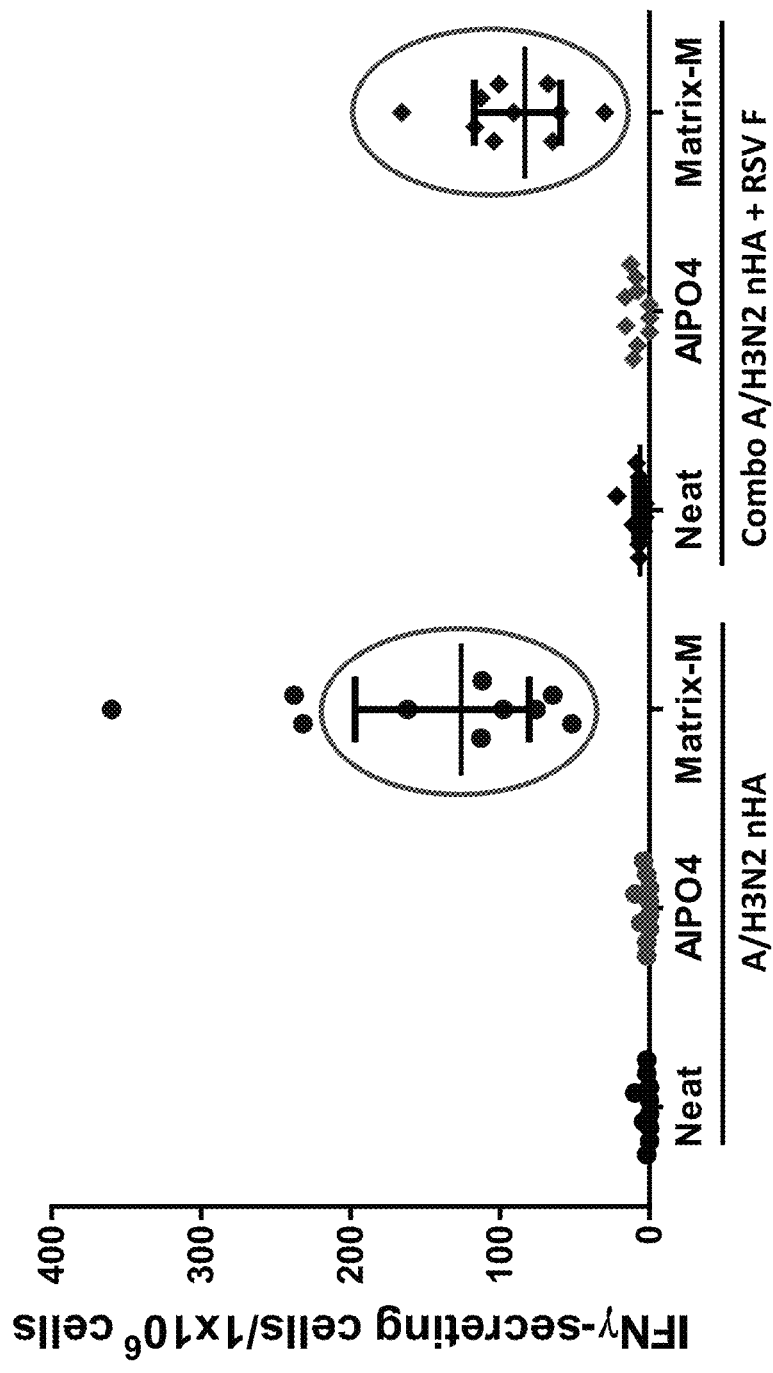

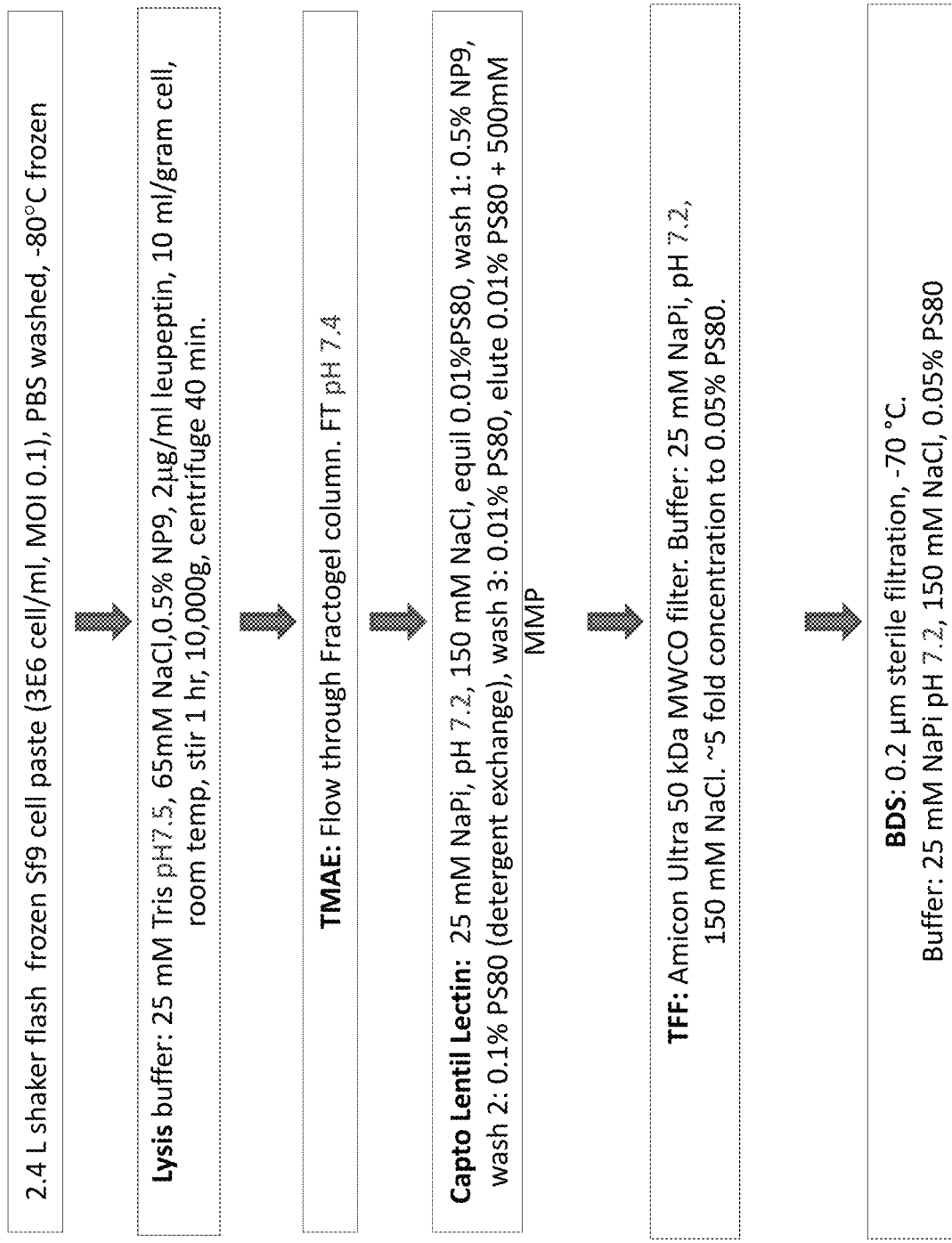
Fig. 24A Enhanced stability HA Nanoparticle purification flow chart neutral pH process

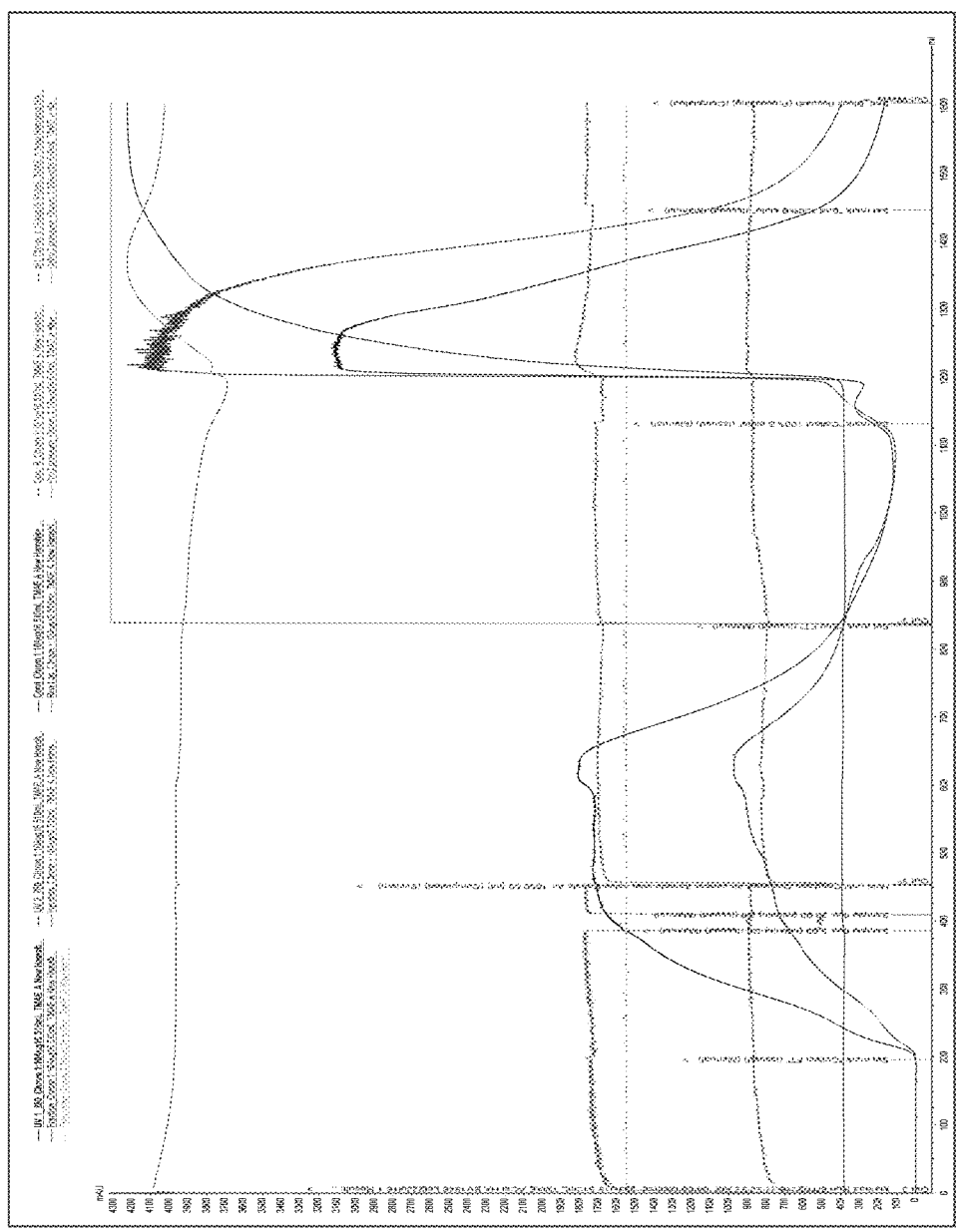
Fig 24B: TMAE Chromatogram of A/New Hampshire/1/2015 (H1N1) HA purification
TMAE XK5x26.5cm, 510 ml
A: 25mM Tris/70mM NaCl/0.02% NP9, pH7.5
B: 25 mM Tris/1.0M NaCl/0.02% NP9, pH7.5
Collect Flow through: 636ml
Elution: 100%B for 2CV
Flow rate: 20 ml/min = 60 cm/hr

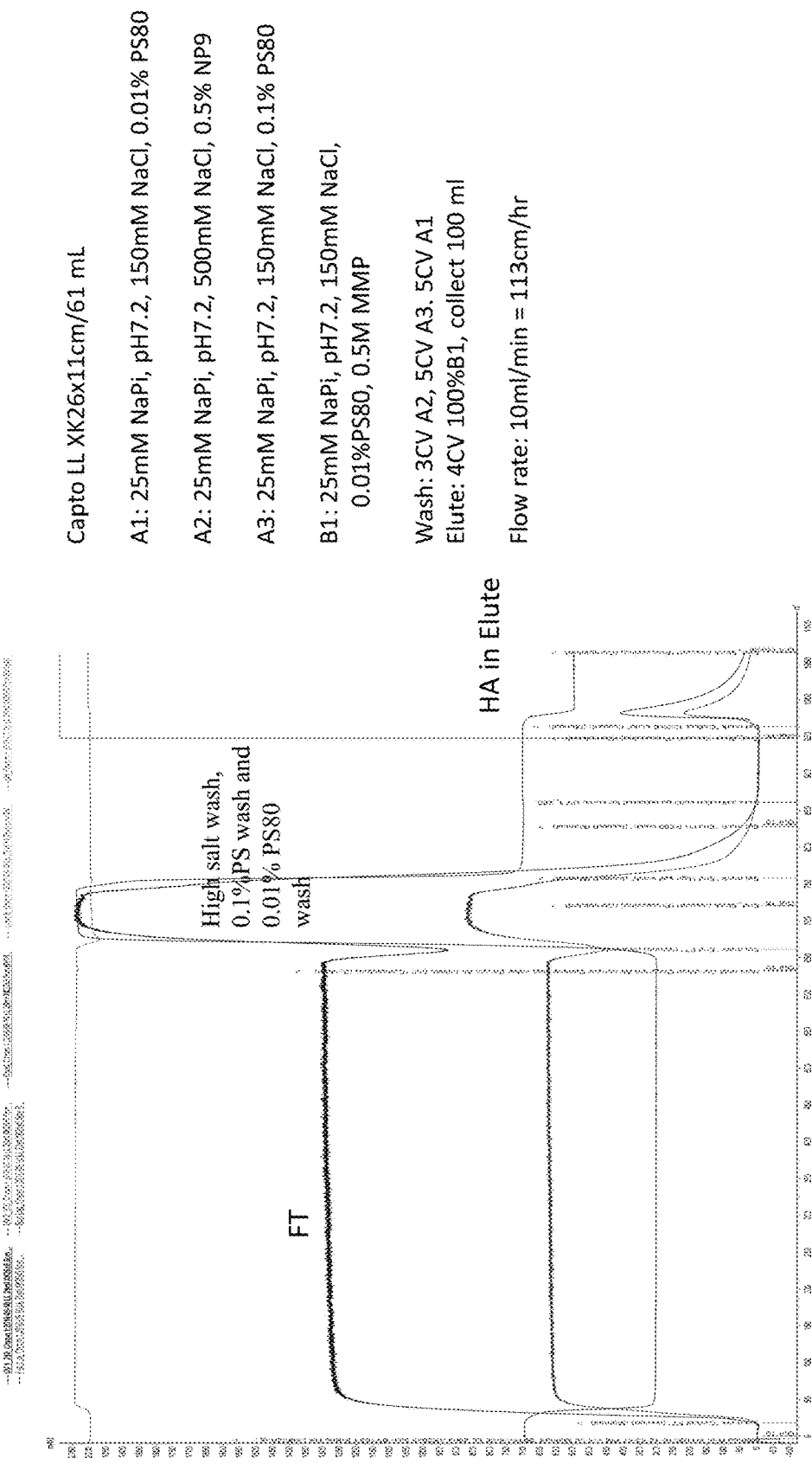
Fig. 24C. Capto Lentil Lectin Chromatogram – BV1849 A/New Hampshire/1/2015 (H1N1) HA Fig 25A. Trypsin-resistant nanoparticles of strain A/New Hampshire/1/2015 (H1N1) HA
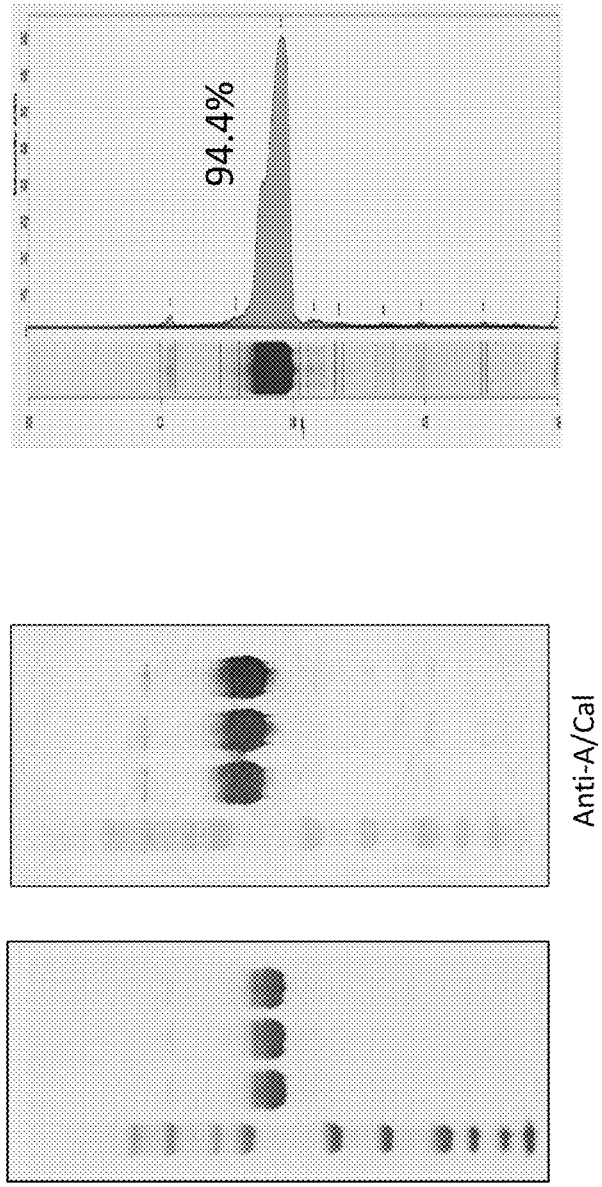
Anti-A/Cal
Concentration by A280:
(A280-A340)x5/1.458=(0.679−0.01)x5/1.458 = 2.27mg/ml
Concentration by SRID with NIBSC reagents = 2.54mg/ml (1.12)
HA Amount =2.27mg/ml×21ml=47.67mg
HA Yield by A280: 47.7mg/2.4L = 19.9mg/L
Bulk Drug Substance (BDS): 25mM NaPi, 150mM NaCl, ~0.05% PS80, pH7.2

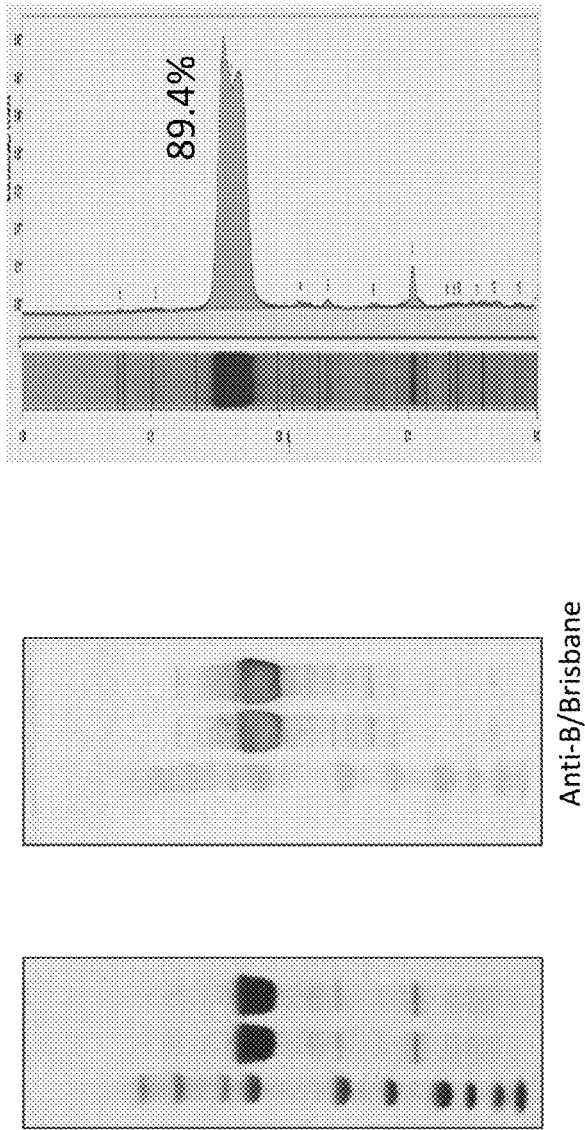
Fig. 25B Trypsin-resistant nanoparticles of strain BV1834 B/Brisbane/60/08 HA
Concentration by A280:
(A280-A340)x5/0.8583=(0.611−0.024)x5/0.8583 = 3.42mg/ml
Concentration by SRID with NIBSC reagents = 3.26 mg/ml (0.95)
Total HA Amount by A280=3.42mg/ml×21ml=71.8mg
HA Yield by A280: 71.8mg/2.4L= 29.9mg/L
BDS: 25mM NaPi, 150mM NaCl, ~0.05% PS80, pH7.2

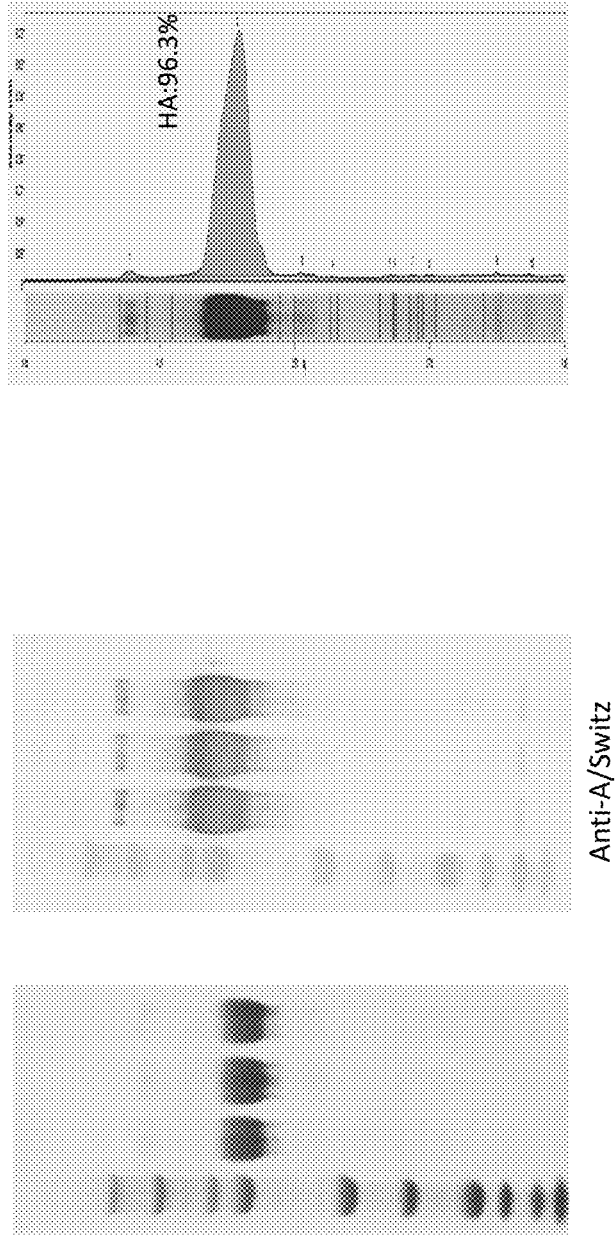
Fig. 25C Trypsin-resistant nanoparticles of strain A/Hong Kong/4801/2014 (H3N2)

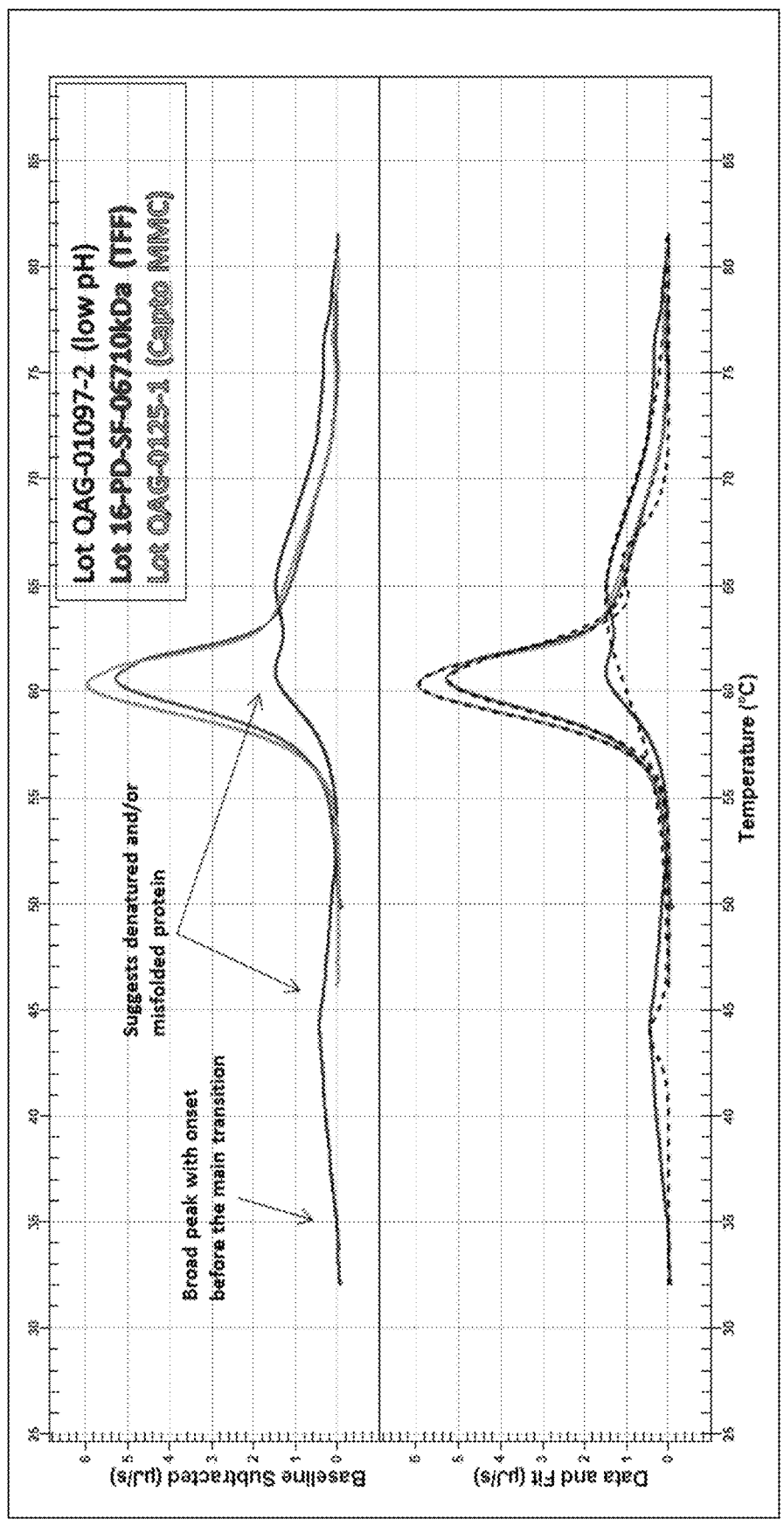
Fig. 25D: Enhanced stability trypsin-resistant HA nanoparticles by nano differential scanning calorimetry (nDSC)

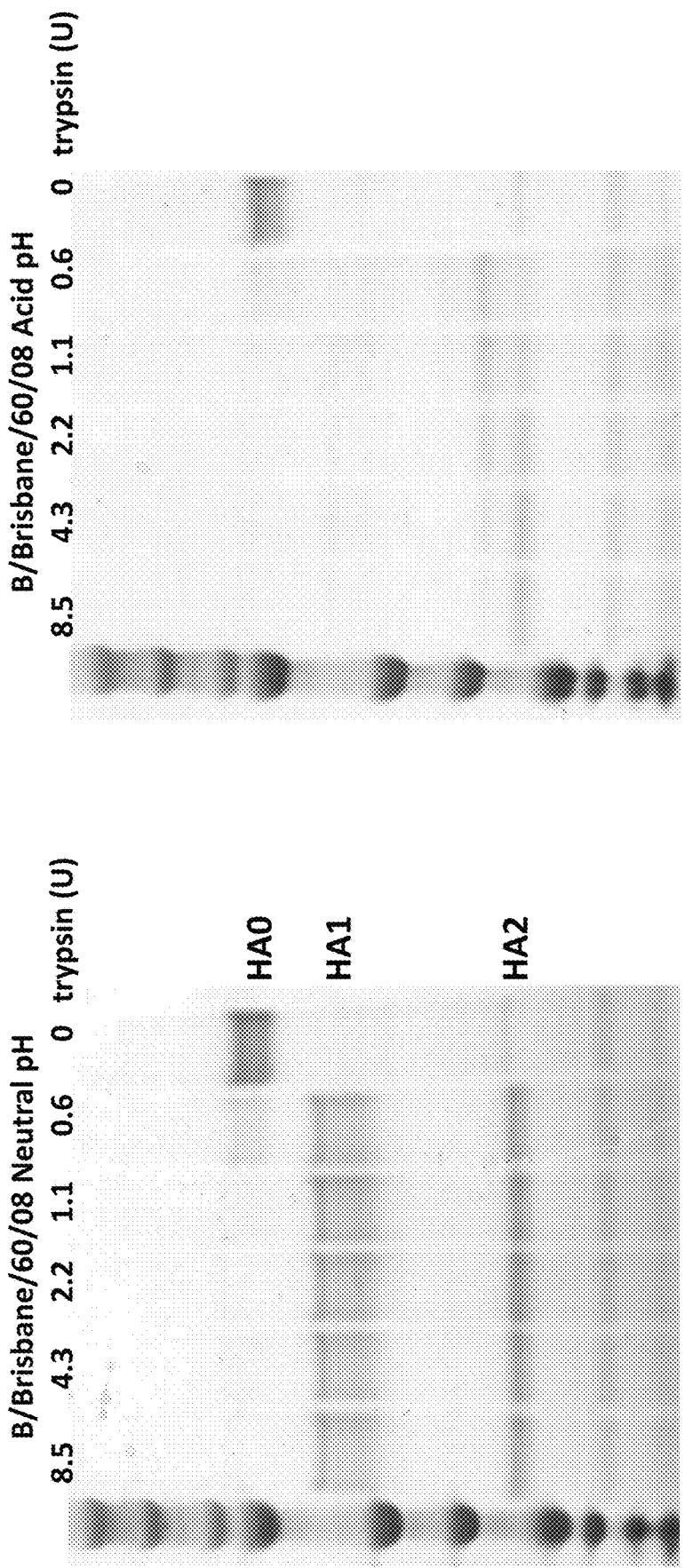
Fig 26A: Comparison of low pH and neutral pH synthesized B strain HA nanoparticles

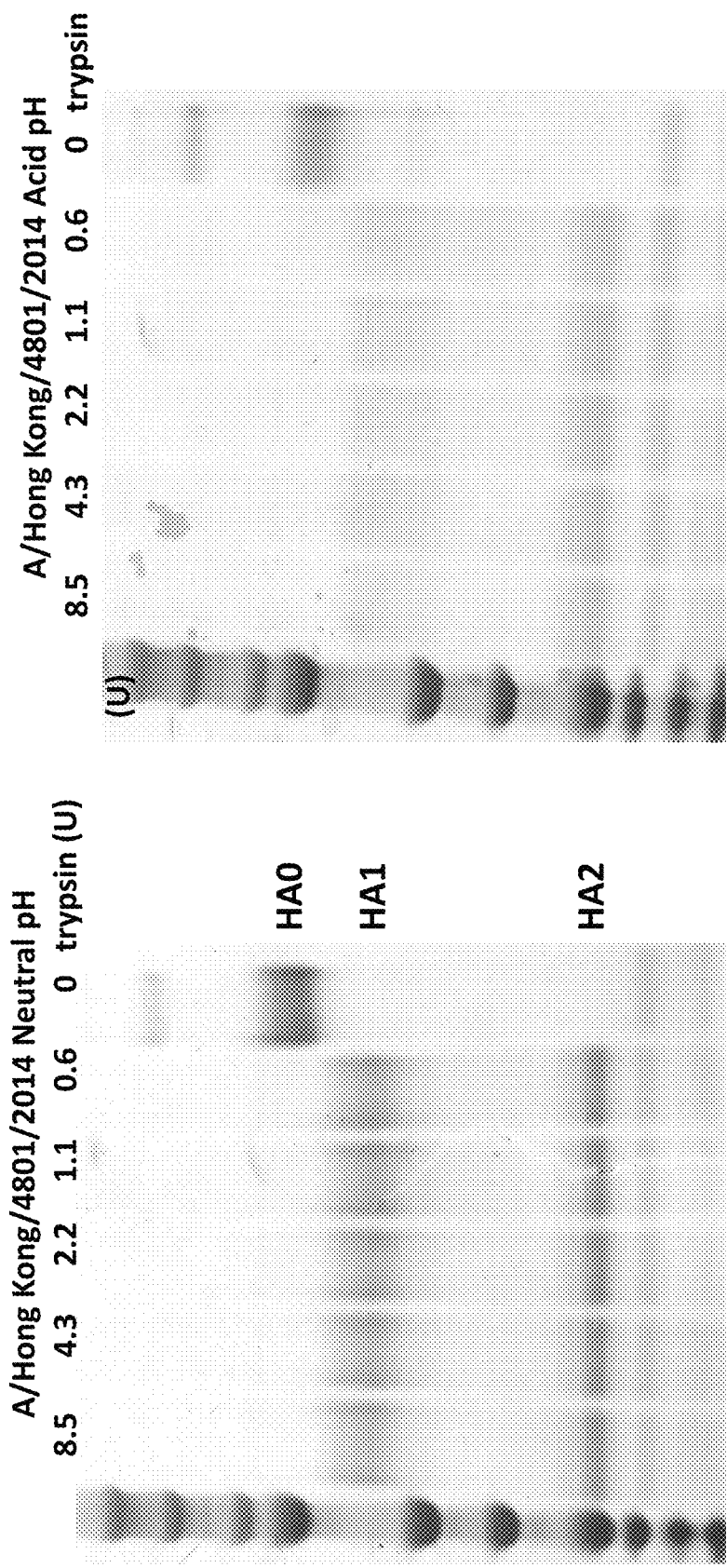
Fig 26B: Comparison of low pH and neutral pH synthesized A/Hong Kong/4801/2014 HA nanoparticles Fig 26C: Trypsin resistance of neutral pH A/New Hampshire/1/2015 (H1N) HA nanoparticles

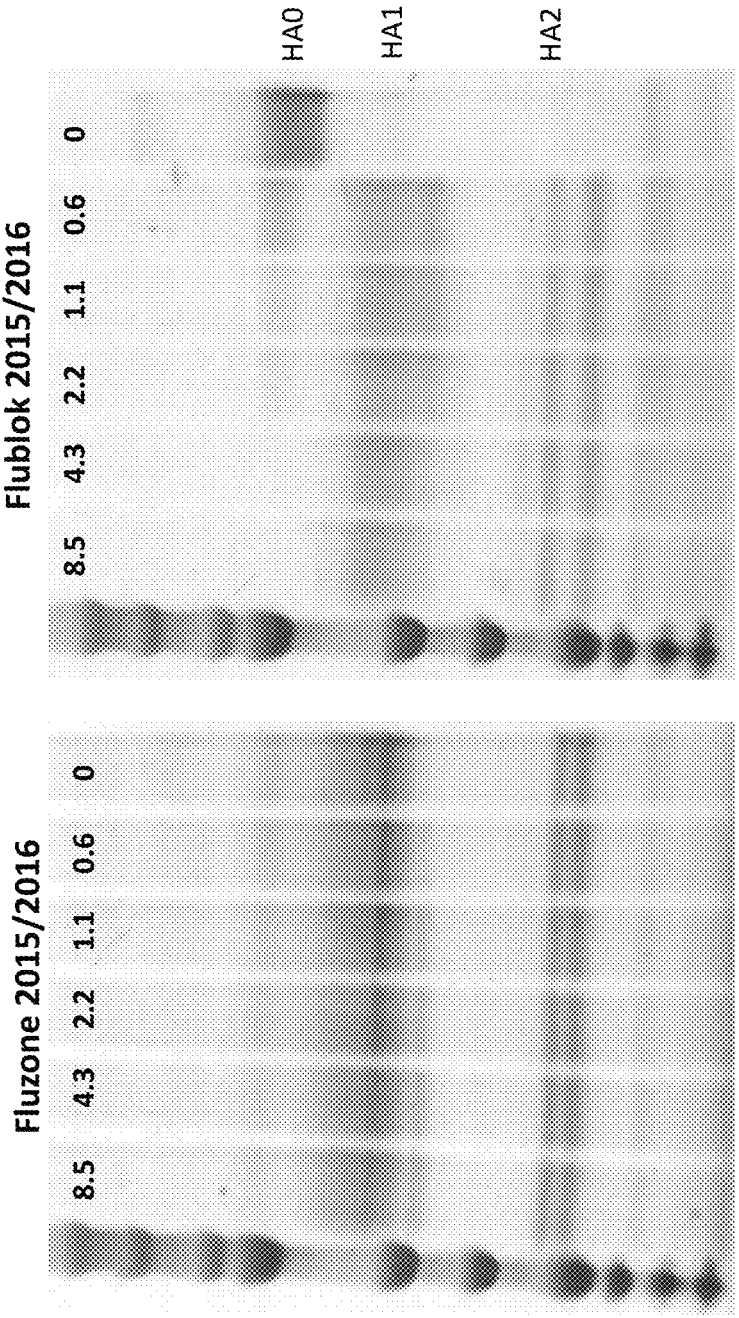
Fig. 27 Trypsin sensitivity of high dose Fluzone and Flublok

Fig. 28A: Ebola nanoparticles induce antibodies and protect against infection

Fig. 28B: Ebola nanoparticles induce antibodies and protect against infection

Fig. 28C: Ebola nanoparticles induce antibodies and protect against infection

| Group | Surviving/Total |
|---|---|
| PBS | 0/10 |
| 5µg EBOV GP | 1/10 |
| 5µg EBOV GP + AlPO$_4$ | 0/10 |
| 5µg EBOV GP + Matrix-M | 9/9* |

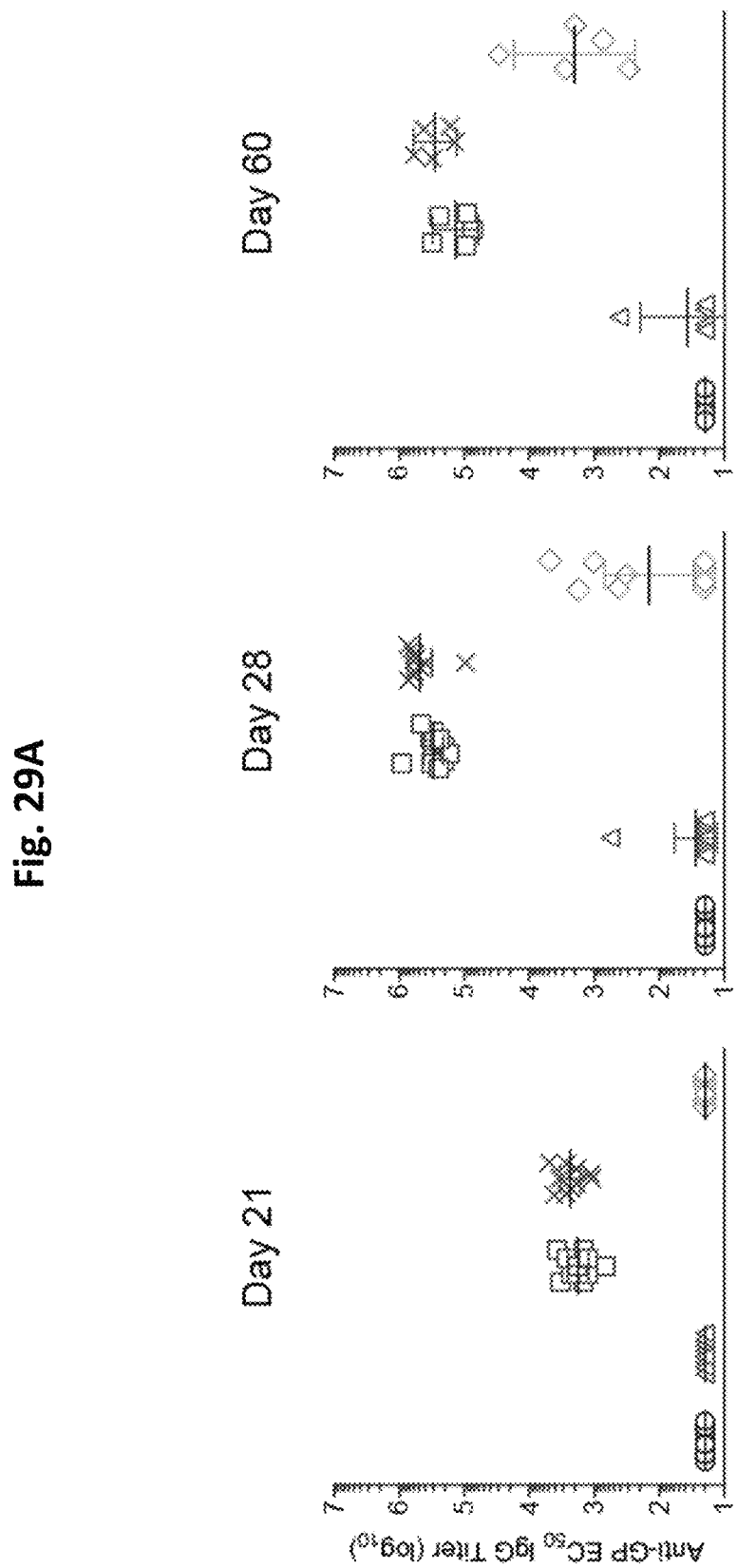

Fig. 29C

Fig. 30A: T cell responses induced by adjuvanted Ebola vaccine

○ PBS
△ 5µg EBOV GP
□ 5µg EBOV GP + 2.5µg Matrix-M

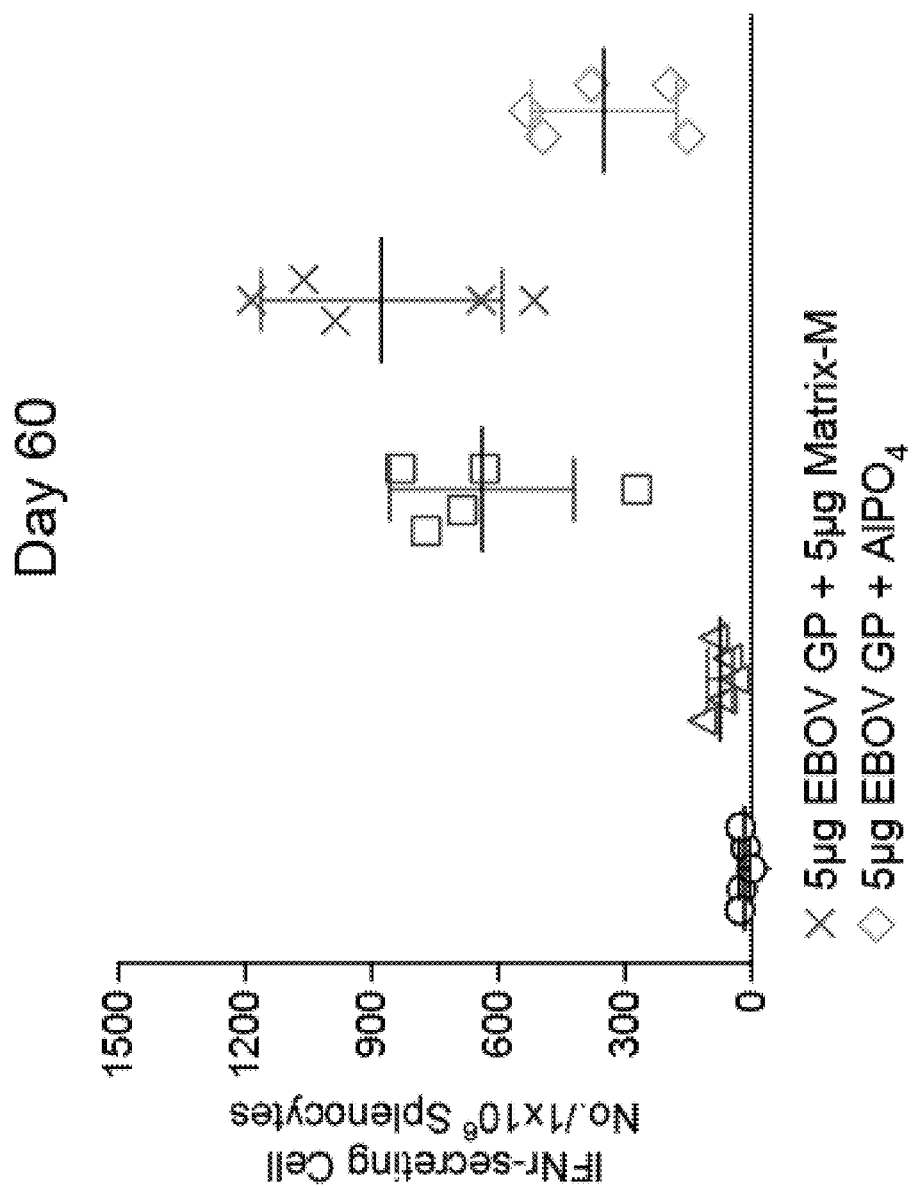

Fig. 30C: T cell responses induced by adjuvanted Ebola vaccine

Fig. 30D: T cell responses induced by adjuvanted Ebola vaccine

Fig. 31E

Day 60

Total GC Cells Per Spleen (x10⁵)

○ PBS △ 5µg EBOV GP ✕ 5µg EBOV GP + 5µg Matrix-M
□ 5µg EBOV GP + 2.5µg Matrix-M ◇ 5µg EBOV GP + AlPO₄

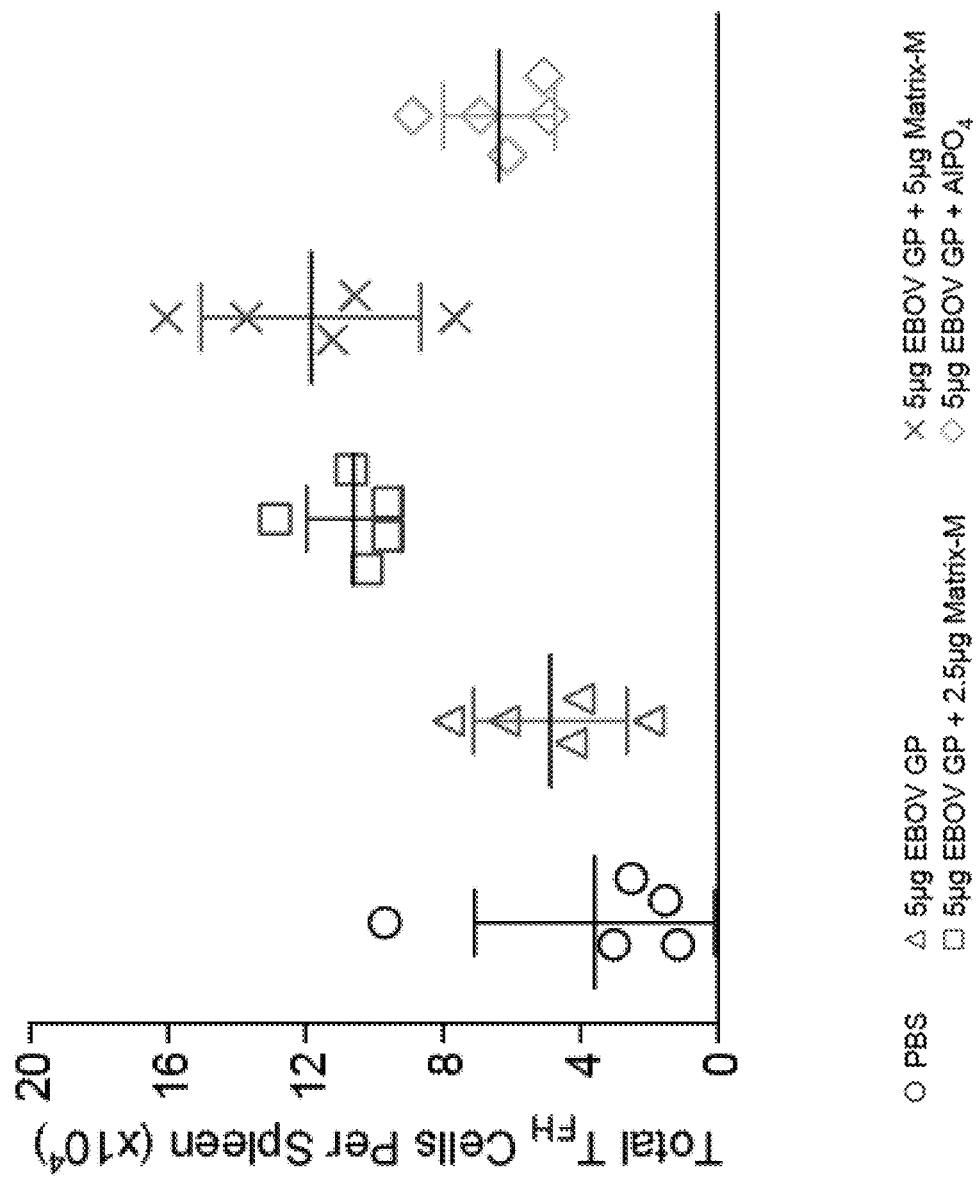

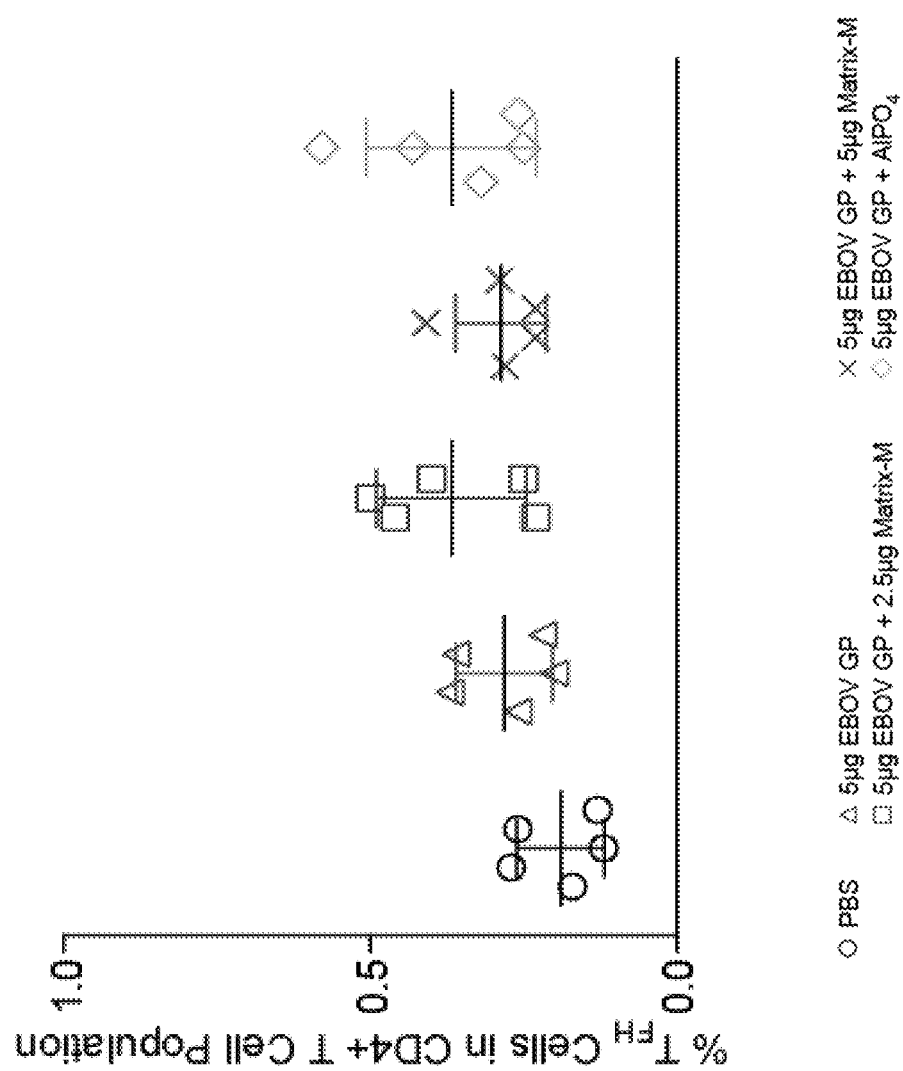

Fig. 33A

Anti-GP IgG-secreting Cell No./1x10⁶ SP Cells

○ PBS
△ 5μg EBOV GP
□ 5μg EBOV GP + 2.5μg Matrix-M
◇ 5μg EBOV GP

Fig. 33B

Anti-GP IgG-secreting Cell No./1x10⁶ BM Cells

× 5μg EBOV GP + 5μg Matrix-M
◇ 5μg EBOV GP + AlPO$_4$

Fig. 34A: Ebola Glycoprotein Structure

Fig. 34B: Ebola Glycoprotein Sequence

Signal peptide | GP1 N-terminus

```
  1 mgvtgilqlp rdrfkrtsff lwviilfqrt fsiplgvihn stlqvsdvdk lvcrdklsst
 61 nqlrsvglnl engvatdvp svtkrwgfrs gvppkvvnye agewaencyn leikkpdgse
121 clpaapdgir gfprcryvhk vsgtgpcagd fafhkegaff lydrlastvi yrgttfaegv
181 vaflilpqak kdffsshplr epvnatedps sgyysttiry qatgfgtnet eylfevdnlt
241 yvqlesrftp qfllqineti yasgkrsntt gkliwkvnpe idttigewaf wetkknitrk
301 irseelsfta vsngpknisg qspartssdp etnttnedhk imasenssam vqvhsqgrka
361 avshittlat istspqppt ktgpdnsthn tpvykldise atqvgqhrr adndstasdt
421 ppattaagpl kaentntsks adsidlattt spqnysetag nnnthhqdtg eesassgklg
481 litntiagva glitggrrtr revivnaqpk cnpnlhywtt qdegaaigla wipyfgpaae
541 giyteglmhn qdglicglrq lanettqalq iflrattelr tfsilnrkai dfllqrwggt
601 chilgpdcci ephdwtknit dkidqiihdf vdktlpdggd ndnwwtgwrq wipagigvtg
661 viiavialfc ickfvf
```

Furin cleavage site → GP2 N-terminus

Fig. 35A: Electron Microscopy Analysis of Nanoparticles

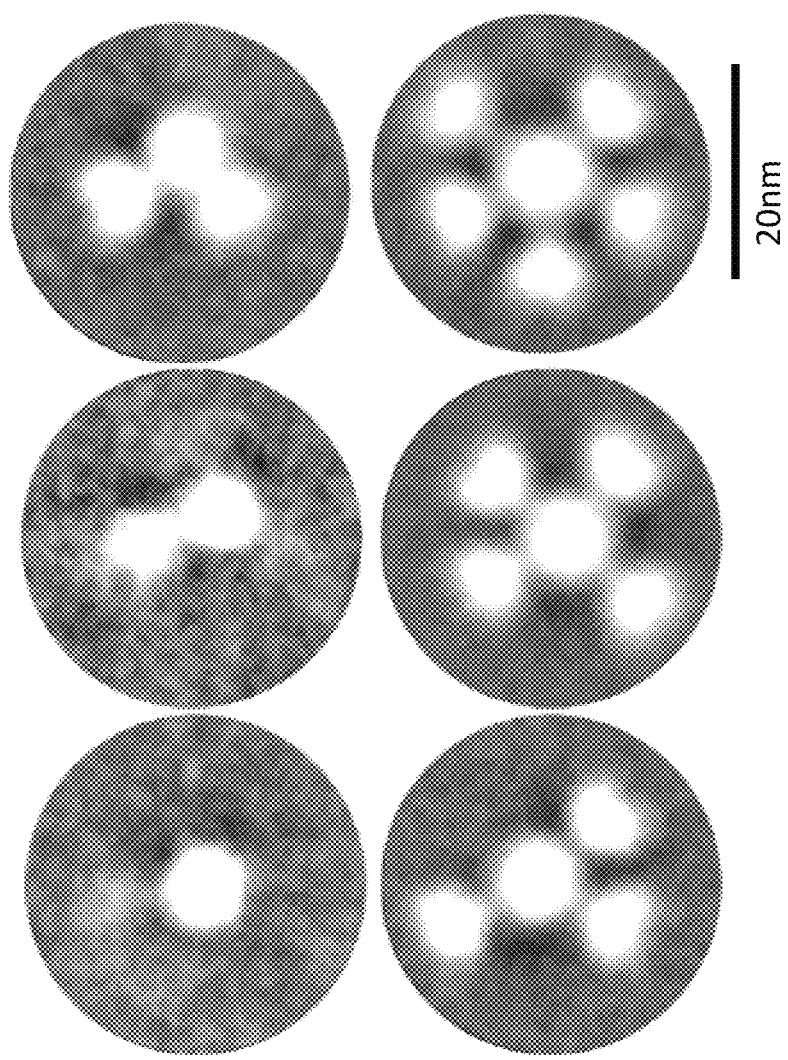
Fig. 35B: Electron Image Showing Exemplary nanoparticles

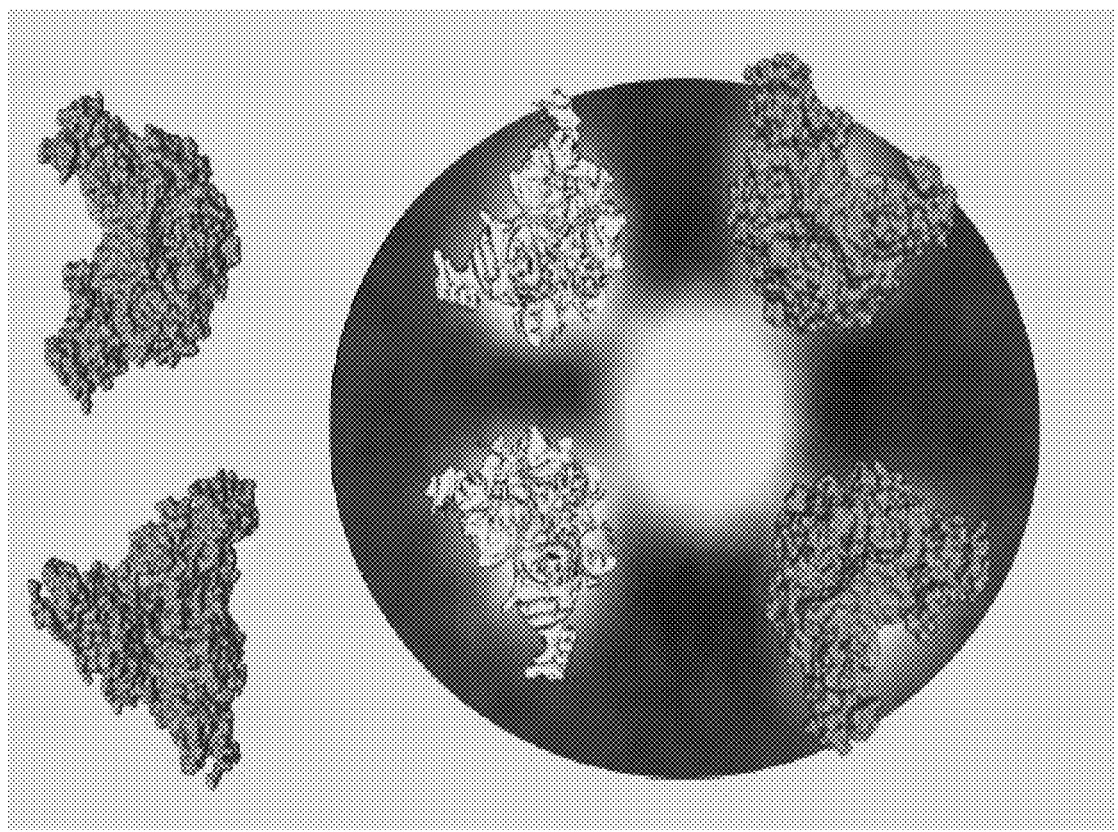
Fig. 35C: Nanoparticle with Docked Trimers

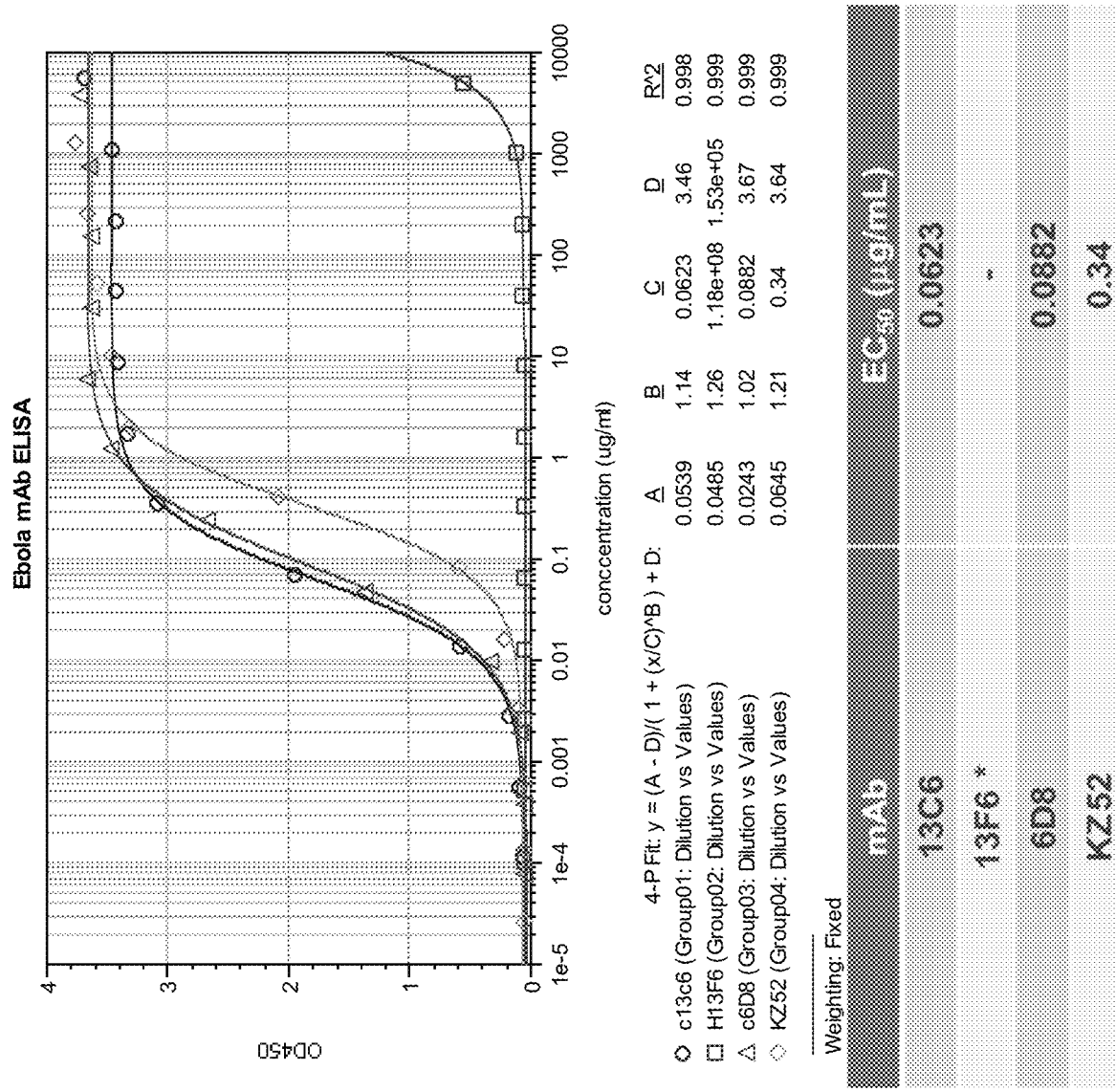
Fig. 36: Anti-Ebola ELISA EC50 of mAb 13C6, 6D8 and KZ52

Fig. 37: Binding kinetics purified recombinant EBOV/Mak GP to functional EBOV mAb

| mAb | EBOV GP Epitope | | SPR $K_D$ (nM) |
|---|---|---|---|
| KZ52 | aa 42-43, 513, 550-553, 556 GP1/GP2 | Conformational Pre-fusion GP2 | 2.36 |
| 13C6 | aa 1-295 GP1 | Conformational In ZMapp | 8.35 |
| 6D8 | aa 389-405 GP1 HNTPVYKLDISEATQVE | Linear | 3.67 |
| 13F6 | aa 401-417 GP1 ATQVEQHHRRTDNDSTA ATQVGQHHRRADNDSTA[1] | Linear Neutralizing | No binding |

Fig. 38: EBOV GP potency assay: Sandwich ELISA based on binding 13C6 mAb

| Sample | 13C6 ELISA (µg/mL) | A280 O.D. (µg/mL) |
|---|---|---|
| EBPV/Mak DP Lot B531P12 | 135.0 | 133.9 |

Fig. 39: Baboon immunogenicity: Nanoparticle vaccine study design

| Group | N | Ebola GP Dose | Adjuvant | Day of Immunization (IM) | Day for Blood Draw |
|---|---|---|---|---|---|
| 1 | 3 | 60µg | No Adjuvant | 0, 21 | 0, 21, 31, 42, 60, 90, 120, 150, 180 |
| 2 | 3 | 60µg | 800µg $AlPO_4$ | | |
| 3 | 3 | 60µg | 50µg Matrix-M | | |
| 4 | 3 | 5µg | 50µg Matrix-M | | |

Fig. 40A: Anti-EBOV/Makona GP ELISA EC90 responses in baboons (Response at Day 21)

Fig. 40B: Anti-EBOV/Makona GP ELISA EC90 responses in baboons
(Response at Day 31)

Fig. 41: Durability of EBOV GP ELISA (EC50) IgG Response

Fig. 42: EBOV/Makona GP vaccine IFNγ-Elispot response in baboons day 31

Fig. 43: Ebola-GP/Matrix-M multifunctional IFNγ TNFα T-cells

Fig. 44 Ebola-GP/Matrix-M multifunctional T-cells and Cytokines

Fig. 45 Ebola-GP/Matrix-M vaccine trial design performed in Cynomolgus macaques

| Group | Vaccine | N | Immunization Day | Challenge¹ Day | End of Study Day |
|---|---|---|---|---|---|
| 1 | 5 µg GP + 50 µg Matrix-M | 3 | 0, 21 | 42 | 60 |
| 2 | control | 1 | -- | 42 | 60 |

1 Challenge virus: 100 pfu wild-type EBOV/Kikwit 9510621

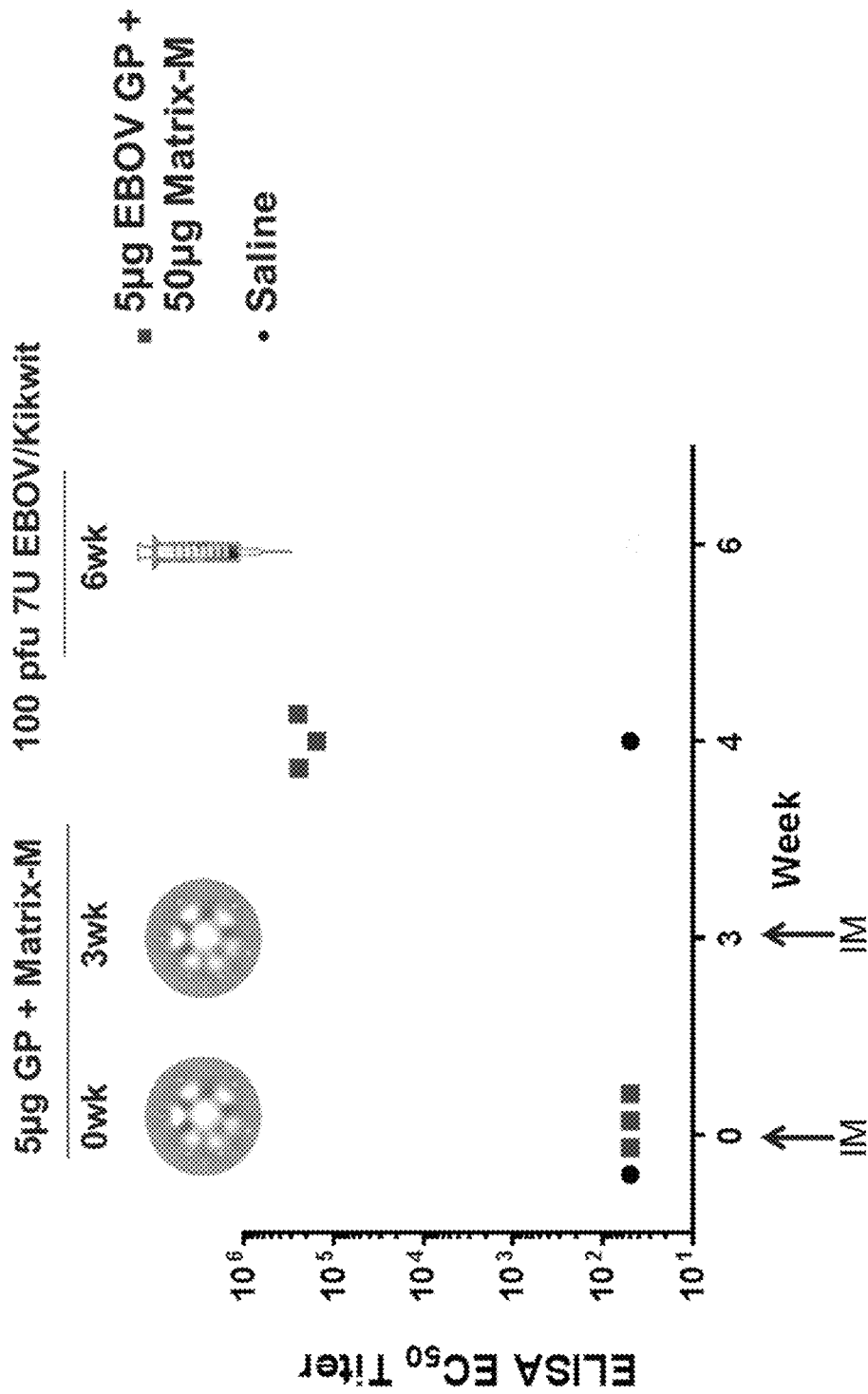

Fig. 47A: Anti-EBOV/Makona GP immune response

Week 0

IFNγ-secreting cells/$10^6$ PBMC

- EZ Cons
- EZ Pool 2
- EZ Pool 1
- DMSO 33355, 33356 placebo, 33360, 33362

Placebo: #33356
Vaccine: #33355, 33360, 33362

Ebola Zaire (EZ) peptide pools
Pool 1: N-terminal GP peptides
Pool 2: C-terminal GP peptides
Con: Zaire/Sudan consensus peptides

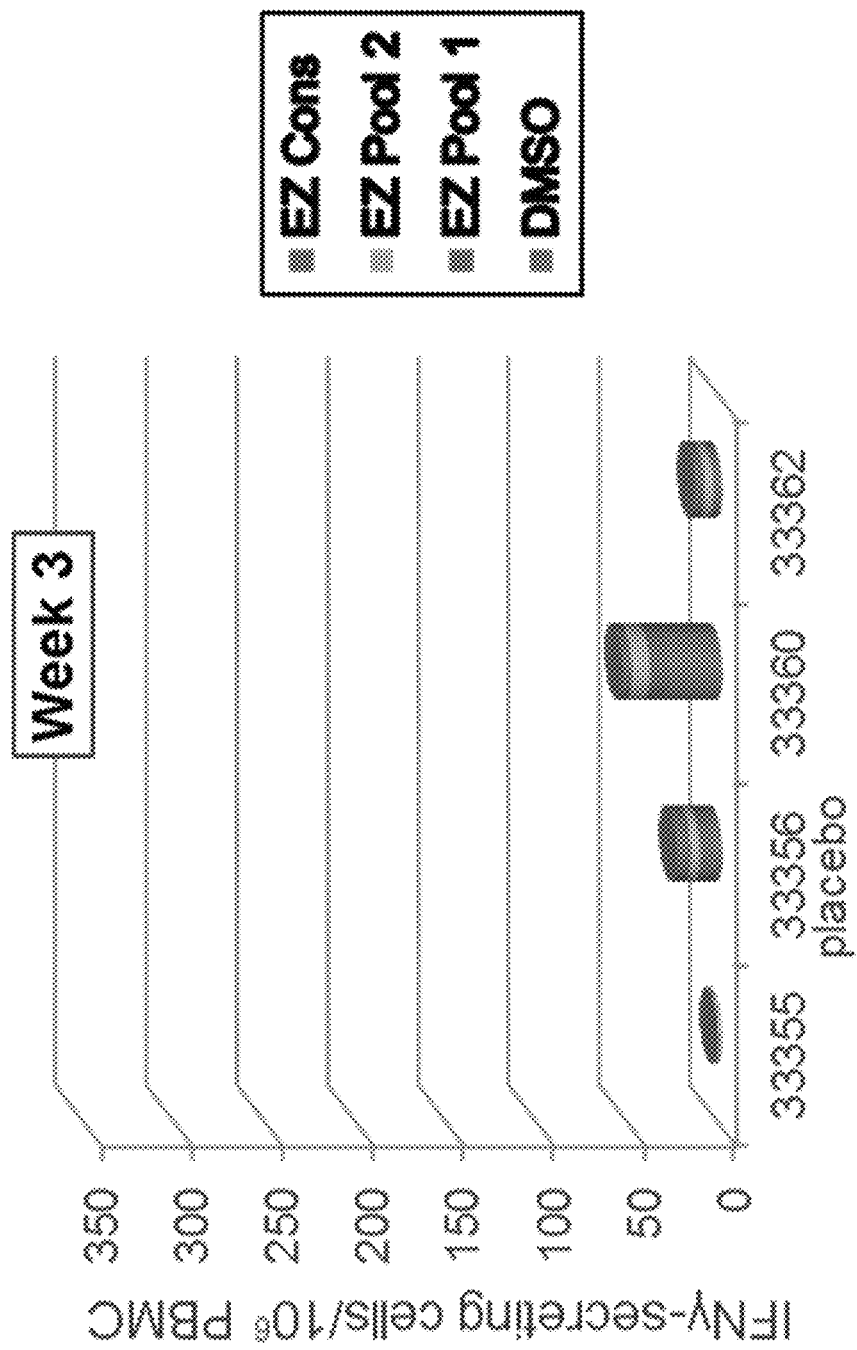

Fig. 47C: Anti-EBOV/Makona GP immune response

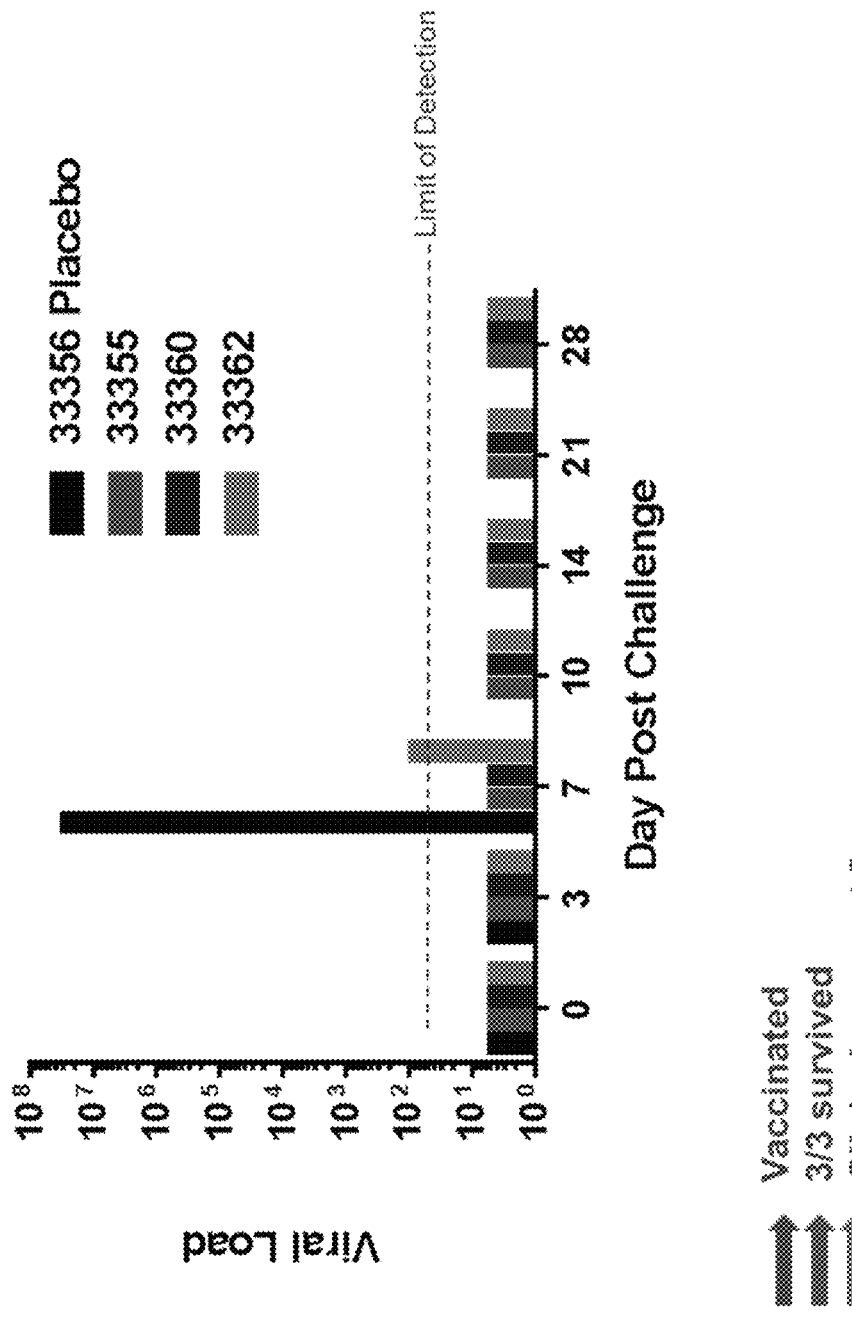

Fig. 49: Second Study of Ebola virus challenge of *Cynomolgus macaques*: Study Design

| Group | Vaccine | N | Immunization wks | Challenge[1] wks |
|---|---|---|---|---|
| F | 5 µg GP + 50 µg Matrix-M | 2 | 0, 6 | 12 |
| G | 5 µg GP + 50 µg Matrix-M | 2 | 0, 3 | 9 |
| A | Control - PBS | 2 | 0, 3, 6 | 12 |

[1]Challenge virus: 100 pfu wild-type 7U EBOV/Kikwit

Fig. 50: Second Study of Ebola virus challenge of *Cynomolgus macaques*: EBOV/Makona vaccine anti-EBOV/Makona GP IgG ELISA (EC50) and NHP survival

VACCINE COMPOSITIONS HAVING IMPROVED STABILITY AND IMMUNOGENICITY

CROSS REFERENCE TO RELATED APPLICATIONS

This application is a divisional filing of U.S. application Ser. No. 15/257,436, filed on Sep. 6, 2016, now issued as U.S. Pat. No. 10,426,829, which claims priority to U.S. Provisional Application No. 62/213,947, filed on Sep. 3, 2015, U.S. Provisional Application No. 62/255,786, filed Nov. 16, 2015, U.S. Provisional Application No. 62/309,216, filed Mar. 16, 2016, and U.S. Provisional Application No. 62/350,973, filed Jun. 16, 2016, each of which is incorporated herein by reference as if set forth in its entirety.

DESCRIPTION OF THE TEXT FILE SUBMITTED ELECTRONICALLY

The contents of the text file submitted electronically herewith are incorporated herein by reference in their entirety: A computer readable format copy of the Sequence Listing (filename: NOVV_060_ 05US_SeqList_ST25.txt, date recorded: Jun. 4, 2019; file size: 90.1 kilobytes).

TECHNICAL FIELD

The present disclosure is generally related to nanoparticles useful for stimulating immune responses. The nanoparticles provide antigens, for example, glycoprotein antigens, associated with a detergent core and are typically produced using recombinant approaches. The nanoparticles have improved stability and enhanced epitope presentation. The disclosure also provides compositions containing the nanoparticles, methods for producing them, and methods of stimulating immune responses.

BACKGROUND

Infectious diseases remain a problem throughout the world. While progress has been made on developing vaccines against some pathogens, many remain a threat to human health. Most notoriously HIV, for which a vaccine remains elusive. Attempts have been made to produce vaccines to certain pathogens but have resulted in failure that caused additional pathology. Other pathogens also remain a problem, including Ebola, which sporadically arises as epidemics—particularly in Africa—and gives rise to loss of life and global economic impact. Influenza virus is yet another virus for which existing vaccine provide some protection but technical challenges in producing the virus mean that seasonal influenza vaccines may provide inadequate protection.

Deploying an effective vaccine relies on a combination of achievements. The vaccine must stimulate an effective immune response that reduces infection or disease by a sufficient amount to be beneficial. A vaccine must also be sufficiently stable to be used in challenging environments where refrigeration may not be available.

Therefore, there is continuing interest in producing vaccines against viruses that present public health issues throughout the globe and there remains an ongoing need to produce effective vaccines with good stability.

SUMMARY OF THE INVENTION

The present disclosure provides nanoparticles suitable for inducing immune responses against pathogens. The nanoparticles offer improved stability, as well as effective immunogenicity. In particular aspects, the pathogen is a virus and, typically, the antigen used to produce a viral nanoparticle is a viral glycoprotein.

In one aspect, the disclosure provides nanoparticles containing viral proteins that have enhanced stability. In some embodiments, the disclosure comprises a vaccine composition comprising a nanoparticle comprising a nonionic detergent, a viral glycoprotein, and a pharmaceutical buffer. In typical embodiments, the nonionic detergent may be selected from the group consisting of PS20, PS40, PS60, PS65, and PS80. In some embodiments, the composition does not comprise any free nonionic detergent. One or more glycoprotein antigen molecules surround a detergent core, which contains the nonionic detergent, and this provides a nanoparticle structure that promotes immunogenicity and inhibits degradation of the antigen.

In some embodiments, antigen is selected from the group consisting of an RSV F protein, an influenza HA protein, an influenza NA protein, and combinations thereof. Other antigens may be used, including Ebola. Typically, the antigen is a glycoprotein.

Optionally, the RSV F protein is a trimeric RSV F protein. The RSV F protein induces the production of neutralizing antibodies. In further embodiments, the neutralizing antibodies recognize the RSV F protein in a post-fusion state and/or a pre-fusion state. In a further aspect, each PS80 particle may comprise between 4 and 7 RSV F proteins.

In some embodiments, an RSV F composition may comprise sodium phosphate at a concentration of between 15 mM and 25 mM; NaCl at a concentration of between 125 mM and 175 mM; histidine between 0.25% and 2% w/v; and the composition pH is between 5.8 and 7.2.

In some embodiments, an HA or NA influenza composition may comprise sodium phosphate at a concentration of between 15 mM and 25 mM; NaCl at a concentration of between 125 mM and 300 mM; histidine between 0.25% and 2% w/v; and the composition pH is above pH6.8 and typically below about pH 8.0.

In some embodiments, the composition comprises an adjuvant. In further embodiments, the adjuvant is alum or Martrix M™. In some embodiments, the composition does not comprise an adjuvant.

In some embodiments, a method of preventing infection comprises administering one or more doses of the vaccine composition. In some embodiments of the method, a single dose of the composition is administered and induces a protective immune response. In some embodiments of the method, each dose consists of between about 100 μg and about 150 μg of the protein antigen. In further embodiments of the method, the one or more doses are administered subcutaneously. In some embodiments of the method, the composition comprises an adjuvant. In a further embodiment of the method, the adjuvant is alum. In some embodiments of the method, the composition is free of adjuvants.

In some embodiments of the method, one or more doses of the composition are administered to an adult. In further embodiments of the method, the adult is a female, and the female may be pregnant. In further embodiments of the method, the adult is over the age of 65 or over 60. In some embodiments of the method, one or more doses of the composition are administered to a child. In further embodiments of the method, the child is a neonate or an infant.

For RSV vaccine, in some embodiments, a composition comprises a heterologous population of at least three RSV F nanoparticle types, wherein each nanoparticle comprises at least one RSV F protein trimer surrounding a detergent-containing core that comprises PS80, and wherein the first RSV F nanoparticle type comprises anisotropic rods, wherein the second RSV F nanoparticle type comprises spherical oligomers, and wherein the third RSV F nanoparticle type comprises intermediates of anisotropic rods and spherical oligomers.

In some embodiments, a method of manufacturing an RSV F protein nanoparticle comprises preparing an RSV F protein extract from a host cell using a first detergent and exchanging the first detergent for a second detergent, wherein the second detergent is PS80, and whereby the nanoparticle exhibits enhanced stability. In a further embodiment of the method, the first detergent is NP-9. In some embodiments of the method, the enhanced stability is selected from protease resistance, oxidative stress resistance, thermal stress resistance, and resistance to agitation. In some embodiments of the method, the molar ratio of PS80: RSV F protein is about 35 to about 65.

In some embodiments, an RSV F nanoparticle comprises one or more RSV F protein trimers associated with a PS80 detergent core. The RSV F nanoparticle, the nanoparticle has an average diameter of about 20 nm to about 60 nm as measured by dynamic light scattering. In some embodiments of the RSV F nanoparticle, each RSV F protein trimer contains an RSV F protein selected from the group consisting of RSV F proteins having a deletion of 1 to 10 amino acids corresponding to residues 137-146 of SEQ ID NO:2. In some embodiments of the RSV F nanoparticle, each RSV F protein trimer contains an RSV F protein selected from the group consisting of RSV F proteins having a deletion of 1 to 10 amino acids corresponding to residues 137-146 of SEQ ID NO:2 and an inactivated primary fusion cleavage site.

In some embodiments of the RSV F nanoparticle, the RSV F protein comprises a deletion of ten amino acids corresponding to residues 137-146 or SEQ ID NO:2, and inactivation of the primary furin cleavage site by mutation of arginine residues at positions 133, 135, and 136 to glutamine. In further embodiments of the RSV F nanoparticle, the RSV F protein comprises or consists of SEQ ID NO:19, which is the mature peptide. In certain embodiments of the RSV F nanoparticle, the RSV F protein comprises or consists of SEQ ID NO:8. Vaccine formulations containing RSV F nanoparticles comprise substantially of the mature peptide with some full-length peptide (SEQ ID NO:8). Over time, small amount of truncated RSV F peptide may arise due to proteolysis. Advantageously, however, the RSV F nanoparticles disclosed herein minimize such degradation and provide extended stability.

This application also discloses enhanced thermostability influenza nanoparticles. Unlike prior influenza nanoparticles the methods and compositions provided here exhibit resistance to trypsin and enhanced thermostability and thus immunogenicity.

For Ebola, the Ebola virus nanoparticles comprise an Ebola virus glycoprotein (GP) trimer attached to a non-ionic detergent core as well as vaccine compositions containing the nanoparticles, optionally in combination with a Matrix M saponin adjuvant. In addition, the disclosure provides for methods of inducing an immune response against Ebola virus in humans by administering a composition containing an Ebola virus nanoparticle and a saponin adjuvant. Methods of protecting against Ebola infection are also provided.

Similarly, nanoparticles containing influenza proteins, either HA, NA or both, are provided. HA nanoparticles showing trypsin-resistance, an indicator of proper folding are provided. Methods of protecting against influenza infection using the influenza nanoparticles in vaccine formulations are also provided.

BRIEF DESCRIPTION OF THE FIGURES

FIGS. 1A and 1B depict primary protein structures of RSV F proteins, accompanied by a polypeptide sequence. FIG. 1A depicts the primary protein structure of wild-type RSV A2 strain versus that of a modified RSV F protein. Furin cleavage sites are indicated by triangles. FIG. 1B depicts the amino acid sequence of a modified RSV F protein (SEQ ID NO:19); with the F1 domain in light-shaded text (residues 1-84), the F2 domain in dark-shaded text (residues 85-539), black lines connecting cysteines that form disulfide bonds, underlined asparagines indicate N-linked glycosylation sites, light-shaded vertical dotted lines indicate a furin cleavage site, and dark-shaded vertical dotted lines indicate a major cleavage site.

FIG. 2 depicts the separation peaks of RSV F proteins by reverse phase HPLC, wherein four major species are identified and correspond to the 4 major peaks. The peak comprising the lowest molecular weight species (~51.2 kDa-~51.3 kDa) is a soluble trimer; the next peak comprises a full length trimer (-64.5 kDa) lacking fatty acids, and the final two major peaks are full length trimers wherein the trimers comprise palmitoleic acid (~64.7 kDa) and palmitic acid (64.788 kDa), respectively.

FIG. 3 depicts the separation of RSV F proteins in a reducing SDS-PAGE. The largest molecular weight proteins comprise high molecular weight species, followed by variants comprising the F1 and F2 domains, then just the F1 domain and variants thereof, followed by just F2 domains.

FIG. 4 depicts a chromatogram output of LC-UV peptide mapping that covers 90% of the amino acids comprising the primary protein structure of the RSV F protein. The combined sequence coverage, including the early-eluting peptides, was found to be 98%, confirming the amino acid sequence of the RSV F protein.

FIG. 5 depicts a glycoanalysis of a purified RSV F protein using HPLC combined with fluorescence detection (FLD). The major glycan structures detected are fucosylated Man3 glycans.

FIG. 6 features an electron micrograph of RSV F nanoparticles with RSV F protein trimers associated with cores of PS80. The figure further depicts a characterization of a single RSV F protein trimer featuring the orientation of the F1 and F2 domains, antigenic site II which is recognized by the Palivizumab antibody, and the C- and N-termini of the F1 domains further comprising fatty acids such as palmitic and palmitoleic acids.

FIG. 7 depicts Dynamic Light Scattering (DLS) measurements of particle size of RSV F nanoparticles. The DLS measurements show that the size of the nanoparticles is modulated by both the available PS80 and the RSV F concentration. An increase in PS80 at a fixed concentration of RSV F concentration results in a decrease in the average nanoparticle size (Z-ave).

FIG. 8 depicts the discrete molecular weight distributions of sample concentration versus molecular weight of the nanoparticles, wherein the concentration of RSV F and the percentage of PS80 is varied. The greatest signal intensity of nanoparticles is achieved with 0.2% PS80 and 1 mg/mL RSV F, suggesting greater uniformity of nanoparticles and confirming the modulation of particle size as a combination of concentrations of PS80 and RSV.

FIGS. 9A and 9B depicts the shape of RSV F nanoparticle types produced with variable PS80 percentages and RSV F concentrations. FIG. 9A reveals that a composition using 0.2% PS80 and 0.22 mg/mL RSV F produces three primary types, monomeric/dimeric anisotropic rods, spherical oligomers, and intermediates thereof. FIG. 9B reveals that a composition using 0.05% PS80 and 0.22 mg/mL RSV F results in a population dominated by monomeric/dimeric anisotropic rods, whereas a composition using 0.05% PS80 and 1.0 mg/mL results in a population dominated by spherical oligomers.

FIG. 10 depicts the effects of the stressors on particular subsections of the RSV F protein in a nanoparticle, as presented in a reduced Lys-C peptide map with relative abundance compared to a control. The stressors are 50° C. for two weeks, pH 3.7 at 25° C. for one week, pH 10 at 25° C. for one week, oxidation of protein by hydrogen peroxide at 25° C. for one week, and agitation at 25° C. for one week.

FIG. 11 illustrates stability of the antigenic site 2 (palivizumab site) exposed to various stress conditions. The percentages are presented as a relative abundance compared to a control. The closer to 100% or over, the greater the resilience in light of the stress conditions. The data illustrate the nanoparticles maintain excellent antigenic site consistency therefore yielding a stable immune response. NSELLSLINDMPITNDQK/K; SEQ ID NO:20 and LMSNN (SEQ ID NO:21) are portions of antigenic site II.

FIGS. 12A, 12B, 12C, and 12D depict the stability of the RSV F nanoparticle composition by showing murine immunogenicity after the nanoparticle compositions were exposed to environmental stress. The mice were sampled at day 21 for anti-RSV F IgG, day 35 for PCA titers, and day 35 for RSV/A neutralizing titers. FIG. 12A depicts the results for the −70° C. control. FIG. 12B depicts the results a composition exposed to 50° C. for two weeks. FIG. 12C depicts the results for a composition exposed to a pH of 10 at 25° C. for two weeks. FIG. 12D depicts the results for a composition exposed to 0.5% hydrogen peroxide at 25° C. for one week.

FIG. 13 depicts the enhanced protease resistance of nanoparticles having higher PS80. Over a period of 18 months, RSV F nanoparticles formulated in the presence of a higher PS80 percentage (0.03%) exhibited less protease degradation versus RSV F nanoparticles formulated in the presence of lower PS80 percentage (0.015%), as evaluated by SDS-PAGE. In addition, fewer high molecular weight (HMW) structures were observed with higher PS80 amounts.

FIG. 14 depicts the comparison of mAbs binding to RSV F nanoparticles versus RSV F A strain viral protein, wherein the equilibrium disassociation constant for site I, II, and IV antibodies reveal that mAbs antibody binding at each of the sites is comparable.

FIG. 15 depicts the results of competitive binding assays in which antibodies present in sera from cotton rats exposed to placebo conditions, RSV/A infection, formaldehyde inactivated RSV, RSV F nanoparticles, and RSV F nanoparticles with alum were compared against one another in binding to site I, II, and IV.

FIG. 16 illustrates a process flow chart for a method of making nanoparticles disclosed herein.

FIG. 17 illustrates a flow chart for a method of making HA nanoparticles disclosed herein. Sf9 cells containing baculovirus-expressed HA are grown and then the HA is extracted using the non-ionic detergent NP9. The extract undergoes sequential purification and a detergent exchange step on Lectin affinity column, and is then filtered and formulated into a bulk drug sub stance.

FIGS. 18A to 18F illustrate steps and results obtained using a method of producing influenza nanoparticles using the HA glycoproteins as an example. FIG. 18A shows sequential purification steps from cell infection, through cell lysis and three columns used to provide purified nanoparticles (TMAE (trimethylaminoethyl) followed by lentil lectin, followed by a sulfate (SO3$^-$) column). FIG. 18B illustrates a chromatogram obtained using a TMAE column. FIG. 18C illustrates a chromatogram obtained using a lentil lectin column purification step. FIG. 18D illustrates a chromatogram obtained using a sulfate column purification step. FIG. 18E shows a gel (upper right panel) of the TMAE and LL columns stages. The bottom panel shows a western blot of the gel. Lanes are as shown in the upper left panel. FIG. 18F shows a gel with eluate from the SO3− column.

FIGS. 19A to 19J illustrate purity analyses of HA nanoparticles produced using different sub-types and in different insect cell lines. FIG. 19A shows a gel, western blot for HA, and gp64 for HA nanoparticles containing A/New Hampshire/1/2015 HA. FIG. 19B shows a quantification of the HA band, and shows that the HA is 99.1% pure by densitometry. FIG. 19C shows a gel, western blot for HA, and gp64 for HA nanoparticles containing A/Switzerland/9715293/2013 HA. FIG. 19D shows a quantification of the HA band and shows that the HA is 94.5% pure by densitometry. FIG. 19E shows a gel, western blot for HA and gp64 for HA nanoparticles containing A/Hong Kong/4801/2014 HA. FIG. 19F shows a quantification of the HA band and shows that the HA is 93.3% pure by densitometry. FIG. 19G shows a gel, western blot for HA, and gp64 for HA nanoparticles containing B/Phuket/3073/2013 HA in Sf9 and Sf22a cells. The right hand panel shows a quantification of the HA band and shows that the HA is 95.4% pure by densitometry. FIG. 19H shows a gel, western blot for HA, and gp64 for HA nanoparticles containing B/Brisbane/60/2008 HA in Sf9 cells. The right hand panel shows a quantification of the HA band and shows that the HA is 96.7% pure by densitometry. FIG. 19I measures HA purity using RP-HPLC. FIG. 19J summarizes the data for HA nanoparticles using three influenza A sub-types and two influenza B sub-types.

FIG. 20 shows HA nanoparticles in electron micrographs.

FIGS. 21A and 21B shows a comparison of docking of HA trimers onto cryoEM structures for HA nanoparticles (FIG. 21A) and for the HA trimers on influenza VLPs containing both HA and NA proteins (FIG. 21B).

FIG. 22 illustrates a study with a combination nanoparticle composition containing RSV F nanoparticles and a representative of HA nanoparticle.

FIGS. 23A to 23F illustrate results obtained according to the study in FIG. 22. FIG. 23A shows HAI titer against the homologous strain. FIG. 23B shows heterologous HAI titer against a heterologous strain. FIG. 23C shows palivizumab competitive antibodies. FIG. 23D shows neutralizing antibodies against the RSV A strain. FIG. 23E shows T cell responses against RSV F protein. The response obtained with Matrix-adjuvanted nanoparticles is prominent. FIG. 23F shows T cell responses against influenza protein.

FIGS. 24A-24C illustrate a process and results for obtaining HA nanoparticles that have enhanced stability. Notably, the pH range during this purification is in a neutral range of pH 7.0 to pH 7.4. FIG. 24A shows purification steps from using thawed cells expressing the HA protein through to the bulk drug substance (BDS) product. FIG. 24B shows a chromatogram trace from a representative nanoparticle using the A/New Hampshire/1/2015 strain. The flow-through from the column is collected, leaving undesirable products behind. FIG. 24C shows a chromatogram trace for the detergent exchange step on a lentil lectin column. The flow-through from this column is discarded as is the wash. Elution is performed with 0.01% PS80. The buffers are as follows: A1: 25 mM sodium phosphate, pH7.2, 150 mM NaCl, 0.01% PS80, A2: 25 mM sodium phosphate, pH7.2, 500 mM NaCl, 0.5% NP9, A3: 25 mM sodium phosphate, pH7.2, 150 mM NaCl, 0.1% PS80, B1: 25 mM sodium phosphate, pH7.2, 150 mM. The HA nanoparticles are then concentrated and stored in 0.05% PS80 buffer as shown in FIG. 24A.

FIGS. 25A-25D show results for purification of trypsin-resistant nanoparticles from several strains. FIG. 25A shows a representative strain for an H1N1 subtype, A/New Hampshire/1/2015. FIG. 25B shows a representative strain for a B type influenza. B/Brisbane/60/08 HA. FIG. 25C shows a representative strain for an H1N1 subtype, A/New Hampshire/1/2015. In each case the data shows high levels of production and excellent purity. FIG. 25D provides a differential scanning calorimetry (DSC) comparison of the trypsin resistant nanoparticles versus nanoparticles produced using a process that exposes them to low pH, about pH 6.0. The DSC data shows greater thermostability with the neutral pH process establishing that the HA protein in the nanoparticle is properly folded.

FIGS. 26A-26C show results for enhanced trypsin resistance of trypsin-resistant nanoparticles from several strains expressed in Sf9 cells. Purified HA nanoparticles made in Sf9 insect cells are HA0. When exposed to trypsin HA0 is cleaved to HA1 and HA2 at Arg AA344 in H1. Correctly folded HA trimers will resist further cleavage when incubated with increasing concentrations of trypsin. FIG. 26A shows neutral pH purified B/Brisbane/60/08 is resistant to trypsin thus is correctly folded (left panel) whereas acid pH purified B/Brisbane/60/08 HA1 is trypsin sensitive thus misfolded (right panel). FIG. 26B shows that acid purified but not neutral-purified HA nanoparticles from A/Hong Kong/4801/2014 are mis-folded. FIG. 26C shows trypsin resistance of neutral pH A/New Hampshire/1/2015 (H1N) HA nanoparticles. Corresponding acid pH purified nanoparticles were trypsin sensitive (not shown).

FIG. 27 shows trypsin sensitivity of a commercial egg-purified influenza vaccine (left panel) and a commercial recombinant influenza (right panel). HA0 is cleaved to HA1 and HA2 in the left panel. Properly folded HA1 is resistant to further trypsin however. In contrast, the commercial recombinant vaccine shows that the HA1 is degraded by trypsin, indicating mis-folded protein is present in the vaccine.

FIGS. 28A-28C shows induction of antibodies and protection from infection. Mice were immunized SC on Days 0, 14, and 28 with 5 µg EBOV/Mak GP, 5 µg EBOV GP adjuvanted with 50 µg AlPO4 or 5 µg EBOV/Mak GP adjuvanted with 5 µg Matrix-M. Serum was obtained on day 28 and evaluated by ELISA for anti-EBOV/Mak GP IgG (FIG. 28A) or anti-Ebola virus neutralizing antibody (FIG. 28B). Black bars represent the group GMT and error bars indicate 95% confidence intervals of the GMT. On day 42, mice were infected with 1,000 pfu mouse adapted Zaire Ebola virus strain 1976 Mayinga. Following challenge, mice were observed daily for morbidity and mortality for a period of 21 days. FIG. 28C shows Kaplan-Meier survival curve for infected mice.

FIGS. 29A-29C show Matrix-M enhanced EBOV/Mak GP-specific IgG and IgG subclass responses. Mice were immunized IM on Days 0 and 21 with 5 µg of EBOV/Mak GP alone or combined with either 2.5 or 5 µg Matrix-M or 50 µg AlPO4. Mice received PBS as placebo control. At days 21, 28 and 60 following the first injection, serum samples were collected and tested for EBOV/Mak GP-IgG (FIG. 29A), IgG1 (FIG. 29B) and IgG2a (FIG. 29C). The results are representative of two separate experiments. Black bars represent the group GMT and error bars indicate 95% confidence intervals of the GMT.

FIGS. 30A-30D show Ebola nanoparticles with Matrix-M induced robust CD4+ T cell and CD8+ T cell responses and multifunctional T cells. Spleen cells were stimulated with Ebola/Mak GP peptide pools covering the entire GP sequence. Culture medium or PMA (50 ng/ml) plus ionomycin (200 ng/ml) were used as negative and positive controls. IFN-γ positive spots from day 28 (FIG. 30A) and 60 (FIG. 30B) were counted and analysed with an ELISPOT reader and associated software. Background numbers of the medium controls were subtracted from the numbers of peptides-stimulated wells and a mean was derived from the triplicates. Cells from all five mice in the same group at day 28 were pooled and incubated with either medium alone, or GP peptide pools, or PMA plus ionomycin for 6 hours at 37° C. with the presence of BD Golgi-stop/Golgi-plug. Cells were then harvested and stained for cell surface markers and intracellular cytokines. Frequency of cytokines was analysed using Flowjo software and Flowjo Boolean function by gating on live CD3+CD44+CD62−CD4+ effector memory T cells or live CD3+CD44+CD62−CD8+ effector memory T cells. (FIGS. 30C and 30D) The value for single cytokines, double cytokines or triple cytokines represent the sum of the frequency of cells expressing any one of the three cytokines (IFN-γ, TNFα and IL-2), any two of the three cytokines or all three cytokines. The result is representative of two separate experiments. Black bars indicate group means and error bars represent standard deviation.

FIGS. 31A-31E show the Matrix-M enhanced Germinal Center (GC) cell response. Fresh splenocytes were stained for GC B cells and data was acquired as described in Materials and Methods. Data was analysed with Flowjo software. Dead cells were excluded from analysis with Invitrogen LIVE/DEAD™ fixable yellow dye. (FIG. 31A), GC cells were defined as CD95+GL-7+ on B220+ B cell gate and the numbers in the dot-plot of representative mice indicate the mean and standard deviation of GC frequency from all five mice in the same group at day 28. GC cell frequencies from individual mice are shown for days 28 (FIG. 31B) and day 60 (FIG. 31C). The absolute GC cell number per spleen from days 28 (FIG. 31D) and 60 (FIG. 31E) was calculated by multiplying the frequency of GC cells within the total number of splenocytes in the spleen. Black bars indicate group means and error bars represent standard deviation.

FIGS. 32A-32E: Matrix-M enhanced the frequency and absolute number of $T_{FH}$ cells in the spleen. $T_{FH}$ cells, defined as CXCR5+PD-1+ T cells within B220−CD49b− CD3+CD4+ T cell gate, were identified in spleens at days 28 and day 60. Representative dot-plot of $T_{FH}$ cell analysis from each group is shown (FIG. 32A). The number in the dot-plot is the average frequency and standard deviation from day 28. The frequency of $T_{FH}$ cells within the CD4+ T cell population from days 28 (FIG. 32B) and 60 (FIG. 32D) is shown. The absolute $T_{FH}$ cell number per spleen from days 28 (FIG. 32C) and 60 (FIG. 32E) was calculated by multiplying the frequency of $T_{FH}$ cells within the total number of splenocytes in the spleen. Black bars indicate group means and error bars represent standard deviation.

FIGS. 33A-33B show Matrix-M induced long-lived plasma cells in bone marrow. Spleen and bone marrow cells were incubated overnight in EBOV/Mak GP coated ELIS- POT plates. The EBOV/Mak GP-specific IgG spots were detected by incubating with goat-anti-mouse IgG-HRP followed by spot development. Spot numbers were counted and analyzed using an ELISPOT reader. The number of antibody secreting cells (ASC) per million cells is shown. (FIG. 33A) day 60 EBOV/Mak GP-IgG ASC number in the spleen; (FIG. 33B) day 60 EBOV/Mak GP-IgG ASC number in the bone marrow. Black bars indicate group means and error bars represent standard deviation.

Figure 34A:
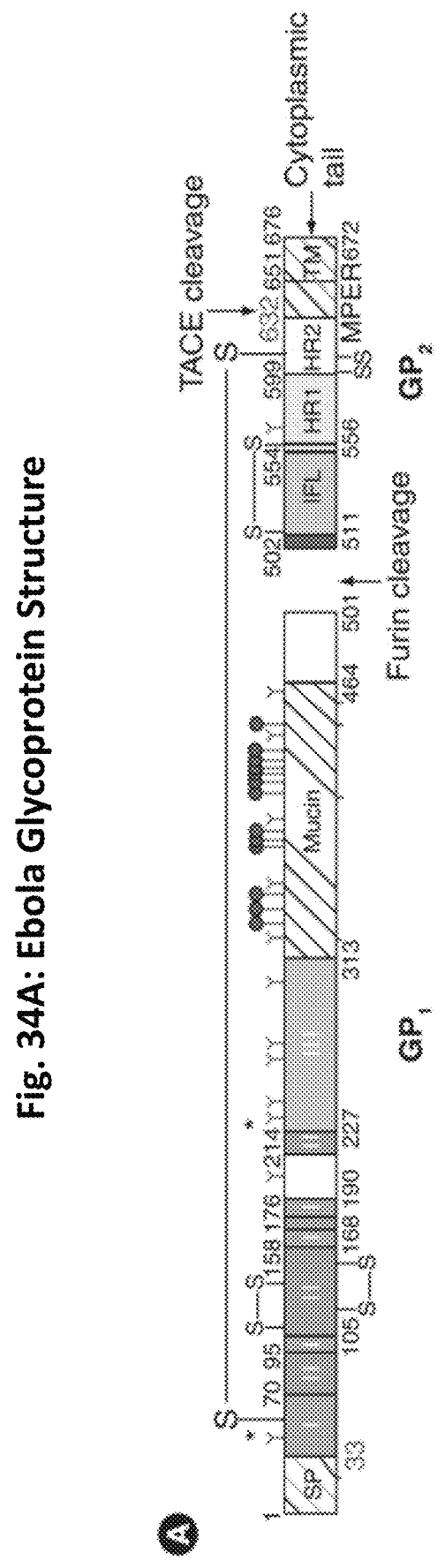

FIGS. 34A-34B show features of an Ebola Glycoprotein. FIG. 34A shows the domain structure. FIG. 34B shows the amino acid sequence of a GP with the cleaved signal peptide and the N- and C-terminii of the mature protein, and the furin cleavage sequence (SEQ ID NO: 22).

FIGS. 35A-35C show electron micrographs of nanoparticles of the disclosure. FIG. 35A illustrates a representative electron micrograph of the nanoparticles. Note that FIG. 35B illustrates the non-ionic detergent core with from up to 5 copies of trimers attached to the core. In some cases, additional trimers are out of the plane of view. FIG. 35C shows a docking study with GP trimers overlaid onto a nanoparticle from a micrograph.

FIG. 36 illustrates the ability of three monoclonal anti-Ebola antibodies to detect the Ebola nanoparticles.

FIG. 37 shows the Surface plasmon resonance (SPR) data for binding of the antibodies to the epitopes of the Ebola GP nanoparticles (SEQ ID NOs:23-25).

FIG. 38 illustrates the high potency of binding of the 13C6 antibody to nanoparticles of the disclosure.

FIG. 39 illustrates a Baboon immunogenicity study design. Group 1 was 60 µg GP nanoparticles with no adjuvant. Group 2 was 60 µg GP nanoparticles with 800 µg AlPO4 adjuvant. Group 3 was 60 µg GP nanoparticles with 50 µg Matrix-M adjuvant. Group 4 was 5 µg GP nanoparticles with 50 µg Matrix-M adjuvant.

FIGS. 40A-40B illustrate results of the Baboon immunogenicity study in FIG. 39. At Day 21, EC90 titers were increased for Groups 2 and 3. FIG. 40A Titers were approximately the same in both groups and also against nanoparticles containing glycoproteins from the Makona Ebola virus and the Mayinga strain, which is the prototypical variant of the Ebola Zaire strain. As shown in FIG. 40B, by Day 31, the immune response was pronounces in all cases and especially for compositions containing GP and Matrix M adjuvant. Notably, the lower dose of GP (5 µg) performed as well as the higher dose (60 µg) underscoring the dose-sparing effect of the Matrix-M.

FIG. 41 illustrates the durable immune response achieved by the nanoparticle compositions. The data shown in the EC50 GMT responses for IgG after administration at Day 0 and Day 21. The nanoparticles with GP and Matrix-M show better responses than an alum adjuvant and the responses remain higher over time.

FIG. 42 illustrates the stimulation of the immune response involving IFNγ releasing cells. The Matrix M combined with 5 µg GP nanoparticles gave the maximum response followed by the higher dose GP nanoparticles (60 µg). Using alum provided a low but detectable increase in peripheral blood mononuclear cells (PBMC) secreting IFN-γ.

FIG. 43 illustrates the IFNγ and TNF-α release profiles from CD4+ and CD8+ T-cells isolated from baboons that were administered vaccine compositions containing the GP nanoparticles disclosed herein.

FIG. 44 illustrates the cytokine release profiles from T-cells isolated from baboons that were administered vaccine compositions containing the GP nanoparticles disclosed herein. The data show that Matrix M-adjuvanted GP nanoparticle compositions stimulate immune responses having broader cytokine release profiles.

FIG. 45 shows a vaccine trial design performed in Cynomolgus macaques. Animals were administered a vaccine composition of 5 µg GP+50 µg Matrix-M at Days 0 and 21 then challenged at Day 42. Animals 33360, 33362, and 33355 were treated with the vaccine composition. Placebo was administered to animal 33356.

FIG. 46 shows the IgG titers obtained in the Cynomolgus macaque trial. By Day 28, EC50 titers had exceeded $10^5$.

FIGS. 47A-47C shows induction of IFN-γ secreting PBMC cells isolated from treated macaques. Peptides derived from Ebola Zaire GP were pooled and used in the assay. A consensus peptide derived from the Zaire and Sudan strains was also tested. The data shown illustrates cells responding to those peptides at Week 0 (FIG. 47A), Week 3 (FIG. 47B), and Week 5 (FIG. 47C). The control animal injected with placebo showed essentially no response. In contrast, vaccine-treated animals showed a robust increase in cells releasing IFN-γ in response to the various peptides tested.

FIG. 48 shows viral load and survival in macaques. By Day 7 post-challenge the placebo animal exhibited a substantial increase in viral nucleic acid, indicating Ebola infection. By Day 9 the animal was euthanized. All vaccinated animals survived. Only animal 33360 exhibited a detectable increase in viral nucleic acid, which was about the limit of detection. By Day 10, even in that one animal, viral RNA levels had dropped beneath the ability of RT-PCR to detect them.

FIG. 49 shows a vaccine trial design for an additional macaque study. Animals were administered saline or 5 µg GP+50 µg Matrix-M. Group F received vaccine at weeks 0 and 6. Group G received vaccine at weeks 0 and 3. Both groups were challenged 6 weeks after administration of the boost vaccine.

FIG. 50 shows the results of the second study. In both groups, substantial increases in anti-Ebola GP were obtained. At Day 18 after challenge with live virus, survival for saline control animals was 0%. In contrast both animals in each of Groups F and G survived, establishing that the vaccine compositions were protective.

DETAILED DESCRIPTION

Figure 29B:
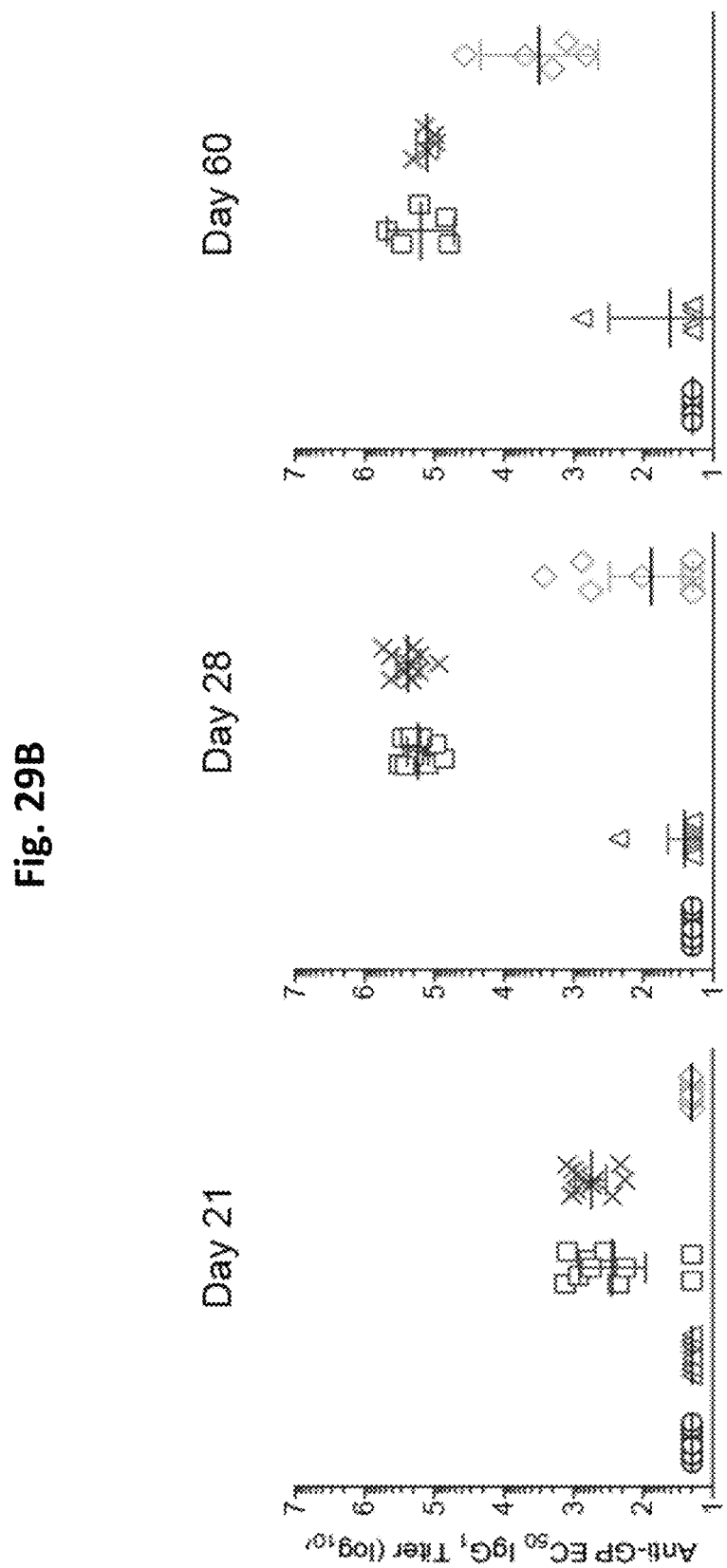

Disclosed herein are nanoparticles for inducing immune responses, methods for producing and administering them and vaccine compositions containing them. The nanoparticle provides antigen surrounding and associated with a detergent core that result in a structure that provides enhanced stability by numerous measures. The detergent core and antigen associate via a physico-chemical interaction mediated by the properties of the antigen and detergent. In addition, the nanoparticles offer especially good antigen presentation to immune systems which, without being bound by theory, is thought to result from the orientation of the antigens around the detergent core.

In one aspect, the disclosure provides compositions containing recombinant viral glycoprotein nanoparticles. In particular aspects, the glycoproteins are recombinantly expressed in a suitable host cell. In one embodiment, the host cell is an insect cell. In an exemplary embodiment, the insect cell is an Sf9 cell.

In particular aspects, the disclosure provides immunogenic compositions comprising one or more viral glycoprotein species in a nanoparticle structure where the glycoprotein is in the form of a trimer and each nanoparticle contains at least one trimer associated with a non-ionic detergent core. In particular aspects, a nanoparticle consists of an antigen, such as a viral glycoprotein, from only one pathogen.

The nanoparticles may be used for the prevention and/or treatment of viral infection. Thus, in another aspect, the disclosure provides a method for eliciting an immune response against a virus. The method involves administering an immunologically effective amount of a composition containing a nanoparticle to a subject.

The disclosure provides vaccine compositions comprising the nanoparticle. Compositions may contain nanoparticles having antigens from multiple pathogens. In some aspects, the vaccine composition may contain nanoparticles with antigens from more than one viral strain from the same species of virus. In aspects, the vaccine composition may contain nanoparticles with antigens from different virus species. In another embodiment, the disclosures provide for a pharmaceutical pack or kit comprising one or more containers filled with one or more of the components of the vaccine compositions.

In another embodiment, the disclosure provides a method of formulating a vaccine composition that induces immunity to an infection or at least one disease symptom thereof to a mammal, comprising adding to the composition an effective dose of a nanoparticle. The disclosed nanoparticles are useful for preparing compositions that stimulate an immune response that confers immunity or substantial immunity to infectious agents. Thus, in one embodiment, the disclosure provides a method of inducing immunity to infections or at least one disease symptom thereof in a subject, comprising administering at least one effective dose of a nanoparticle.

In some embodiments, the nanoparticles are administered with an adjuvant. In other aspects, the nanoparticles are administered without an adjuvant. In some aspects, the adjuvant may be bound to the nanoparticle, such as by a non-covalent interaction. In other aspects, the adjuvant is co-administered with the nanoparticle but the adjuvant and nanoparticle do not interact substantially.

Also provided herein are methods of manufacturing the nanoparticles and vaccine compositions. Advantageously, the methods provide nanoparticles that are substantially free from contamination by other proteins, such as proteins associated with recombinant expression of proteins in baculovirus/Sf9 systems.

DEFINITIONS

As used herein, and in the appended claims, the singular forms "a", "an", and "the" include plural referents unless the context clearly dictates otherwise. Thus, for example, reference to "a protein" can refer to one protein or to mixtures of such protein, and reference to "the method" includes reference to equivalent steps and/or methods known to those skilled in the art, and so forth.

As used herein, the term "adjuvant" refers to a compound that, when used in combination with an immunogen, augments or otherwise alters or modifies the immune response induced against the immunogen. Modification of the immune response may include intensification or broadening the specificity of either or both antibody and cellular immune responses.

As used herein, the term "about" or "approximately" when preceding a numerical value indicates the value plus or minus a range of 10%. For example, "about 100" encompasses 90 and 110.

As used herein, the terms "immunogen," "antigen," and "epitope" refer to substances such as proteins, including glycoproteins, and peptides that are capable of eliciting an immune response.

As used herein, an "immunogenic composition" is a composition that comprises an antigen where administration of the composition to a subject results in the development in the subject of a humoral and/or a cellular immune response to the antigen.

As used herein, a "subunit" composition, for example a vaccine, that includes one or more selected antigens but not all antigens from a pathogen. Such a composition is substantially free of intact virus or the lysate of such cells or particles and is typically prepared from at least partially purified, often substantially purified immunogenic polypeptides from the pathogen. The antigens in the subunit composition disclosed herein are typically prepared recombinantly, often using a baculovirus system.

As used herein, "substantially" refers to isolation of a substance (e.g. a compound, polynucleotide, or polypeptide) such that the substance forms the majority percent of the sample in which it is contained. For example, in a sample, a substantially purified component comprises 85%, preferably 85%-90%, more preferably at least 95%-99.5%, and most preferably at least 99% of the sample. If a component is substantially replaced the amount remaining in a sample is less than or equal to about 0.5% to about 10%, preferably less than about 0.5% to about 1.0%

The terms "treat," "treatment," and "treating," as used herein, refer to an approach for obtaining beneficial or desired results, for example, clinical results. For the purposes of this disclosure, beneficial or desired results may include inhibiting or suppressing the initiation or progression of an infection or a disease; ameliorating, or reducing the development of, symptoms of an infection or disease; or a combination thereof.

"Prevention," as used herein, is used interchangeably with "prophylaxis" and can mean complete prevention of an infection or disease, or prevention of the development of symptoms of that infection or disease; a delay in the onset of an infection or disease or its symptoms; or a decrease in the severity of a subsequently developed infection or disease or its symptoms.

As used herein an "effective dose" or "effective amount" refers to an amount of an immunogen sufficient to induce an immune response that reduces at least one symptom of pathogen infection. An effective dose or effective amount may be determined e.g., by measuring amounts of neutralizing secretory and/or serum antibodies, e.g., by plaque neutralization, complement fixation, enzyme-linked immunosorbent (ELISA), or microneutralization assay.

As used herein, the term "vaccine" refers to an immunogenic composition, such as an immunogen derived from a pathogen, which is used to induce an immune response against the pathogen that provides protective immunity (e.g., immunity that protects a subject against infection with the pathogen and/or reduces the severity of the disease or condition caused by infection with the pathogen). The protective immune response may include formation of antibodies and/or a cell-mediated response. Depending on context, the term "vaccine" may also refer to a suspension or solution of an immunogen that is administered to a vertebrate to produce protective immunity.

As used herein, the term "subject" includes humans and other animals. Typically, the subject is a human. For example, the subject may be an adult, a teenager, a child (2 years to 14 years of age), an infant (1 month to 24 months), or a neonate (up to 1 month). In some aspects, the adults are seniors about 65 years or older, or about 60 years or older. In some aspects, the subject is a pregnant woman or a woman intending to become pregnant. In other aspects, subject is not a human; for example a non-human primate; for example, a baboon, a chimpanzee, a gorilla, or a macaque. In certain aspects, the subject may be a pet, such as a dog or cat.

As used herein, the term "pharmaceutically acceptable" means being approved by a regulatory agency of a U.S. Federal or a state government or listed in the U.S. Pharmacopeia, European Pharmacopeia or other generally recognized pharmacopeia for use in mammals, and more particularly in humans. These compositions can be useful as a vaccine and/or antigenic compositions for inducing a protective immune response in a vertebrate.

As used herein, the term "about" means plus or minus 10% of the indicated numerical value.

Overview

Antigens derived from pathogens are combined with non-ionic detergents to provide nanoparticles surrounding a detergent core that have improved stability and excellent immunogenicity. The disclosure also provides for methods and compositions for vaccinating a subject against pathogens. In particular aspects, the pathogen is a virus. The antigen is typically a protein, often a glycoprotein. Also disclosed are compositions containing the nanoparticles which find use as vaccine compositions. Methods of producing the nanoparticles and producing the vaccine compositions are also disclosed.

Nanoparticle Structure and Morphology

Nanoparticles of the present disclosure comprise antigens associated with non-ionic detergent core. FIG. 6 upper panel illustrates an example of multiple RSV F antigens associated with the detergent core. FIGS. 35 shows Ebola nanoparticles. Advantageously, the nanoparticles have improved resistance to environmental stresses such that they provide enhanced stability.

In particular embodiments, the nanoparticles are composed of multiple protein trimers surrounding a non-ionic detergent core. For example, each nanoparticle may contain 1, 2, 3, 4, 5, 6, 7, 8, 9, 10, 11, 12, or 15 trimers. Typically, each nanoparticle contains 2 to 9 trimers. In particular embodiments, each nanoparticle contains 2 to 6 trimers. Compositions disclosed herein may contain nanoparticles having different numbers of trimers. For example, a composition may contain nanoparticles where the number of trimers ranges from 2-9; in other embodiments, the nanoparticles in a composition may contain from 2-6 trimers. In particular embodiments, the compositions contain a heterogeneous population of nanoparticles having 2 to 6 trimers per nanoparticle, or 2 to 9 trimers per nanoparticle. In other embodiments, the compositions may contain a substantially homogenous population of nanoparticles. For example, the population may contain about 95% nanoparticles having 5 trimers.

The antigens are associated with the non-ionic detergent-containing core of the nanoparticle. Typically, the detergent is selected from polysorbate-20 (PS20), polysorbate-40 (PS40), polysorbate-60 (PS60), polysorbate-65 (PS65) and polysorbate-80 (PS80). The presence of the detergent facilitates formation of the nanoparticles by forming a core that organizes and presents the antigens. Thus, in certain embodiments, the nanoparticles may contain the antigens assembled into multi-oligomeric glycoprotein-PS80 protein-detergent nanoparticles with the head regions projecting outward and hydrophobic regions and PS80 detergent forming a central core surrounded by the antigens.

The nanoparticles disclosed herein range in Z-ave size from about 20 nm to about 60 nm, about 20 nm to about 50 nm, about 20 nm to about 45 nm, or about 25 nm to about 45 nm. Particle size (Z-ave) is measured by dynamic light scattering (DLS) using a Malvern Zetasizer, unless otherwise specified.

Several nanoparticle types may be included in vaccine compositions disclosed herein. In some aspects, the nanoparticle type is in the form of an anisotropic rod, which may be a dimer or a monomer. In other aspects, the nanoparticle type is a spherical oligomer. In yet other aspects, the nanoparticle may be described as an intermediate nanoparticle, having sedimentation properties intermediate between the first two types. Formation of nanoparticle types may be regulated by controlling detergent and protein concentration during the production process. Nanoparticle type may be determined by measuring sedimentation co-efficient. See FIGS. 9A and 9B, for examples showing RSV F nanoparticles. See also, FIG. 8 illustrating control over nanoparticle size by adjusting detergent and protein concentrations.

Nanoparticle Production

The nanoparticles of the present disclosure are non-naturally occurring products, the components of which do not occur together in nature. Generally, the methods disclosed herein use a detergent exchange approach wherein a first detergent is used to isolate a protein and then that first detergent is exchanged for a second detergent to form the nanoparticles.

The antigens contained in the nanoparticles are typically produced by recombinant expression in host cells. Standard recombinant techniques may be used. Typically, the proteins are expressed in insect host cells using a baculovirus system. In preferred embodiments, the baculovirus is a cathepsin-L knock-out baculovirus. In other preferred embodiments, the bacuolovirus is a chitinase knock-out baculovirus. In yet other preferred embodiments, the baculovirus is a double knock-out for both cathepsin-L and chitinase. High level expression may be obtained in insect cell expression systems. Non limiting examples of insect cells are, *Spodoptera frugiperda* (Sf) cells, e.g. Sf9, Sf21, *Trichoplusia ni* cells, e.g. High Five cells, and *Drosophila S2* cells.

Typical transfection and cell growth methods can be used to culture the cells. Vectors, e.g., vectors comprising polynucleotides that encode fusion proteins, can be transfected into host cells according to methods well known in the art. For example, introducing nucleic acids into eukaryotic cells can be achieved by calcium phosphate co-precipitation, electroporation, microinjection, lipofection, and transfection employing polyamine transfection reagents. In one embodiment, the vector is a recombinant baculovirus.

Methods to grow host cells include, but are not limited to, batch, batch-fed, continuous and perfusion cell culture techniques. Cell culture means the growth and propagation of cells in a bioreactor (a fermentation chamber) where cells propagate and express protein (e.g. recombinant proteins) for purification and isolation. Typically, cell culture is performed under sterile, controlled temperature and atmospheric conditions in a bioreactor. A bioreactor is a chamber used to culture cells in which environmental conditions such as temperature, atmosphere, agitation and/or pH can be monitored. In one embodiment, the bioreactor is a stainless steel chamber. In another embodiment, the bioreactor is a pre-sterilized plastic bag (e.g. Cellbag®, Wave Biotech, Bridgewater, N.J.). In other embodiment, the pre-sterilized plastic bags are about 50 L to 3500 L bags.

Detergent Extraction and Purification of Nanoparticles

After growth of the host cells, the protein may be harvested from the host cells using detergents and purification protocols. Once the host cells have grown for 48 to 96 hours, the cells are isolated from the media and a detergent-containing solution is added to solubilize the cell membrane, releasing the protein in a detergent extract. Triton X-100 and tergitol, also known as NP-9, are each preferred detergents for extraction. The detergent may be added to a final concentration of about 0.1% to about 1.0%. For example, the concentration may be about 0.1%, about 0.2%, about 0.3%, about 0.5%, about 0.7%, about 0.8%, or about 1.0%. In certain embodiments, the range may be about 0.1% to about 0.3%. Preferably, the concentration is about 0.5%.

In other aspects, different first detergents may be used to isolate the protein from the host cell. For example, the first detergent may be Bis(polyethylene glycol bis[imidazoylcarbonyl]), nonoxynol-9, Bis(polyethylene glycol bis[imidazoyl carbonyl]), Brij® 35, Brij ®56, Brij® 72, Brij® 76, Brij® 92V, Brij® 97, Brij® 58P, Cremophor® EL, Decaethyleneglycol monododecyl ether, N-Decanoyl-N-methylglucamine, n-Decyl alpha-Dglucopyranoside, Decyl beta-D-maltopyranoside, n-Dodecanoyl-N-methylglucamide, nDodecyl alpha-D-maltoside, n-Dodecyl beta-D-maltoside, n-Dodecyl beta-D-maltoside, Heptaethylene glycol monodecyl ether, Heptaethylene glycol monododecyl ether, Heptaethylene glycol monotetradecyl ether, n-Hexadecyl beta-D-maltoside, Hexaethylene glycol monododecyl ether, Hexaethylene glycol monohexadecyl ether, Hexaethylene glycol monooctadecyl ether, Hexaethylene glycol monotetradecyl ether, Igepal CA-630,Igepal CA -630, Methyl-6-0-(N -heptylcarbamoyl)-alpha-D-glucopyranoside, Nonaethylene glycol monododecyl ether, N-Nonanoyl-N-methylglucamine, N-NonanoylN-methylglucamine, Octaethylene glycol monodecyl ether, Octaethylene glycol-monododecyl ether, Octaethylene glycol monohexadecyl ether, Octaethylene glycol monooctadecyl ether, Octaethylene glycol monotetradecyl ether, Octyl-beta-D glucopyranoside, Pentaethylene glycol monodecyl ether, Pentaethylene glycol monododecyl ether, Pentaethylene glycol monohexadecyl ether, Pentaethylene glycol monohexyl ether, Pentaethylene glycol monooctadecyl ether, Pentaethylene glycol monooctyl ether, Polyethylene glycol diglycidyl ether, Polyethylene glycol ether W-1, Polyoxyethylene 10 tridecyl ether, Polyoxyethylene 100 stearate, Polyoxyethylene 20 isohexadecyl ether, Polyoxyethylene 20 oleyl ether, Polyoxyethylene 40 stearate, Polyoxyethylene 50 stearate, Polyoxyethylene 8 stearate, Polyoxyethylene bis (imidazolyl carbonyl), Polyoxyethylene 25 propylene glycol stearate, Saponin from *Quillaja* bark, Span® 20, Span® 40, Span® 60, Span® 65, Span® 80, Span® 85, Tergitol Type 15-S-12, Tergitol Type 15-S-30, Tergitol Type 15-S-5, Tergitol Type 15-S-7, Tergitol Type 15-S-9, Tergitol Type NP-10, Tergitol Type NP-4, Tergitol Type NP-40, Tergitol, Type NP-7 Tergitol Type NP-9, Tergitol Type TMN-10, Tergitol Type TMN-6, Triton X-100 or combinations thereof.

The nanoparticles may then be isolated from cellular debris using centrifugation. In some embodiments, gradient centrifugation, such as using cesium chloride, sucrose and iodixanol, may be used. Other techniques may be used as alternatives or in addition, such as standard purification techniques including, e.g., ion exchange, affinity, and gel filtration chromatography.

For example, the first column may be an ion exchange chromatography resin, such as Fractogel® EMD TMAE (EMD Millipore), the second column may be a lentil (*Lens culinaris*) lectin affinity resin, and the third column may be a cation exchange column such as a Fractogel® EMD SO3 (EMD Millipore) resin. In other aspects, the cation exchange column may be an MMC column or a Nuvia C Prime column (Bio-Rad Laboratories, Inc). Preferably, the methods disclosed herein do not use a detergent extraction column; for example a hydrophobic interaction column. Such a column is often used to remove detergents during purification but may negatively impact the methods disclosed here.

Detergent Exchange

To form nanoparticles, the first detergent, used to extract the protein from the host cell is substantially replaced with a second detergent to arrive at the nanoparticle structure. NP-9 is a preferred extraction detergent. Typically, the nanoparticles do not contain detectable NP-9 when measured by HPLC. The second detergent is typically selected from the group consisting of PS20, PS40, PS60, PS65, and PS80. Preferably, the second detergent is PS80. To maintain the stability of the nanoparticle formulations, the ratio of the second detergent and protein is maintained within a certain range.

In particular aspects, detergent exchange is performed using affinity chromatography to bind glycoproteins via their carbohydrate moiety. For example, the affinity chromatography may use a legume lectin column. Legume lectins are proteins originally identified in plants and found to interact specifically and reversibly with carbohydrate residues. See, for example, Sharon and Lis, "Legume lectins—a large family of homologous proteins," FASEB J. 1990 November; 4(14):3198-208; Liener, "The Lectins: Properties, Functions, and Applications in Biology and Medicine," Elsevier, 2012. Suitable lectins include concanavalin A (con A), pea lectin, sainfoin lect, and lentil lectin. Lentil lectin is a preferred column for detergent exchange due to its binding properties. See, for instance, Example 10. Lectin columns are commercially available; for example, Capto Lentil Lectin, is available from GE Healthcare. In certain aspects, the lentil lectin column may use a recombinant lectin. At the molecular level, it is thought that the carbohydrate moieties bind to the lentil lectin, freeing the amino acids of the protein to coalesce around the detergent resulting in the formation of a detergent core providing nanoparticles having multiple copies of the antigen, e.g., glycoprotein oligomers which can be dimers, trimers, or tetramers anchored in the detergent.

The detergent, when incubated with the protein to form the nanoparticles during detergent exchange, may be present at up to about 0.1% (w/v) during early purifications steps and this amount is lowered to achieve the final nanoparticles having optimum stability. For example, the non-ionic detergent (e.g., PS80) may be about 0.03% to about 0.1%. Preferably, for improved stability, the nanoparticle contains about 0.03% to about 0.05% PS80. Amounts below about 0.03% PS80 in formulations do not show as good stability. Further, if the PS80 is present above about 0.05%, aggregates are formed. Accordingly, about 0.03% to about 0.05%

PS80 provides structural and stability benefits that allow for long-term stability of nanoparticles with reduced degradation.

Detergent exchange may be performed with proteins purified as discussed above and purified, frozen for storage, and then thawed for detergent exchange.

Enhanced Stability and Enhanced Immunogenicity of Nanoparticles

Without being bound by theory, it is thought that associating the antigen with a non-ionic detergent core offers superior stability and antigen presentation. The nanoparticles disclosed herein provide surprisingly good stability and immunogenicity. Advantageous stability is especially useful for vaccines used in countries lacking proper storage; for example, certain locations in Africa may lack refrigeration and so vaccines for diseases prevalent in areas facing difficult storage conditions, such as Ebola virus and RSV, benefit particularly from improved stability. Further, the HA influenza nanoparticles produced using the neutral pH approach exhibit superior folding to known recombinant flu vaccines.

Notably, prior approaches to using detergents to produce RSV vaccines including split vaccines such as described in US 2004/0028698 to Colau et al. failed to produce effective structures. Rather than nanoparticles having proteins surrounding a detergent core as disclosed herein, Colau et al's compositions contained amorphous material lacking identifiable viral structures, presumably resulting in failure to present epitopes to the immune system effectively. In addition, the disclosed nanoparticles have particularly enhanced stability because the orientation of the antigens, often glycoproteins, around the detergent core sterically hinders access of enzymes and other chemicals that cause protein degradation.

The nanoparticles have enhanced stability as determined by their ability to maintain immunogenicity after exposure to varied stress. Stability may be measured in a variety of ways. In one approach, a peptide map may be prepared to determine the integrity of the antigen protein after various treatments designed to stress the nanoparticles by mimicking harsh storage conditions. Thus, a measure of stability is the relative abundance of antigen peptides in a stressed sample compared to a control sample. FIG. 12 shows that even after various different stresses to an RSV F nanoparticle composition, robust immune responses are achieved. FIG. 13 illustrates the improved protease resistance provided by the nanoparticles using PS80 levels above 0.015%. Notably, at 18 months PS80 at 0.03% shows a 50% reduction in formation of truncated species compared to 0.015% PS80. The nanoparticles disclosed herein are stable at 2-8° C. Advantageously, however, they are also stable at 25° C. for at least 2 months. In some embodiments, the compositions are stable at 25° C. for at least 3 months, at least 6 months, at least 12 months, at least 18 months, or at least 24 months. For RSV-F nanoparticles, stability may be determined by measuring formation of truncated F1 protein, as shown in FIG. 13. Advantageously, the RSV-F nanoparticles disclosed herein advantageously retain an intact antigenic site II at an abundance of 90 to 100% as measured by peptide mapping compared to the control RSV-F protein in response to various stresses including pH (pH3.7), high pH (pH10), elevated temperature (50° C. for 2 weeks), and even oxidation by peroxide as shown in FIG. 12.

It is thought that the position of the glycoprotein anchored into the detergent core provides enhanced stability by reducing undesirable interactions. For example, the improved protection against protease-based degradation may be achieved through a shielding effect whereby anchoring the glycoproteins into the core at the molar ratios disclosed herein results in steric hindrance blocking protease access.

Thus, in particular aspects, disclosed herein are RSV-F nanoparticles, and compositions containing the same, that retain 90% to 100%, of intact Site II peptide, compared to untreated control, in response to one or more treatments selected from the group consisting of incubation at 50° C. for 2 weeks, incubation at pH 3.7 for 1 week at 25° C., incubation at pH 10 for 1 week at 25° C., agitation for 1 week at 25° C., and incubation with an oxidant, such as hydrogen peroxide, for 1 week at 25° C. Additionally, after such treatments, the compositions functionality is retained. See FIGS. 12A-12D. For example, neutralizing antibody, anti-RSV IgG and PCA titers are preserved compared to control.

Enhanced immunogenicity is exemplified by the cross-neutralization achieved by the influenza nanoparticles. It is thought that the orientation of the influenza antigens projecting from the core provides a more effective presentation of epitopes to the immune system.

Nanoparticle Antigens

In typical embodiments, the antigens used to produce the nanoparticles are viral proteins. In some aspects, the proteins may be modified but retain the ability to stimulate immune responses against the natural peptide. In some aspects, the protein inherently contains or is adapted to contain a transmembrane domain to promote association of the protein into a detergent core. Often the protein is naturally a glycoprotein.

RSV Antigens

In one aspect, the virus is Respiratory Syncytial Virus (RSV) and the viral antigen is the Fusion (F) glycoprotein. The structure and function of RSV F proteins is well characterized. See FIG. 1, for an example of wild-type structure. Suitable RSV-F proteins for use in the compositions described herein can be derived from RSV strains such as A2, Long, ATCC VR-26, 19, 6265, E49, E65, B65, RSB89-6256, RSB89-5857, RSB89-6190, and RSB89-6614. In certain embodiments, RSV F proteins are mutated compared to their natural variants. These mutations confer desirable characteristics, such as improved protein expression, enhanced immunogenicity and the like. Additional information describing RSV-F protein structure can be found at Swanson et al. A Monomeric Uncleaved Respiratory Syncytial Virus F Antigen Retains Prefusion-Specific Neutralizing Epitopes. Journal of Virology, 2014, 88, 11802-11810. Jason S. McLellan et al. Structure of RSV Fusion Glycoprotein Trimer Bound to a Prefusion-Specific Neutralizing Antibody. Science, 2013, 340, 1113-1117.

The primary fusion cleavage is located at residues 131 to 136 corresponding to SEQ ID NO:2. Inactivation of the primary fusion cleavage site may be achieved by mutating residues in the site, with the result that furin can no longer recognize the consensus site. For example, inactivation of the primary furin cleavage site may be accomplished by introducing at least one amino acid substitution at positions corresponding to arginine 133, arginine 135, and arginine 136 of the wild-type RSV F protein (SEQ ID NO:2). In particular aspects, one, two, or all three of the arginines are mutated to glutamine. In other aspects, inactivation is accomplished by mutating the wild-type site to one of the following sequences: KKQKQQ (SEQ ID NO: 14), QKQKQQ (SEQ ID NO:15), KKQKRQ (SEQ ID NO: 16), and GRRQQR (SEQ ID NO: 17).

In particular aspects, from 1 to 10 amino acids of the corresponding to acids 137 to 145 of SEQ ID NO: 2 may be deleted, including the particular examples of suitable RSV F proteins shown below. Each of SEQ ID NOS 3-13 may optionally be prepared with an active primary fusion cleavage site KKRKRR (SEQ ID NO:18). The wild type strain in SEQ ID NO:2 has sequencing errors (A to P, V to I, and V to M) that are corrected in SEQ ID NOS:3-13. Following expression of the RSV-F protein in a host cell, the N-terminal signal peptide is cleaved to provide the final sequences. Typically, the signal peptide is cleaved by host cell proteases. In other aspects, however, the full-length protein may be isolated from the host cell and the signal peptide cleaved subsequently. The N-terminal RSV F signal peptide consists of amino acids of SEQ ID NO: 26 (MELLILKANAITTILTAVTFCFASG). Thus, for example, following cleavage of the signal peptide from SEQ ID NO:8 during expression and purification, a mature protein having the sequence of SEQ ID NO: 19 is obtained and used to produce a RSV F nanoparticle vaccine. See FIG. 1B. Optionally, one or more up to all of the RSV F signal peptide amino acids may be deleted, mutated, or the entire signal peptide may be deleted and replaced with a different signal peptide to enhance expression. An initiating methionine residue is maintained to initiate expression.

| Expressed Protein SEQ ID NO: | Fusion Domain Deletion | Primary Fusion Cleavage Site sequence |
|---|---|---|
| 1 | Wild type Strain A2 (nucleic) | KKRKRR (active) |
| 2 | Wild type Strain A2 (protein) | KKRKRR (active) |
| 3 | Deletion of 137 (Δ1) | KKQKQQ (inactive) |
| 4 | Deletion of 137-138 (Δ2) | KKQKQQ (inactive) |
| 5 | Deletion of 137-139 (Δ3) | KKQKQQ (inactive) |
| 6 | Deletion of 137-140 (Δ4) | KKQKQQ (inactive) |
| 7 | Deletion of 137-141 (Δ5) | KKQKQQ (inactive) |
| 8 | Deletion of 137-146 (Δ10) | KKQKQQ (inactive) |
| 9 | Deletion of 137-142 (Δ6) | KKQKQQ (inactive) |
| 10 | Deletion of 137-143 (Δ7) | KKQKQQ (inactive) |
| 11 | Deletion of 137-144 (Δ8) | KKQKQQ (inactive) |
| 12 | Deletion of 137-145 (Δ9) | KKQKQQ (inactive) |
| 13 | Deletion of 137-145 (Δ9) | KKRKRR (active) |

In some aspects, the RSV F protein disclosed herein is only altered from a wild-type strain by deletions in the fusion domain, optionally with inactivation of the primary cleavage site. In other aspects, additional alterations to the RSV F protein may be made. Typically, the cysteine residues are mutated. Typically, the N-linked glycosylation sites are not mutated. See FIG. 1B. Additionally, the antigenic site II, also referred to herein as the Palivizumab site because of the ability of the palivizumab antibody to bind to that site, is preserved. The Motavizumab antibody also binds at site II. Additional suitable RSV-F proteins, incorporated by reference, are found in U.S. Publication US 2011/0305727, including in particular, RSV-F proteins containing the sequences spanning residues 100 to 150 as disclosed in FIG. 1C therein.

In certain other aspects, the RSV F1 or F2 domains may have modifications relative to the wild-type strain as shown in SEQ ID NO:2. For example, the F1 domain may have 1, 2, 3, 4, 5, 6, 7, 8, 9, or 10 alterations, which may be mutations or deletions. Similarly, the F2 domain may have 1, 2, 3, 4, 5, 6, 7, 8, 9, or 10 alterations, which may be mutations or deletions. The F1 and F2 domains may each independently retain at least 90%, at least 94% at least 95% at least 96% at least 98% at least 99%, or 100% identity to the wild-type sequence.

In a particular example, an RSV nanoparticle drug product may contain about 0.025% to about 0.03% PS80 with RSV F at a range of about 270 μg/mL to about 300 μg/mL, or about 60 μg/mL to about 300 μg/mL. In other aspects, the nanoparticle drug product may contain about 0.035% to about 0.04% PS80 in a composition with RSV F at 300 μg/mL to about 500 μg/mL. In yet other aspects, the nanoparticle drug product may contain about 0.035% to about 0.04% PS80 in a composition with RSV F at 350-500 μg/mL.

Because the concentrations of antigen and detergent can vary, the amounts of each may be referred as a molar ratio of non-ionic detergent: protein. For example, the molar ratio of PS80 to protein is calculated by using the PS80 concentration and protein concentration of the antigen measured by ELISA/A280 and their respective molecular weights. The molecular weight of PS80 used for the calculation is 1310 and, using RSV F as an example, the molecular weight for RSV F is 65 kD. Molar ratio is calculated as a follows: (PS80 concentration×10×65000)÷(1310×RSV F concentration in mg/mL). Thus, for example, as shown FIG. 13, the nanoparticle concentration, measured by protein, is 270 μg/mL and the PS80 concentrations are 0.015% and 0.03%. These have a molar ratio of PS80 to RSV F protein of 27:1 (that is, 0.015×10×65000/(1310×0.27)) and 55:1, respectively.

In particular aspects, the molar ratio is in a range of about 30:1 to about 80:1, about 30:1 to about 70:1, about 30:1 to about 60:1, about 40:1 to about 70:1, or about 40:1 to about 50:1. Often, the replacement non-ionic detergent is PS80 and the molar ratio is about 30:1 to about 50:1, PS80: protein. For RSV-F glycoprotein, nanoparticles having a molar ratio in a range of 35:1 to about 65:1, and particularly a ratio of about 45:1, are especially stable.

Influenza Antigens

The nanoparticle platform is especially useful for presenting influenza antigens to the immune system of a subject. Previous approaches to producing influenza nanoparticle vaccines have used hydrophobic interaction columns to remove detergent or have contained only minimal amounts of detergent to reduce non-specific interactions that arose during product purification. It has now been discovered, however, that by performing a detergent exchange step nanoparticles having a non-ionic detergent core having excellent properties can be produced. The nanoparticles show excellent stability as evidenced by resistance to degradation by environmental stresses, which permits extended storage periods, as especially useful property for vaccines. In addition, the nanoparticle structure is such that it presents the antigens in a particularly advantageous fashion.

The influenza nanoparticles are especially useful as vaccines as the antibodies they induce contain broadly neutralizing antibodies. Thus, antibodies induced by a nanoparticle administered in one year can neutralize influenza viral strains arising from the "drift" process in subsequent years. It is thought that these epitopes that induce these broadly neutralizing antibodies have not been exposed at all, or exposed effectively, in prior influenza vaccines, or that the epitopes were insufficiently stable in prior formulations. The nanoparticles disclosed herein resolve those problems by presenting cross-protective epitopes anchored around a non-ionic detergent core with enhanced stability.

Finally, the methods disclosed herein provide for especially high yield influenza nanoparticles with good purity, which is advantageous economically in general and especially valuable for viruses that require rapid production of large amounts, such as pandemic influenza virus.

In certain embodiments, a nanoparticle may contain an HA or an NA protein. For example, a nanoparticle may contain a HA protein selected from the sub-types H1, H2, H3, H4, H5, H6, H7, H8, H9, H10, H11, H12, H13, H14, H15, and H16. A nanoparticle may contain an NA protein selected from the sub-types N1, N2, N3, N4, N5, N6, N7, N8 and N9. Phylogenetically, the HA and NA proteins are split into groups. For HA, Group 1 contains H1, H2, H5, H6, H8, H9, H11, H12, H13, and H16, and group 2 contains H3, H4, H7, H10, H14, and H15. NAs also form two groups: Group 1 contains N1, N4, N5, and N8, and Group 2 contains N2, N3, N6, N7, and N9. In certain aspects, the antigen may have at least 90% identity, at least 95% identity, at least 97% identity, or at least 99% to the native influenza HA protein or the NA protein.

The HA and NA proteins used for the nanoparticles are typically full-length sequences. In certain aspects, portions of the C-terminus may be removed.

Advantageously, compositions having influenza can induce responses against heterologous strains of influenza, even when additional pathogen nanoparticles disclosed herein are co-administered. By inducing responses against heterologous influenza strains, broader protection is achieved. Thus, in particular aspects, the homologous HAI titer induced with Matrix M-adjuvanted compositions is about 800 to about 2000. In particular aspects, the heterologous HAI titer is about 1300. In particular aspects, the heterologous HAI titer induced with Matrix M-adjuvanted compositions is about 200 to about 400; for example, the heterologous HAI titer may be about 300.

In certain aspects, the influenza nanoparticles are trypsin-resistant nanoparticles produced using neutral pH purification. Trypsin resistance is achieved by neutral pH range of above 6.8 to 8.5 during purification and formulation of the HA nanoparticles. In particular aspects, the pH range during purification and formulation of the HA nanoparticles is 7.0 to 8.5, 7.0 to 7.5, or 7.2 to 7.5. HA nanoparticle stability may be measured by Differential Scanning calorimetry (DSC). DSC measures the thermodynamic profile of macromolecules in solution, specifically, by measuring the difference in heat energy uptake between a sample solution and appropriate reference (buffer/solvent) by varying the temperature in a controlled manner. DSC provides data as transition midpoints (Tm), defined as temperatures where half the protein is denatured/unfolded and half in the native/folded state. In certain aspects, the trypsin-resistant HA nanoparticles herein have a Tm peak in a range of about 60° C. to 75° C.; for example, the Tm may be 60° C., 65° C., 70° C. or 75° C.

Trypsin resistance indicates that the HA protein is properly folded and thus provides a vaccine product having better stability and immunogenicity. The sensitivity of HA proteins varies from strain-to-strain and the neutral pH production disclosed herein thus provides a process for maximizing immunogenicity for all strains, especially pH sensitive strains. Without being bound by theory it is thought that the combination of the detergent exchange and neutral pH levels preserve the HA protein in a structure that renders it resistant to proteases, particularly trypsin. Thus, by having the HA protein associated around a non-ionic detergent core combined with neutral pH purification, HA proteins of particularly good stability and immunogenicity are achieved. In addition, the methods of producing the nanoparticles provide excellent levels of protein for use in a vaccine. In particular aspects, the HA nanoparticles are produced, as measured by A280, at about 10 mg/L of cell culture to about 30 mg/L, or higher, at about 20 mg/L to about 30 mg/L.

The trypsin-resistant HA nanoparticles may be prepared as described in FIG. 24. Briefly, the various steps, including detergent exchanges are performed with buffers above pH 7.0; often in the range of about pH 7.2 to about pH 7.4. FIG. 25D provides an example of the better thermostability achieved with trypsin resistant nanoparticles. The TFF and MMC production lots were obtained using neutral pH whereas the misfolded low pH lot is substantially degraded and/or misfolded.

Ebola Antigens

The disclosure also provided methods and compositions for treating, ameliorating, or preventing Ebola virus infection and/or disease. In particular, the compositions are vaccine compositions. Advantageously, the vaccine compositions disclosed herein provide for 100% survival to lethal challenge in animal models. The compositions also maintain a viral load about or below the detectable limit when using RT-PCR to detect viral nucleic acid.

In one aspect, the disclosure provides compositions containing recombinant Ebola virus Glycoprotein (GP) nanoparticles in combination with saponin-based adjuvants.

In particular aspects, the disclosure provides immunogenic compositions comprising one or Ebola virus GP proteins in a nanoparticle structure where the GP protein is in the form of a trimer and each nanoparticle contains at least one trimer attached to a non-ionic detergent core.

The Ebola GP nanoparticles may be used for the prevention and/or treatment of Ebola infection. In another aspect, the present disclosure provides pharmaceutically acceptable vaccine compositions comprising an Ebola GP nanoparticle. In some aspects, nanoparticles from more than one strain are in the vaccine. In another embodiment, the disclosures provides for a pharmaceutical pack or kit comprising one or more containers filled with one or more of the ingredients of the vaccine formulations.

Ebola Glycoproteins

The Ebola antigen use to prepare the nanoparticle is typically an Ebola Glycoprotein (GP) antigen. The antigen may be derived from a variety of strains. The compositions disclosed herein may contain nanoparticles from one, two, three, four, five, or six separate Ebola strains. For example, the strain may be Makona, Sudan, Zaire, Reston. In other aspects, the Ebola GP may share amino acid or nucleic acid identity with one or more of these strains. For example, the GP may be about 80% identical, about 85% identical, about 90% identical, about 95% identical, about 97% identical, about 98% identical, or about 99% identical to one or more of the GPs from the Makona, Sudan, Zaire, or Reston viruses, wherein identity is measured over the full length of the protein or nucleic acid. In some aspects, the Ebola GP may comprise, or consist of, SEQ ID NO:27 or 28, or a protein having identity thereto.

A representative Zaire strain sequence is provided at GenBank Accession No. AAB81004 (SEQ ID NO:27). The first underlined portion shows the N-terminus for the GP1 protein. The preceding signal peptide is cleaved off during processing following expression in the cell prior to purification and formulation into a vaccine. Shown in bold is the furin cleavage site. Following the bold text, the N-terminus for the GP2 protein is shown. FIG. 7A shows a cartoon of the protein structure.

MGVTGILQLPRDRFKRTSFFLWVIILFQRTFS<u>IPLGVIHNSTLQVSDV

DKLVCRDKLSSTNQLRSVGLNLEGNGVATDVPSATKRWGFRSGV

PPKVVNYEAGEWAENCYNLEIKKPDGSECLPAAPDGIRGFPRCRY

VHKVSGTGPCAGDFAFHKEGAFFLYDRLASTVIYRGTTFAEGVVA

FLILPQAKKDFFSSHPLREPVNATEDPSSGYYSTTIRYQATGFGTNE

TEYLFEVDNLTYVQLESRFTPQFLLQLNETIYTSGKRSNTTGKLIW

KVNPEIDTTIGEWAFWETKKNLTRKIRSEELSFTVVSNGAKNISGQ

SPARTSSDPGTNTTTEDHKIMASENSSAMVQVHSQGREAAVSHLT

TLATISTSPQSLTTKPGPDNSTHNTPVYKLDISEATQVEQHHRRTD

NDSTASDTPSATTAAGPPKAENTNTSKSTDFLDPATTTSPQNHSET

AGNNNTHHQDTGEESASSGKLGLITNTIAGVAGLITGGRRTRREAI

VN</u>AQPKCNPNLHYWTTQDEGAAIGLAWIPYFGPAAEGIYIEGLMH

NQDGLICGLRQLANETTQALQLFLRATTELRTFSILNRKAIDFLLQR

WGGTCHILGPDCCIEPHDWTKNITDKIDQIIHDFVDKTLPDQGDND

NWWTGWRQWIPAGIGVTGVIIAVIALFCICKFVF

The Makona isolate sequence is provided at GenBank Accession No. AJG44192 (SEQ ID NO:28). As above, the first underlined portion shows the N-terminus for the GP1 protein. The preceding signal peptide is cleaved off during processing. Shown in bold is the furin cleavage site. Following the bold text, the N-terminus for the GP2 protein is shown. See also FIG. 7B.

MGVTGILQLPRDRFKRTSFFLWVIILFQRTFS<u>IPLGVIHNSTLQVSDV

DKLVCRDKLSSTNQLRSVGLNLEGNGVATDVPSVTKRWGFRSGV

PPKVVNYEAGEWAENCYNLEIKKPDGSECLPAAPDGIRGFPRCRY

VHKVSGTGPCAGDFAFHKEGAFFLYDRLASTVIYRGTTFAEGVVA

FLILPQAKKDFFSSHPLREPVNATEDPSSGYYSTTIRYQATGFGTNE

TEYLFEVDNLTYVQLESRFTPQFLLQLNETIYASGKRSNTTGKLIW

KVNPEIDTTIGEWAFWETKKNLTRKIRSEELSFTAVSNGPKNISGQS

PARTSSDPETNTTNEDHKIMASENSSAMVQVHSQGRKAAVSHLTT

LATISTSPQPPTTKTGPDNSTHNTPVYKLDISEATQVGQHHRRADN

DSTASDTPPATTAAGPLKAENTNTSKSADSLDLATTTSPQNYSETA

GNNNTHHQDTGEESASSGKLGLITNTIAGVAGLITGGRRTRREVIV

N</u>AQPKCNPNLHYWTTQDEGAAIGLAWIPYFGPAAEGIYTEGLMH

NQDGLICGLRQLANETTQALQLFLRATTELRTFSILNRKAIDFLLQR

WGGTCHILGPDCCIEPHDWTKNITDKIDQIIHDFVDKTLPDQGDND

NWWTGWRQWIPAGIGVTGVIIAVIALFCICKFVF

The ability of the vaccine compositions to stimulate immune responses was confirmed in three animal models. First, a mouse model was used. A recombinant EBOV/Mak full length GP nanoparticle vaccine formulated with Matrix-M, AlPO$_4$ or saline was evaluated. Immunization of mice with non-adjuvanted or AlPO$_4$ adjuvanted EBOV/Mak GP induced modest antibody and cellular responses; however, when adjuvanted with Matrix-M, purified EBOV/Mak GP nanoparticles were highly immunogenic and protective in a murine challenge model. Immunization of mice with Matrix-M adjuvanted EBOV/Mak GP resulted in a significant increase in anti-EBOV/Mak GP IgG and Ebola virus neutralizing antibody. Immunization with the Matrix-M adjuvanted EBOV/Mak GP conferred 100% protection from a lethal Ebola virus challenge while unadjuvanted EBOV/Mak GP was only 10% protective and no protection was observed in mice immunized with EBOV/Mak GP with AlPO$_4$. Thus, in particular aspects, the compositions disclosed herein prevent Ebola infection.

Co-administration of the EBOV/Mak GP with Matrix-M induced the production of a balanced IgG1 and IgG2a subclass response. In the absence of adjuvant or with AlPO$_4$, minimal IgG2a antibody was detected. Blaney et al. Antibody quality and protection from lethal Ebola virus challenge in nonhuman primates immunized with rabies virus based bivalent vaccine. PLoS Pathog. 2013; 9(5):, showed in a rabies/EBOV chimera vaccine model in non-human primates (NHP) that the antibody isotype played a role in virus neutralization and protection against Ebola virus challenge. Murine IgG2a antibody is the equivalent of human IgG1 antibody that binds efficiently to IgG-Fc receptors (FcγR) and complement (C1q) (Bruhns, P. Properties of mouse and human IgG receptors and their contribution to disease models Blood. 2012; 119: 5640-5649; Vidarsson G, Dekkers G, Rispens T. IgG subclasses and allotypes: from structure to effector functions. Front. Immunol. 2014; 5:520) and may help resolving viral infections e.g., through antibody-dependent cell-mediated cytotoxicity. All antibodies that were completely protective in vivo were of the IgG2a subclass; i.e. the same as human IgG1. Thus, the compositions disclosed herein stimulate production of IgG1 antibodies as part of a protective immune response.

The use of the Matrix-M adjuvant provided a dose dependent increase in the frequency of CD4+ and CD8+ cytokine secreting T cells as well as the number of multifunctional T cells producing more than one cytokine. The observation that protection from a lethal Ebola virus challenge was observed only in the Matrix-M adjuvanted EBOV/Mak GP group correlated with the enhanced production of multifunctional T cells.

The use of Matrix-M increased the frequency of GC B cells in the spleen and long lived plasma cells in the bone marrow. GCs are the micro-anatomic locations for B cell differentiation, somatic hypermutation, antibody class-switching and formation of memory B cells. Co-administration of the EBOV/Mak GP with the saponin adjuvant Matrix-M also resulted in an increase of the numbers of $T_{FH}$ cells which facilitate GC B cell differentiation and development. The increased frequencies of GC and $T_{FH}$ cells induced by Matrix-M adjuvantation correlated with the enhanced magnitude of the antibody response and the induction of a greater numbers of long-lived plasma cell, suggesting the Matrix-M adjuvanted EBOV/Mak GP vaccine may induce an especially durable antibody response.

Each dose of Ebola GP may be combined with adjuvant. Administering Matrix-M adjuvant with purified EBOV/Mak GP nanoparticles provides robust stimulation of the anti-EBOV/Mak GP immune response resulting in 100% protective efficacy in the mouse model. The compositions and methods disclosed herein provide a more rapid onset of anti-EBOV/Mak GP IgG and Ebola virus neutralization antibodies, increased concentration of IgG2a, as well as increased frequency of multifunctional CD4+ and CD8+ T cells, $T_{FH}$ cells, germinal center B cells and persistence of EBOV/Mak GP-specific plasma B cells in the bone marrow.

Analysis of the mouse study thus confirms that the compositions disclosed herein provided complete protection. To further establish the protective effect, studies were performed in two separate non-human primate models: Baboon and macaques. See Perry et al., "The Baboon (*Papio* spp.) as a model of human Ebola virus infection," Viruses. 2012 October 23; 4(10):2400-16; Geisbert et al., "Pathogenesis of Ebola hemorrhagic fever in cynomolgus macaques: evidence that dendritic cells are early and sustained targets of infection," Am J Pathol. 2003 December; 163(6):2347-70. Accordingly, in some aspects of the disclosure a protective effect includes a reduction on viral load beneath the ability of RT-PCR to detect after about 7 days, about 10 days, about 14 days, or about 21 days, after virus exposure.

The non-human primate studies further confirmed that the compositions disclosed herein are protective. Ebola GP nanoparticles were evaluated without adjuvant and with either Alum or Matrix M adjuvants. See Example 23. The immune responses in baboons were extremely robust and sustained. Notably, the inclusion of Matrix M led to a greater immune response than with Alum. The results with the macaque model were particularly unexpected. See Examples 24 and 24. The compositions not only protected against challenge with live Ebola vaccine, the amount of Ebola RNA was undetectable at Day 10 following challenge with live virus. See FIG. 48. Notably, in one macaque subject, there was a small signal about Day 7; however, by Day 10, levels had returned below the limit of detection. In contrast, exposure of untreated animals to live Ebola virus resulted in infection and disease such that the subject was euthanized at Day 9.

Modified Antigens

The antigens disclosed herein encompass variations and mutants of those antigens. In certain aspects, the antigen may share identity to a disclosed antigen. Generally, and unless specifically defined in context of a specifically identified antigens, the percentage identity may be at least 80%, at least 90%, at least 95%, at least 97%, or at least 98%. Percentage identity can be calculated using the alignment program ClustalW2, available at www.ebi.ac.uk/Tools/msa/clustalw2/. The following default parameters may be used for Pairwise alignment: Protein Weight Matrix=Gonnet; Gap Open=10; Gap Extension=0.1.

In particular aspects, the protein contained in the nanoparticles consists of that protein. In other aspects, the protein contained in the nanoparticles comprise that protein. Additions to the protein itself may be for various purposes. In some aspects, the antigen may be extended at the N-terminus, the C-terminus, or both. In some aspects, the extension is a tag useful for a function, such as purification or detection. In some aspects the tag contains an epitope. For example, the tag may be a polyglutamate tag, a FLAG-tag, a HA-tag, a polyHis-tag (having about 5-10 histidines), a Myc-tag, a Glutathione-S-transferase-tag, a Green fluorescent protein-tag, Maltose binding protein-tag, a Thioredoxin-tag, or an Fc-tag. In other aspects, the extension may be an N-terminal signal peptide fused to the protein to enhance expression. While such signal peptides are often cleaved during expression in the cell, some nanoparticles may contain the antigen with an intact signal peptide. Thus, when a nanoparticle comprises an antigen, the antigen may contain an extension and thus may be a fusion protein when incorporated into nanoparticles. For the purposes of calculating identity to the sequence, extensions are not included.

In some aspects, the antigen may be truncated. For example, the N-terminus may be truncated by about 10 amino acids, about 30 amino acids, about 50 amino acids, about 75 amino acids, about 100 amino acids, or about 200 amino acids. The C-terminus may be truncated instead of or in addition to the N-terminus. For example, the C-terminus may be truncated by about 10 amino acids, about 30 amino acids, about 50 amino acids, about 75 amino acids, about 100 amino acids, or about 200 amino acids. For purposes of calculating identity to the protein having truncations, identity is measured over the remaining portion of the protein.

Combination Nanoparticles

A combination nanoparticle, as used herein, refers to a nanoparticle that induces immune responses against two or more different pathogens. Depending on the particular combination, the pathogens may be different strains or sub-types of the same species or the pathogens may be different species. To prepare a combination nanoparticle, glycoproteins from multiple pathogens may be combined into a single nanoparticle by binding them at the detergent exchange stage. The binding of the glycoproteins to the column followed by detergent exchange permits multiple glycoproteins types to form around a detergent core, to provide a combination nanoparticle.

The disclosure also provides for vaccine compositions that induce immune responses against two or more different pathogens by combining two or more nanoparticles that each induce a response against a different pathogen. Optionally, vaccine compositions may contain one or more combination nanoparticles alone or in combination with additional nanoparticles with the purpose being to maximize the immune response against multiple pathogens while reducing the number of vaccine compositions administered to the subject.

Such compositions are particularly desirable when the pathogens are connected in some aspect. In one example, a composition may contain nanoparticles against the strains identified annually by authorities as forming a particular year's seasonal influenza. Typically, for a seasonal influenza vaccine, a vaccine composition contains HA and/or NA nanoparticles that induce immune responses against a strain of three, four, or five influenza sub-types. Thus, different strains of influenza may be combined in a vaccine composition. In some aspects, the combination nanoparticle may contain an HA protein from a first strain and an NA protein from a second strain. In other aspects, a nanoparticle may contain one or more HA and one or more NA proteins from the same or different sub-types. For example, a nanoparticle may contain one or more HA nanoparticles selected from the sub-types H1, H2, H3, H4, H5, H6, H7, H8, H9, H10, H11, H12, H13, H14, H15 and H16 and/or one or more NA nanoparticles selected from the sub-types N1, N2, N3, N4, N5, N6, N7, N8 and N9. Phylogenetically, the HA and NA proteins are split into groups. For HA, Group 1 contains H1, H2, H5, H6, H8, H9, H11, H12, H13, and H16, and group 2 contains H3, H4, H7, H10, H14, and H15. NA proteins also form two groups: Group 1 contains N1, N4, N5, and N8, and Group 2 contains N2, N3, N6, N7, and N9. In certain aspects, the antigen may have at least 90% identity, at least 95% identity, at least 97% identity, or at least 99% to the native influenza HA protein and/or to the NA protein.

In another example, influenza and RSV both cause respiratory disease and HA, NA, and/or RSV F may therefore be mixed into a combination nanoparticle or multiple nanoparticles may be combined in a vaccine composition to induce responses against RSV and one or more influenza strains.

Vaccine Compositions

Compositions disclosed herein may be used either prophylactically or therapeutically, but will typically be prophylactic. Accordingly, the disclosure includes methods for treating or preventing infection. The methods involve administering to the subject a therapeutic or prophylactic amount of the immunogenic compositions of the disclosure. Preferably, the pharmaceutical composition is a vaccine composition that provides a protective effect. In other aspects, the protective effect may include amelioration of a symptom associated with infection in a percentage of the exposed population. For example, depending on the pathogen, the composition may prevent or reduce one or more virus disease symptoms selected from: fever fatigue, muscle pain, headache, sore throat, vomiting, diarrhea, rash, symptoms of impaired kidney and liver function, internal bleeding and external bleeding, compared to an untreated subject.

The nanoparticles may be formulated for administration as vaccines in the presence of various excipients, buffers, and the like. For example, the vaccine compositions may contain sodium phosphate, sodium chloride, and/or histidine. Sodium phosphate may be present at about 10 mM to about 50 mM, about 15 mM to about 25 mM, or about 25 mM; in particular cases, about 22 mM sodium phosphate is present. Histidine may be present about 0.1% (w/v), about 0.5% (w/v), about 0.7% (w/v), about 1% (w/v), about 1.5% (w/v), about 2% (w/v), or about 2.5% (w/v). Sodium chloride, when present, may be about 150 mM. In certain compositions, for example influenza vaccines, the sodium chloride may be present at higher amounts, including about 200 mM, about 300 mM, or about 350 mM.

Certain nanoparticles, particularly RSV F nanoparticles, have improved stability at slightly acidic pH levels. For example, the pH range for composition containing the nanoparticles may be about pH 5.8 to about pH 7.0, about pH 5.9 to about pH 6.8, about pH 6.0 to about pH 6.5, about pH 6.1 to about pH 6.4, about pH 6.1 to about pH 6.3, or about pH 6.2. Typically, the composition for RSV F protein nanoparticles is about pH 6.2. In other nanoparticles, the composition may tend towards neutral; for example, influenza nanoparticles may be about pH 7.0 to pH 7.4; often about pH 7.2.

Adjuvants

In certain embodiments, the compositions disclosed herein may be combined with one or more adjuvants to enhance an immune response. In other embodiments, the compositions are prepared without adjuvants, and are thus available to be administered as adjuvant-free compositions. Advantageously, adjuvant-free compositions disclosed herein may provide protective immune responses when administered as a single dose. Alum-free compositions that induce robust immune responses are especially useful in adults about 60 and older.

Aluminum-Based Adjuvants

In some embodiments, the adjuvant may be alum (e.g. $AlPO_4$ or $Al(OH)_3$). Typically, the nanoparticle is substantially bound to the alum. For example, the nanoparticle may be at least 80% bound, at least 85% bound, at least 90% bound or at least 95% bound to the alum. Often, the nanoparticle is 92% to 97% bound to the alum in a composition. The amount of alum is present per dose is typically in a range between about 400 µg to about 1250 µg. For example, the alum may be present in a per dose amount of about 300 µg to about 900 µg, about 400 µg to about 800 µg, about 500 µg to about 700 µg, about 400 µg to about 600 µg, or about 400 µg to about 500 µg. Typically, the alum is present at about 400 µg for a dose of 120 µg of the protein nanoparticle.

Saponin Adjuvants

Adjuvants containing saponin may also be combined with the immunogens disclosed herein. Saponins are glycosides derived from the bark of the *Quillaja saponaria* Molina tree. Typically, saponin is prepared using a multi-step purification process resulting in multiple fractions. As used, herein, the term "a saponin fraction from *Quillaja saponaria* Molina" is used generically to describe a semi-purified or defined saponin fraction of *Quillaja saponaria* or a substantially pure fraction thereof.

Saponin Fractions

Several approaches for producing saponin fractions are suitable. Fractions A, B, and C are described in U.S. Pat. No. 6,352,697 and may be prepared as follows. A lipophilic fraction from Quil A, a crude aqueous *Quillaja saponaria* Molina extract, is separated by chromatography and eluted with 70% acetonitrile in water to recover the lipophilic fraction. This lipophilic fraction is then separated by semipreparative HPLC with elution using a gradient of from 25% to 60% acetonitrile in acidic water. The fraction referred to herein as "Fraction A" or "QH-A" is, or corresponds to, the fraction, which is eluted at approximately 39% acetonitrile. The fraction referred to herein as "Fraction B" or "QH-B" is, or corresponds to, the fraction, which is eluted at approximately 47% acetonitrile. The fraction referred to herein as "Fraction C" or "QH-C" is, or corresponds to, the fraction, which is eluted at approximately 49% acetonitrile. Additional information regarding purification of Fractions is found in U.S. Pat. No. 5,057,540. When prepared as described herein, Fractions A, B and C of *Quillaja saponaria* Molina each represent groups or families of chemically closely related molecules with definable properties. The chromatographic conditions under which they are obtained are such that the batch-to-batch reproducibility in terms of elution profile and biological activity is highly consistent.

Other saponin fractions have been described. Fractions B3, B4 and B4b are described in EP 0436620. Fractions QA1-QA22 are described EP03632279 B2, Q-VAC (Nor-Feed, AS Denmark), *Quillaja saponaria* Molina Spikoside (Isconova AB, Ultunaallén 2B, 756 51 Uppsala, Sweden). Fractions QA-1, QA-2, QA-3, QA-4, QA-5, QA-6, QA-7, QA-8, QA-9, QA-10, QA-11, QA-12, QA-13, QA-14, QA-15, QA-16, QA-17, QA-18, QA-19, QA-20, QA-21, and QA-22 of EP 0 3632 279 B2, especially QA-7, QA-17, QA-18, and QA-21 may be used. They are obtained as described in EP 0 3632 279 B2, especially at page 6 and in Example 1 on page 8 and 9.

The saponin fractions described herein and used for forming adjuvants are often substantially pure fractions; that is, the fractions are substantially free of the presence of contamination from other materials. In particular aspects, a substantially pure saponin fraction may contain up to 40% by weight, up to 30% by weight, up to 25% by weight, up to 20% by weight, up to 15% by weight, up to 10% by weight, up to 7% by weight, up to 5% by weight, up to 2% by weight, up to 1% by weight, up to 0.5% by weight, or up to 0.1% by weight of other compounds such as other saponins or other adjuvant materials.

ISCOM Structures

Saponin fractions may be administered in the form of a cage-like particle referred to as an ISCOM (Immune Stimulating COMplex). ISCOMs may be prepared as described in EP0109942B1, EP0242380B1 and EP0180546 B1. In particular embodiments a transport and/or a passenger antigen may be used, as described in EP 9600647-3 (PCT/SE97/00289).

Matrix Adjuvants

In some aspects, the ISCOM is an ISCOM matrix complex. An ISCOM matrix complex comprises at least one saponin fraction and a lipid. The lipid is at least a sterol, such as cholesterol. In particular aspects, the ISCOM matrix complex also contains a phospholipid. The ISCOM matrix complexes may also contain one or more other immuno-modulatory (adjuvant-active) substances, not necessarily a glycoside, and may be produced as described in EP0436620B 1.

In other aspects, the ISCOM is an ISCOM complex. An ISCOM complex contains at least one saponin, at least one lipid, and at least one kind of antigen or epitope. The ISCOM complex contains antigen associated by detergent treatment such that that a portion of the antigen integrates into the particle. In contrast, ISCOM matrix is formulated as an admixture with antigen and the association between ISCOM matrix particles and antigen is mediated by electrostatic and/or hydrophobic interactions.

According to one embodiment, the saponin fraction integrated into an ISCOM matrix complex or an ISCOM complex, or at least one additional adjuvant, which also is integrated into the ISCOM or ISCOM matrix complex or mixed therewith, is selected from fraction A, fraction B, or fraction C of *Quillaja saponaria*, a semipurified preparation of *Quillaja saponaria*, a purified preparation of *Quillaja saponaria*, or any purified sub-fraction e.g., QA 1-21.

In particular aspects, each ISCOM particle may contain at least two saponin fractions. Any combinations of weight % of different saponin fractions may be used. Any combination of weight % of any two fractions may be used. For example, the particle may contain any weight % of fraction A and any weight % of another saponin fraction, such as a crude saponin fraction or fraction C, respectively. Accordingly, in particular aspects, each ISCOM matrix particle or each ISCOM complex particle may contain from 0.1 to 99.9 by weight, 5 to 95% by weight, 10 to 90% by weight 15 to 85% by weight, 20 to 80% by weight, 25 to 75% by weight, 30 to 70% by weight, 35 to 65% by weight, 40 to 60% by weight, 45 to 55% by weight, 40 to 60% by weight, or 50% by weight of one saponin fraction, e.g. fraction A and the rest up to 100% in each case of another e.g. any crude fraction or any other faction e.g. fraction C. The weight is calculated as the total weight of the saponin fractions. Examples of ISCOM matrix complex and ISCOM complex adjuvants are disclosed in U.S Published Application No. 2013/0129770.

In particular embodiments, the ISCOM matrix or ISCOM complex comprises from 5-99% by weight of one fraction, e.g. fraction A and the rest up to 100% of weight of another fraction e.g. a crude saponin fraction or fraction C. The weight is calculated as the total weight of the saponin fractions.

In another embodiment, the ISCOM matrix or ISCOM complex comprises from 40% to 99% by weight of one fraction, e.g. fraction A and from 1% to 60% by weight of another fraction, e.g. a crude saponin fraction or fraction C. The weight is calculated as the total weight of the saponin fractions.

In yet another embodiment, the ISCOM matrix or ISCOM complex comprises from 70% to 95% by weight of one fraction e.g., fraction A, and from 30% to 5% by weight of another fraction, e.g., a crude saponin fraction, or fraction C. The weight is calculated as the total weight of the saponin fractions. In other embodiments, the saponin fraction from *Quillaja saponaria* Molina is selected from any one of QA 1-21.

In addition to particles containing mixtures of saponin fractions, ISCOM matrix particles and ISCOM complex particles may each be formed using only one saponin fraction. Compositions disclosed herein may contain multiple particles wherein each particle contains only one saponin fraction. That is, certain compositions may contain one or more different types of ISCOM-matrix complexes particles and/or one or more different types of ISCOM complexes particles, where each individual particle contains one saponin fraction from *Quillaja saponaria* Molina, wherein the saponin fraction in one complex is different from the saponin fraction in the other complex particles.

In particular aspects, one type of saponin fraction or a crude saponin fraction may be integrated into one ISCOM matrix complex or particle and another type of substantially pure saponin fraction, or a crude saponin fraction, may be integrated into another ISCOM matrix complex or particle. A composition or vaccine may comprise at least two types of complexes or particles each type having one type of saponins integrated into physically different particles.

In the compositions, mixtures of ISCOM matrix complex particles and/or ISCOM complex particles may be used in which one saponin fraction Quillaja saponaria Molina and another saponin fraction Quillaja saponaria Molina are separately incorporated into different ISCOM matrix complex particles and/or ISCOM complex particles.

The ISCOM matrix or ISCOM complex particles, which each have one saponin fraction, may be present in composition at any combination of weight %. In particular aspects, a composition may contain 0.1% to 99.9% by weight, 5% to 95% by weight, 10% to 90% by weight, 15% to 85% by weight, 20% to 80% by weight, 25% to 75% by weight, 30% to 70% by weight, 35% to 65% by weight, 40% to 60% by weight, 45% to 55% by weight, 40 to 60% by weight, or 50% by weight, of an ISCOM matrix or complex containing a first saponin fraction with the remaining portion made up by an ISCOM matrix or complex containing a different saponin fraction. In some aspects, the remaining portion is one or more ISCOM matrix or complexes where each matrix or complex particle contains only one saponin fraction. In other aspects, the ISCOM matrix or complex particles may contain more than one saponin fraction.

In particular compositions, the saponin fraction in a first ISCOM matrix or ISCOM complex particle is Fraction A and the saponin fraction in a second ISCOM matrix or ISCOM complex particle is Fraction C.

Preferred compositions comprise a first ISCOM matrix containing Fraction A and a second ISCOM matrix containing Fraction C, wherein the Fraction A ISCOM matrix constitutes about 70% per weight of the total saponin adjuvant, and the Fraction C ISCOM matrix constitutes about 30% per weight of the total saponin adjuvant. In another preferred composition, the Fraction A ISCOM matrix constitutes about 85% per weight of the total saponin adjuvant, and the Fraction C ISCOM matrix constitutes about 15% per weight of the total saponin adjuvant. Thus, in certain compositions, the Fraction A ISCOM matrix is present in a range of about 70% to about 85%, and Fraction C ISCOM matrix is present in a range of about 15% to about 30%, of the total weight amount of saponin adjuvant in the composition. Exemplary QS-7 and QS-21 fractions, their production and their use is described in U.S Pat. Nos. 5,057,540; 6,231,859; 6,352,697; 6,524,584; 6,846,489; 7,776,343, and 8,173,141, which are incorporated by reference for those disclosures.

Other Adjuvants

In some, compositions other adjuvants may be used in addition or as an alternative. The inclusion of any adjuvant described in Vogel et al., "A Compendium of Vaccine Adjuvants and Excipients (2nd Edition)," herein incorporated by reference in its entirety for all purposes, is envisioned within the scope of this disclosure. Other adjuvants include complete Freund's adjuvant (a non-specific stimulator of the immune response containing killed Mycobacterium tuberculosis), incomplete Freund's adjuvants and aluminum hydroxide adjuvant. Other adjuvants comprise GMCSP, BCG, MDP compounds, such as thur-MDP and nor-MDP, CGP (MTP-PE), lipid A, and monophosphoryl lipid A (MPL), MF-59, RIBI, which contains three components extracted from bacteria, MPL, trehalose dimycolate (TDM) and cell wall skeleton (CWS) in a 2% squalene/Tween® 80 emulsion. In some embodiments, the adjuvant may be a paucilamellar lipid vesicle; for example, Novasomes®. Novasomes® are paucilamellar nonphospholipid vesicles ranging from about 100 nm to about 500 nm. They comprise Brij 72, cholesterol, oleic acid and squalene. Novasomes have been shown to be an effective adjuvant (see, U.S. Pat. Nos. 5,629,021, 6,387,373, and 4,911,928.

Administration and Dosage

Compositions disclosed herein may be administered via a systemic route or a mucosal route or a transdermal route or directly into a specific tissue. As used herein, the term "systemic administration" includes parenteral routes of administration. In particular, parenteral administration includes subcutaneous, intraperitoneal, intravenous, intraarterial, intramuscular, or intrasternal injection, intravenous, or kidney dialytic infusion techniques. Typically, the systemic, parenteral administration is intramuscular injection. As used herein, the term "mucosal administration" includes oral, intranasal, intravaginal, intra-rectal, intra-tracheal, intestinal and ophthalmic administration. Preferably, administration is intramuscular.

Compositions may be administered on a single dose schedule or a multiple dose schedule. Multiple doses may be used in a primary immunization schedule or in a booster immunization schedule. In a multiple dose schedule the various doses may be given by the same or different routes e.g., a parenteral prime and mucosal boost, a mucosal prime and parenteral boost, etc. In some aspects, a follow-on boost dose is administered about 2 weeks, about 3 weeks, about 4 weeks, about 5 weeks, or about 6 weeks after the prior dose. Typically, however, the compositions disclosed herein are administered only once yet still provide a protective immune response.

In some embodiments, the dose, as measured in µg, may be the total weight of the dose including the solute, or the weight of the RSV F nanoparticles, or the weight of the RSV F protein. Dose is measured using protein concentration assay either A280 or ELISA.

The dose of antigen, including for pediatric administration, may be in the range of about 30 µg to about 300 µg, about 90 µg to about 270 µg, about 100 µg to about 160 µg, about 110 µg to about 150 µg, about 120 µg to about 140 µg, or about 140 µg to about 160 µg. In particular embodiments, the dose is about 120 µg, administered with alum. In some aspects, a pediatric dose may be in the range of about 30 µg to about 90 µg. Certain populations may be administered with or without adjuvants. For example, when administered to seniors, preferably there is no alum. In certain aspects, compositions may be free of added adjuvant. In such circumstances, the dose may be increased by about 10%.

In some embodiments, the dose may be administered in a volume of about 0.1 mL to about 1.5 mL, about 0.3 mL to about 1.0 mL, about 0.4 mL to about 0.6 mL, or about 0.5 mL, which is a typical amount.

In particular embodiments for an RSV vaccine, the dose may comprise an RSV F protein concentration of about 175 µg/mL to about 325 µg/mL, about 200 µg/mL to about 300 µg/mL, about 220 µg/mL to about 280 µg/mL, or about 240 µg/mL to about 260 µg/mL.

All patents, patent applications, references, and journal articles cited in this disclosure are expressly incorporated herein by reference in their entireties for all purposes.

EXAMPLES

Example 1

Expression and Purification of an RSV F Protein

An RSV F protein having SEQ ID NO: 8 was expressed in a baculovirus expression system and recombinant plaques expressing the RSV F protein were picked and confirmed. The recombinant virus was then amplified by infection of Sf9 insect cells. A culture of insect cells was infected at ~3 MOI (Multiplicity of infection=virus ffu or pfu/cell) with baculovirus. The culture and supernatant were harvested 48-72 hrs post-infection. The crude cell harvest, approximately 30 mL, was clarified by centrifugation for 15 minutes at approximately 800×g. The resulting crude cell harvests containing the RSV F protein were purified as described below.

Non-ionic surfactant Tergitol® NP-9 (Nonylphenol Ethoxylate) was used in the membrane protein extraction protocol. NP-9 was Crude extraction was further purified by passing through anion exchange chromatography, lentil lectin affinity/HIC and cation exchange chromatography. The washed cells were lysed by detergent treatment and then subjected to low pH treatment which leads to precipitation of BV and Sf9 host cell DNA and protein. The neutralized low pH treatment lysate is clarified and further purified on anion exchange and affinity chromatography before a second low pH treatment is performed.

Affinity chromatography was used to remove Sf9/BV proteins, DNA and NP-9, as well as concentrate the RSV F protein. Briefly, lentil lectin is a metalloprotein containing calcium and manganese, which reversibly binds polysaccharides and glycosylated proteins containing glucose or mannose. The RSV F-containing anion exchange flow through fraction was loaded onto the lentil lectin affinity chromatography resin (Capto Lentil Lectin, GE Healthcare). The glycosylated RSV F protein selectively binds to the resin while non-glycosylated proteins and DNA are removed in the column flow through. Weakly bound glycoproteins were removed by buffers containing high salt and low molar concentration of methyl alpha-D-mannopyranoside (MMP).

In addition, the column washes were also used to detergent exchange the NP-9 detergent with the surfactant polysorbate 80 (PS80). To perform the detergent exchange, the column was incubated with 0.1% PS80 after binding of the RSV F glycoprotein to the lentil lectin column. The RSV F protein was eluted from the lentil lectin column with a high concentration of MMP. After elution, the RSV F protein trimers are assembled into micelle nanoparticles composed of RSV F protein trimers and PS80 contained in a detergent core. After detergent exchange there was a low pH inactivation step followed by incubation on a sulfate column in the presence of buffer with PS80 at 0.1%.

The eluted material was diluted in a solution containing PS80 adequate to provide a Drug Substance (DS) for bulk storage with a molar ratio of PS80:RSV F protein of about 50. The adequate composition of the DS was achieved by combining the RSV F nanoparticles in a solution comprising phosphate buffer at 22 mM sodium phosphate, 0.03% PS80, and a pH of 6.2. At each step during and after detergent exchange, the antigen to PS80 ratio in the composition was maintained at a molar ratio between 35 and 60. The molar ratio was calculated using the PS80 concentration and RSV F concentration, as measured by ELISA/A280, and their respective molecular weights. The molecular weight of PS80 is 1310 and for RSV is 65 kD.

Example 2

Preparation of a Vaccine Composition

To provide nanoparticles for an administered vaccine product, the Drug Substance was diluted into a Drug Product, with a PS80:RSV protein molar ratio of about 50. Drug Substance was thawed, diluted and filled into glass vials or pre-filled syringes for storage at 2-8° C. prior to administration. The nanoparticles bound to alum adjuvant. The alum adjuvant was added and mixed to ensure about 95% of the nanoparticles are bound to the alum is bound, meaning about 0.4 mg per 120 µg dose of RSV F nanoparticle in a 0.5 mL volume.

Example 3

Characterization of RSV F Glycoproteins in Nanoparticles

Figure 3:
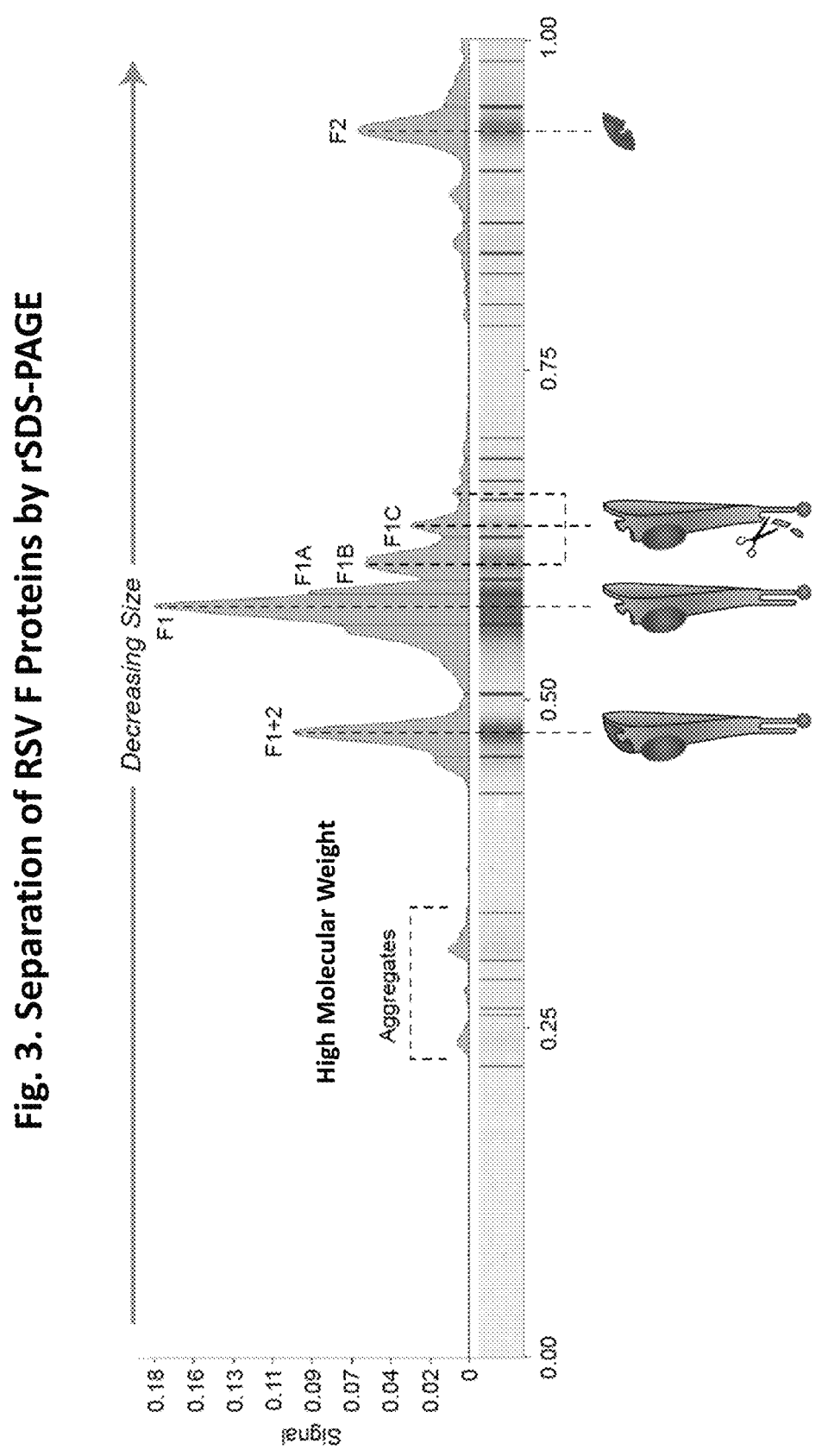

We analyzed protein structure in the nanoparticles by various analytical techniques. FIG. 3 shows that the highest peak of RSV F protein produced contains palmitoleic acid (Peak 2A). The second largest peak contains palmitic acid (Peak 2B). Residual peaks were obtained lacking either fatty acid (Peak 5) and in soluble form (Peak 1). Analysis on SDS-PAGE gel separated additional variants, including the F1+2 protein, F1, F1A, F1B, and F1C portions as well as F2. See FIG. 4. Analysis of the peptide structure was performed using peptide mapping. See FIG. 5. To assess the glycan structures on the RSV F glycoproteins, HPLC-FLD was performed. The results demonstrated that the major glycan structures are fucosylated.

Example 4

Examination of RSV F Nanoparticles by Electron Microscopy

Nanoparticles as prepared in Example 1 were visualized by electron microscope. The results confirmed formation of nanoparticles containing the RSV F glycoproteins surrounding the detergent core. The precise composition of the detergent core remains unclear. FIG. 6 illustrates the types of nanoparticles obtained. The RSV F proteins maintained trimer structure even after the detergent exchange. Several types of nanoparticles were obtained that vary in the number of trimers/nanoparticle and in morphology. FIG. 6 shows that multiple trimers can be found around the detergent core. In the highlighted portion seven trimers are shown surrounding the detergent. The main panel in FIG. 6 illustrates the range of trimers around the detergent core that are produced. The cartoon structure of the RSV F protein trimer in the bottom left panel illustrates the orientation of the trimers with the bottom portion associated with to the detergent core, facilitated by the fatty acids attached to each RSV F glycoprotein.

Example 5

Particle Characterization of RSV F Nanoparticles

Dynamic light scattering (DLS) was utilized to determine the size distribution profile of the nanoparticles by measuring changes in light scattering patterns of particles in Brownian motion. Nanoparticle sizes were able to be determined as a linear function of the concentration of ionic detergent versus the concentration of the RSV F nanoparticles (see FIGS. 7 and 8).

Analytical ultracentrifugation (AUC) was used to measure the progression of the sample concentration versus the axis of rotation profile as a result of the applied centrifugal field. FIG. 8 reveals that predominantly two shapes of nanoparticles emerge based upon the concentration of nanoparticles present. Nanoparticle types obtained include monomeric and dimeric anisotropic rods, and spherical oligomers. Structure intermediates between these two nanoparticle types form at concentrations between those that result in anisotropic rods and spherical oligomers. FIG. 9 shows that nanoparticle type can be controlled by modulating the concentration of the RSV F protein, with higher concentrations (1 mg/mL) resulting in a predominant population of spherical oligomers, while lower concentrations (0.22 mg/mL) resulting in predominant populations of monomeric/dimeric anisotropic rods. These data illustrate that the detergent amounts and the RSV F concentration can be controlled to arrive at nanoparticle have a particular diameter (z-ave) from 20 nm to 60 nm.

Example 6

Enhanced Stability of Nanoparticles: Molecular Characterization

The five stressors utilized were thermal stress at 50° C. with time points at 48 hours, one week, and two weeks; low pH (3.7 at 25° C.) with time points at 48 hours, four days, and one week; high pH (10 at 25° C.) with time points at 24 hours, 48 hours, and one week; hydrogen peroxide oxidation at 25° C. with time points at 12 hours, 48 hours, and one week; and physical agitation at 25° C. with time points at four hours, 24 hours, and one week.

After the various stress treatments differences in the primary structure were assessed. FIG. 10 shows a comparison of how particular regions survived stress relative to a control. The data show that the nanoparticles have excellent stability across the entire protein, and that only the especially harsh oxidation test using hydrogen peroxide was able to degrade the protein to any particular extent. However, even that treatment did not reduce the structural integrity of antigenic site II, which is the target of palivizumab. Indeed, even with the harsh oxidation the RSV-F protein only deteriorated structurally at positions 63-82, 237-258, and 360-364. Accordingly, even after being subjected to harsh stress, the nanoparticles remained substantially intact.

FIG. 11 further quantifies nanoparticle stability regarding antigenic site II. The data show that in response to each of thermal stress, low pH, high pH, and agitation that the antigenic site II remained intact to the extent of 90% in each of the samples.

Example 7

Enhanced Stability of Nanoparticles: Maintained Immunogenic Properties

The stressed vaccine compositions described in Example 6 were evaluated for immunogenicity in a murine model. The vaccines were administered to mice via two intramuscular injections across a range of RSV F doses consisting of 0.15, 0.45, 1.3, 4, and 12 µg/mL of RSV F protein. RSV F composition stressed under the following conditions, accompanied by a control (thawed from storage at −70° C.), were administered: 50° C. for two weeks, the pH 10 at 25° C. for one week, 0.5% hydrogen peroxide at 25° C. for one week.

The immune response was evaluated with regard to the presence of anti-RSV F IgG, PCA titers, and the presence of RSV A neutralizing antibodies. The physical and chemical stressors did not significantly affect, in vivo, the RSV F protein immunogenicity. The stressed samples induced similar anti-RSV F IgG antibody titers and comparable functional PCA and RSV A neutralizing titers to those of the unstressed RSV F nanoparticle vaccine composition control. (See FIGS. 12A-12D). Collectively, these forced degradation studies indicate that even when exposed to severe environmental stresses the nanoparticles induce potent immune responses.

Example 8

Protease Resistance of Nanoparticles

Formation of nanoparticles with improved stability is dependent on the amount of PS80 used to produce the nanoparticle. FIG. 13 illustrates a dramatic improvement in stability up to 18 months when nanoparticles were formed with 0.03% PS80 (i.e. a molar ratio of 55) compared to 0.015% (i.e. a molar ratio of 27). The left panel shows an SDS-PAGE of nanoparticles produced at the two concentrations at time zero. The data shows that similar results to a reference preparation were obtained for both the nanoparticle preparation. Specifically, both show robust signals for F1, and F1+2 illustrating essentially no degradation. Aliquots of each preparation were then incubated at 4° C. for 18 months and then run again on SDS-PAGE. The data on the right panel as well as the table illustrates that nanoparticles containing only 0.015% in the particle resulted in truncated F1. In contrast, nanoparticles prepared with 0.03% in the particle illustrated excellent resistance to protease. We think that maintaining a correct ratio of detergent and protein results in a nanoparticle having an orientation of glycoprotein with protease-sensitive portions protected, possibly via some steric hindrance mechanism. We further observed that concentrations of PS80 at or above 0.06% increased aggregate formation. Taken together the data show that optimum PS80 levels are about 0.03% to about 0.05% for nanoparticle stability.

Example 9

Purification of HA Nanoparticles

The TMAE column was pre-equilibrated with Buffer A1 (25 mM Tris pH7.5, 70 mM NaCl, 0.02% NP9 for 0.5 CV at Flow Rate: 91.7 cm 30 mL/min. Sample was loaded at 20 mL/min (25 min resident time) and then washed with EQ buffer A1 (25 mM Tris pH7.5, 70 mM NaCl, 0.02% NP-9). The purified sample was then eluted using 1.25 CV 15% Buffer B (25 mM Tris pH8, 1M NaCl, 0.02% NP9) followed 1.1 cv 100%B. A representative chromatogram is shown in FIG. 18B. The product from the TMAE column was applied to a Lentil lectin affinity chromatography column pre-equilibrated with Buffer A11: 25 mM sodium phosphate pH6.0, 10 mM NaCl, 0.05% PS80 for 3 CV (Flow Rate: 147 cm/h 13 mL/min). Sample was loaded at 9.4 min resident time—6.5 mL/min-73.5 cm/h. After loading, high-salt washing was performed with 3 CV Buffer A12 (25 mM sodium phosphate pH6.0, 500 mM NaCl, 0.5% NP-9). After the first wash, detergent exchange was performed by washing the column with 6CV of Buffer A11 (25 mM sodium phosphate pH6.0, 10 mM NaCl, 0.05% PS80). Nanoparticles containing PS80 were then eluted with 100% B for 3 CV, B1: Buffer B: 25 mM sodium phosphate pH6.0, 10 mM NaCl, 0.05% PS80, 500 mM Methyl-alpha-D-Mannopyronoside. A representative chromatogram trace is shown in FIG. 18C. The product from the lentil lectin column was applied to a sulfate column with 3 CV Buffer A1 (25 mM sodium phosphate pH6.0, 10 mM NaCl, 0.05% PS80), washed with 2 CV Buffer A1 then eluted with 100% Buffer B1 (25 mM sodium phosphate pH 7.5, 500 mM NaCl, 0.05% PS80). The eluted product was then combined 1:1 with 50 mM sodium phosphate pH 9 and sterile filtered. The final product was at pH 7.2. A chromatogram is shown in FIG. 18D. FIG. 18E provides a gel and western blot of various products obtained during the purification process from the TMAE and LL columns. FIG. 18F shows eluate from the SO3− column.

Example 10

Analysis of HA Nanoparticle Purity

HA nanoparticles were prepared as outlined in FIGS. 17 and 18. We measured purity of multiple HA nanoparticle preparations using HA sequences derived from various strains (A/New Hampshire/1/2015, A/Switzerland/9715293/2013, A/Hong Kong/4801/2014, B/Phuket/3073/2013, and B/Brisbane/60/2008). The data showed that high purity preparations were obtained in all cases. Analysis by gel densitometry showed purity above 93% and ranging from 93% to 97%. See FIGS. 19A to 19H. We also analyzed purity of the three A subtype strains by RP-HPLC and found that purity was 83% to 85%. See FIG. 19I. In addition, we measured nanoparticle size. The nanoparticles showed a diameter between 22.0 nm and 29.9 nm. See FIG. 19.

Example 11

Analysis of HA Ultrastructure

Electron microscopy was performed to assess the structure of the HA nanoparticles. We found that, like other glycoproteins, the HA glycoproteins formed trimers that were associated with the PS80 detergent core. Each detergent core contained multiple trimers. See FIG. 20. Using cryo-EM 2D class averaging we docked the HA trimers onto nanoparticles. FIG. 21A shows results of these in silico docking experiments. The upper panels show the fit for an HA trimer onto a first nanoparticle. The lower panel shows the fit onto another stalk of a nanoparticle For comparison, docking on VLPs was performed. The VLPs contain a lipid bilayer into which the HA protein is anchored. See FIG. 21B. The center panels show HA protein structure overlaid onto the stalk emanating from the bilayer. The right hand upper and lower panels shows free HA EM micrograph looking straight down onto the HA trimers, alone (upper panel) and with the corresponding HA structure overlaid on the EM picture (lower panel).

Example 12

Immunogenicity Analysis of HA Nanoparticles Co-Administered with RSV F Nanoparticles Immunogenicity of nanoparticles in vaccines in a mouse model was assessed. A combination of nanoparticles containing two antigens (influenza HA protein from A/Switzerland H3 sub-type and RSV F protein) was administered. Each nanoparticle was also administered separately. The vaccines were administered alone or with adjuvants AlPO$_4$ or Matrix M saponin adjuvant. FIG. 22 shows the treatments administered to groups 1-10. Group 10, the control, was not treated. Treatments were administered at Days 0 and 21. We measured HAI against heterologous and homologous challenges. See FIGS. 23A and 23B. FIG. 23A shows that Matrix-adjuvanted HA nanoparticles stimulated particularly robust responses against homologous challenge. FIG. 23B shows that a robust HAI response was also obtained against heterologous influenza strain A/Texas/50/2012 when administered with Matrix M, and this response was not affected by co-administration with the RSV F nanoparticle.

We also measured the ability of the RSV F nanoparticle component to induce formation of antibodies that compete with Palivizumab. FIG. 23C. The data shows that RSV F nanoparticles administered alone and with either AlPO$_4$ or Matrix M induced substantial antibody titer of 80 μg/mL to around 700 μg/mL. When both RSV F and influenza nanoparticle were induced a lowered response of around 20 μg/mL to 40 μg/mL was obtained in the absence of adjuvant or with AlPO$_4$. With Matrix M, however, the RSV F response was robust when administered alone or in combination with the HA nanoparticle. Measurement of RSV neutralizing antibodies showed a similar pattern to PCA antibodies. See FIG. 23D.

In addition, to antibody responses, we measured T cell responses induced by the vaccines against RSV and against influenza A/Switzerland/9715293/2013. FIGS. 23E and 23F. The data show robust induction of IFNγ against both targets when Matrix M was used as adjuvant.

Example 13

Trypsin-Resistant Nanoparticle Production

Certain approaches to producing influenza can result in trypsin sensitivity of the HA protein, which alters folding leading to reduced immunogencity and stability of vaccine formulations. To produce a trypsin-resistant HA nanoparticle we used a detergent exchange approach employing neutral pH buffers. See FIGS. 24A-C.

SF9 cells were infected with HA nanoparticle BV vectors MOI=0.1; 3E6 cells/ml. Cells were harvested on day 3 and lysed with buffered 0.5% NP9; pH 7.5. We next performed anion exchange chromatography (Fractogel TMAE; EMD). FIG. 24B shows an illustrative chromatogram. The flow through contains the HA. Following anion exchange column, detergent exchange was performed using a Capto Lentil Lectin column (GE) using a high salt/detergent wash containing 0.01% PS80; pH 7.2 and eluted also in 0.01% PS80. FIG. 24C shows an illustrative chromatogram for the detergent exchange process. Finally, we used Tangential flow filtration (TFF): 50 kD MWCO filter; pH 7.2 to produce the bulk drug substance (BDS) used to store the product. At the TFF stage and afterwards PS80 was maintained in 0.05%, in a buffer with pH 7.2.

Example 14

Trypsin-Resistant Nanoparticle Analysis

HA nanoparticles from various strains using the process described in Example 13 and production was assessed. FIG. 25A shows that yield of strain A/New Hampshire/1/2015 (H1N1) was about 20 mg/L. B strain influenza nanoparticles also had excellent productivity and purity. FIG. 25B shows yield and purity of a B strain, B/Brisbane/60/08 HA, assessed as the bulk drug substance. Yield was about 30 mg/L. FIG. 25C shows yield of an H3N2 strain showing the process gave about 96% purity and a yield of about 20 mg/L.

Thermodynamic Stability Analysis

FIG. 25D provides a thermodynamic profile comparison between HA nanoparticles produced using the trypsin-resistant neutral pH approach in Example 13 versus approaches using low pH purifications steps, such shown in FIG. 18. The Differential Scanning calorimetry (DSC) method was used to determine the thermodynamic profile of macromolecules in solution, specifically, by measuring the difference in heat energy uptake between a sample solution and appropriate reference (buffer/solvent) by varying the temperature in a controlled manner. In relation to Flu HA samples, DSC has allowed us to visualize transition midpoints (Tm's), defined as temperatures where half the protein is denatured/unfolded and half in the native/folded state.

Additionally, DSC has given us information regarding protein conformation and the estimated stability profiles can be roughly extrapolated for each HA strain undergoing differing process conditions. The difference between HA purified by a process step that exposed the HA to pH 6.0 during purification vs HA purified via an alternate step (e.g. MMC resin or TFF membrane) is shown using the B/Brisbane HA as an example. The data shows Tm values are higher in intensity, show a shift to higher onset of Tm for the main peak and sharper peaks suggesting proper folding of the HA when purified by the alternate step. The data for the HA exposed to pH 6.0, however shows Tm values that have either greatly diminished in intensity, show earlier onset for the Tm of the main peak, have significantly broadened peaks displaying slow asymmetrical unfolding, and/or contain misfolded proteins and aggregation peaks at higher temperatures. Similar profiles were observed for the other strains (A/Cal, A/Hong Kong, A/ New Hampshire). While low pH gives rise to nanoparticles as discussed above, and while they may have certain application, based on these three observations in the DSC data, we conclude that the alternate process steps/conditions using neutral pH yield HA protein with significantly better thermodynamic and potentially improved stability profiles.

Trypsin Resistance

FIG. 26 illustrates the improved trypsin resistance obtained when nanoparticles were produced as described in Example 13. To test trypsin sensitivity, HA samples were diluted to 0.24 mg/mL, incubated with decreasing trypsin at 37° C. for 60 min, Trypsin inhibitor was added to stop the digestion, and then SDS-PAGE analysis was performed. Comparing the left panel and right panel of FIG. 26 illustrates the enhanced trypsin resistance. Purified HA nanoparticles made in SD insect cells are HA0. When exposed to trypsin HA0 is cleaved to HA1 and HA2 at Arg AA344 in H1. Correctly folded HA trimers will resist further cleavage when incubated with increasing concentrations of trypsin. Neutral pH purified B/Brisbane/60/08 is resistant to trypsin and is correctly folded (left panel). Acid pH purified B/Brisbane/60/08 HA1 is trypsin sensitive and misfolded (right panel). FIGS. 26B and 26C illustrate that trypsin resistance is achieved for a variety of strains. FIG. 26B shows strain A/Hong Kong/4801/2014. Neutral pH purified A/Hong Kong/4801/2014 (H3N2) is resistant to trypsin and thus is correctly folded (left panel). Acid pH purified A/Hong Kong/4801/2014 (H3N2) HA1 is trypsin sensitive and not correctly folded (right panel).

Similar data was obtained with A/New Hampshire/1/2015, and H1N1 sub-type. Like the other strains, acid-purified H1N1 was misfolded (data not shown) whereas the neutral pH purified protein was trypsin-resistant and correctly folded.

Comparison with Commercial Flu Vaccines

Previous approaches to producing recombinant influenza vaccines have not met with widespread success. To investigate whether egg-produced or recombinantly-produced flu vaccine exhibited trypsin-resistance we compared trypsin-sensitivity in egg-produced and recombinant vaccines (Fluzone® and Flublok®, respectively) using the same protocols as above. Specifically, undiluted vaccines were incubated with varying amounts of trypsin at 37° C. for 60 min, then trypsin inhibitor was added, 2× Sample Buffer was added, and heated at 70° C. for 10 min before SDS page.

We found that the egg-produced variant showed trypsin resistance. Specifically, commercial trivalent egg-derived high dose Fluzone vaccine, which is cleaved to HA1 and HA2 and HA1, is resistant to trypsin digestion. In contrast, commercial trivalent recombinant HA Flublok vaccine when exposed to trypsin is converted to HA1 and HA2 and HAI polypeptides, and is sensitive to trypsin. FIG. 27 (right panel). These results demonstrate at least one of the strains is denatured possibly due to purification at pH 5.89 (See for example, Wang et al. Vaccine. 24 (2006); 2176.).

Thus, recombinant influenza vaccines that are commercially available suffer from misfolding that may arise from production under low pH conditions and likely explains, at least in part, their poor immunogenicity and the lack of widespread adoption to date.

In contrast the methods disclosed herein confirm that purifying HA nanoparticles using buffers of at least pH7.0 reduces or eliminates misfolding of the HA protein that occurs when HA proteins are exposed to acid conditions during purification.

Example 15

Construction of Ebola Virus Glycoprotein Nanoparticles

The wild-type full-length, unmodified EBOV glycoprotein (GP) gene from the 2014 Makona Ebola virus was cloned into recombinant baculovirus and expressed in *Spodoptera frugiperda* Sf9 insect cells. After expression, the N-terminal signal peptide is cleaved and the mature protein is purified and formed into nanoparticles. Purified Ebola virus GP (EBOV/Mak GP) nanoparticles are composed of multiple GP trimers assembled into spherical particles 36±4 nm (as measured by dynamic light scattering). Recombinant GP nanoparticles have a core region which contains the glycoprotein 2 (GP2) 'fusion subunits' with 2-9 or up to 15 "chalice-like" glycoprotein 1 (GP1) trimers 'attachment subunits' extending outward.

For co-administering Matrix-M, a saponin-based adjuvant consisting of two populations of individually formed 40 nm sized Matrix particles, was used. The Matrix-M used was 85% Matrix-A and 15% Matrix-C. The Matrix particles were formed by formulating purified saponin from *Quillaja saponaria* Molina with cholesterol and phospholipid.

Example 16

Immunization and Protocols

Balb/c mice (6-8 weeks old; Harlan Laboratories Inc., Frederick, Md.) were housed in groups of 10 and immunized by subcutaneous (SC) or intramuscular (IM) administration. Phosphate buffered saline (PBS) was used as placebo. Blood samples for serum were collected via the retro-orbital route. Prior to blood collection, animals were anesthetized with isoflurane.

Mice (n=10 per group) were immunized by IM administration (50 µl injection volume) at Days 0 and 21 with EBOV/Mak GP alone or mixed with $AlPO_4$ (50 µg) or Matrix-M adjuvant (2.5 µg or 5 µg). Blood samples were collected at Days 0, 14, 21, 28 and 60. Spleen and bone marrow samples were collected at days 28 and 60. Spleen and bone marrow samples were suspended in PBS containing 2% fetal bovine serum (FBS) for further preparation.

Serum samples from day 28 were evaluated for anti-EBOV/Mak neutralizing antibody responses at U.S. Army Medical Research Institute of Infectious Diseases, Fredrick, Md. using a pseudovirion neutralization reporter assay. A hantavirus pulmonary syndrome (HPS) DNA vaccine delivered using a spring-powered jet injector elicits a potent neutralizing antibody response in rabbits and nonhuman primates. Curr Gene Ther. 2014;14: 200-210. For this assay, the vesicular stomatitis virus G protein was removed and replaced with luciferase reporter. This VSV luciferase expressing core was pseudotyped using the plasmid pWRG/EBOV-Z76 (opt) that expresses the Zaire Ebola virus 1976 (Mayinga) GP. The plasmid used to provide the pseudotyping Ebola GP was pWRG/EBOV/Mak-Z76 (opt) expressing the Zaire Ebola virus 1976 (Mayinga) GP. PsVs were prepared in 293T cells. Mouse sera were heat-inactivated at 56° C. for 30 minutes and then an initial 1:20 dilution was prepared followed by five-fold serial dilutions in Eagle's Minimum Essential Medium (EMEM) (Life Technologies) supplemented with 10% (vol/vol) heat inactivated FBS, 100 IU/mL penicillin, and 100 µg/mL streptomycin (cEMEM). Ebola GP PsVs were diluted in cEMEM. An equal volume of PsVs solution containing $4\times10^3$ focus-forming units and 10% guinea pig complement (Cedarlane) was added to the sera dilutions for a final starting dilution of 1:40 and then incubated overnight at 4° C. Vero cell monolayers seeded in clear-bottom black 96-well plates (Corning) were infected with 50 µl of each PsVs-serum mixture and then incubated at 37° C. for an additional 18-24 hours. The medium was discarded, the cells were lysed, and luciferase substrate was added according to the Renilla Luciferase Assay System protocol (Promega #E2820). The flash luciferase signal was measured using a Tecan M200 microplate reader. Raw values were exported to GraphPad Prism version 6.04, where the data were baseline-corrected to the untreated PsVs signal. The data were fit to four parameter logistic nonlinear regression models using GraphPad Prism and then PsVNA 50% (PsVNA50) neutralization titers were interpolated from the curves for each sample. Each sample was analyzed in triplicate. The assay positive control was serum from a rabbit vaccinated three times with the pWRG/EBOV-Z76 (opt), a Zaire Ebola virus 1976 Mayinga GP DNA vaccine.

EBOV/Mak GP specific serum antibodies were quantitated by enzyme linked immunosorbent assay (ELISA). Briefly, NUNC MaxiSorp microtiter plates were coated with 2 µg/mL of EBOV/Mak GP (Novavax) overnight at 2-8° C. Unreacted surface was blocked with StartingBlock Blocking Buffer (Pierce) for one hour at room temperature (RT). The plates were reacted sequentially at RT with 5-fold serial dilutions of serum samples starting from 1:100 (two hours), goat anti-mouse IgG (or IgG1 and IgG2a) conjugated to horseradish peroxidase (HRP) (Southern Biotech) (one hour), peroxidase substrate 3,3,5,5-Tetramethylbenzidine (TMB) (Sigma) (ten minutes) and TMB Stop Buffer (Scy Tek Laboratories). The plates were washed three times with PBS/Tween (Quality Biologicals) before addition of the HRP conjugate and TMB reagent.

The plates were read at 450 nm in SpectraMax plus plate readers (Molecular Devices). SoftMax pro software (Molecular Devices) was used to fit concentration-responses to a 4-parameter fit curve. Antibody titers were defined as the reciprocal of the highest dilution in which there was a 50% maximum antibody binding ($EC_{50}$) response. If the serum IgG titer is out of the lower detection range, then a titer of <100 (starting dilution) was reported and a value of 50 assigned to the sample to calculate the group geometric mean titer (GMT). Mouse anti-EBOV/Mak GP monoclonal antibody (mAb) (4F3) from IBT Biosciences (Gaithersburg, Md.) was used as the positive control.

ELISPOT Assay, Assessing IFN-γ and EBOV/Mak GP-Specific IgG-Secreting Cells

Single cell suspensions were prepared from individual spleens by gently grinding the tissues using the plunger of a syringe. Single bone marrow cell suspension was prepared by flushing PBS containing 2% FBS through the bone using a syringe with a 21-gauge needle. Cells were washed twice with PBS containing 2% FBS and counted. IFN-γ ELISPOT assays were performed using mouse IFN-γ ELISPOT kits (eBioscience, San Diego, Calif.) according to the manufacturer's procedure. Briefly, anti-IFN-γ antibody (15 µg/ml in PBS) was used to coat ELISPOT plates (Millipore, Darmstadt, Germany) at 100 µl/well, overnight at 4° C. The plates were washed four times with PBS and blocked with RPMI1640 medium plus 5% FBS for 1-2 hours at room temperature. A total of $3\times10^5$ splenocytes in a volume of 200 µl were stimulated with pools of 15-mer EBOV GP peptides with 11 overlapping amino acids (2.5 µg/ml) covering the entire EBOV GP sequence. Phorbol myristic acetate (PMA) (50 ng/ml) plus ionomycin (200 ng/ml) was used as positive control and medium as negative control. Each stimulation condition was carried out in triplicate. Assay plates were incubated overnight at 37° C. in a 5% $CO_2$ incubator and the signals were developed based on manufacturer's instructions. Spots were counted and analyzed using an ELISPOT reader and Immunospot software (Cellular Technology, Ltd., Shaker Heights, Ohio). The Ebola-GP specific spot number was obtained by subtracting the background number in the medium controls from the GP-peptide stimulated wells. Data shown in the graph are the average of triplicate wells. To measure GP-specific IgG-secreting cells, ELISPOT plates were coated with EBOV/Mak GP (2.5 µg/ml in PBS) and incubated overnight at 4° C. Plates were washed and blocked as described above. Triplicates of $3-5\times10^5$ splenocytes or bone marrow cells per well were plated and the plates were incubated overnight at 37° C. On the second day the plates were washed, and goat anti-mouse IgG-HRP was added and incubated for 1.5 hours. Spots were developed and counted as described above. The average spot number from triplicate wells were calculated and presented.

Surface Staining for Cell Phenotypes and Intracellular Staining for Cytokines For surface staining, cells were first incubated with anti-CD16/32 antibody (clone 2.4 G2) to block the Fc receptor.

To characterize the germinal center cells, 1×10⁶ of fresh splenocytes were incubated at 4° C. for 30 min with a mixture of the following antibodies: B220-PerCP, CD19-APC, GL7-BV421, CD95-PE-Cy7 (BD Biosciences, CA) and the yellow LIVE/DEAD® dye (Life Technologies, NY). Cells were washed twice and suspended in PBS containing 2% FBS for analysis. To stain T follicular helper cells, 1×10⁶ fresh splenocytes were incubated with CXCR5-Biotin, washed two times, then incubated with a mixture of antibodies including CD3-BV650, B220-PerCP, CD4-PE-Cy7, Streptavidin-BV421, PD-1-APC, CD69-FITC and CD49b-PE (BD Biosciences, CA) and the yellow LIVE/DEAD® dye (Life Technologies). Cells were washed twice and suspended in PBS containing 2% FBS for analysis.

For intracellular staining for cytokines, splenocytes were cultured in a 96-well U-bottom plate at 1×10⁶ cells per well. The peptide stimulation was performed as described for the ELISPOT cultures. The plate was incubated 6 hours at 37° C. in the presence of BD GolgiPlug™ and BD GolgiStop™ (BD Biosciences). Cells were washed twice, incubated for 20 min at 4° C. with a mixture of antibodies for cell surface markers, including CD3-BV 650, CD4-PerCP, CD8-FITC, CD44-APC-Cy7 and CD62L-PE-Cy7 (BD Pharmingen, CA) and the yellow LIVE/DEAD® dye (Life Technologies, NY). After two washes, cells were fixed with Cytofix/Cytoperm (BD Biosciences) for 30 min at 4° C., followed by two washes with BD Perm/Wash™ (BD Biosciences). Cells were incubated with antibodies to IFN-γ-APC, IL-2-BV 421 and TNFα-PE (BD Biosciences) overnight at 4° C. The cells were washed and re-suspended in 1×BD Perm/Wash buffer for data acquisition. All staining samples were acquired using a LSR-Fortessa flow cytometer (Becton Dickinson, San Jose, Calif.) and the data were analysed with Flowjo software version Xv10 (Tree Star Inc., Ashland, Oreg.).

Statistical analysis was performed using SAS software version 9.4. Pairwise comparisons with Tukey's adjustment from ANOVA used group as the independent variable and log-transformed titer result as the dependent variable to determine significance between groups.

Example 17

EBOV/Mak GP Induced Antibody Response and Protective Efficacy

The immunogenicity of the EBOV/Mak GP nanoparticle vaccine was evaluated with and without adjuvant in a mouse model. Mice were vaccinated on Days 0, 14 and 28 by SC injection with 5 µg of EBOV/Mak GP alone or EBOV/Mak GP formulated in Matrix-M or AlPO₄ adjuvant. Analysis of sera obtained on day 28 (14 days post second immunization) indicated that the Matrix-M adjuvanted EBOV/Mak GP induced high levels of antigen-specific IgG antibodies against the Mayinga GP with a geometric mean titer (GMT) of 26,991. The response obtained following immunization with EBOV/Mak GP with Matrix-M was significantly higher than those induced by EBOV/Mak GP alone (GMT=266, p=0.001) or EBOV/Mak GP adjuvanted with AlPO₄ (GMT=436, p=0.0001) (FIG. 28A). The AlPO₄ adjuvant offered only marginal increase in anti-EBOV/Mak GP IgG in comparison to the EBOV/Mak GP alone.

The neutralization activity of day 28 sera was analysed using Ebola GP pseudovirions (PsVs) (FIG. 28B). In the absence of adjuvant, neutralization GMT titer in sera from mice immunized with the EBOV/Mak GP alone were 197 and when EBOV/Mak GP was adjuvanted with AlPO₄, lower titers were observed (GMT=49, p=0.1). Neutralization titers observed in sera from mice immunized with EBOV/Mak GP with Matrix-M had a GMT of 6,463, thirty-two-fold higher than that obtained with EBOV/Mak GP alone. In this assay, PsVs expressing the EBOV 1976 Mayinga strain GP were used as PsVs expressing the EBOV/Mak 2014 strain GP were not available. Thus, the assay is measuring the cross-neutralizing activity of anti-EBOV/Mak GP against the Mayinga GP.

On day 42, two weeks after the third vaccination given on day 28, mice were challenged by an intraperitoneal inoculation of 1,000 pfu mouse adapted Zaire Ebola virus strain 1976 Mayinga. Control mice started to succumb to infection after three days while mice vaccinated with EBOV/Mak GP alone or EBOB/Mak GP adjuvanted with AlPO₄ succumbed at day five or six, respectively. Twenty-one days after challenge infection, all mice vaccinated with Matrix-M adjuvanted EBOV/Mak GP and one mouse vaccinated with EBOV/Mak GP alone was alive and healthy. In contrast, all other mice were dead or had been euthanized by day 8 due to Ebola virus infection (FIG. 28C).

Example 18

Kinetics of Ebola-GP IgG, IgG1 and IgG2a Responses

In order to further characterize the immune responses to Matrix-M-adjuvanted EBOV/Mak GP in more detail, two groups of Balb/c mice (10/group) were injected with 5 µg EBOV/Mak GP adjuvanted with either 2.5 or 5 µg of Matrix-M. Groups of mice injected with PBS, EBOV/Mak GP alone or EBOV/Mak GP with AlPO₄ served as controls. At days 14, 21, 28 and 60, EBOV/Mak GP-specific IgG and IgG subclasses (IgG1 and IgG2a) were measured by ELISA.

At day 14 following the first injection, all mice injected with EBOV/Mak GP with Matrix-M (2.5 or 5 µg) responded with EBOV/Mak GP-specific IgG (GMT=755 and 1,499 respectively, data not shown). None of the 10 mice in the EBOV/Mak GP group and EBOV/Mak GP with AlPO₄ group generated EBOV/Mak GP specific IgG (data not shown). By day 21, the IgG response to EBOV/Mak GP increased further in the Matrix-M-adjuvanted groups (FIG. 29A). There was still no response in the groups given EBOV/Mak GP alone or with EBOV/Mak GP with AlPO₄. All mice received a second injection at day 21. At day 28 there was a robust increase in IgG responses in the mice receiving Matrix-M (2.5 or 5 µg) with ELISA GMT titers of 3.0×10⁵ and 4.9×10⁵ respectively (FIG. 29A). At days 28 and 60 in the EBOV/Mak GP alone and with AlPO₄ groups, specific IgG responses were detected in some of the mice, but were significantly lower than in the mice immunized with EBOV/Mak GP with Matrix-M (FIG. 29A). By day 60, the anti-GP IgG titers induced by EBOV/Mak GP with 2.5 or 5 µg Matrix-M were not significantly reduced compared to day 28 and were 67-fold and 139-fold higher, respectively, than in the EBOV/Mak GP with AlPO₄ groups (FIG. 29A).

Figure 29C:
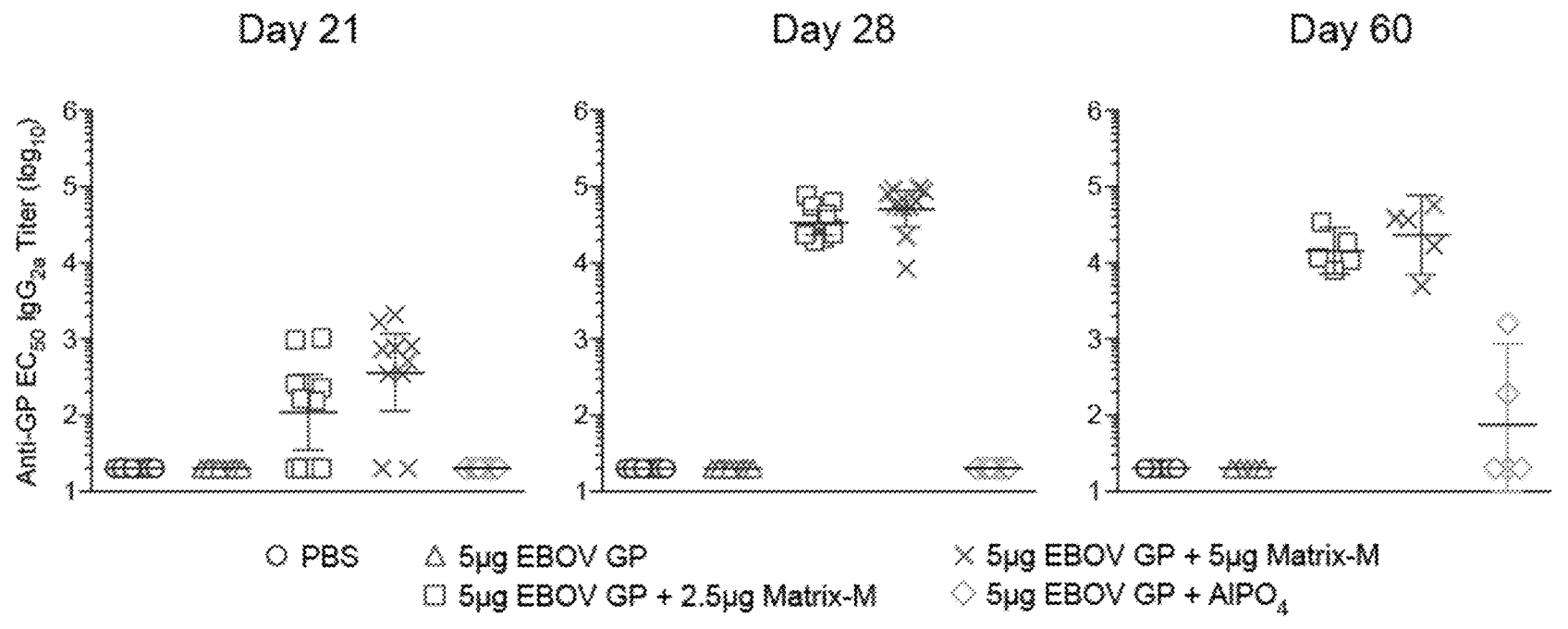

The EBOV/Mak GP-specific IgG1 and IgG2a responses were also determined. Similar to total IgG, Matrix-M adjuvanted EBOV/Mak GP vaccine induced high anti-GP IgG1 and IgG2a levels at days 28 and 60 (FIG. 29B and 29C). In contrast, only one out of 10 mice given EBOV/Mak GP alone and four of 10 mice given EBOV/Mak GP with AlPO₄ produced low levels of IgG1 at day 28 (FIG. 29B). At day 60, antigen-specific IgG1 was detected in serum from all five remaining mice in the group given EBOV/Mak GP with AlPO₄, but the average titer was 51- and 41-fold lower than in the groups given EBOV/Mak GP with 2.5 or 5.0 µg Matrix-M (FIG. 29B), respectively. Furthermore, EBOV/Mak GP alone did not induce detectable IgG2a antibody at days 28 and 60.

Example 19

CD4+, CD8+, and Multifunctional T cell Response

We next assessed the T cell response to the different EBOV/Mak GP formulations by measuring the number of IFN-γ secreting T cells after ex vivo stimulation of spleen cells with EBOV/Mak GP peptides in an ELISPOT assay. At day 28, IFN-γ secreting cells increased in a Matrix-M dose-dependent manner in spleens from mice immunized with EBOV/Mak GP with Matrix-M (FIG. 30A, 30B). The average number of IFN-γ-secreting cells in groups receiving EBOV/Mak GP with 5.0 and 2.5 µg of Matrix-M were 17- and 10-fold higher respectively than in the group receiving EBOV/Mak GP alone and 8- and 5-fold higher respectively than in the group receiving EBOV/Mak GP with AlPO$_4$ (FIG. 30A).

By day 60, the number of IFN-γ secreting cells in spleens from mice immunized with EBOV/Mak GP with 5 µg of Matrix-M was still 12-fold higher than in spleens from mice immunized with EBOV/Mak GP alone and 3-fold higher than in spleens from mice immunized with EBOV/Mak GP with AlPO$_4$ (FIG. 30B). The increased numbers of IFN-γ secreting cells in spleens from mice immunized with EBOV/Mak GP with 2.5 µg Matrix-M were also maintained at day 60 but at a lower level than with 5 µg Matrix-M.

We further assessed Matrix-M induced CD4+ and CD8+ T cell responses by intracellular staining of cytokines combined with cell surface markers. Analysis of splenocytes by flowcytometric staining at day 28 showed that both CD4+ and CD8+ T cells from EBOV/Mak GP with Matrix-M groups secreted IFN-γ, TNFα and IL-2 (FIG. 30C and 30D). The frequency of cytokine-secreting CD4+ and CD8+ T cells was much higher in spleens from the EBOV/Mak GP with Matrix-M groups than the baseline or minimal responses observed in control mice, mice receiving EBOV/Mak GP alone or EBOV/Mak GP with AlPO$_4$ (FIG. 30C and 30D). The frequency of T cells that simultaneously produce two or more cytokines (IFN-γ, TNFα and IL-2) was also evaluated at day 28. Both CD4+ and CD8+ T cells producing either two or three cytokines were detected at marked levels only in spleens from the mice immunized with EBOV/Mak GP with Matrix-M.

Example 20

Germinal Center and T Follicular Helper Cell Responses

Figure 31A:
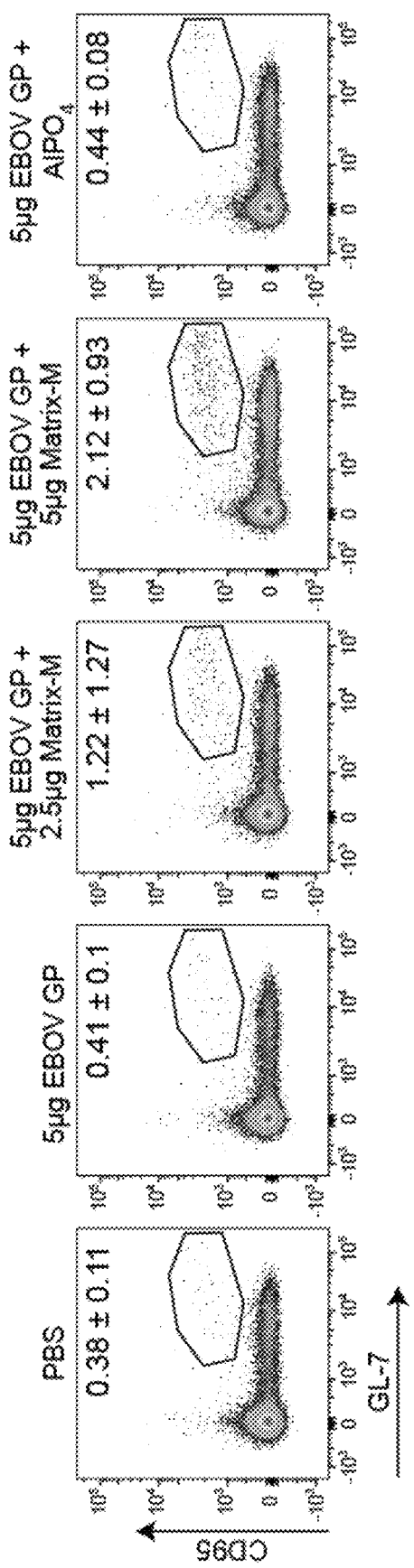
Figure 31B:
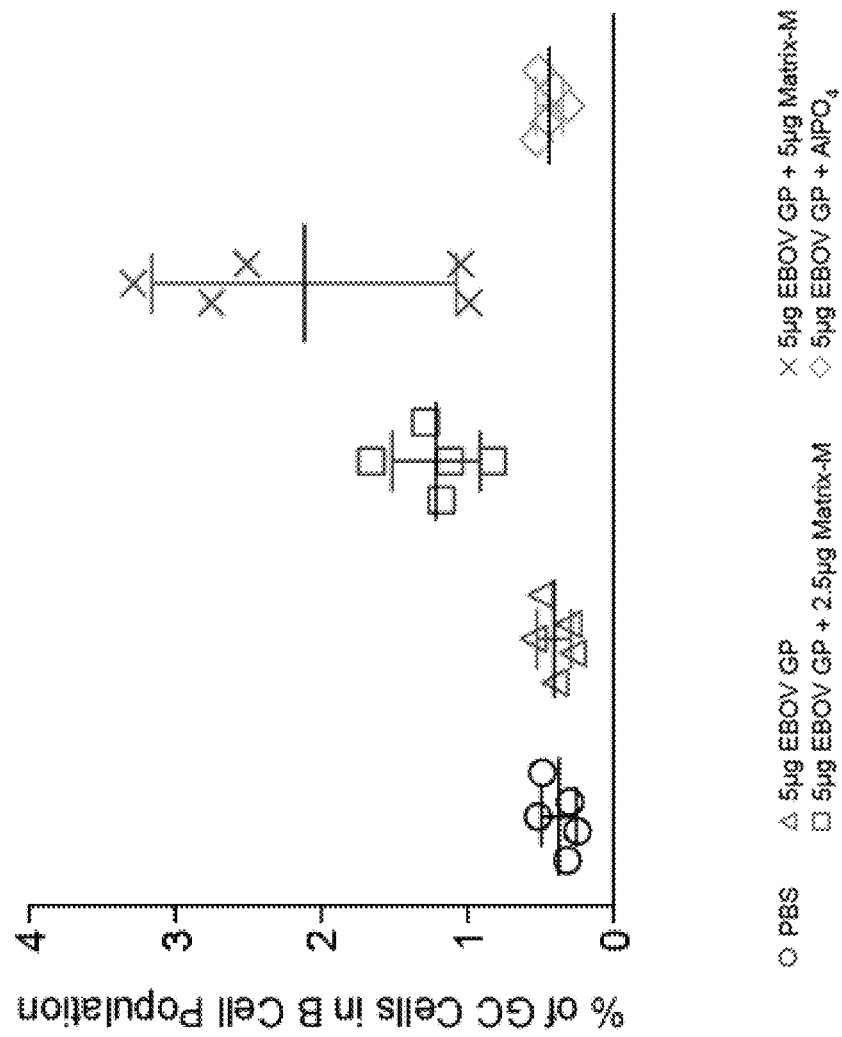
Figure 31C:
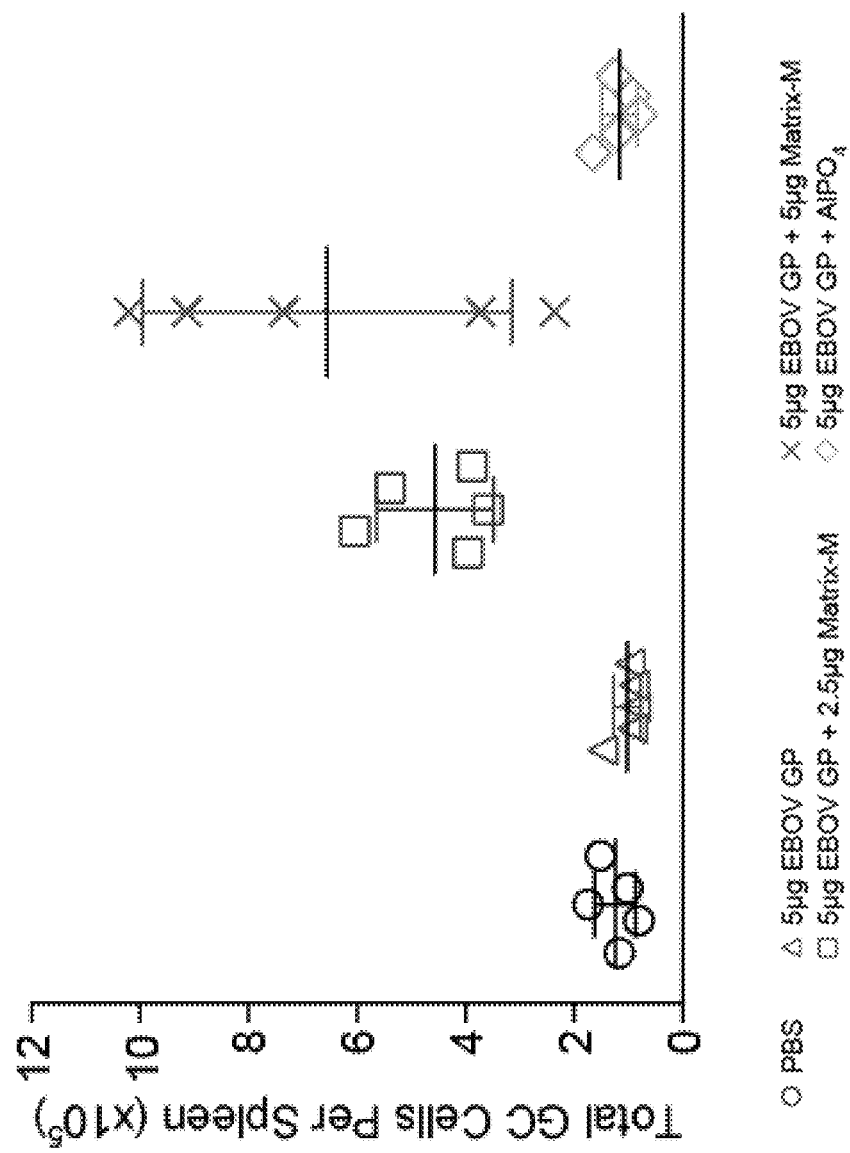
Figure 31D:
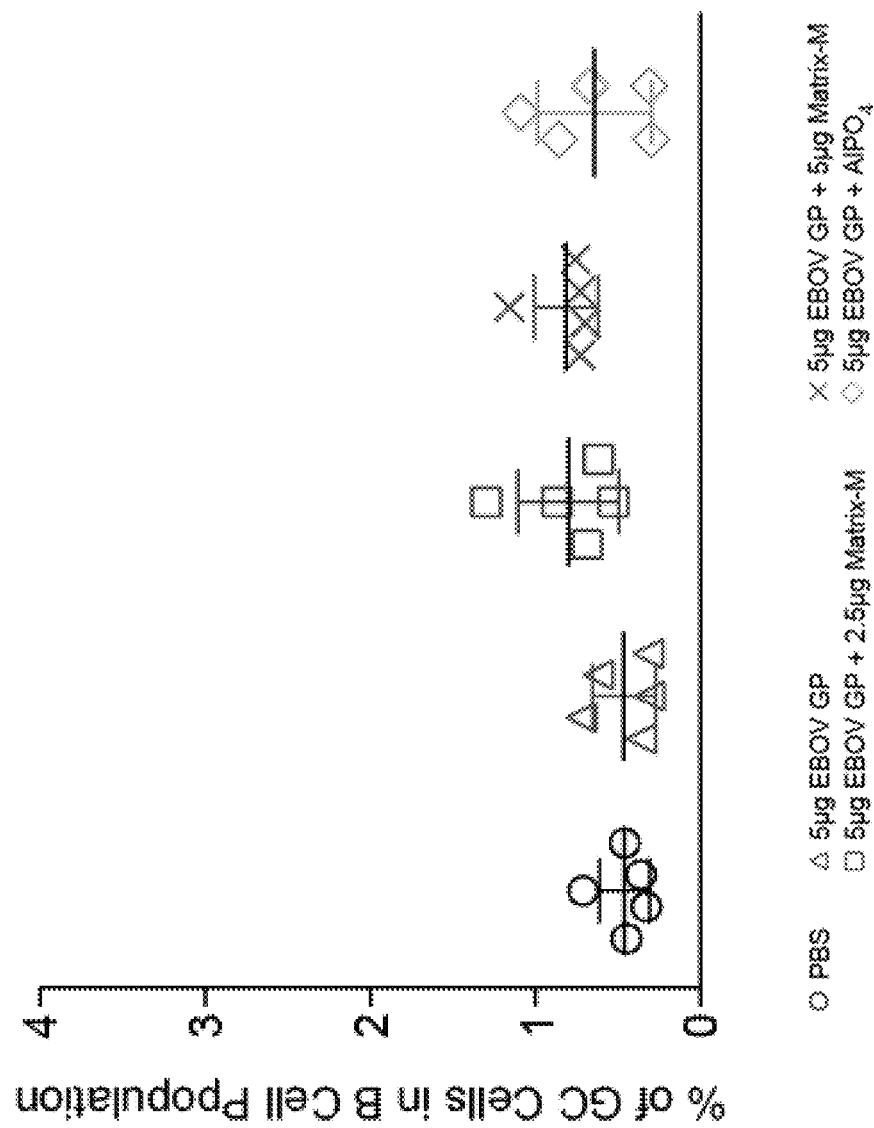

The frequency and absolute number of GC B cells in the spleen were analysed by flowcytometric staining (FIG. 31A). The analysis showed that at day 28 (seven days after the 2$^{nd}$ injection of vaccine), EBOV/Mak GP adjuvanted with 2.5 and 5 µg of Matrix-M induced responses with a GC frequency of 1.22 and 2.12% respectively in comparison to placebo, EBOV/Mak GP alone or EBOV/Mak GP with AlPO$_4$ (0.38, 0.41 and 0.44% respectively) (FIG. 31B). Accordingly, the absolute GC cell number in the spleen also increased in the groups receiving Matrix-M (FIG. 31C). By day 60, the frequency and absolute number returned to background level (FIG. 31D and 31E)

Figure 32A:
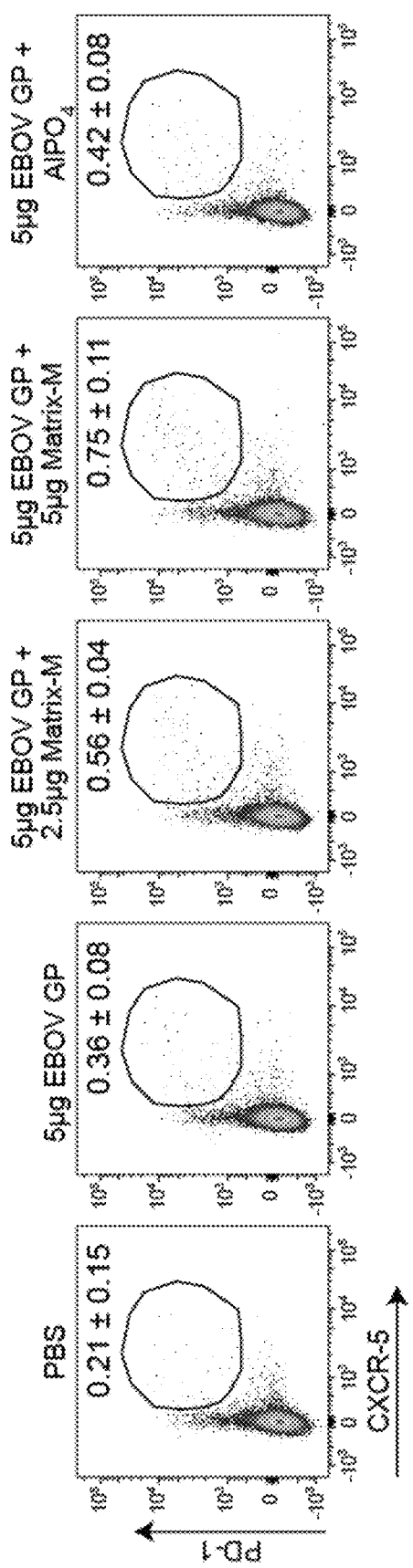
Figure 32B:
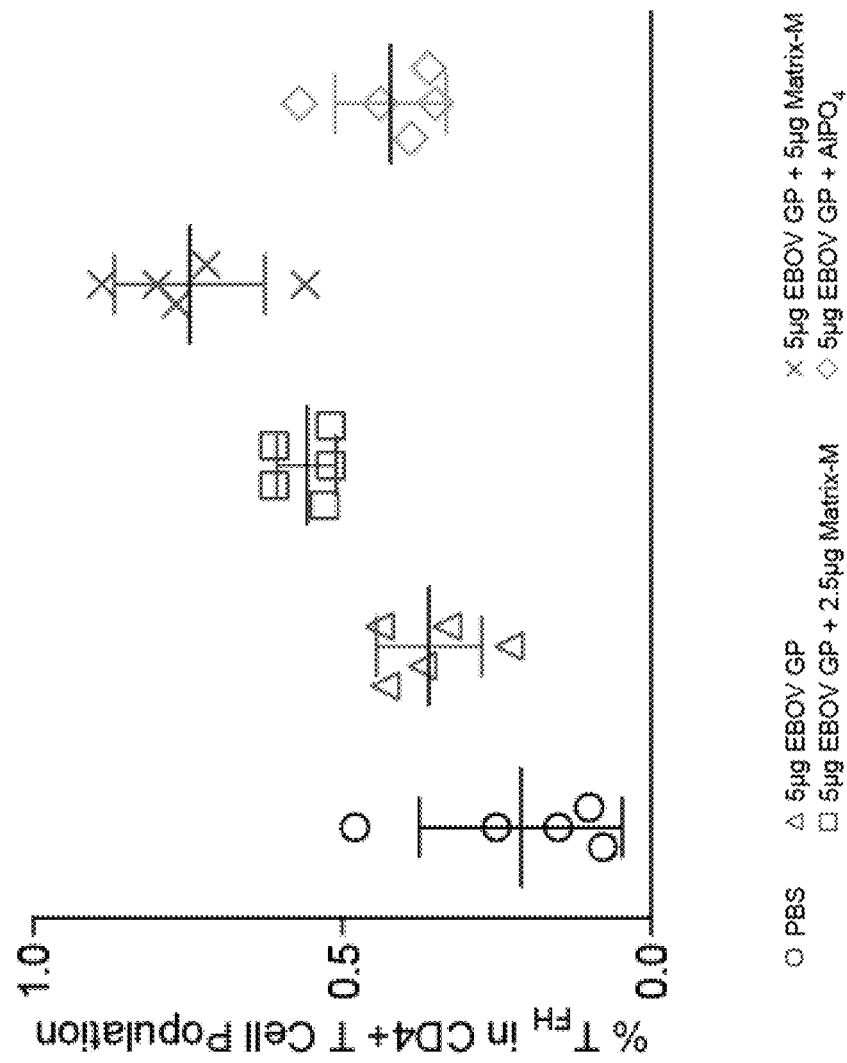
Figure 32E:
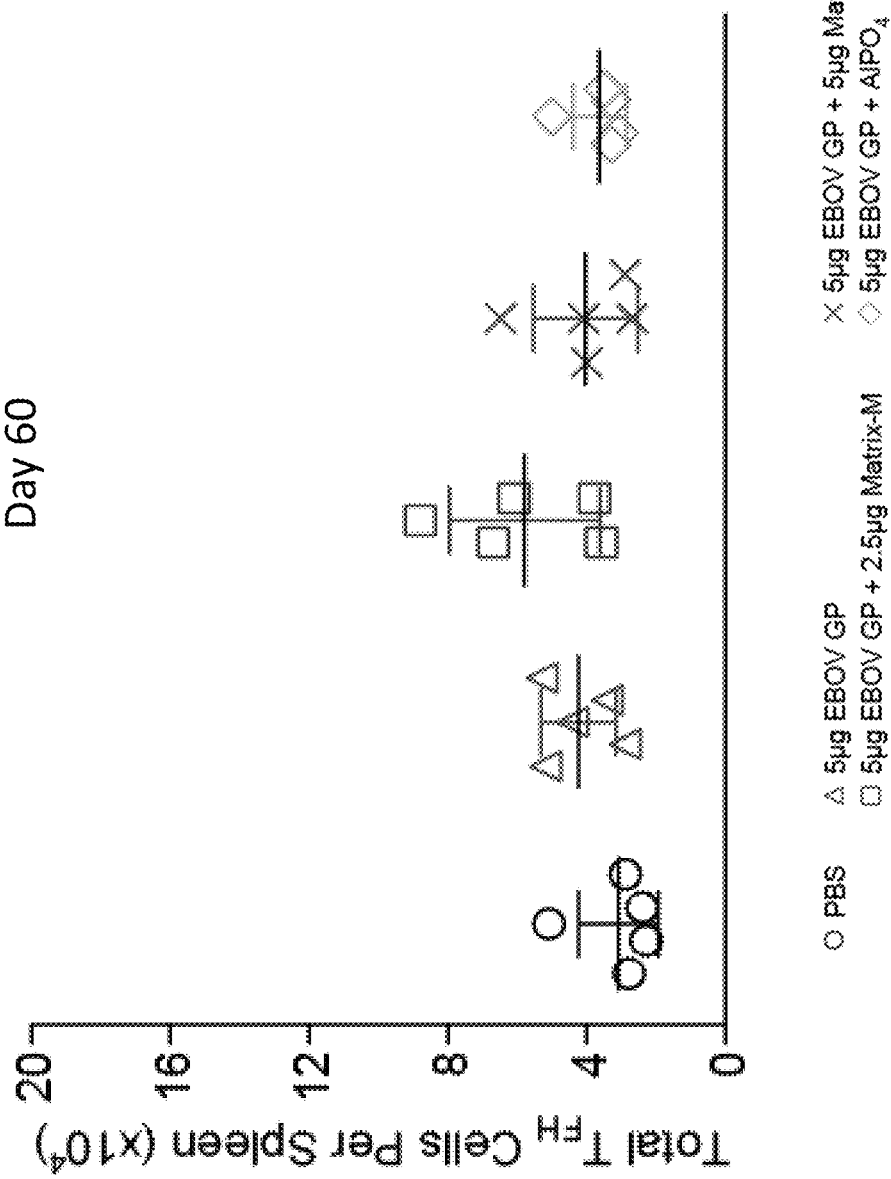

Analysis of T$_{FH}$ cells frequencies at day 28 showed that EBOV/Mak GP with 2.5 or 5 µg of Matrix-M induced higher frequencies of T$_{FH}$ cells than the EBOV/Mak GP alone or with AlPO$_4$ (FIG. 32A and 32B). Accordingly, the absolute number of T$_{FH}$ cells was also enhanced by EBOV/Mak GP with Matrix-M compared to EBOV/Mak GP alone or with AlPO$_4$ (FIG. 32C). By day 60, the frequency and absolute number of T$_{FH}$ cells retracted to near background levels (FIGS. 32D and 32E).

Example 21

EBOV/Mak GP-Specific Plasma Cells

In order to assess the influence of Matrix-M on the EBOV/Mak GP-specific plasma cells, the number of IgG-producing cells in spleen and bone marrow was analysed at day 60 after immunization. The analysis at day 60 demonstrated only a few EBOV/Mak GP-specific IgG-secreting cells (<6/10$^6$ splenocytes) in the spleens from mice immunized with Matrix-M adjuvanted EBOV/Mak GP vaccine (FIG. 33A). No IgG-secreting cells were detected in the spleens from mice immunized with EBOV/Mak GP alone and EBOV/Mak GP with AlPO$_4$ (FIG. 33A). In contrast, high numbers of EBOV/Mak GP-specific IgG-secreting cells appeared in bone marrow from mice that received Matrix-M adjuvanted EBOV/Mak GP (FIG. 33B), demonstrating the formation of long-lived plasma B cells.

Example 22

Characterization of Antibody Binding to the Nanoparticles

We tested the ability of several anti-Ebola antibodies to bind to the nanoparticles. The antibodies are 13C6, 13F6, 6D8 and KZ52. The EC50 curve and values are shown in FIG. 36 and additional binding kinetic data are shown in FIG. 37. FIG. 38 shows potency data using the 13C6 as a reference. Three of four antibodies exhibited excellent binding to the GP.

Example 23

Non-Human Primate study: Baboon

Figure 41:
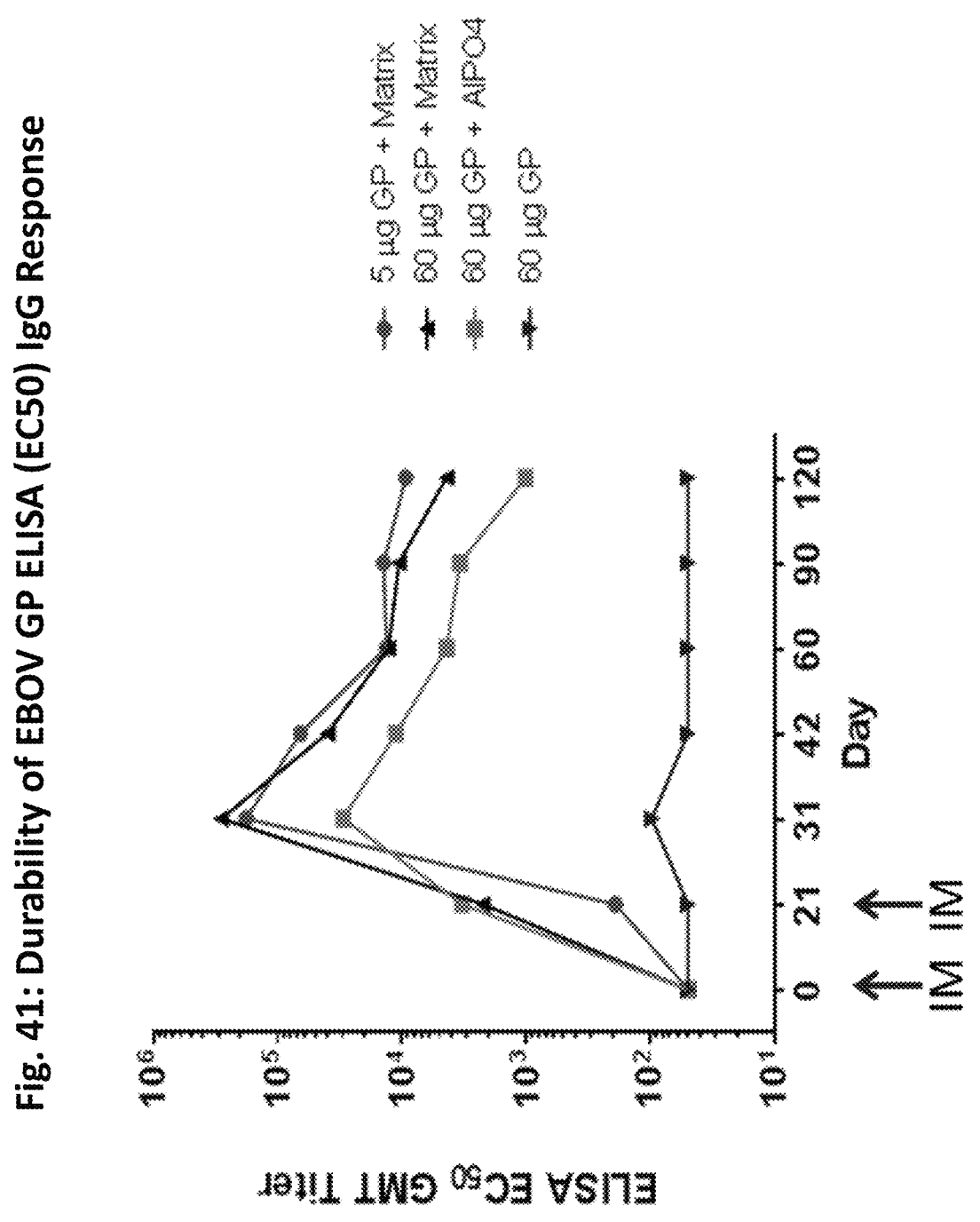

To confirm the results obtained in mice in a non-human primate model, a baboon study was performed. The study was designed as shown in FIG. 39. Four groups were formed. Group 1 was the control. Group 2 received antigen with AlPO$_4$. Groups 2 and 3 received antigen, 60 µg and 5 µg, respectively with Matrix-M at 50 Baboons were immunized at 0 and 21 days. Robust responses were obtained against both Makona GP and Mayinga GP. See FIG. 40. Additional analysis confirmed that the response was long-lasting. FIG. 41 shows EC50 values for IgG against Makona at later timepoints. The data establish the response is sustained.

Figure 43:
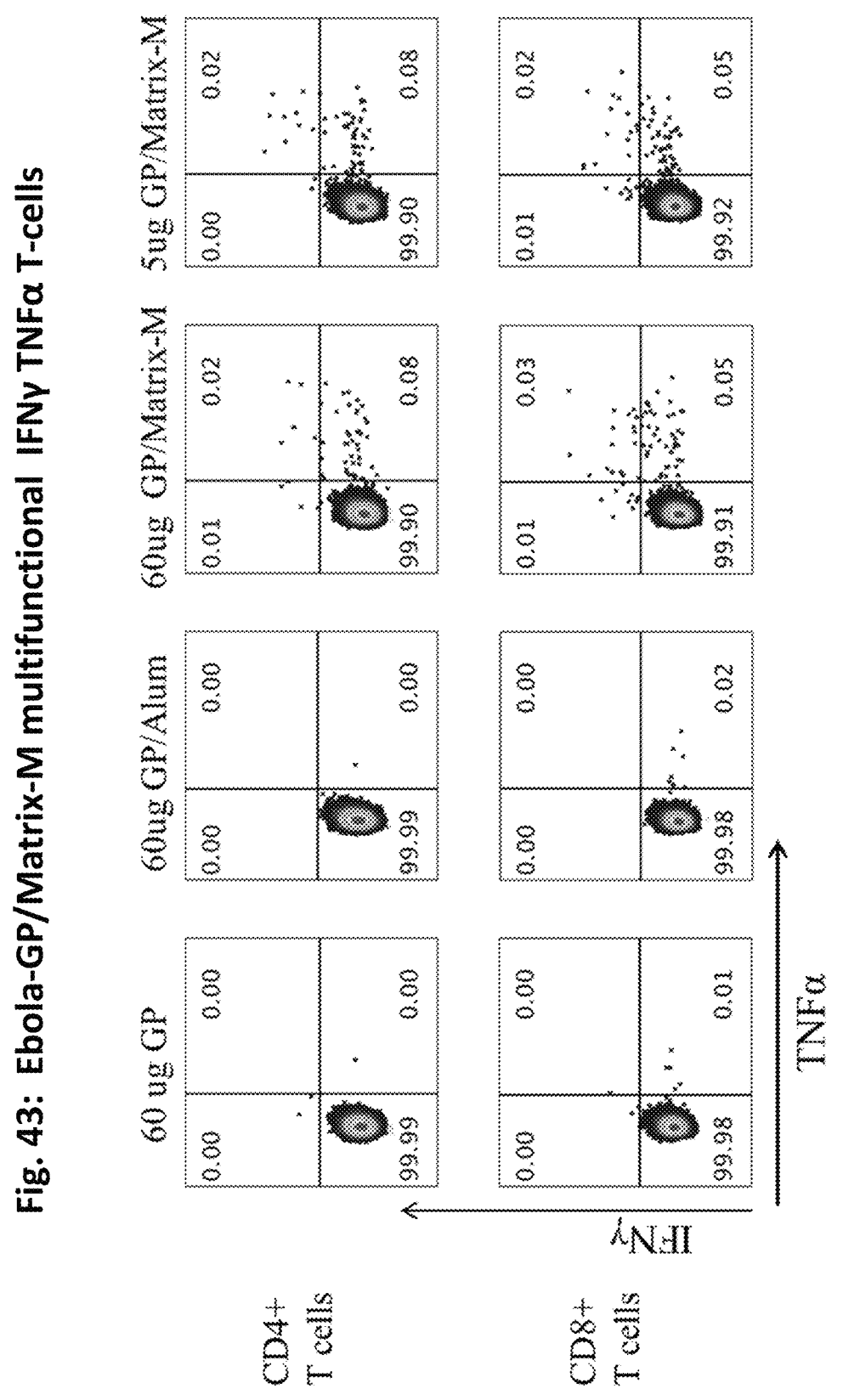

Additional studies confirm that IFN-γ levels increase substantially following immunization. FIG. 42 shows that Matrix M in combination with GP increased more so than with an alum adjuvant. Interestingly, the lower dose of GP, 5 µg, gave a more pronounced increase in IFN-γ levels. TNF-α and IFN-γ responses in T-cells are shown in FIG. 43 with cytokines responses shown in FIG. 44. Again, the response is more pronounced with GP and Matrix M in each case than with alum. These data underscore the robust immune response of the disclosed formulations in the baboon model.

Example 24

Non-Human Primate Study: Macaque Study 1

Figure 47C:
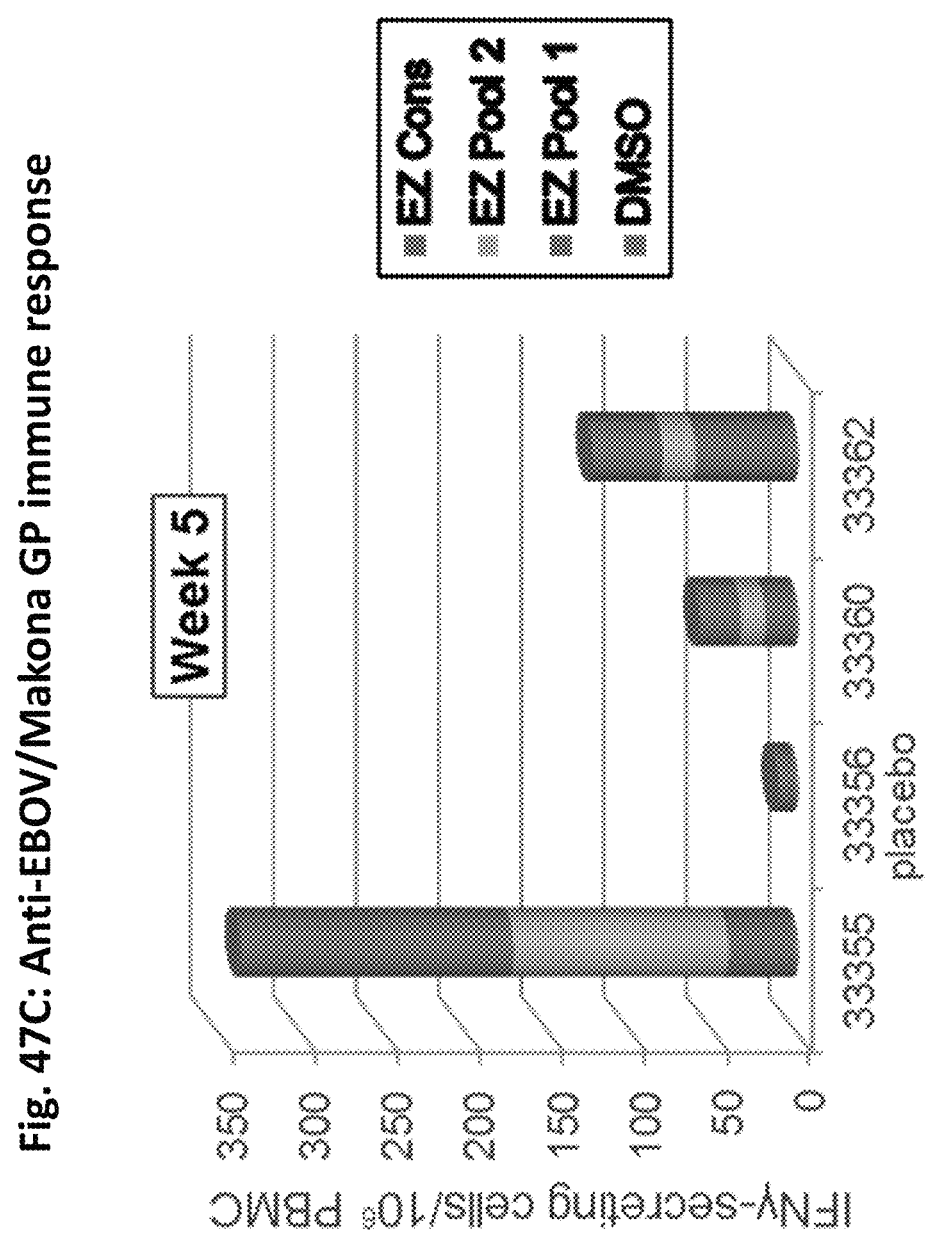

To further confirm the protective effect of the nanoparticles, a macaques study was performed as indicated in FIG. 45. Macaques were immunized intramuscularly at days 0 and 21 with vaccine as shown and challenged at Day 42. Anti-GP responses were measure at Day 0 and 28. As FIG. 46 shows, immunized macques showed a dramatic induction of anti-IgG antibodies. The immune response was characterized as shown in FIG. 47. IFN-γ secreting cells in response to various peptides pools was measured at weeks 0, 3, and 5. The results demonstrate that immunized macaques induced IFN-γ-secreting cells in immunized macaques.

Animal survival was remarkable. FIG. 48. By day 7, the Ebola viral load in placebo-treated macaques was $10^7$. By Day 9, the placebo animal was euthanized. In contrast, 100% of treated animals survived. Remarkably, the immune response was able to render the viral load undetectable by RT-PCR in almost all animals at almost all time points. Animal 33362 showed viral load at day 7 that was about 10% above the detectable limit. By Day 10, however, levels had dropped beneath the ability of the assay to detect them.

Example 25

Non-Human Primate study: Macaque Study 2

A second study was performed in Macaques. Animals were dosed with 5 μg GP+50 μg Matrix-M at zero weeks, with a follow-on boost at either 3 weeks or 6 weeks. Immunized animals were then challenged with wild-type Ebola virus at 9 weeks and 12 weeks, respectively. FIG. 49.

ELISA data for IgG are shown in FIG. 50. The left panel shows that 3 weeks after the first injection, high titers had developed and were sustained. The right panel illustrates results in animals with a 6-week gap between administrations. Those animals showed a substantial increase two weeks after the second, booster administration, illustrating the beneficial effect of a prime-boost approach.

The vaccine composition was fully protective in macaques. 18 days after challenge with live virus, the saline control-treated mice were all dead. In contrast, 100% of macaques immunized with the vaccine compositions survived challenge. Collectively, these data confirm that the immune responses stimulated by the compositions are protective whether a boost administration occurs within 3 weeks or within 6 weeks.

The invention claimed is:

1. A method of stimulating an immune response in a subject comprising administering a vaccine composition comprising:
   (i) a nanoparticle comprising a non-ionic detergent core and a viral glycoprotein, wherein the viral glycoprotein is associated with the core; wherein the non-ionic detergent is PS80; wherein the viral glycoprotein is an RSV F glycoprotein and the molar ratio of PS80 to viral glycoprotein is about 30:1 to about 60:1; and
   (ii) a pharmaceutically acceptable buffer.

2. The method of claim 1, wherein the vaccine composition is administered intramuscularly.

3. The method of claim 1, wherein a single dose of the vaccine composition is administered.

4. The method of claim 1, wherein multiple doses of the vaccine composition are administered.

5. The method of claim 1, wherein a dose of the vaccine composition comprises between about 30 μg and about 150 μg of the RSV F glycoprotein.

6. The method of claim 1, wherein the subject is selected from the group consisting of an adult, a senior adult, a pregnant female adult, a child, a neonate, and an infant.

7. The method of claim 1, wherein the composition comprises an adjuvant.

8. The method of claim 7, wherein the adjuvant comprises at least two iscom particles, wherein: the first iscom particle comprises fraction A of *Quillaja Saponaria* Molina and not fraction C of *Quillaja Saponaria* Molina; and the second iscom particle comprises fraction C of *Quillaja Saponaria* Molina and not fraction A of *Quillaja Saponaria* Molina.

9. The method of claim 8, wherein the two iscom matrix particles are present in a composition of about 70% (w/w) of the first iscom particle and about 30% (w/w) of the second iscom particle.

10. The method of claim 8, wherein the two iscom matrix particles are present in a composition of about 85% (w/w) of the first iscom particle and about 15% (w/w) of the second iscom particle.

11. The method of claim 7, wherein the adjuvant comprises iscom matrix particles comprising a mixture of fraction A of *Quillaja Saponaria* Molina and fraction C of *Quillaja Saponaria* Molina.

12. The method of claim 11, wherein the mixture comprises about 70% (w/w) of fraction A of *Quillaja Saponaria* Molina and about 30% (w/w) of fraction C of *Quillaja Saponaria* Molina.

13. The method of claim 11, wherein the mixture comprises about 85% (w/w) of fraction A of *Quillaja Saponaria* Molina and about 15% (w/w) of fraction C of *Quillaja Saponaria* Molina.

14. The method of claim 7, wherein the adjuvant is an alum adjuvant.

15. The method of claim 1, wherein the composition contains no added adjuvant.

16. The method of claim 1, wherein a dose of the vaccine composition is administered in a volume of about 0.5 mL.

17. The method of claim 1, wherein a dose of the vaccine composition comprises about 87.5 μg to about 162.5 μg of an RSV F glycoprotein.

18. The method of claim 1, wherein a dose of the vaccine composition comprises about 100 μg to about 300 μg of an RSV F glycoprotein.

19. The method of claim 1, wherein a dose of the vaccine composition comprises about 120 μg to about 130 μg of an RSV F glycoprotein.

20. The method of claim 1, wherein the RSV F glycoprotein comprises a deletion of 1 to 10 amino acids corresponding to amino acids 137-146 of SEQ ID NO:2 and an inactivated primary furin cleavage site corresponding to amino acids 131 to 136 of SEQ ID NO: 2, wherein the primary furin cleavage site is inactivated by mutation.

21. The method of claim 20, wherein the RSV F glycoprotein is selected from the group consisting of SEQ ID NOS:3-12 and variants of SEQ ID NOS:3-12 lacking part or all of the N-terminal signal peptide.

22. The method of claim 21, wherein the RSV F glycoprotein comprises SEQ ID NO:19.

23. The method of claim 21, wherein the RSV F glycoprotein consists of SEQ ID NO:19.

24. The method of claim 1, wherein the molar ratio is about 50:1.

25. The method of claim 1, wherein the pharmaceutically acceptable buffer comprises
  (i) sodium phosphate at about 15 mM to about 25 mM;
  (ii) sodium chloride at about 150 mM;
  (iii) histidine at 0.25% w/v to 2% w/v;
wherein the pH of the composition is between 5.8 and 6.4.

26. The method of claim 1, wherein the pharmaceutically acceptable buffer comprises
  (i) sodium phosphate at about 22 mM;
  (ii) sodium chloride at about 150 mM;
  (iii) histidine at about 1% w/v;
wherein the pH of the composition is about 6.2.

27. The method of claim 1, wherein the RSV F glycoprotein comprises an RSV F1 and an RSV F2 domain connected by a disulfide bond.

\* \* \* \* \*

SEQUENCE LISTING

```
<160> NUMBER OF SEQ ID NOS: 29

<210> SEQ ID NO 1
<211> LENGTH: 1725
<212> TYPE: DNA
<213> ORGANISM: Respiratory syncytial virus

<400> SEQUENCE: 1
atggagttgc taatcctcaa agcaaatgca attaccacaa tcctcactgc agtcacattt      60
tgttttgctt ctggtcaaaa catcactgaa gaattttatc aatcaacatg cagtgcagtt     120
agcaaaggct atcttagtgc tctgagaact ggttggtata ccagtgttat aactatagaa     180
ttaagtaata tcaaggaaaa taagtgtaat ggaacagatg ctaaggtaaa attgataaaa     240
caagaattag ataaatataa aaatgctgta acagaattgc agttgctcat gcaaagcaca     300
ccaccaacaa acaatcgagc cagaagagaa ctaccaaggt ttatgaatta tacactcaac     360
aatgccaaaa aaaccaatgt aacattaagc aagaaaagga aagaagatt tcttggtttt     420 ttgttaggtg ttggatctgc aatcgccagt ggcgttgctg tatctaaggt cctgcaccta     480 gaagggaag tgaacaagat caaaagtgct ctactatcca caaacaaggc tgtagtcagc     540
ttatcaaatg gagttagtgt cttaaccagc aaagtgttag acctcaaaaa ctatatagat     600
aaacaattgt tacctattgt gaacaagcaa agctgcagca tatcaaatat agaaactgtg     660
atagagttcc aacaaaagaa caacagacta ctagagatta ccagggaatt tagtgttaat     720
gcaggtgtaa ctacacctgt aagcacttac atgttaacta atagtgaatt attgtcatta     780
atcaatgata tgcctataac aaatgatcag aaaaagttaa tgtccaacaa tgttcaaata     840
gttagacagc aaagttactc tatcatgtcc ataataaaag aggaagtctt agcatatgta     900
gtacaattac cactatatgg tgttatagat acaccctgtt ggaaactaca cacatcccct     960
ctatgtacaa ccaacacaaa agaagggtcc aacatctgtt taacaagaac tgacagagga    1020
tggtactgtg acaatgcagg atcagtatct ttcttcccac aagctgaaac atgtaaagtt    1080
```

```
caatcaaatc gagtattttg tgacacaatg aacagtttaa cattaccaag tgaaataaat    1140
ctctgcaatg ttgacatatt caaccccaaa tatgattgta aaattatgac ttcaaaaaca    1200
gatgtaagca gctccgttat cacatctcta ggagccattg tgtcatgcta tggcaaaact    1260
aaatgtacag catccaataa aaatcgtgga atcataaaga catttttcaa cgggtgcgat    1320
tatgtatcaa ataaagggat ggacactgtg tctgtaggta acacattata ttatgtaaat    1380
aagcaagaag gtaaaagtct ctatgtaaaa ggtgaaccaa taataaattt ctatgaccca    1440
ttagtattcc cctctgatga atttgatgca tcaatatctc aagtcaacga aagattaac    1500 cagagcctag catttattcg taaatccgat gaattattac ataatgtaaa tgctggtaaa    1560
tccaccacaa atatcatgat aactactata attatagtga ttatagtaat attgttatca    1620
ttaattgctg ttggactgct cttatactgt aaggccagaa gcacaccagt cacactaagc    1680
aaagatcaac tgagtggtat aaataatatt gcatttagta actaa                    1725
```

<210> SEQ ID NO 2
<211> LENGTH: 574
<212> TYPE: PRT
<213> ORGANISM: Respiratory syncytial virus

<400> SEQUENCE: 2

```
Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
            20                  25                  30

Tyr Gln Ser Thr Cys Ser Ala Val Ser Lys Gly Tyr Leu Ser Ala Leu
        35                  40                  45

Arg Thr Gly Trp Tyr Thr Ser Val Ile Thr Ile Glu Leu Ser Asn Ile
    50                  55                  60

Lys Glu Asn Lys Cys Asn Gly Thr Asp Ala Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gln Ser Thr Pro Pro Thr Asn Asn Arg Ala Arg Arg Glu Leu Pro
            100                 105                 110

Arg Phe Met Asn Tyr Thr Leu Asn Asn Ala Lys Lys Thr Asn Val Thr
        115                 120                 125

Leu Ser Lys Lys Arg Lys Arg Arg Phe Leu Gly Phe Leu Leu Gly Val
    130                 135                 140

Gly Ser Ala Ile Ala Ser Gly Val Ala Val Ser Lys Val Leu His Leu
145                 150                 155                 160

Glu Gly Glu Val Asn Lys Ile Lys Ser Ala Leu Leu Ser Thr Asn Lys
                165                 170                 175

Ala Val Val Ser Leu Ser Asn Gly Val Ser Val Leu Thr Ser Lys Val
            180                 185                 190

Leu Asp Leu Lys Asn Tyr Ile Asp Lys Gln Leu Leu Pro Ile Val Asn
        195                 200                 205

Lys Gln Ser Cys Ser Ile Ser Asn Ile Glu Thr Val Ile Glu Phe Gln
    210                 215                 220

Gln Lys Asn Asn Arg Leu Leu Glu Ile Thr Arg Glu Phe Ser Val Asn
225                 230                 235                 240

Ala Gly Val Thr Thr Pro Val Ser Thr Tyr Met Leu Thr Asn Ser Glu
                245                 250                 255
```

-continued

```
Leu Leu Ser Leu Ile Asn Asp Met Pro Ile Thr Asn Asp Gln Lys Lys
            260                 265                 270

Leu Met Ser Asn Asn Val Gln Ile Val Arg Gln Gln Ser Tyr Ser Ile
        275                 280                 285

Met Ser Ile Ile Lys Glu Glu Val Leu Ala Tyr Val Val Gln Leu Pro
    290                 295                 300

Leu Tyr Gly Val Ile Asp Thr Pro Cys Trp Lys Leu His Thr Ser Pro
305                 310                 315                 320

Leu Cys Thr Thr Asn Thr Lys Glu Gly Ser Asn Ile Cys Leu Thr Arg
                325                 330                 335

Thr Asp Arg Gly Trp Tyr Cys Asp Asn Ala Gly Ser Val Ser Phe Phe
            340                 345                 350

Pro Gln Ala Glu Thr Cys Lys Val Gln Ser Asn Arg Val Phe Cys Asp
        355                 360                 365

Thr Met Asn Ser Leu Thr Leu Pro Ser Glu Ile Asn Leu Cys Asn Val
    370                 375                 380

Asp Ile Phe Asn Pro Lys Tyr Asp Cys Lys Ile Met Thr Ser Lys Thr
385                 390                 395                 400

Asp Val Ser Ser Ser Val Ile Thr Ser Leu Gly Ala Ile Val Ser Cys
                405                 410                 415

Tyr Gly Lys Thr Lys Cys Thr Ala Ser Asn Lys Asn Arg Gly Ile Ile
            420                 425                 430

Lys Thr Phe Ser Asn Gly Cys Asp Tyr Val Ser Asn Lys Gly Met Asp
        435                 440                 445

Thr Val Ser Val Gly Asn Thr Leu Tyr Tyr Val Asn Lys Gln Glu Gly
    450                 455                 460

Lys Ser Leu Tyr Val Lys Gly Glu Pro Ile Ile Asn Phe Tyr Asp Pro
465                 470                 475                 480

Leu Val Phe Pro Ser Asp Glu Phe Asp Ala Ser Ile Ser Gln Val Asn
                485                 490                 495

Glu Lys Ile Asn Gln Ser Leu Ala Phe Ile Arg Lys Ser Asp Glu Leu
            500                 505                 510

Leu His Asn Val Asn Ala Gly Lys Ser Thr Thr Asn Ile Met Ile Thr
        515                 520                 525

Thr Ile Ile Ile Val Ile Ile Val Ile Leu Leu Ser Leu Ile Ala Val
    530                 535                 540

Gly Leu Leu Leu Tyr Cys Lys Ala Arg Ser Thr Pro Val Thr Leu Ser
545                 550                 555                 560

Lys Asp Gln Leu Ser Gly Ile Asn Asn Ile Ala Phe Ser Asn
                565                 570
```

<210> SEQ ID NO 3
<211> LENGTH: 573
<212> TYPE: PRT
<213> ORGANISM: Artificial Sequence
<220> FEATURE:
<223> OTHER INFORMATION: Deletion of 137 (delta 1)

<400> SEQUENCE: 3

```
Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
            20                  25                  30

Tyr Gln Ser Thr Cys Ser Ala Val Ser Lys Gly Tyr Leu Ser Ala Leu
        35                  40                  45
```

-continued

```
Arg Thr Gly Trp Tyr Thr Ser Val Ile Thr Ile Glu Leu Ser Asn Ile
    50                  55                  60

Lys Glu Asn Lys Cys Asn Gly Thr Asp Ala Lys Val Lys Leu Ile Lys
 65              70                  75                      80

Gln Glu Leu Asp Lys Tyr Lys Asn Ala Val Thr Glu Leu Gln Leu Leu
                 85                  90                  95

Met Gln Ser Thr Pro Ala Thr Asn Asn Arg Ala Arg Arg Glu Leu Pro
            100             105             110

Arg Phe Met Asn Tyr Thr Leu Asn Asn Ala Lys Lys Thr Asn Val Thr
        115                 120             125

Leu Ser Lys Lys Gln Lys Gln Gln Leu Gly Phe Leu Leu Gly Val Gly
    130             135                 140

Ser Ala Ile Ala Ser Gly Val Ala Val Ser Lys Val Leu His Leu Glu
145             150             155                     160

Gly Glu Val Asn Lys Ile Lys Ser Ala Leu Leu Ser Thr Asn Lys Ala
                165             170                 175

Val Val Ser Leu Ser Asn Gly Val Ser Val Leu Thr Ser Lys Val Leu
            180             185             190

Asp Leu Lys Asn Tyr Ile Asp Lys Gln Leu Leu Pro Ile Val Asn Lys
        195             200             205

Gln Ser Cys Ser Ile Ser Asn Ile Glu Thr Val Ile Glu Phe Gln Gln
    210             215             220

Lys Asn Asn Arg Leu Leu Glu Ile Thr Arg Glu Phe Ser Val Asn Ala
225             230             235                     240

Gly Val Thr Thr Pro Val Ser Thr Tyr Met Leu Thr Asn Ser Glu Leu
            245             250             255

Leu Ser Leu Ile Asn Asp Met Pro Ile Thr Asn Asp Gln Lys Lys Leu
        260             265             270

Met Ser Asn Asn Val Gln Ile Val Arg Gln Gln Ser Tyr Ser Ile Met
    275             280             285

Ser Ile Ile Lys Glu Glu Val Leu Ala Tyr Val Val Gln Leu Pro Leu
    290             295             300

Tyr Gly Val Ile Asp Thr Pro Cys Trp Lys Leu His Thr Ser Pro Leu
305             310             315                     320

Cys Thr Thr Asn Thr Lys Glu Gly Ser Asn Ile Cys Leu Thr Arg Thr
            325             330             335

Asp Arg Gly Trp Tyr Cys Asp Asn Ala Gly Ser Val Ser Phe Phe Pro
        340             345             350

Gln Ala Glu Thr Cys Lys Val Gln Ser Asn Arg Val Phe Cys Asp Thr
    355             360             365

Met Asn Ser Leu Thr Leu Pro Ser Glu Val Asn Leu Cys Asn Val Asp
    370             375             380

Ile Phe Asn Pro Lys Tyr Asp Cys Lys Ile Met Thr Ser Lys Thr Asp
385             390             395                     400

Val Ser Ser Ser Val Ile Thr Ser Leu Gly Ala Ile Val Ser Cys Tyr
            405             410             415

Gly Lys Thr Lys Cys Thr Ala Ser Asn Lys Asn Arg Gly Ile Ile Lys
        420             425             430

Thr Phe Ser Asn Gly Cys Asp Tyr Val Ser Asn Lys Gly Val Asp Thr
    435             440             445

Val Ser Val Gly Asn Thr Leu Tyr Tyr Val Asn Lys Gln Glu Gly Lys
    450             455             460

Ser Leu Tyr Val Lys Gly Glu Pro Ile Ile Asn Phe Tyr Asp Pro Leu
```

```
                465                 470                 475                 480
Val Phe Pro Ser Asp Glu Phe Asp Ala Ser Ile Ser Gln Val Asn Glu
                485                 490                 495

Lys Ile Asn Gln Ser Leu Ala Phe Ile Arg Lys Ser Asp Glu Leu Leu
            500                 505                 510

His Asn Val Asn Ala Gly Lys Ser Thr Thr Asn Ile Met Ile Thr Thr
        515                 520                 525

Ile Ile Ile Val Ile Ile Val Ile Leu Leu Ser Leu Ile Ala Val Gly
    530                 535                 540

Leu Leu Leu Tyr Cys Lys Ala Arg Ser Thr Pro Val Thr Leu Ser Lys
545                 550                 555                 560

Asp Gln Leu Ser Gly Ile Asn Asn Ile Ala Phe Ser Asn
                565                 570

<210> SEQ ID NO 4
<211> LENGTH: 572
<212> TYPE: PRT
<213> ORGANISM: Artificial Sequence
<220> FEATURE:
<223> OTHER INFORMATION: Deletion of 137-138 (delta 2)

<400> SEQUENCE: 4

Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
            20                  25                  30

Tyr Gln Ser Thr Cys Ser Ala Val Ser Lys Gly Tyr Leu Ser Ala Leu
        35                  40                  45

Arg Thr Gly Trp Tyr Thr Ser Val Ile Thr Ile Glu Leu Ser Asn Ile
    50                  55                  60

Lys Glu Asn Lys Cys Asn Gly Thr Asp Ala Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gln Ser Thr Pro Ala Thr Asn Asn Arg Ala Arg Arg Glu Leu Pro
            100                 105                 110

Arg Phe Met Asn Tyr Thr Leu Asn Asn Ala Lys Lys Thr Asn Val Thr
        115                 120                 125

Leu Ser Lys Lys Gln Lys Gln Gly Phe Leu Leu Gly Val Gly Ser
    130                 135                 140

Ala Ile Ala Ser Gly Val Ala Val Ser Lys Val Leu His Leu Glu Gly
145                 150                 155                 160

Glu Val Asn Lys Ile Lys Ser Ala Leu Leu Ser Thr Asn Lys Ala Val
                165                 170                 175

Val Ser Leu Ser Asn Gly Val Ser Val Leu Thr Ser Lys Val Leu Asp
            180                 185                 190

Leu Lys Asn Tyr Ile Asp Lys Gln Leu Leu Pro Ile Val Asn Lys Gln
        195                 200                 205

Ser Cys Ser Ile Ser Asn Ile Glu Thr Val Ile Glu Phe Gln Gln Lys
    210                 215                 220

Asn Asn Arg Leu Leu Glu Ile Thr Arg Glu Phe Ser Val Asn Ala Gly
225                 230                 235                 240

Val Thr Thr Pro Val Ser Thr Tyr Met Leu Thr Asn Ser Glu Leu Leu
                245                 250                 255

Ser Leu Ile Asn Asp Met Pro Ile Thr Asn Asp Gln Lys Lys Leu Met
```

```
            260                 265                 270
Ser Asn Asn Val Gln Ile Val Arg Gln Gln Ser Tyr Ser Ile Met Ser
            275                 280             285

Ile Ile Lys Glu Glu Val Leu Ala Tyr Val Val Gln Leu Pro Leu Tyr
        290                 295                 300

Gly Val Ile Asp Thr Pro Cys Trp Lys Leu His Thr Ser Pro Leu Cys
305                 310                 315                 320

Thr Thr Asn Thr Lys Glu Gly Ser Asn Ile Cys Leu Thr Arg Thr Asp
                325                 330                 335

Arg Gly Trp Tyr Cys Asp Asn Ala Gly Ser Val Ser Phe Phe Pro Gln
                340                 345                 350

Ala Glu Thr Cys Lys Val Gln Ser Asn Arg Val Phe Cys Asp Thr Met
            355                 360                 365

Asn Ser Leu Thr Leu Pro Ser Glu Val Asn Leu Cys Asn Val Asp Ile
        370                 375                 380

Phe Asn Pro Lys Tyr Asp Cys Lys Ile Met Thr Ser Lys Thr Asp Val
385                 390                 395                 400

Ser Ser Ser Val Ile Thr Ser Leu Gly Ala Ile Val Ser Cys Tyr Gly
                405                 410                 415

Lys Thr Lys Cys Thr Ala Ser Asn Lys Asn Arg Gly Ile Ile Lys Thr
                420                 425                 430

Phe Ser Asn Gly Cys Asp Tyr Val Ser Asn Lys Gly Val Asp Thr Val
            435                 440                 445

Ser Val Gly Asn Thr Leu Tyr Tyr Val Asn Lys Gln Glu Gly Lys Ser
450                 455                 460

Leu Tyr Val Lys Gly Glu Pro Ile Ile Asn Phe Tyr Asp Pro Leu Val
465                 470                 475                 480

Phe Pro Ser Asp Glu Phe Asp Ala Ser Ile Ser Gln Val Asn Glu Lys
                485                 490                 495

Ile Asn Gln Ser Leu Ala Phe Ile Arg Lys Ser Asp Glu Leu Leu His
            500                 505                 510

Asn Val Asn Ala Gly Lys Ser Thr Thr Asn Ile Met Ile Thr Thr Ile
        515                 520                 525

Ile Ile Val Ile Ile Val Ile Leu Leu Ser Leu Ile Ala Val Gly Leu
    530                 535                 540

Leu Leu Tyr Cys Lys Ala Arg Ser Thr Pro Val Thr Leu Ser Lys Asp
545                 550                 555                 560

Gln Leu Ser Gly Ile Asn Asn Ile Ala Phe Ser Asn
                565                 570

<210> SEQ ID NO 5
<211> LENGTH: 571
<212> TYPE: PRT
<213> ORGANISM: Artificial Sequence
<220> FEATURE:
<223> OTHER INFORMATION: Deletion of 137-139 (delta 3)

<400> SEQUENCE: 5

Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
            20                  25                  30

Tyr Gln Ser Thr Cys Ser Ala Val Ser Lys Gly Tyr Leu Ser Ala Leu
        35                  40                  45

Arg Thr Gly Trp Tyr Thr Ser Val Ile Thr Ile Glu Leu Ser Asn Ile
```

```
            50                  55                  60
Lys Glu Asn Lys Cys Asn Gly Thr Asp Ala Lys Val Lys Leu Ile Lys
 65                  70                  75                  80

Gln Glu Leu Asp Lys Tyr Lys Asn Ala Val Thr Glu Leu Gln Leu Leu
                 85                  90                  95

Met Gln Ser Thr Pro Ala Thr Asn Asn Arg Ala Arg Arg Glu Leu Pro
                100                 105                 110

Arg Phe Met Asn Tyr Thr Leu Asn Asn Ala Lys Lys Thr Asn Val Thr
            115                 120                 125

Leu Ser Lys Lys Gln Lys Gln Gln Phe Leu Leu Gly Val Gly Ser Ala
        130                 135                 140

Ile Ala Ser Gly Val Ala Val Ser Lys Val Leu His Leu Glu Gly Glu
145                 150                 155                 160

Val Asn Lys Ile Lys Ser Ala Leu Leu Ser Thr Asn Lys Ala Val Val
                165                 170                 175

Ser Leu Ser Asn Gly Val Ser Val Leu Thr Ser Lys Val Leu Asp Leu
            180                 185                 190

Lys Asn Tyr Ile Asp Lys Gln Leu Leu Pro Ile Val Asn Lys Gln Ser
        195                 200                 205

Cys Ser Ile Ser Asn Ile Glu Thr Val Ile Glu Phe Gln Gln Lys Asn
210                 215                 220

Asn Arg Leu Leu Glu Ile Thr Arg Glu Phe Ser Val Asn Ala Gly Val
225                 230                 235                 240

Thr Thr Pro Val Ser Thr Tyr Met Leu Thr Asn Ser Glu Leu Leu Ser
                245                 250                 255

Leu Ile Asn Asp Met Pro Ile Thr Asn Asp Gln Lys Lys Leu Met Ser
            260                 265                 270

Asn Asn Val Gln Ile Val Arg Gln Gln Ser Tyr Ser Ile Met Ser Ile
        275                 280                 285

Ile Lys Glu Glu Val Leu Ala Tyr Val Val Gln Leu Pro Leu Tyr Gly
290                 295                 300

Val Ile Asp Thr Pro Cys Trp Lys Leu His Thr Ser Pro Leu Cys Thr
305                 310                 315                 320

Thr Asn Thr Lys Glu Gly Ser Asn Ile Cys Leu Thr Arg Thr Asp Arg
                325                 330                 335

Gly Trp Tyr Cys Asp Asn Ala Gly Ser Val Ser Phe Phe Pro Gln Ala
            340                 345                 350

Glu Thr Cys Lys Val Gln Ser Asn Arg Val Phe Cys Asp Thr Met Asn
        355                 360                 365

Ser Leu Thr Leu Pro Ser Glu Val Asn Leu Cys Asn Val Asp Ile Phe
370                 375                 380

Asn Pro Lys Tyr Asp Cys Lys Ile Met Thr Ser Lys Thr Asp Val Ser
385                 390                 395                 400

Ser Ser Val Ile Thr Ser Leu Gly Ala Ile Val Ser Cys Tyr Gly Lys
                405                 410                 415

Thr Lys Cys Thr Ala Ser Asn Lys Asn Arg Gly Ile Ile Lys Thr Phe
            420                 425                 430

Ser Asn Gly Cys Asp Tyr Val Ser Asn Lys Gly Val Asp Thr Val Ser
        435                 440                 445

Val Gly Asn Thr Leu Tyr Tyr Val Asn Lys Gln Glu Gly Lys Ser Leu
450                 455                 460

Tyr Val Lys Gly Glu Pro Ile Ile Asn Phe Tyr Asp Pro Leu Val Phe
465                 470                 475                 480
```

Pro Ser Asp Glu Phe Asp Ala Ser Ile Ser Gln Val Asn Glu Lys Ile
              485                 490                 495

Asn Gln Ser Leu Ala Phe Ile Arg Lys Ser Asp Glu Leu Leu His Asn
            500                 505                 510

Val Asn Ala Gly Lys Ser Thr Thr Asn Ile Met Ile Thr Thr Ile Ile
        515                 520                 525

Ile Val Ile Ile Val Ile Leu Leu Ser Leu Ile Ala Val Gly Leu Leu
    530                 535                 540

Leu Tyr Cys Lys Ala Arg Ser Thr Pro Val Thr Leu Ser Lys Asp Gln
545                 550                 555                 560

Leu Ser Gly Ile Asn Asn Ile Ala Phe Ser Asn
                565                 570

<210> SEQ ID NO 6
<211> LENGTH: 570
<212> TYPE: PRT
<213> ORGANISM: Artificial Sequence
<220> FEATURE:
<223> OTHER INFORMATION: Deletion of 137-140 (delta 4)

<400> SEQUENCE: 6

Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
            20                  25                  30

Tyr Gln Ser Thr Cys Ser Ala Val Ser Lys Gly Tyr Leu Ser Ala Leu
        35                  40                  45

Arg Thr Gly Trp Tyr Thr Ser Val Ile Thr Ile Glu Leu Ser Asn Ile
    50                  55                  60

Lys Glu Asn Lys Cys Asn Gly Thr Asp Ala Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gln Ser Thr Pro Ala Thr Asn Asn Arg Ala Arg Arg Glu Leu Pro
            100                 105                 110

Arg Phe Met Asn Tyr Thr Leu Asn Asn Ala Lys Lys Thr Asn Val Thr
        115                 120                 125

Leu Ser Lys Lys Gln Lys Gln Gln Leu Leu Gly Val Gly Ser Ala Ile
    130                 135                 140

Ala Ser Gly Val Ala Val Ser Lys Val Leu His Leu Glu Gly Glu Val
145                 150                 155                 160

Asn Lys Ile Lys Ser Ala Leu Leu Ser Thr Asn Lys Ala Val Val Ser
                165                 170                 175

Leu Ser Asn Gly Val Ser Val Leu Thr Ser Lys Val Leu Asp Leu Lys
            180                 185                 190

Asn Tyr Ile Asp Lys Gln Leu Leu Pro Ile Val Asn Lys Gln Ser Cys
        195                 200                 205

Ser Ile Ser Asn Ile Glu Thr Val Ile Glu Phe Gln Gln Lys Asn Asn
    210                 215                 220

Arg Leu Leu Glu Ile Thr Arg Glu Phe Ser Val Asn Ala Gly Val Thr
225                 230                 235                 240

Thr Pro Val Ser Thr Tyr Met Leu Thr Asn Ser Glu Leu Leu Ser Leu
                245                 250                 255

Ile Asn Asp Met Pro Ile Thr Asn Asp Gln Lys Lys Leu Met Ser Asn
            260                 265                 270

```
Asn Val Gln Ile Val Arg Gln Ser Tyr Ser Ile Met Ser Ile Ile
        275                 280                 285

Lys Glu Glu Val Leu Ala Tyr Val Val Gln Leu Pro Leu Tyr Gly Val
        290                 295                 300

Ile Asp Thr Pro Cys Trp Lys Leu His Thr Ser Pro Leu Cys Thr Thr
305                 310                 315                 320

Asn Thr Lys Glu Gly Ser Asn Ile Cys Leu Thr Arg Thr Asp Arg Gly
                325                 330                 335

Trp Tyr Cys Asp Asn Ala Gly Ser Val Ser Phe Phe Pro Gln Ala Glu
                340                 345                 350

Thr Cys Lys Val Gln Ser Asn Arg Val Phe Cys Asp Thr Met Asn Ser
        355                 360                 365

Leu Thr Leu Pro Ser Glu Val Asn Leu Cys Asn Val Asp Ile Phe Asn
        370                 375                 380

Pro Lys Tyr Asp Cys Lys Ile Met Thr Ser Lys Thr Asp Val Ser Ser
385                 390                 395                 400

Ser Val Ile Thr Ser Leu Gly Ala Ile Val Ser Cys Tyr Gly Lys Thr
                405                 410                 415

Lys Cys Thr Ala Ser Asn Lys Asn Arg Gly Ile Ile Lys Thr Phe Ser
        420                 425                 430

Asn Gly Cys Asp Tyr Val Ser Asn Lys Gly Val Asp Thr Val Ser Val
        435                 440                 445

Gly Asn Thr Leu Tyr Tyr Val Asn Lys Gln Glu Gly Lys Ser Leu Tyr
        450                 455                 460

Val Lys Gly Glu Pro Ile Ile Asn Phe Tyr Asp Pro Leu Val Phe Pro
465                 470                 475                 480

Ser Asp Glu Phe Asp Ala Ser Ile Ser Gln Val Asn Glu Lys Ile Asn
                485                 490                 495

Gln Ser Leu Ala Phe Ile Arg Lys Ser Asp Glu Leu Leu His Asn Val
        500                 505                 510

Asn Ala Gly Lys Ser Thr Thr Asn Ile Met Ile Thr Thr Ile Ile Ile
        515                 520                 525

Val Ile Ile Val Ile Leu Leu Ser Leu Ile Ala Val Gly Leu Leu Leu
        530                 535                 540

Tyr Cys Lys Ala Arg Ser Thr Pro Val Thr Leu Ser Lys Asp Gln Leu
545                 550                 555                 560

Ser Gly Ile Asn Asn Ile Ala Phe Ser Asn
                565                 570

<210> SEQ ID NO 7
<211> LENGTH: 569
<212> TYPE: PRT
<213> ORGANISM: Artificial Sequence
<220> FEATURE:
<223> OTHER INFORMATION: Deletion of 137-141 (delta 5)

<400> SEQUENCE: 7

Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
                20                  25                  30

Tyr Gln Ser Thr Cys Ser Ala Val Ser Lys Gly Tyr Leu Ser Ala Leu
        35                  40                  45

Arg Thr Gly Trp Tyr Thr Ser Val Ile Thr Ile Glu Leu Ser Asn Ile
        50                  55                  60
```

```
Lys Glu Asn Lys Cys Asn Gly Thr Asp Ala Lys Val Lys Leu Ile Lys
 65                  70                  75                  80

Gln Glu Leu Asp Lys Tyr Lys Asn Ala Val Thr Glu Leu Gln Leu Leu
             85                  90                  95

Met Gln Ser Thr Pro Ala Thr Asn Asn Arg Ala Arg Arg Glu Leu Pro
            100                 105                 110

Arg Phe Met Asn Tyr Thr Leu Asn Asn Ala Lys Lys Thr Asn Val Thr
            115                 120                 125

Leu Ser Lys Lys Gln Lys Gln Gln Leu Gly Val Gly Ser Ala Ile Ala
            130                 135                 140

Ser Gly Val Ala Val Ser Lys Val Leu His Leu Glu Gly Glu Val Asn
145                 150                 155                 160

Lys Ile Lys Ser Ala Leu Leu Ser Thr Asn Lys Ala Val Val Ser Leu
            165                 170                 175

Ser Asn Gly Val Ser Val Leu Thr Ser Lys Val Leu Asp Leu Lys Asn
            180                 185                 190

Tyr Ile Asp Lys Gln Leu Leu Pro Ile Val Asn Lys Gln Ser Cys Ser
            195                 200                 205

Ile Ser Asn Ile Glu Thr Val Ile Glu Phe Gln Gln Lys Asn Asn Arg
210                 215                 220

Leu Leu Glu Ile Thr Arg Glu Phe Ser Val Asn Ala Gly Val Thr Thr
225                 230                 235                 240

Pro Val Ser Thr Tyr Met Leu Thr Asn Ser Glu Leu Leu Ser Leu Ile
            245                 250                 255

Asn Asp Met Pro Ile Thr Asn Asp Gln Lys Lys Leu Met Ser Asn Asn
            260                 265                 270

Val Gln Ile Val Arg Gln Gln Ser Tyr Ser Ile Met Ser Ile Ile Lys
            275                 280                 285

Glu Glu Val Leu Ala Tyr Val Val Gln Leu Pro Leu Tyr Gly Val Ile
290                 295                 300

Asp Thr Pro Cys Trp Lys Leu His Thr Ser Pro Leu Cys Thr Thr Asn
305                 310                 315                 320

Thr Lys Glu Gly Ser Asn Ile Cys Leu Thr Arg Thr Asp Arg Gly Trp
            325                 330                 335

Tyr Cys Asp Asn Ala Gly Ser Val Ser Phe Phe Pro Gln Ala Glu Thr
            340                 345                 350

Cys Lys Val Gln Ser Asn Arg Val Phe Cys Asp Thr Met Asn Ser Leu
            355                 360                 365

Thr Leu Pro Ser Glu Val Asn Leu Cys Asn Val Asp Ile Phe Asn Pro
            370                 375                 380

Lys Tyr Asp Cys Lys Ile Met Thr Ser Lys Thr Asp Val Ser Ser Ser
385                 390                 395                 400

Val Ile Thr Ser Leu Gly Ala Ile Val Ser Cys Tyr Gly Lys Thr Lys
            405                 410                 415

Cys Thr Ala Ser Asn Lys Asn Arg Gly Ile Ile Lys Thr Phe Ser Asn
            420                 425                 430

Gly Cys Asp Tyr Val Ser Asn Lys Gly Val Asp Thr Val Ser Val Gly
            435                 440                 445

Asn Thr Leu Tyr Tyr Val Asn Lys Gln Glu Gly Lys Ser Leu Tyr Val
            450                 455                 460

Lys Gly Glu Pro Ile Ile Asn Phe Tyr Asp Pro Leu Val Phe Pro Ser
465                 470                 475                 480
```

-continued

```
Asp Glu Phe Asp Ala Ser Ile Ser Gln Val Asn Glu Lys Ile Asn Gln
                485                 490                 495

Ser Leu Ala Phe Ile Arg Lys Ser Asp Glu Leu Leu His Asn Val Asn
            500                 505                 510

Ala Gly Lys Ser Thr Thr Asn Ile Met Ile Thr Ile Ile Val
            515                 520                 525

Ile Ile Val Ile Leu Leu Ser Leu Ile Ala Val Gly Leu Leu Leu Tyr
            530                 535                 540

Cys Lys Ala Arg Ser Thr Pro Val Thr Leu Ser Lys Asp Gln Leu Ser
545                 550                 555                 560

Gly Ile Asn Asn Ile Ala Phe Ser Asn
                565

<210> SEQ ID NO 8
<211> LENGTH: 564
<212> TYPE: PRT
<213> ORGANISM: Artificial Sequence
<220> FEATURE:
<223> OTHER INFORMATION: Deletion of 137-146 (delta 10)

<400> SEQUENCE: 8

Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
            20                  25                  30

Tyr Gln Ser Thr Cys Ser Ala Val Ser Lys Gly Tyr Leu Ser Ala Leu
        35                  40                  45

Arg Thr Gly Trp Tyr Thr Ser Val Ile Thr Ile Glu Leu Ser Asn Ile
    50                  55                  60

Lys Glu Asn Lys Cys Asn Gly Thr Asp Ala Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gln Ser Thr Pro Ala Thr Asn Asn Arg Ala Arg Arg Glu Leu Pro
            100                 105                 110

Arg Phe Met Asn Tyr Thr Leu Asn Asn Ala Lys Lys Thr Asn Val Thr
        115                 120                 125

Leu Ser Lys Lys Gln Lys Gln Ala Ile Ala Ser Gly Val Ala Val
130                 135                 140

Ser Lys Val Leu His Leu Glu Gly Glu Val Asn Lys Ile Lys Ser Ala
145                 150                 155                 160

Leu Leu Ser Thr Asn Lys Ala Val Val Ser Leu Ser Asn Gly Val Ser
                165                 170                 175

Val Leu Thr Ser Lys Val Leu Asp Leu Lys Asn Tyr Ile Asp Lys Gln
            180                 185                 190

Leu Leu Pro Ile Val Asn Lys Gln Ser Cys Ser Ile Ser Asn Ile Glu
        195                 200                 205

Thr Val Ile Glu Phe Gln Gln Lys Asn Asn Arg Leu Leu Glu Ile Thr
    210                 215                 220

Arg Glu Phe Ser Val Asn Ala Gly Val Thr Thr Pro Val Ser Thr Tyr
225                 230                 235                 240

Met Leu Thr Asn Ser Glu Leu Leu Ser Leu Ile Asn Asp Met Pro Ile
                245                 250                 255

Thr Asn Asp Gln Lys Lys Leu Met Ser Asn Asn Val Gln Ile Val Arg
            260                 265                 270
```

```
Gln Gln Ser Tyr Ser Ile Met Ser Ile Ile Lys Glu Glu Val Leu Ala
            275                 280                 285

Tyr Val Val Gln Leu Pro Leu Tyr Gly Val Ile Asp Thr Pro Cys Trp
290                 295                 300

Lys Leu His Thr Ser Pro Leu Cys Thr Thr Asn Thr Lys Glu Gly Ser
305                 310                 315                 320

Asn Ile Cys Leu Thr Arg Thr Asp Arg Gly Trp Tyr Cys Asp Asn Ala
                325                 330                 335

Gly Ser Val Ser Phe Phe Pro Gln Ala Glu Thr Cys Lys Val Gln Ser
            340                 345                 350

Asn Arg Val Phe Cys Asp Thr Met Asn Ser Leu Thr Leu Pro Ser Glu
        355                 360                 365

Val Asn Leu Cys Asn Val Asp Ile Phe Asn Pro Lys Tyr Asp Cys Lys
370                 375                 380

Ile Met Thr Ser Lys Thr Asp Val Ser Ser Val Ile Thr Ser Leu
385                 390                 395                 400

Gly Ala Ile Val Ser Cys Tyr Gly Lys Thr Lys Cys Thr Ala Ser Asn
                405                 410                 415

Lys Asn Arg Gly Ile Ile Lys Thr Phe Ser Asn Gly Cys Asp Tyr Val
            420                 425                 430

Ser Asn Lys Gly Val Asp Thr Val Ser Val Gly Asn Thr Leu Tyr Tyr
        435                 440                 445

Val Asn Lys Gln Glu Gly Lys Ser Leu Tyr Val Lys Gly Glu Pro Ile
450                 455                 460

Ile Asn Phe Tyr Asp Pro Leu Val Phe Pro Ser Asp Glu Phe Asp Ala
465                 470                 475                 480

Ser Ile Ser Gln Val Asn Glu Lys Ile Asn Gln Ser Leu Ala Phe Ile
                485                 490                 495

Arg Lys Ser Asp Glu Leu Leu His Asn Val Asn Ala Gly Lys Ser Thr
            500                 505                 510

Thr Asn Ile Met Ile Thr Thr Ile Ile Ile Val Ile Ile Val Ile Leu
        515                 520                 525

Leu Ser Leu Ile Ala Val Gly Leu Leu Leu Tyr Cys Lys Ala Arg Ser
530                 535                 540

Thr Pro Val Thr Leu Ser Lys Asp Gln Leu Ser Gly Ile Asn Asn Ile
545                 550                 555                 560

Ala Phe Ser Asn

<210> SEQ ID NO 9
<211> LENGTH: 568
<212> TYPE: PRT
<213> ORGANISM: Artificial Sequence
<220> FEATURE:
<223> OTHER INFORMATION: Deletion of 137-142 (delta 6)

<400> SEQUENCE: 9

Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
            20                  25                  30

Tyr Gln Ser Thr Cys Ser Ala Val Ser Lys Gly Tyr Leu Ser Ala Leu
        35                  40                  45

Arg Thr Gly Trp Tyr Thr Ser Val Ile Thr Ile Glu Leu Ser Asn Ile
    50                  55                  60

Lys Glu Asn Lys Cys Asn Gly Thr Asp Ala Lys Val Lys Leu Ile Lys
```

```
                65                  70                  75                  80
            Gln Glu Leu Asp Lys Tyr Lys Asn Ala Val Thr Glu Leu Gln Leu Leu
                            85                  90                  95

Met Gln Ser Thr Pro Ala Thr Asn Asn Arg Ala Arg Arg Glu Leu Pro
                            100                 105                 110

Arg Phe Met Asn Tyr Thr Leu Asn Asn Ala Lys Lys Thr Asn Val Thr
                            115                 120                 125

Leu Ser Lys Lys Gln Lys Gln Gln Gly Val Gly Ser Ala Ile Ala Ser
                            130                 135                 140

Gly Val Ala Val Ser Lys Val Leu His Leu Glu Gly Glu Val Asn Lys
            145                 150                 155                 160

Ile Lys Ser Ala Leu Leu Ser Thr Asn Lys Ala Val Val Ser Leu Ser
                            165                 170                 175

Asn Gly Val Ser Val Leu Thr Ser Lys Val Leu Asp Leu Lys Asn Tyr
                            180                 185                 190

Ile Asp Lys Gln Leu Leu Pro Ile Val Asn Lys Gln Ser Cys Ser Ile
                            195                 200                 205

Ser Asn Ile Glu Thr Val Ile Glu Phe Gln Gln Lys Asn Asn Arg Leu
                            210                 215                 220

Leu Glu Ile Thr Arg Glu Phe Ser Val Asn Ala Gly Val Thr Thr Pro
            225                 230                 235                 240

Val Ser Thr Tyr Met Leu Thr Asn Ser Glu Leu Leu Ser Leu Ile Asn
                            245                 250                 255

Asp Met Pro Ile Thr Asn Asp Gln Lys Lys Leu Met Ser Asn Asn Val
                            260                 265                 270

Gln Ile Val Arg Gln Gln Ser Tyr Ser Ile Met Ser Ile Ile Lys Glu
                            275                 280                 285

Glu Val Leu Ala Tyr Val Val Gln Leu Pro Leu Tyr Gly Val Ile Asp
                            290                 295                 300

Thr Pro Cys Trp Lys Leu His Thr Ser Pro Leu Cys Thr Thr Asn Thr
            305                 310                 315                 320

Lys Glu Gly Ser Asn Ile Cys Leu Thr Arg Thr Asp Arg Gly Trp Tyr
                            325                 330                 335

Cys Asp Asn Ala Gly Ser Val Ser Phe Phe Pro Gln Ala Glu Thr Cys
                            340                 345                 350

Lys Val Gln Ser Asn Arg Val Phe Cys Asp Thr Met Asn Ser Leu Thr
                            355                 360                 365

Leu Pro Ser Glu Val Asn Leu Cys Asn Val Asp Ile Phe Asn Pro Lys
                            370                 375                 380

Tyr Asp Cys Lys Ile Met Thr Ser Lys Thr Asp Val Ser Ser Ser Val
            385                 390                 395                 400

Ile Thr Ser Leu Gly Ala Ile Val Ser Cys Tyr Gly Lys Thr Lys Cys
                            405                 410                 415

Thr Ala Ser Asn Lys Asn Arg Gly Ile Ile Lys Thr Phe Ser Asn Gly
                            420                 425                 430

Cys Asp Tyr Val Ser Asn Lys Gly Val Asp Thr Val Ser Val Gly Asn
                            435                 440                 445

Thr Leu Tyr Tyr Val Asn Lys Gln Glu Gly Lys Ser Leu Tyr Val Lys
                            450                 455                 460

Gly Glu Pro Ile Ile Asn Phe Tyr Asp Pro Leu Val Phe Pro Ser Asp
            465                 470                 475                 480

Glu Phe Asp Ala Ser Ile Ser Gln Val Asn Glu Lys Ile Asn Gln Ser
                            485                 490                 495
```

```
Leu Ala Phe Ile Arg Lys Ser Asp Glu Leu His Asn Val Asn Ala
                500                 505                 510

Gly Lys Ser Thr Thr Asn Ile Met Ile Thr Thr Ile Ile Val Ile
                515                 520                 525

Ile Val Ile Leu Leu Ser Leu Ile Ala Val Gly Leu Leu Leu Tyr Cys
                530                 535                 540

Lys Ala Arg Ser Thr Pro Val Thr Leu Ser Lys Asp Gln Leu Ser Gly
545                 550                 555                 560

Ile Asn Asn Ile Ala Phe Ser Asn
                565

<210> SEQ ID NO 10
<211> LENGTH: 567
<212> TYPE: PRT
<213> ORGANISM: Artificial Sequence
<220> FEATURE:
<223> OTHER INFORMATION: Deletion of 137-143 (delta 7)

<400> SEQUENCE: 10

Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
                20                  25                  30

Tyr Gln Ser Thr Cys Ser Ala Val Ser Lys Gly Tyr Leu Ser Ala Leu
            35                  40                  45

Arg Thr Gly Trp Tyr Thr Ser Val Ile Thr Ile Glu Leu Ser Asn Ile
        50                  55                  60

Lys Glu Asn Lys Cys Asn Gly Thr Asp Ala Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gln Ser Thr Pro Ala Thr Asn Asn Arg Ala Arg Arg Glu Leu Pro
                100                 105                 110

Arg Phe Met Asn Tyr Thr Leu Asn Asn Ala Lys Lys Thr Asn Val Thr
            115                 120                 125

Leu Ser Lys Lys Gln Lys Gln Gln Val Gly Ser Ala Ile Ala Ser Gly
        130                 135                 140

Val Ala Val Ser Lys Val Leu His Leu Glu Gly Glu Val Asn Lys Ile
145                 150                 155                 160

Lys Ser Ala Leu Leu Ser Thr Asn Lys Ala Val Val Ser Leu Ser Asn
                165                 170                 175

Gly Val Ser Val Leu Thr Ser Lys Val Leu Asp Leu Lys Asn Tyr Ile
                180                 185                 190

Asp Lys Gln Leu Leu Pro Ile Val Asn Lys Gln Ser Cys Ser Ile Ser
            195                 200                 205

Asn Ile Glu Thr Val Ile Glu Phe Gln Gln Lys Asn Asn Arg Leu Leu
        210                 215                 220

Glu Ile Thr Arg Glu Phe Ser Val Asn Ala Gly Val Thr Thr Pro Val
225                 230                 235                 240

Ser Thr Tyr Met Leu Thr Asn Ser Glu Leu Leu Ser Leu Ile Asn Asp
                245                 250                 255

Met Pro Ile Thr Asn Asp Gln Lys Lys Leu Met Ser Asn Asn Val Gln
                260                 265                 270

Ile Val Arg Gln Gln Ser Tyr Ser Ile Met Ser Ile Ile Lys Glu Glu
            275                 280                 285
```

```
Val Leu Ala Tyr Val Val Gln Leu Pro Leu Tyr Gly Val Ile Asp Thr
        290                 295                 300

Pro Cys Trp Lys Leu His Thr Ser Pro Leu Cys Thr Thr Asn Thr Lys
305                 310                 315                 320

Glu Gly Ser Asn Ile Cys Leu Thr Arg Thr Asp Arg Gly Trp Tyr Cys
                325                 330                 335

Asp Asn Ala Gly Ser Val Ser Phe Phe Pro Gln Ala Glu Thr Cys Lys
                340                 345                 350

Val Gln Ser Asn Arg Val Phe Cys Asp Thr Met Asn Ser Leu Thr Leu
        355                 360                 365

Pro Ser Glu Val Asn Leu Cys Asn Val Asp Ile Phe Asn Pro Lys Tyr
    370                 375                 380

Asp Cys Lys Ile Met Thr Ser Lys Thr Asp Val Ser Ser Val Ile
385                 390                 395                 400

Thr Ser Leu Gly Ala Ile Val Ser Cys Tyr Gly Lys Thr Lys Cys Thr
                405                 410                 415

Ala Ser Asn Lys Asn Arg Gly Ile Ile Lys Thr Phe Ser Asn Gly Cys
                420                 425                 430

Asp Tyr Val Ser Asn Lys Gly Val Asp Thr Val Ser Val Gly Asn Thr
        435                 440                 445

Leu Tyr Tyr Val Asn Lys Gln Glu Gly Lys Ser Leu Tyr Val Lys Gly
    450                 455                 460

Glu Pro Ile Ile Asn Phe Tyr Asp Pro Leu Val Phe Pro Ser Asp Glu
465                 470                 475                 480

Phe Asp Ala Ser Ile Ser Gln Val Asn Glu Lys Ile Asn Gln Ser Leu
                485                 490                 495

Ala Phe Ile Arg Lys Ser Asp Glu Leu Leu His Asn Val Asn Ala Gly
                500                 505                 510

Lys Ser Thr Thr Asn Ile Met Ile Thr Thr Ile Ile Ile Val Ile Ile
        515                 520                 525

Val Ile Leu Leu Ser Leu Ile Ala Val Gly Leu Leu Leu Tyr Cys Lys
    530                 535                 540

Ala Arg Ser Thr Pro Val Thr Leu Ser Lys Asp Gln Leu Ser Gly Ile
545                 550                 555                 560

Asn Asn Ile Ala Phe Ser Asn
                565
```

<210> SEQ ID NO 11
<211> LENGTH: 566
<212> TYPE: PRT
<213> ORGANISM: Artificial Sequence
<220> FEATURE:
<223> OTHER INFORMATION: Deletion of 137-144 (delta 8)

<400> SEQUENCE: 11

```
Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
            20                  25                  30

Tyr Gln Ser Thr Cys Ser Ala Val Ser Lys Gly Tyr Leu Ser Ala Leu
        35                  40                  45

Arg Thr Gly Trp Tyr Thr Ser Val Ile Thr Ile Glu Leu Ser Asn Ile
    50                  55                  60

Lys Glu Asn Lys Cys Asn Gly Thr Asp Ala Lys Val Lys Leu Ile Lys
65                  70                  75                  80
```

```
Gln Glu Leu Asp Lys Tyr Lys Asn Ala Val Thr Leu Gln Leu Leu
                85                  90                  95

Met Gln Ser Thr Pro Ala Thr Asn Asn Arg Ala Arg Arg Glu Leu Pro
            100                 105                 110

Arg Phe Met Asn Tyr Thr Leu Asn Asn Ala Lys Lys Thr Asn Val Thr
            115                 120                 125

Leu Ser Lys Lys Gln Lys Gln Gln Gly Ser Ala Ile Ala Ser Gly Val
130                 135                 140

Ala Val Ser Lys Val Leu His Leu Glu Gly Glu Val Asn Lys Ile Lys
145                 150                 155                 160

Ser Ala Leu Leu Ser Thr Asn Lys Ala Val Val Ser Leu Ser Asn Gly
                165                 170                 175

Val Ser Val Leu Thr Ser Lys Val Leu Asp Leu Lys Asn Tyr Ile Asp
            180                 185                 190

Lys Gln Leu Leu Pro Ile Val Asn Lys Gln Ser Cys Ser Ile Ser Asn
            195                 200                 205

Ile Glu Thr Val Ile Glu Phe Gln Gln Lys Asn Asn Arg Leu Leu Glu
            210                 215                 220

Ile Thr Arg Glu Phe Ser Val Asn Ala Gly Val Thr Thr Pro Val Ser
225                 230                 235                 240

Thr Tyr Met Leu Thr Asn Ser Glu Leu Leu Ser Leu Ile Asn Asp Met
                245                 250                 255

Pro Ile Thr Asn Asp Gln Lys Lys Leu Met Ser Asn Asn Val Gln Ile
            260                 265                 270

Val Arg Gln Gln Ser Tyr Ser Ile Met Ser Ile Ile Lys Glu Glu Val
            275                 280                 285

Leu Ala Tyr Val Val Gln Leu Pro Leu Tyr Gly Val Ile Asp Thr Pro
290                 295                 300

Cys Trp Lys Leu His Thr Ser Pro Leu Cys Thr Thr Asn Thr Lys Glu
305                 310                 315                 320

Gly Ser Asn Ile Cys Leu Thr Arg Thr Asp Arg Gly Trp Tyr Cys Asp
                325                 330                 335

Asn Ala Gly Ser Val Ser Phe Phe Pro Gln Ala Glu Thr Cys Lys Val
            340                 345                 350

Gln Ser Asn Arg Val Phe Cys Asp Thr Met Asn Ser Leu Thr Leu Pro
            355                 360                 365

Ser Glu Val Asn Leu Cys Asn Val Asp Ile Phe Asn Pro Lys Tyr Asp
            370                 375                 380

Cys Lys Ile Met Thr Ser Lys Thr Asp Val Ser Ser Ser Val Ile Thr
385                 390                 395                 400

Ser Leu Gly Ala Ile Val Ser Cys Tyr Gly Lys Thr Lys Cys Thr Ala
                405                 410                 415

Ser Asn Lys Asn Arg Gly Ile Ile Lys Thr Phe Ser Asn Gly Cys Asp
            420                 425                 430

Tyr Val Ser Asn Lys Gly Val Asp Thr Val Ser Val Gly Asn Thr Leu
            435                 440                 445

Tyr Tyr Val Asn Lys Gln Glu Gly Lys Ser Leu Tyr Val Lys Gly Glu
450                 455                 460

Pro Ile Ile Asn Phe Tyr Asp Pro Leu Val Phe Pro Ser Asp Glu Phe
465                 470                 475                 480

Asp Ala Ser Ile Ser Gln Val Asn Glu Lys Ile Asn Gln Ser Leu Ala
                485                 490                 495
```

Phe Ile Arg Lys Ser Asp Glu Leu Leu His Asn Val Asn Ala Gly Lys
                  500                 505                 510

Ser Thr Thr Asn Ile Met Ile Thr Ile Ile Val Ile Ile Val
        515                 520                 525

Ile Leu Leu Ser Leu Ile Ala Val Gly Leu Leu Tyr Cys Lys Ala
        530                 535                 540

Arg Ser Thr Pro Val Thr Leu Ser Lys Asp Gln Leu Ser Gly Ile Asn
545                 550                 555                 560

Asn Ile Ala Phe Ser Asn
                565

<210> SEQ ID NO 12
<211> LENGTH: 565
<212> TYPE: PRT
<213> ORGANISM: Artificial Sequence
<220> FEATURE:
<223> OTHER INFORMATION: Deletion of 137-145 (delta 9)

<400> SEQUENCE: 12

Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
            20                  25                  30

Tyr Gln Ser Thr Cys Ser Ala Val Ser Lys Gly Tyr Leu Ser Ala Leu
        35                  40                  45

Arg Thr Gly Trp Tyr Thr Ser Val Ile Thr Ile Glu Leu Ser Asn Ile
    50                  55                  60

Lys Glu Asn Lys Cys Asn Gly Thr Asp Ala Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gln Ser Thr Pro Ala Thr Asn Asn Arg Ala Arg Arg Glu Leu Pro
            100                 105                 110

Arg Phe Met Asn Tyr Thr Leu Asn Asn Ala Lys Lys Thr Asn Val Thr
        115                 120                 125

Leu Ser Lys Lys Gln Lys Gln Gln Ser Ala Ile Ala Ser Gly Val Ala
    130                 135                 140

Val Ser Lys Val Leu His Leu Glu Gly Glu Val Asn Lys Ile Lys Ser
145                 150                 155                 160

Ala Leu Leu Ser Thr Asn Lys Ala Val Val Ser Leu Ser Asn Gly Val
                165                 170                 175

Ser Val Leu Thr Ser Lys Val Leu Asp Leu Lys Asn Tyr Ile Asp Lys
            180                 185                 190

Gln Leu Leu Pro Ile Val Asn Lys Gln Ser Cys Ser Ile Ser Asn Ile
        195                 200                 205

Glu Thr Val Ile Glu Phe Gln Gln Lys Asn Asn Arg Leu Leu Glu Ile
    210                 215                 220

Thr Arg Glu Phe Ser Val Asn Ala Gly Val Thr Thr Pro Val Ser Thr
225                 230                 235                 240

Tyr Met Leu Thr Asn Ser Glu Leu Leu Ser Leu Ile Asn Asp Met Pro
                245                 250                 255

Ile Thr Asn Asp Gln Lys Lys Leu Met Ser Asn Asn Val Gln Ile Val
            260                 265                 270

Arg Gln Gln Ser Tyr Ser Ile Met Ser Ile Ile Lys Glu Glu Val Leu
        275                 280                 285

```
Ala Tyr Val Val Gln Leu Pro Leu Tyr Gly Val Ile Asp Thr Pro Cys
    290                 295                 300

Trp Lys Leu His Thr Ser Pro Leu Cys Thr Thr Asn Thr Lys Glu Gly
305                 310                 315                 320

Ser Asn Ile Cys Leu Thr Arg Thr Asp Arg Gly Trp Tyr Cys Asp Asn
                325                 330                 335

Ala Gly Ser Val Ser Phe Phe Pro Gln Ala Glu Thr Cys Lys Val Gln
            340                 345                 350

Ser Asn Arg Val Phe Cys Asp Thr Met Asn Ser Leu Thr Leu Pro Ser
        355                 360                 365

Glu Val Asn Leu Cys Asn Val Asp Ile Phe Asn Pro Lys Tyr Asp Cys
370                 375                 380

Lys Ile Met Thr Ser Lys Thr Asp Val Ser Ser Val Ile Thr Ser
385                 390                 395                 400

Leu Gly Ala Ile Val Ser Cys Tyr Gly Lys Thr Lys Cys Thr Ala Ser
                405                 410                 415

Asn Lys Asn Arg Gly Ile Ile Lys Thr Phe Ser Asn Gly Cys Asp Tyr
            420                 425                 430

Val Ser Asn Lys Gly Val Asp Thr Val Ser Val Gly Asn Thr Leu Tyr
        435                 440                 445

Tyr Val Asn Lys Gln Glu Gly Lys Ser Leu Tyr Val Lys Gly Glu Pro
    450                 455                 460

Ile Ile Asn Phe Tyr Asp Pro Leu Val Phe Pro Ser Asp Glu Phe Asp
465                 470                 475                 480

Ala Ser Ile Ser Gln Val Asn Glu Lys Ile Asn Gln Ser Leu Ala Phe
                485                 490                 495

Ile Arg Lys Ser Asp Glu Leu Leu His Asn Val Asn Ala Gly Lys Ser
            500                 505                 510

Thr Thr Asn Ile Met Ile Thr Thr Ile Ile Val Ile Ile Val Ile
        515                 520                 525

Leu Leu Ser Leu Ile Ala Val Gly Leu Leu Leu Tyr Cys Lys Ala Arg
    530                 535                 540

Ser Thr Pro Val Thr Leu Ser Lys Asp Gln Leu Ser Gly Ile Asn Asn
545                 550                 555                 560

Ile Ala Phe Ser Asn
                565

<210> SEQ ID NO 13
<211> LENGTH: 565
<212> TYPE: PRT
<213> ORGANISM: Artificial Sequence
<220> FEATURE:
<223> OTHER INFORMATION: Deletion of 137-145 (delta 9) with wild type
      fusion cleavage site

<400> SEQUENCE: 13

Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
            20                  25                  30

Tyr Gln Ser Thr Cys Ser Ala Val Ser Lys Gly Tyr Leu Ser Ala Leu
        35                  40                  45

Arg Thr Gly Trp Tyr Thr Ser Val Ile Thr Ile Glu Leu Ser Asn Ile
    50                  55                  60

Lys Glu Asn Lys Cys Asn Gly Thr Asp Ala Lys Val Lys Leu Ile Lys
65                  70                  75                  80
```

Gln Glu Leu Asp Lys Tyr Lys Asn Ala Val Thr Glu Leu Gln Leu Leu
                    85                  90                  95

Met Gln Ser Thr Pro Ala Thr Asn Asn Arg Ala Arg Arg Glu Leu Pro
                100                 105                 110

Arg Phe Met Asn Tyr Thr Leu Asn Asn Ala Lys Lys Thr Asn Val Thr
            115                 120                 125

Leu Ser Lys Lys Arg Lys Arg Arg Ser Ala Ile Ala Ser Gly Val Ala
130                 135                 140

Val Ser Lys Val Leu His Leu Glu Gly Glu Val Asn Lys Ile Lys Ser
145                 150                 155                 160

Ala Leu Leu Ser Thr Asn Lys Ala Val Val Ser Leu Ser Asn Gly Val
                165                 170                 175

Ser Val Leu Thr Ser Lys Val Leu Asp Leu Lys Asn Tyr Ile Asp Lys
                180                 185                 190

Gln Leu Leu Pro Ile Val Asn Lys Gln Ser Cys Ser Ile Ser Asn Ile
            195                 200                 205

Glu Thr Val Ile Glu Phe Gln Gln Lys Asn Asn Arg Leu Leu Glu Ile
210                 215                 220

Thr Arg Glu Phe Ser Val Asn Ala Gly Val Thr Thr Pro Val Ser Thr
225                 230                 235                 240

Tyr Met Leu Thr Asn Ser Glu Leu Leu Ser Leu Ile Asn Asp Met Pro
                245                 250                 255

Ile Thr Asn Asp Gln Lys Lys Leu Met Ser Asn Asn Val Gln Ile Val
            260                 265                 270

Arg Gln Gln Ser Tyr Ser Ile Met Ser Ile Ile Lys Glu Glu Val Leu
            275                 280                 285

Ala Tyr Val Val Gln Leu Pro Leu Tyr Gly Val Ile Asp Thr Pro Cys
290                 295                 300

Trp Lys Leu His Thr Ser Pro Leu Cys Thr Thr Asn Thr Lys Glu Gly
305                 310                 315                 320

Ser Asn Ile Cys Leu Thr Arg Thr Asp Arg Gly Trp Tyr Cys Asp Asn
                325                 330                 335

Ala Gly Ser Val Ser Phe Phe Pro Gln Ala Glu Thr Cys Lys Val Gln
            340                 345                 350

Ser Asn Arg Val Phe Cys Asp Thr Met Asn Ser Leu Thr Leu Pro Ser
            355                 360                 365

Glu Val Asn Leu Cys Asn Val Asp Ile Phe Asn Pro Lys Tyr Asp Cys
            370                 375                 380

Lys Ile Met Thr Ser Lys Thr Asp Val Ser Ser Ser Val Ile Thr Ser
385                 390                 395                 400

Leu Gly Ala Ile Val Ser Cys Tyr Gly Lys Thr Lys Cys Thr Ala Ser
                405                 410                 415

Asn Lys Asn Arg Gly Ile Ile Lys Thr Phe Ser Asn Gly Cys Asp Tyr
            420                 425                 430

Val Ser Asn Lys Gly Val Asp Thr Val Ser Val Gly Asn Thr Leu Tyr
            435                 440                 445

Tyr Val Asn Lys Gln Glu Gly Lys Ser Leu Tyr Val Lys Gly Glu Pro
450                 455                 460

Ile Ile Asn Phe Tyr Asp Pro Leu Val Phe Pro Ser Asp Glu Phe Asp
465                 470                 475                 480

Ala Ser Ile Ser Gln Val Asn Glu Lys Ile Asn Gln Ser Leu Ala Phe
                485                 490                 495

-continued

```
Ile Arg Lys Ser Asp Glu Leu Leu His Asn Val Asn Ala Gly Lys Ser
                500                 505                 510

Thr Thr Asn Ile Met Ile Thr Thr Ile Ile Val Ile Ile Val Ile
            515                 520                 525

Leu Leu Ser Leu Ile Ala Val Gly Leu Leu Leu Tyr Cys Lys Ala Arg
        530                 535                 540

Ser Thr Pro Val Thr Leu Ser Lys Asp Gln Leu Ser Gly Ile Asn Asn
545                 550                 555                 560

Ile Ala Phe Ser Asn
                565

<210> SEQ ID NO 14
<211> LENGTH: 6
<212> TYPE: PRT
<213> ORGANISM: Artificial Sequence
<220> FEATURE:
<223> OTHER INFORMATION: mutated furin cleavage site

<400> SEQUENCE: 14

Lys Lys Gln Lys Gln Gln
1               5

<210> SEQ ID NO 15
<211> LENGTH: 6
<212> TYPE: PRT
<213> ORGANISM: Artificial Sequence
<220> FEATURE:
<223> OTHER INFORMATION: mutated furin cleavage site

<400> SEQUENCE: 15

Gln Lys Gln Lys Gln Gln
1               5

<210> SEQ ID NO 16
<211> LENGTH: 6
<212> TYPE: PRT
<213> ORGANISM: Artificial Sequence
<220> FEATURE:
<223> OTHER INFORMATION: mutated furin cleavage site

<400> SEQUENCE: 16

Lys Lys Gln Lys Arg Gln
1               5

<210> SEQ ID NO 17
<211> LENGTH: 6
<212> TYPE: PRT
<213> ORGANISM: Artificial Sequence
<220> FEATURE:
<223> OTHER INFORMATION: mutated furin cleavage site

<400> SEQUENCE: 17

Gly Arg Arg Gln Gln Arg
1               5

<210> SEQ ID NO 18
<211> LENGTH: 6
<212> TYPE: PRT
<213> ORGANISM: Unknown
<220> FEATURE:
<223> OTHER INFORMATION: furin cleavage site

<400> SEQUENCE: 18

Lys Lys Arg Lys Arg Arg
1               5
```

```
<210> SEQ ID NO 19
<211> LENGTH: 539
<212> TYPE: PRT
<213> ORGANISM: Artificial Sequence
<220> FEATURE:
<223> OTHER INFORMATION: modified RSV F protein

<400> SEQUENCE: 19
```

| | | | | | | | | | | | | | | |
|---|---|---|---|---|---|---|---|---|---|---|---|---|---|---|
| Gln | Asn | Ile | Thr | Glu | Glu | Phe | Tyr | Gln | Ser | Thr | Cys | Ser | Ala | Val | Ser |
| 1 | | | | 5 | | | | | 10 | | | | | 15 |

Lys Gly Tyr Leu Ser Ala Leu Arg Thr Gly Trp Tyr Thr Ser Val Ile
           20                  25                  30

Thr Ile Glu Leu Ser Asn Ile Lys Glu Asn Lys Cys Asn Gly Thr Asp
               35                  40                  45

Ala Lys Val Lys Leu Ile Lys Gln Glu Leu Asp Lys Tyr Lys Asn Ala
 50                  55                  60

Val Thr Glu Leu Gln Leu Leu Met Gln Ser Thr Pro Ala Thr Asn Asn
 65                  70                  75                  80

Arg Ala Arg Arg Glu Leu Pro Arg Phe Met Asn Tyr Thr Leu Asn Asn
                 85                  90                  95

Ala Lys Lys Thr Asn Val Thr Leu Ser Lys Lys Arg Lys Arg Arg Phe Leu Gly Phe Leu Leu Gly Val Gly Ser Ala
           100                 105                 110

Ile Ala Ser Gly Val Ala Val Ser Lys Val Leu His Leu Glu Gly Glu
           115                 120                 125

Val Asn Lys Ile Lys Ser Ala Leu Leu Ser Thr Asn Lys Ala Val Val
 130                 135                 140

Ser Leu Ser Asn Gly Val Ser Val Leu Thr Ser Lys Val Leu Asp Leu
145                 150                 155                 160

Lys Asn Tyr Ile Asp Lys Gln Leu Leu Pro Ile Val Asn Lys Gln Ser
                 165                 170                 175

Cys Ser Ile Ser Asn Ile Glu Thr Val Ile Glu Phe Gln Gln Lys Asn
             180                 185                 190

Asn Arg Leu Leu Glu Ile Thr Arg Glu Phe Ser Val Asn Ala Gly Val
         195                 200                 205

Thr Thr Pro Val Ser Thr Tyr Met Leu Thr Asn Ser Glu Leu Leu Ser
210                 215                 220

Leu Ile Asn Asp Met Pro Ile Thr Asn Asp Gln Lys Lys Leu Met Ser
225                 230                 235                 240

Asn Asn Val Gln Ile Val Arg Gln Gln Ser Tyr Ser Ile Met Ser Ile
                 245                 250                 255

Ile Lys Glu Glu Val Leu Ala Tyr Val Val Gln Leu Pro Leu Tyr Gly
             260                 265                 270

Val Ile Asp Thr Pro Cys Trp Lys Leu His Thr Ser Pro Leu Cys Thr
         275                 280                 285

Thr Asn Thr Lys Glu Gly Ser Asn Ile Cys Leu Thr Arg Thr Asp Arg
     290                 295                 300

Gly Trp Tyr Cys Asp Asn Ala Gly Ser Val Ser Phe Phe Pro Gln Ala
305                 310                 315                 320

Glu Thr Cys Lys Val Gln Ser Asn Arg Val Phe Cys Asp Thr Met Asn
                 325                 330                 335

Ser Leu Thr Leu Pro Ser Glu Val Asn Leu Cys Asn Val Asp Ile Phe
             340                 345                 350

Asn Pro Lys Tyr Asp Cys Lys Ile Met Thr Ser Lys Thr Asp Val Ser
         355                 360                 365

Ser Ser Val Ile Thr Ser Leu Gly Ala Ile Val Ser Cys Tyr Gly Lys
        370                 375                 380

Thr Lys Cys Thr Ala Ser Asn Lys Asn Arg Gly Ile Ile Lys Thr Phe
385                 390                 395                 400

Ser Asn Gly Cys Asp Tyr Val Ser Asn Lys Gly Val Asp Thr Val Ser
            405                 410                 415

Val Gly Asn Thr Leu Tyr Tyr Val Asn Lys Gln Glu Gly Lys Ser Leu
            420                 425                 430

Tyr Val Lys Gly Glu Pro Ile Ile Asn Phe Tyr Asp Pro Leu Val Phe
            435                 440                 445

Pro Ser Asp Glu Phe Asp Ala Ser Ile Ser Gln Val Asn Glu Lys Ile
            450                 455                 460

Asn Gln Ser Leu Ala Phe Ile Arg Lys Ser Asp Glu Leu Leu His Asn
465                 470                 475                 480

Val Asn Ala Gly Lys Ser Thr Thr Asn Ile Met Ile Thr Thr Ile Ile
            485                 490                 495

Ile Val Ile Ile Val Ile Leu Leu Ser Leu Ile Ala Val Gly Leu Leu
            500                 505                 510

Leu Tyr Cys Lys Ala Arg Ser Thr Pro Val Thr Leu Ser Lys Asp Gln
            515                 520                 525

Leu Ser Gly Ile Asn Asn Ile Ala Phe Ser Asn
        530                 535

<210> SEQ ID NO 20
<211> LENGTH: 19
<212> TYPE: PRT
<213> ORGANISM: Artificial Sequence
<220> FEATURE:
<223> OTHER INFORMATION: portions of antigenic site II

<400> SEQUENCE: 20

Asn Ser Glu Leu Leu Ser Leu Ile Asn Asp Met Pro Ile Thr Asn Asp
1               5                   10                  15

Gln Lys Lys

<210> SEQ ID NO 21
<211> LENGTH: 5
<212> TYPE: PRT
<213> ORGANISM: Artificial Sequence
<220> FEATURE:
<223> OTHER INFORMATION: portions of antigenic site II

<400> SEQUENCE: 21

Leu Met Ser Asn Asn
1               5

<210> SEQ ID NO 22
<211> LENGTH: 676
<212> TYPE: PRT
<213> ORGANISM: Ebola virus

<400> SEQUENCE: 22

Met Gly Val Thr Gly Ile Leu Gln Leu Pro Arg Asp Arg Phe Lys Arg
1               5                   10                  15

Thr Ser Phe Phe Leu Trp Val Ile Ile Leu Phe Gln Arg Thr Phe Ser
                20                  25                  30

Ile Pro Leu Gly Val Ile His Asn Ser Thr Leu Gln Val Ser Asp Val
            35                  40                  45

-continued

```
Asp Lys Leu Val Cys Arg Asp Lys Leu Ser Ser Thr Asn Gln Leu Arg
    50                  55                  60

Ser Val Gly Leu Asn Leu Glu Gly Asn Gly Val Ala Thr Asp Val Pro
65                  70                  75                  80

Ser Val Thr Lys Arg Trp Gly Phe Arg Ser Gly Val Pro Pro Lys Val
                85                  90                  95

Val Asn Tyr Glu Ala Gly Glu Trp Ala Glu Asn Cys Tyr Asn Leu Glu
            100                 105                 110

Ile Lys Lys Pro Asp Gly Ser Glu Cys Leu Pro Ala Ala Pro Asp Gly
        115                 120                 125

Ile Arg Gly Phe Pro Arg Cys Arg Tyr Val His Lys Val Ser Gly Thr
    130                 135                 140

Gly Pro Cys Ala Gly Asp Phe Ala Phe His Lys Glu Gly Ala Phe Phe
145                 150                 155                 160

Leu Tyr Asp Arg Leu Ala Ser Thr Val Ile Tyr Arg Gly Thr Thr Phe
                165                 170                 175

Ala Glu Gly Val Val Ala Phe Leu Ile Leu Pro Gln Ala Lys Lys Asp
            180                 185                 190

Phe Phe Ser Ser His Pro Leu Arg Glu Pro Val Asn Ala Thr Glu Asp
        195                 200                 205

Pro Ser Ser Gly Tyr Tyr Ser Thr Thr Ile Arg Tyr Gln Ala Thr Gly
    210                 215                 220

Phe Gly Thr Asn Glu Thr Glu Tyr Leu Phe Glu Val Asp Asn Leu Thr
225                 230                 235                 240

Tyr Val Gln Leu Glu Ser Arg Phe Thr Pro Gln Phe Leu Leu Gln Leu
                245                 250                 255

Asn Glu Thr Ile Tyr Ala Ser Gly Lys Arg Ser Asn Thr Thr Gly Lys
            260                 265                 270

Leu Ile Trp Lys Val Asn Pro Glu Ile Asp Thr Thr Ile Gly Glu Trp
        275                 280                 285

Ala Phe Trp Glu Thr Lys Lys Asn Leu Thr Arg Lys Ile Arg Ser Glu
    290                 295                 300

Glu Leu Ser Phe Thr Ala Val Ser Asn Gly Pro Lys Asn Ile Ser Gly
305                 310                 315                 320

Gln Ser Pro Ala Arg Thr Ser Ser Asp Pro Glu Thr Asn Thr Thr Asn
                325                 330                 335

Glu Asp His Lys Ile Met Ala Ser Glu Asn Ser Ser Ala Met Val Gln
            340                 345                 350

Val His Ser Gln Gly Arg Lys Ala Ala Val Ser His Leu Thr Thr Leu
        355                 360                 365

Ala Thr Ile Ser Thr Ser Pro Gln Pro Pro Thr Thr Lys Thr Gly Pro
    370                 375                 380

Asp Asn Ser Thr His Asn Thr Pro Val Tyr Lys Leu Asp Ile Ser Glu
385                 390                 395                 400

Ala Thr Gln Val Gly Gln His Arg Arg Ala Asp Asn Asp Ser Thr
                405                 410                 415

Ala Ser Asp Thr Pro Pro Ala Thr Thr Ala Ala Gly Pro Leu Lys Ala
            420                 425                 430

Glu Asn Thr Asn Thr Ser Lys Ser Ala Asp Ser Leu Asp Leu Ala Thr
        435                 440                 445

Thr Thr Ser Pro Gln Asn Tyr Ser Glu Thr Ala Gly Asn Asn Asn Thr
    450                 455                 460

His His Gln Asp Thr Gly Glu Glu Ser Ala Ser Ser Gly Lys Leu Gly
```

-continued

```
            465                 470                 475                 480
Leu Ile Thr Asn Thr Ile Ala Gly Val Ala Gly Leu Ile Thr Gly Gly
                485                 490                 495

Arg Arg Thr Arg Arg Glu Val Ile Val Asn Ala Gln Pro Lys Cys Asn
            500                 505                 510

Pro Asn Leu His Tyr Trp Thr Thr Gln Asp Glu Gly Ala Ala Ile Gly
            515                 520                 525

Leu Ala Trp Ile Pro Tyr Phe Gly Pro Ala Ala Glu Gly Ile Tyr Thr
            530                 535                 540

Glu Gly Leu Met His Asn Gln Asp Gly Leu Ile Cys Gly Leu Arg Gln
545                 550                 555                 560

Leu Ala Asn Glu Thr Thr Gln Ala Leu Gln Leu Phe Leu Arg Ala Thr
                565                 570                 575

Thr Glu Leu Arg Thr Phe Ser Ile Leu Asn Arg Lys Ala Ile Asp Phe
            580                 585                 590

Leu Leu Gln Arg Trp Gly Gly Thr Cys His Ile Leu Gly Pro Asp Cys
            595                 600                 605

Cys Ile Glu Pro His Asp Trp Thr Lys Asn Ile Thr Asp Lys Ile Asp
        610                 615                 620

Gln Ile Ile His Asp Phe Val Asp Lys Thr Leu Pro Asp Gln Gly Asp
625                 630                 635                 640

Asn Asp Asn Trp Trp Thr Gly Trp Arg Gln Trp Ile Pro Ala Gly Ile
                645                 650                 655

Gly Val Thr Gly Val Ile Ile Ala Val Ile Ala Leu Phe Cys Ile Cys
            660                 665                 670

Lys Phe Val Phe
        675
```

<210> SEQ ID NO 23
<211> LENGTH: 17
<212> TYPE: PRT
<213> ORGANISM: Ebola virus

<400> SEQUENCE: 23

```
His Asn Thr Pro Val Tyr Lys Leu Asp Ile Ser Glu Ala Thr Gln Val
1               5                   10                  15

Glu
```

<210> SEQ ID NO 24
<211> LENGTH: 17
<212> TYPE: PRT
<213> ORGANISM: Ebola virus

<400> SEQUENCE: 24

```
Ala Thr Gln Val Glu Gln His His Arg Arg Thr Asp Asn Asp Ser Thr
1               5                   10                  15

Ala
```

<210> SEQ ID NO 25
<211> LENGTH: 17
<212> TYPE: PRT
<213> ORGANISM: Ebola virus

<400> SEQUENCE: 25

```
Ala Thr Gln Val Gly Gln His His Arg Arg Ala Asp Asn Asp Ser Thr
1               5                   10                  15

Ala
```

<210> SEQ ID NO 26
<211> LENGTH: 25
<212> TYPE: PRT
<213> ORGANISM: Respiratory syncytial virus

<400> SEQUENCE: 26

Met Glu Leu Leu Ile Leu Lys Ala Asn Ala Ile Thr Thr Ile Leu Thr
1               5                   10                  15

Ala Val Thr Phe Cys Phe Ala Ser Gly
            20                  25

<210> SEQ ID NO 27
<211> LENGTH: 676
<212> TYPE: PRT
<213> ORGANISM: Ebola virus

<400> SEQUENCE: 27

Met Gly Val Thr Gly Ile Leu Gln Leu Pro Arg Asp Arg Phe Lys Arg
1               5                   10                  15

Thr Ser Phe Phe Leu Trp Val Ile Ile Leu Phe Gln Arg Thr Phe Ser
            20                  25                  30

Ile Pro Leu Gly Val Ile His Asn Ser Thr Leu Gln Val Ser Asp Val
        35                  40                  45

Asp Lys Leu Val Cys Arg Asp Lys Leu Ser Ser Thr Asn Gln Leu Arg
50                  55                  60

Ser Val Gly Leu Asn Leu Glu Gly Asn Gly Val Ala Thr Asp Val Pro
65                  70                  75                  80

Ser Ala Thr Lys Arg Trp Gly Phe Arg Ser Gly Val Pro Pro Lys Val
                85                  90                  95

Val Asn Tyr Glu Ala Gly Glu Trp Ala Glu Asn Cys Tyr Asn Leu Glu
            100                 105                 110

Ile Lys Lys Pro Asp Gly Ser Glu Cys Leu Pro Ala Ala Pro Asp Gly
        115                 120                 125

Ile Arg Gly Phe Pro Arg Cys Arg Tyr Val His Lys Val Ser Gly Thr
130                 135                 140

Gly Pro Cys Ala Gly Asp Phe Ala Phe His Lys Glu Gly Ala Phe Phe
145                 150                 155                 160

Leu Tyr Asp Arg Leu Ala Ser Thr Val Ile Tyr Arg Gly Thr Thr Phe
                165                 170                 175

Ala Glu Gly Val Val Ala Phe Leu Ile Leu Pro Gln Ala Lys Lys Asp
            180                 185                 190

Phe Phe Ser Ser His Pro Leu Arg Glu Pro Val Asn Ala Thr Glu Asp
        195                 200                 205

Pro Ser Ser Gly Tyr Tyr Ser Thr Thr Ile Arg Tyr Gln Ala Thr Gly
210                 215                 220

Phe Gly Thr Asn Glu Thr Glu Tyr Leu Phe Glu Val Asp Asn Leu Thr
225                 230                 235                 240

Tyr Val Gln Leu Glu Ser Arg Phe Thr Pro Gln Phe Leu Leu Gln Leu
                245                 250                 255

Asn Glu Thr Ile Tyr Thr Ser Gly Lys Arg Ser Asn Thr Thr Gly Lys
            260                 265                 270

Leu Ile Trp Lys Val Asn Pro Glu Ile Asp Thr Thr Ile Gly Glu Trp
        275                 280                 285

Ala Phe Trp Glu Thr Lys Lys Asn Leu Thr Arg Lys Ile Arg Ser Glu
290                 295                 300

```
Glu Leu Ser Phe Thr Val Val Ser Asn Gly Ala Lys Asn Ile Ser Gly
305                 310                 315                 320

Gln Ser Pro Ala Arg Thr Ser Asp Pro Gly Thr Asn Thr Thr Thr
            325                 330                 335

Glu Asp His Lys Ile Met Ala Ser Glu Asn Ser Ser Ala Met Val Gln
                340                 345                 350

Val His Ser Gln Gly Arg Glu Ala Ala Val Ser His Leu Thr Thr Leu
            355                 360                 365

Ala Thr Ile Ser Thr Ser Pro Gln Ser Leu Thr Thr Lys Pro Gly Pro
370                 375                 380

Asp Asn Ser Thr His Asn Thr Pro Val Tyr Lys Leu Asp Ile Ser Glu
385                 390                 395                 400

Ala Thr Gln Val Glu Gln His His Arg Arg Thr Asp Asn Asp Ser Thr
                405                 410                 415

Ala Ser Asp Thr Pro Ser Ala Thr Thr Ala Ala Gly Pro Pro Lys Ala
            420                 425                 430

Glu Asn Thr Asn Thr Ser Lys Ser Thr Asp Phe Leu Asp Pro Ala Thr
            435                 440                 445

Thr Thr Ser Pro Gln Asn His Ser Glu Thr Ala Gly Asn Asn Asn Thr
450                 455                 460

His His Gln Asp Thr Gly Glu Glu Ser Ala Ser Ser Gly Lys Leu Gly
465                 470                 475                 480

Leu Ile Thr Asn Thr Ile Ala Gly Val Ala Gly Leu Ile Thr Gly Gly
                485                 490                 495

Arg Arg Thr Arg Arg Glu Ala Ile Val Asn Ala Gln Pro Lys Cys Asn
            500                 505                 510

Pro Asn Leu His Tyr Trp Thr Thr Gln Asp Glu Gly Ala Ala Ile Gly
            515                 520                 525

Leu Ala Trp Ile Pro Tyr Phe Gly Pro Ala Ala Glu Gly Ile Tyr Ile
530                 535                 540

Glu Gly Leu Met His Asn Gln Asp Gly Leu Ile Cys Gly Leu Arg Gln
545                 550                 555                 560

Leu Ala Asn Glu Thr Thr Gln Ala Leu Gln Leu Phe Leu Arg Ala Thr
                565                 570                 575

Thr Glu Leu Arg Thr Phe Ser Ile Leu Asn Arg Lys Ala Ile Asp Phe
            580                 585                 590

Leu Leu Gln Arg Trp Gly Gly Thr Cys His Ile Leu Gly Pro Asp Cys
            595                 600                 605

Cys Ile Glu Pro His Asp Trp Thr Lys Asn Ile Thr Asp Lys Ile Asp
610                 615                 620

Gln Ile Ile His Asp Phe Val Asp Lys Thr Leu Pro Asp Gln Gly Asp
625                 630                 635                 640

Asn Asp Asn Trp Trp Thr Gly Trp Arg Gln Trp Ile Pro Ala Gly Ile
                645                 650                 655

Gly Val Thr Gly Val Ile Ile Ala Val Ile Ala Leu Phe Cys Ile Cys
            660                 665                 670

Lys Phe Val Phe
            675

<210> SEQ ID NO 28
<211> LENGTH: 676
<212> TYPE: PRT
<213> ORGANISM: Ebola virus
```

```
<400> SEQUENCE: 28

Met Gly Val Thr Gly Ile Leu Gln Leu Pro Arg Asp Arg Phe Lys Arg
1               5                   10                  15

Thr Ser Phe Phe Leu Trp Val Ile Ile Leu Phe Gln Arg Thr Phe Ser
            20                  25                  30

Ile Pro Leu Gly Val Ile His Asn Ser Thr Leu Gln Val Ser Asp Val
        35                  40                  45

Asp Lys Leu Val Cys Arg Asp Lys Leu Ser Ser Thr Asn Gln Leu Arg
50                  55                  60

Ser Val Gly Leu Asn Leu Glu Gly Asn Gly Val Ala Thr Asp Val Pro
65                  70                  75                  80

Ser Val Thr Lys Arg Trp Gly Phe Arg Ser Gly Val Pro Lys Val
                85                  90                  95

Val Asn Tyr Glu Ala Gly Glu Trp Ala Glu Asn Cys Tyr Asn Leu Glu
            100                 105                 110

Ile Lys Lys Pro Asp Gly Ser Glu Cys Leu Pro Ala Ala Pro Asp Gly
            115                 120                 125

Ile Arg Gly Phe Pro Arg Cys Arg Tyr Val His Lys Val Ser Gly Thr
        130                 135                 140

Gly Pro Cys Ala Gly Asp Phe Ala Phe His Lys Glu Gly Ala Phe Phe
145                 150                 155                 160

Leu Tyr Asp Arg Leu Ala Ser Thr Val Ile Tyr Arg Gly Thr Thr Phe
                165                 170                 175

Ala Glu Gly Val Val Ala Phe Leu Ile Leu Pro Gln Ala Lys Lys Asp
            180                 185                 190

Phe Phe Ser Ser His Pro Leu Arg Glu Pro Val Asn Ala Thr Glu Asp
            195                 200                 205

Pro Ser Ser Gly Tyr Tyr Ser Thr Thr Ile Arg Tyr Gln Ala Thr Gly
        210                 215                 220

Phe Gly Thr Asn Glu Thr Glu Tyr Leu Phe Glu Val Asp Asn Leu Thr
225                 230                 235                 240

Tyr Val Gln Leu Glu Ser Arg Phe Thr Pro Gln Phe Leu Leu Gln Leu
                245                 250                 255

Asn Glu Thr Ile Tyr Ala Ser Gly Lys Arg Ser Asn Thr Thr Gly Lys
            260                 265                 270

Leu Ile Trp Lys Val Asn Pro Glu Ile Asp Thr Thr Ile Gly Glu Trp
            275                 280                 285

Ala Phe Trp Glu Thr Lys Lys Asn Leu Thr Arg Lys Ile Arg Ser Glu
        290                 295                 300

Glu Leu Ser Phe Thr Ala Val Ser Asn Gly Pro Lys Asn Ile Ser Gly
305                 310                 315                 320

Gln Ser Pro Ala Arg Thr Ser Ser Asp Pro Glu Thr Asn Thr Thr Asn
                325                 330                 335

Glu Asp His Lys Ile Met Ala Ser Glu Asn Ser Ser Ala Met Val Gln
            340                 345                 350

Val His Ser Gln Gly Arg Lys Ala Ala Val Ser His Leu Thr Thr Leu
        355                 360                 365

Ala Thr Ile Ser Thr Ser Pro Gln Pro Pro Thr Thr Lys Thr Gly Pro
370                 375                 380

Asp Asn Ser Thr His Asn Thr Pro Val Tyr Lys Leu Asp Ile Ser Glu
385                 390                 395                 400

Ala Thr Gln Val Gly Gln His His Arg Arg Ala Asp Asn Asp Ser Thr
                405                 410                 415
```

```
Ala Ser Asp Thr Pro Ala Thr Thr Ala Ala Gly Pro Leu Lys Ala
            420                 425                 430

Glu Asn Thr Asn Thr Ser Lys Ser Ala Asp Ser Leu Asp Leu Ala Thr
                435                 440                 445

Thr Thr Ser Pro Gln Asn Tyr Ser Glu Thr Ala Gly Asn Asn Asn Thr
450                 455                 460

His His Gln Asp Thr Gly Glu Glu Ser Ala Ser Ser Gly Lys Leu Gly
465                 470                 475                 480

Leu Ile Thr Asn Thr Ile Ala Gly Val Ala Gly Leu Ile Thr Gly Gly
                485                 490                 495

Arg Arg Thr Arg Arg Glu Val Ile Val Asn Ala Gln Pro Lys Cys Asn
                500                 505                 510

Pro Asn Leu His Tyr Trp Thr Thr Gln Asp Glu Gly Ala Ala Ile Gly
            515                 520                 525

Leu Ala Trp Ile Pro Tyr Phe Gly Pro Ala Ala Glu Gly Ile Tyr Thr
530                 535                 540

Glu Gly Leu Met His Asn Gln Asp Gly Leu Ile Cys Gly Leu Arg Gln
545                 550                 555                 560

Leu Ala Asn Glu Thr Thr Gln Ala Leu Gln Leu Phe Leu Arg Ala Thr
                565                 570                 575

Thr Glu Leu Arg Thr Phe Ser Ile Leu Asn Arg Lys Ala Ile Asp Phe
                580                 585                 590

Leu Leu Gln Arg Trp Gly Gly Thr Cys His Ile Leu Gly Pro Asp Cys
            595                 600                 605

Cys Ile Glu Pro His Asp Trp Thr Lys Asn Ile Thr Asp Lys Ile Asp
610                 615                 620

Gln Ile Ile His Asp Phe Val Asp Lys Thr Leu Pro Asp Gln Gly Asp
625                 630                 635                 640

Asn Asp Asn Trp Trp Thr Gly Trp Arg Gln Trp Ile Pro Ala Gly Ile
                645                 650                 655

Gly Val Thr Gly Val Ile Ile Ala Val Ile Ala Leu Phe Cys Ile Cys
                660                 665                 670

Lys Phe Val Phe
        675

<210> SEQ ID NO 29
<211> LENGTH: 644
<212> TYPE: PRT
<213> ORGANISM: Ebola virus

<400> SEQUENCE: 29

Ile Pro Leu Gly Val Ile His Asn Ser Thr Leu Gln Val Ser Asp Val
1               5                   10                  15

Asp Lys Leu Val Cys Arg Asp Lys Leu Ser Ser Thr Asn Gln Leu Arg
                20                  25                  30

Ser Val Gly Leu Asn Leu Glu Gly Asn Gly Val Ala Thr Asp Val Pro
            35                  40                  45

Ser Val Thr Lys Arg Trp Gly Phe Arg Ser Gly Val Pro Pro Lys Val
        50                  55                  60

Val Asn Tyr Glu Ala Gly Glu Trp Ala Glu Asn Cys Tyr Asn Leu Glu
65                  70                  75                  80

Ile Lys Lys Pro Asp Gly Ser Glu Cys Leu Pro Ala Ala Pro Asp Gly
                85                  90                  95

Ile Arg Gly Phe Pro Arg Cys Arg Tyr Val His Lys Val Ser Gly Thr
```

```
                100             105             110
Gly Pro Cys Ala Gly Asp Phe Ala Phe His Lys Glu Gly Ala Phe Phe
        115             120             125

Leu Tyr Asp Arg Leu Ala Ser Thr Val Ile Tyr Arg Gly Thr Thr Phe
130             135             140

Ala Glu Gly Val Val Ala Phe Leu Ile Leu Pro Gln Ala Lys Lys Asp
145             150             155             160

Phe Phe Ser Ser His Pro Leu Arg Glu Pro Val Asn Ala Thr Glu Asp
            165             170             175

Pro Ser Ser Gly Tyr Tyr Ser Thr Thr Ile Arg Tyr Gln Ala Thr Gly
        180             185             190

Phe Gly Thr Asn Glu Thr Glu Tyr Leu Phe Glu Val Asp Asn Leu Thr
        195             200             205

Tyr Val Gln Leu Glu Ser Arg Phe Thr Pro Gln Phe Leu Leu Gln Leu
    210             215             220

Asn Glu Thr Ile Tyr Ala Ser Gly Lys Arg Ser Asn Thr Thr Gly Lys
225             230             235             240

Leu Ile Trp Lys Val Asn Pro Glu Ile Asp Thr Thr Ile Gly Glu Trp
            245             250             255

Ala Phe Trp Glu Thr Lys Lys Asn Leu Thr Arg Lys Ile Arg Ser Glu
            260             265             270

Glu Leu Ser Phe Thr Ala Val Ser Asn Gly Pro Lys Asn Ile Ser Gly
        275             280             285

Gln Ser Pro Ala Arg Thr Ser Ser Asp Pro Glu Thr Asn Thr Thr Asn
        290             295             300

Glu Asp His Lys Ile Met Ala Ser Glu Asn Ser Ser Ala Met Val Gln
305             310             315             320

Val His Ser Gln Gly Arg Lys Ala Ala Val Ser His Leu Thr Thr Leu
            325             330             335

Ala Thr Ile Ser Thr Ser Pro Gln Pro Pro Thr Thr Lys Thr Gly Pro
            340             345             350

Asp Asn Ser Thr His Asn Thr Pro Val Tyr Lys Leu Asp Ile Ser Glu
            355             360             365

Ala Thr Gln Val Gly Gln His His Arg Arg Ala Asp Asn Asp Ser Thr
            370             375             380

Ala Ser Asp Thr Pro Pro Ala Thr Thr Ala Ala Gly Pro Leu Lys Ala
385             390             395             400

Glu Asn Thr Asn Thr Ser Lys Ser Ala Asp Ser Leu Asp Leu Ala Thr
            405             410             415

Thr Thr Ser Pro Gln Asn Tyr Ser Glu Thr Ala Gly Asn Asn Asn Thr
            420             425             430

His His Gln Asp Thr Gly Glu Glu Ser Ala Ser Ser Gly Lys Leu Gly
        435             440             445

Leu Ile Thr Asn Thr Ile Ala Gly Val Ala Gly Leu Ile Thr Gly Gly
        450             455             460

Arg Arg Thr Arg Arg Glu Val Ile Val Asn Ala Gln Pro Lys Cys Asn
465             470             475             480

Pro Asn Leu His Tyr Trp Thr Thr Gln Asp Glu Gly Ala Ala Ile Gly
            485             490             495

Leu Ala Trp Ile Pro Tyr Phe Gly Pro Ala Ala Glu Gly Ile Tyr Thr
            500             505             510

Glu Gly Leu Met His Asn Gln Asp Gly Leu Ile Cys Gly Leu Arg Gln
            515             520             525
```

```
Leu Ala Asn Glu Thr Thr Gln Ala Leu Gln Leu Phe Leu Arg Ala Thr
        530                 535                 540
Thr Glu Leu Arg Thr Phe Ser Ile Leu Asn Arg Lys Ala Ile Asp Phe
545                 550                 555                 560
Leu Leu Gln Arg Trp Gly Gly Thr Cys His Ile Leu Gly Pro Asp Cys
                565                 570                 575
Cys Ile Glu Pro His Asp Trp Thr Lys Asn Ile Thr Asp Lys Ile Asp
                580                 585                 590
Gln Ile Ile His Asp Phe Val Asp Lys Thr Leu Pro Asp Gln Gly Asp
            595                 600                 605
Asn Asp Asn Trp Trp Thr Gly Trp Arg Gln Trp Ile Pro Ala Gly Ile
        610                 615                 620
Gly Val Thr Gly Val Ile Ile Ala Val Ile Ala Leu Phe Cys Ile Cys
625                 630                 635                 640
Lys Phe Val Phe
```